United States Patent
Aukerman et al.

(10) Patent No.: US 8,541,650 B2
(45) Date of Patent: Sep. 24, 2013

(54) PLANTS HAVING ALTERED AGRONOMIC CHARACTERISTICS UNDER NITROGEN LIMITING CONDITIONS AND RELATED CONSTRUCTS AND METHODS INVOLVING GENES ENCODING LNT1 POLYPEPTIDES AND HOMOLOGS THEREOF

(75) Inventors: Milo Aukerman, Newark, DE (US); Stephen M. Allen, Wilmington, DE (US); Dale Loussaert, Clive, IA (US); Stanley Luck, Wilmington, DE (US); Hajime Sakai, Newark, DE (US); Scott V. Tingey, Wilmington, DE (US)

(73) Assignees: E. I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 252 days.

(21) Appl. No.: 12/999,074

(22) PCT Filed: Jul. 8, 2009

(86) PCT No.: PCT/US2009/049878
§ 371 (c)(1),
(2), (4) Date: Dec. 15, 2010

(87) PCT Pub. No.: WO2010/006010
PCT Pub. Date: Jan. 14, 2010

(65) Prior Publication Data
US 2011/0099667 A1 Apr. 28, 2011

Related U.S. Application Data

(60) Provisional application No. 61/078,949, filed on Jul. 8, 2008.

(51) Int. Cl.
*A01H 1/00* (2006.01)
*C12N 5/04* (2006.01)
*C12N 15/00* (2006.01)
*C12N 15/82* (2006.01)
*C12Q 1/68* (2006.01)
*C07H 21/04* (2006.01)

(52) U.S. Cl.
USPC ......... 800/278; 800/295; 435/6.1; 435/320.1; 435/419; 530/370; 536/23.1; 536/23.6

(58) Field of Classification Search
None
See application file for complete search history.

(56) References Cited

U.S. PATENT DOCUMENTS

| 2004/0031072 | A1 | 2/2004 | La Rosa et al. | |
|---|---|---|---|---|
| 2004/0214272 | A1 | 10/2004 | LaRosa et al. | |
| 2004/0216190 | A1* | 10/2004 | Kovalic | 800/289 |
| 2007/0011783 | A1 | 1/2007 | Liu et al. | |
| 2009/0087878 | A9 | 4/2009 | LaRosa et al. | |

OTHER PUBLICATIONS

Detlef Weigel et al., Activation Tagging in *Arabidopsis*, Plant Physiology, Apr. 2000, pp. 1003-1013, vol. 122.
National Center for Biotechnology Information General Identifier No. 145337238, May 28, 2011, Accession No. NM105376, A. Theologis et al, Sequence and analysis of chromosome 1 of the plant *Arabidopsis thaliana*.
National Center for Biotechnology Information General Identifier No. 157341431, Oct. 8, 2007, Accession No. CA049338, O. Jaillon et al., The grapevine genome sequencce suggests ancestral hexaploidization in major angiosperm phyla.
National Center for Biotechnology Information General Identifier No. 157343572, Oct. 8, 2007, Accession No. CA068078, O. Jaillon et al., The grapevine genome sequence suggests ancestral hexaploidization in major angiosperm phyla.
National Center for Biotechnology Information General Identifier No. 212275704, Jun. 16, 2012, Accession No. NP_001130069, C. Soderlund et al., Sequencing, mapping, and analysis of 27,455 maize full-length cDNAs.
National Center for Biotechnology Information General Identifier No. 42563004, May 28, 2011, Accession No. NP_176877, A. Theologis et al., Sequence and analysis of chromosome 1 of the plant *Arabidopsis thaliana*.

* cited by examiner

*Primary Examiner* — Brent T Page
*Assistant Examiner* — Matthew Keogh

(57) ABSTRACT

Isolated polynucleotides and polypeptides and recombinant DNA constructs particularly useful for altering agronomic characteristics of plants under nitrogen limiting conditions, compositions (such as plants or seeds) comprising these recombinant DNA constructs, and methods utilizing these recombinant DNA constructs. The recombinant DNA construct comprises a polynucleotide operably linked to a promoter functional in a plant, wherein said polynucleotide encodes an LNT1 polypeptide.

10 Claims, 24 Drawing Sheets

FIG. 11

| O 3 | O 4 | O 2 | O 1 | O 5 | O 3 | O C1 | O 4 |
|---|---|---|---|---|---|---|---|
| O 4 | O 2 | O 1 | O 5 | O 3 | O C1 | O 4 | O 2 |
| O 2 | O 1 | O 5 | O 3 | O C1 | O 4 | O 2 | O 5 |
| O 1 | O 5 | O 3 | O C1 | O 4 | O 2 | O 5 | O 4 |
| O 5 | O 3 | O C1 | O 1 | O 2 | O 5 | O 4 | O 3 |
| O 3 | O C1 | O 1 | O 2 | O 5 | O 4 | O 3 | O 1 |
| O C1 | O 1 | O 2 | O 5 | O 4 | O 3 | O 1 | O C1 |
| O 1 | O 2 | O 5 | O 4 | O 3 | O 1 | O C1 | O 2 |

Typical grid pattern for 5 lines (labeled 1 through 5), plus wild-type control C1, used in screens.

FIG. 13

**Modified Hoagland's solutions -
16X concentrations for semi-hydroponics maize growth.**

| Nutrient | 1 mM KNO$_3$ | 2 mM KNO$_3$ | 3 mM KNO$_3$ | 4 mM KNO$_3$ |
|---|---|---|---|---|
| KNO$_3$ | 16 mM | 32 mM | 48 mM | 64 mM |
| KCl | 48 mM | 32 mM | 16 mM | --- |
| KH$_2$PO$_4$ | 11 mM | 11 mM | 11 mM | 11 mM |
| MgSO$_4$ | 16 mM | 16 mM | 16 mM | 16 mM |
| CaCl$_2$·2H$_2$O | 16 mM | 16 mM | 16 mM | 16 mM |
| Sprint 330 | 1.6 g/L | 1.6 g/L | 1.6 g/L | 1.6 g/L |
| H$_3$BO$_3$ | 24 µM | 24 µM | 24 µM | 24 µM |
| 5 mM MnCl$_2$·4H$_2$O | 8 µM | 8 µM | 8 µM | 8 µM |
| 5 mM ZnSO$_4$·7 H$_2$O | 8 M | 8 µM | 8 µM | 8 µM |
| 0.5 mM CuSO$_4$·5 H$_2$O | 800 nM | 800 nM | 800 nM | 800 nM |
| 0.5 mM H$_2$MoO$_4$·H$_2$O | 800 nM | 800 nM | 800 nM | 800 nM |

Dilute 16X with tap water and determine the pH of the final mixture.
Add 3-12 mL H$_2$SO$_4$ if the pH is above 6.5.
Optimum pH is 5.0 - 5.5

FIG. 14

The effect of different nitrate concentrations on the growth and development of Gaspe Bay Flint derived maize lines (see Example 18).

| [nitrate] | root (g dwt) | shoot (g dwt) | total vegetative (g dwt) | ear & husk (g dwt) | tassel (g dwt) | tiller # | tiller (g dwt) |
|---|---|---|---|---|---|---|---|
| 1 week after emergence | | | | | | | |
| 1 mM | 0.070a | 0.105b | 0.175b | | | | |
| 2 mM | 0.073a | 0.137ab | 0.209ab | | | | |
| 3 mM | 0.056a | 0.120ab | 0.176ab | | | | |
| 4 mM | 0.074a | 0.157a | 0.231a | | | | |
| 2 weeks after emergence | | | | | | | |
| 1 mM | 0.331ab | 0.544c | 0.875c | | | | |
| 2 mM | 0.266b | 0.951b | 1.217b | | | | |
| 3 mM | 0.352a | 1.171a | 1.523a | | | | |
| 4 mM | 0.303ab | 1.209a | 1.512a | | | | |
| 3 weeks after emergence | | | | | | | |
| 1 mM | 0.757a | 1.283b | 2.040b | 0.379c | 0.239c | 0.8c | 0.080b |
| 2 mM | 0.785a | 2.033a | 2.819a | 0.718a | 0.363bc | 2.3 | 0.506a |
| 3 mM | 0.664a | 1.911a | 2.574a | 0.451bc | 0.403ab | 2.8ab | 0.441a |
| 4 mM | 0.845a | 2.129a | 2.974a | 0.650ab | 0.506a | 3.3a | 0.688a |
| 4 weeks after emergence | | | | | | | |
| 1 mM | 0.842b | 2.010b | 2.852b | 1.318b | 0.677b | * | * |
| 2 mM | 1.493a | 3.772a | 5.265a | 3.130a | 1.018a | * | * |
| 3 mM | 1.232ab | 3.563a | 4.795a | 3.060a | 0.875ab | * | * |
| 4 mM | 1.010b | 2.943a | 3.952a | 2.787a | 0.891ab | * | * |

* Tillers removed 3 weeks after emergence
Means with similar letters are not different by protected Least Significant Difference (LSD) (0.05)

FIG. 15A

```
      M---PNWELRXCCDHDQXIFXATVGVFTVVILLLWRTFLLTPFKLITVFLH Majority
               10        20        30        40        50

1   MA--VNWELQGCCHRDQRIFIAAVGVSTVVILLLWRTFLLTPFKLITVFLH   SEQ ID NO:18 (maize)
  1   MA--VNWELRGCCCDHDQRIFIAAVGVSTVVILLLWRTFLLTPFKLITVFLH  SEQ ID NO:20 (maize)
  1   M---PNWELRNCCDHDQKVFIACVAAFTVVILVLWRTFLLTPFKLITVFLH   SEQ ID NO:22 (soybean)
  1   M---PNWELRNCCDHDQKIFIACVAAFTVVILVLWRTFLLTPFKLITVFLH   SEQ ID NO:24 (soybean)
  1   MTSPNWELKNCCDRDQKFFLATVGIYSLVILALWRTFLLTPFKLITVFLH    SEQ ID NO:26 (sunflower)
  1   MA--NWELRDCCNHDQLLFLITLAFCVIVILALWRTIVLLPFKLVTIFLH    SEQ ID NO:28 (sunflower)
  1   M--------------------------------------------------  SEQ ID NO:30 (rice)
  1   MDSPNWELRGCCNRMQNTFLITIGVFTVVILLLWRTFLLTPFKLITVFLH    SEQ ID NO:32 (Arabidopsis)
  1   M---ANWELKNCCKHDQVVFLATIGVFTVVILLLWRTFLLTPFKLITVFLH   SEQ ID NO:33 (grape)
  1   M---ANWELKKCCNHEQVVFLTTISICTVVILALWRTILLITPFKLVTVFLH  SEQ ID NO:34 (grape)
  1   MA--VNWELQGCCHRDQRIFIAAVGVSTVVILLLWRTFLLTPFKLITVFLH   SEQ ID NO:37 (maize)

EASHAIACKLTCGDVEGMQVHANEGGVTQTRGGIYWXILPAGYLGSSFWG Majority
               60        70        80        90       100

50   ETSHALACKLTCGDVEGMQVHANEGGVTQTRGGIYWIILPAGYLGSSFWG    SEQ ID NO:18 (maize)
 50   ETSHALACKLTCGDVEGMQVHANEGGVTQTRGGIYWIILPAGYLGSSFWG    SEQ ID NO:20 (maize)
 49   EASHAIACWLTCGKVEGIQVHANEGGVTQTRGGIYWVILPAGYLGSSFWG    SEQ ID NO:22 (soybean)
 49   EASHAIACWLTCGKVEGIQVHANEGGVTQTRGGIYWVILPAGYLGSSFWG    SEQ ID NO:24 (soybean)
 51   EASHAIACKLTCGEVMGMEVHANEGGVTQTRGGVYWLILPAGYLGSSFWG    SEQ ID NO:26 (sunflower)
 49   EASHAVACKLTCGHVEGMQIFADEGGMTQTRGGVYWFILPAGYLGSSFWG    SEQ ID NO:28 (sunflower)
  2   -------QVHPNEGGVTQTRGGIYWIILPAGYLGSSFWG              SEQ ID NO:30 (rice)
 51   EASHAVACKLTCGDVEGMEVNANEGSSTTRGGIYWLILPAGYLGSSFWG     SEQ ID NO:32 (Arabidopsis)
 49   EASHAIACKLTCGQVEGINVNADEGGVTQTRGGVYWNLILPAGYLGSSFWG   SEQ ID NO:33 (grape)
 49   EASHAIACKLTCGHVEGIQVHADEGTTQTRGGIYWLILPAGYLGSSFWG     SEQ ID NO:34 (grape)
 50   ETSHALACKLTCGDVEGMQVHANEGGVTQTRGGIYWIILPAGYLGSSFWG    SEQ ID NO:37 (maize)
```

FIG. 15B

```
    MVLILASTNLLLTARIAAGCFILALFIVLFVAKNWTLRGLCIGFIVFIAVV Majority
                110       120       130       140       150
100 MVFILASTNLLTTRIAAGCFILALFIVLFVADNWFLRWLCLGFIVFIAVV SEQ ID NO:18  (maize)
100 MVFILASTNLLTTRIAAGCFILALFIVLFVAENWFLRWLCLGFIVFIAVV SEQ ID NO:20  (maize)
 99 MALILASTNLLTAKIAAGCFIAALIVVLFLAKNWTLRGLCIGFIVFIAVI SEQ ID NO:22  (soybean)
 99 MVLILASTNLLTAKIAAGCFIAALIVVLFLAKNWTLRGLCIGFIVFIAVI SEQ ID NO:24  (soybean)
101 MLLILASTDLLTARIAAGCLAAALLIVLFLAKNWTLRGLCIGFIVFLAIV SEQ ID NO:26  (sunflower)
 99 MVLILASTNLIAARVAAGCLAAALIIVLFVAKNWFLRWLCIGFIVLAVV  SEQ ID NO:28  (sunflower)
 34 MVFILASTNLLTTRIAAGCFILALFIVLFVAKNWFLRWLCIGFIVFLAVV SEQ ID NO:30  (rice)
101 MALILASTNLLTTRIAAAGLGLALFIVILGFTAKNWTLRGLCIGFIFLAII SEQ ID NO:32  (Arabidopsis)
 99 MVFILASTNLLTSRIAAGCFEAVALIVVLFIAKNWTLRGLCIGFIIFLAII SEQ ID NO:33  (grape)
 99 MVLIASTNVLTAKIAAGCFAFALLIVVLFVAKNWTLRGLCIGFIVFIAVI SEQ ID NO:34  (grape)
100 MVFILASTNLLTTRIAAGCFILALFIVLFVADNWFLRWLCLGFIVFIAVV SEQ ID NO:37  (maize)

WVLIQEFTTVHILRYVILFIGVMNSLFSVYDIYDDLISRRVHSSDAEKFAE Majority
                160       170       180       190       200
150 WVIQEFTSFHILKYVILFIGVMNSLFSVYDIYDDLISRRVNTSDAEKFAE SEQ ID NO:18  (maize)
150 WVIQEFTSFHVLKYVILFIGVMNSLFSVYDIYDDLISRRVNTSDAEKFAE SEQ ID NO:20  (maize)
149 WVLQEKTTVHVLRYVILFIGVMNSLFSVYDIYDDLISRRVHSSDAEKFAE SEQ ID NO:22  (soybean)
149 WLLQEKT-VHVLRYVILFIGVMNSLFSVYDIYDDLISRRVHSSDAEKFAE SEQ ID NO:24  (soybean)
151 WLLQEFTTVRILRYVILFIGVMNSLFSVFSIYDIYDDLISRRVNSSDAEKFAE SEQ ID NO:26  (sunflower)
149 WLLQEFTTKVRILRYIIMFIGVMNSVFSIYDIYDDLISRQVHTSDAEKFAE SEQ ID NO:28  (sunflower)
 84 WIQEFTKFHSLKYVILFIGVMNSLFSVYDIYDDLISRRVHSSDAEKFAE SEQ ID NO:30  (rice)
151 WVLQELTTVKILRYVILFIGVMNSLFSVYDIYDDLISRRVHSSDAEKFAE SEQ ID NO:32  (Arabidopsis)
149 WVLQETTKVRILREFILFMGVMNSLFSVYDIYDDLISRRVNSSDAEKFAE SEQ ID NO:33  (grape)
149 WLLQETTEIRILRYIILFIGVMNSLFSVYDIYDDLISRRVNSSDAEKFAE SEQ ID NO:34  (grape)
150 WVIQEFTSFHILKYVILFIGVMNSLFSVYDIYDDLISRRVNTSDAEKFAE SEQ ID NO:37  (maize)
```

FIG. 15C

```
    ICPCPCNGFGWGVIWGMISFIFLCASIYLGLVILS---                 Majority

200 ICPCPCNGFAWGVIWGFISFIFLCASIYLGLVILS.                   SEQ ID NO:18 (maize)
200 ICPCPCNGFAWGVIWGFISFIFLCASIYLGLVILS.                   SEQ ID NO:20 (maize)
199 VCPCPCNGFGWGVIWGMISFAFLCASLYLGLVILSG.                  SEQ ID NO:22 (soybean)
199 VCPCPCNGFGWGVIWGMISFAFLCASLYLGLVILSG.                  SEQ ID NO:24 (soybean)
201 ICPCPCNGVAWGVIWGMISFTFLSASVYLGLVILS.                   SEQ ID NO:26 (sunflower)
199 VCPCPCNGVGWGVIWGLISLIFLGIATYFGLVILSQV.                 SEQ ID NO:28 (sunflower)
134 ICPCPCNGCAWGVIWGFISFIFLCASIYLGLVILS.                   SEQ ID NO:30 (rice)
201 ICPC-CTGCGWGVIWGMISFAFLCASLYLGLVILS.                   SEQ ID NO:32 (Arabidopsis)
199 ICPCPCNGVGWGVIWGMISFIFLAAAMYIGLVIL---S                 SEQ ID NO:33 (grape)
199 VCPCPCNGVGWGVIWGLISFLFLCGAMYLGLVIL---S                 SEQ ID NO:34 (grape)
200 ICPCPCNGFAWGVIWGFISFIFICASIYLGLVIL---S                 SEQ ID NO:37 (maize)
         210       220       230
```

FIG. 16

Percent Identity

|   | 1 | 2 | 3 | 4 | 5 | 6 | 7 | 8 | 9 | 10 | 11 | |
|---|---|---|---|---|---|---|---|---|---|----|----|---|
| 1 |   | 97.4 | 79.6 | 80.4 | 78.3 | 68.9 | 92.9 | 77.4 | 78.1 | 75.1 | 100.0 | SEQ ID NO:18 (maize) |
| 2 | 2.2 |   | 81.3 | 82.1 | 77.9 | 69.4 | 92.9 | 77.0 | 78.1 | 75.1 | 97.9 | SEQ ID NO:20 (maize) |
| 3 | 22.4 | 20.1 |   | 98.7 | 82.6 | 72.8 | 84.0 | 80.4 | 82.8 | 81.1 | 79.9 | SEQ ID NO:22 (soybean) |
| 4 | 21.2 | 19.0 | 0.9 |   | 82.6 | 73.2 | 84.6 | 80.0 | 82.8 | 81.1 | 80.8 | SEQ ID NO:24 (soybean) |
| 5 | 24.6 | 25.2 | 18.4 | 18.4 |   | 73.7 | 81.1 | 81.3 | 82.8 | 79.4 | 78.6 | SEQ ID NO:26 (sunflower) |
| 6 | 37.6 | 36.9 | 32.9 | 32.2 | 30.3 |   | 74.0 | 71.1 | 76.4 | 78.5 | 69.2 | SEQ ID NO:28 (sunflower) |
| 7 | 6.9 | 6.9 | 16.6 | 15.9 | 21.2 | 31.3 |   | 78.7 | 81.7 | 78.1 | 92.9 | SEQ ID NO:30 (rice) |
| 8 | 23.6 | 24.1 | 19.1 | 19.6 | 19.5 | 32.4 | 21.4 |   | 80.3 | 75.1 | 77.8 | SEQ ID NO:32 (Arabidopsis) |
| 9 | 25.5 | 25.5 | 19.6 | 19.6 | 19.1 | 28.7 | 19.8 | 20.3 |   | 83.7 | 78.1 | SEQ ID NO:33 (grape) |
| 10 | 29.8 | 29.8 | 21.9 | 21.9 | 23.7 | 25.6 | 24.6 | 27.4 | 18.4 |   | 75.1 | SEQ ID NO:34 (grape) |
| 11 | 0.0 | 2.2 | 22.5 | 21.3 | 24.7 | 37.8 | 6.9 | 23.7 | 25.3 | 29.7 |   | SEQ ID NO:37 (maize) |
|   | 1 | 2 | 3 | 4 | 5 | 6 | 7 | 8 | 9 | 10 | 11 | |

FIG. 17A Evaluation of Individual Gaspe Flint Derived Maize Lines Transformed with PHP30116

| Treatment | Event name | % green_end exponential | % green_harvest | % lightgreen_end exponential | % lightgreen_harvest |
|---|---|---|---|---|---|
| 1.0 mMol KNO3 | EA2393.375.1.1 | [0.021] | [0.035] | 0.012 | 0.059 |
| 1.0 mMol KNO3 | EA2393.375.1.11 | [0.074] | NS | 0.074 | 0.023 |
| 1.0 mMol KNO3 | EA2393.375.1.3 | 0.079 | NS | [0.046] | NS |
| 1.0 mMol KNO3 | EA2393.375.1.6 | 0.059 | NS | NS | NS |
| 1.0 mMol KNO3 | EA2393.375.1.7 | [0.009] | NS | 0.023 | NS |
| 1.0 mMol KNO3 | EA2393.375.1.9 | NS | NS | NS | NS |
| 6.5 mMol KNO3 | EA2393.375.1.1 | NS | NS | NS | NS |
| 6.5 mMol KNO3 | EA2393.375.1.11 | 0.000 | 0.000 | 0.016 | 0.000 |
| 6.5 mMol KNO3 | EA2393.375.1.3 | [0.011] | NS | NS | NS |
| 6.5 mMol KNO3 | EA2393.375.1.6 | NS | NS | [0.083] | NS |
| 6.5 mMol KNO3 | EA2393.375.1.7 | NS | [0.091] | NS | NS |
| 6.5 mMol KNO3 | EA2393.375.1.9 | NS | [0.034] | NS | 0.021 |

Significant positive results have p-values less than or equal to 0.1.
Significant negative results are in brackets.
"NS" when difference not significant.

FIG. 17B Evaluation of Individual Gaspe Flint Derived Maize Lines Transformed with PHP30116

| Treatment | Event name | area_end exponential | area_harvest | days to emergence | ear diameter |
|---|---|---|---|---|---|
| 1.0 mMol KNO3 | EA2393.375.1.1 | NS | NS | NS | NS |
| 1.0 mMol KNO3 | EA2393.375.1.11 | NS | NS | NS | NS |
| 1.0 mMol KNO3 | EA2393.375.1.3 | NS | NS | NS | NS |
| 1.0 mMol KNO3 | EA2393.375.1.6 | NS | NS | NS | [0.020] |
| 1.0 mMol KNO3 | EA2393.375.1.7 | 0.028 | 0.009 | NS | NS |
| 1.0 mMol KNO3 | EA2393.375.1.9 | NS | [0.059] | NS | NS |
| 6.5 mMol KNO3 | EA2393.375.1.1 | 0.091 | NS | NS | 0.074 |
| 6.5 mMol KNO3 | EA2393.375.1.11 | [0.085] | [0.046] | NS | NS |
| 6.5 mMol KNO3 | EA2393.375.1.3 | [0.001] | [0.001] | NS | NS |
| 6.5 mMol KNO3 | EA2393.375.1.6 | [0.087] | NS | NS | 0.037 |
| 6.5 mMol KNO3 | EA2393.375.1.7 | NS | NS | NS | [0.058] |
| 6.5 mMol KNO3 | EA2393.375.1.9 | NS | NS | NS | [0.080] |

Significant positive results have p-values less than or equal to 0.1.
Significant negative results are in brackets.
"NS" when difference not significant.

FIG. 17C Evaluation of Individual Gaspe Flint Derived Maize Lines Transformed with PHP30116

| Treatment | Event name | ear dry weight | ear fresh weight | maximum area | sgr - r2 > 0.9 |
|---|---|---|---|---|---|
| 1.0 mMol KNO3 | EA2393.375.1.1 | NS | NS | NS | 0.035 |
| 1.0 mMol KNO3 | EA2393.375.1.11 | NS | NS | NS | NS |
| 1.0 mMol KNO3 | EA2393.375.1.3 | NS | NS | NS | NS |
| 1.0 mMol KNO3 | EA2393.375.1.6 | NS | NS | NS | NS |
| 1.0 mMol KNO3 | EA2393.375.1.7 | NS | NS | 0.055 | NS |
| 1.0 mMol KNO3 | EA2393.375.1.9 | NS | NS | [0.071] | [0.048] |
| 6.5 mMol KNO3 | EA2393.375.1.1 | 0.019 | 0.016 | NS | NS |
| 6.5 mMol KNO3 | EA2393.375.1.11 | NS | NS | [0.048] | NS |
| 6.5 mMol KNO3 | EA2393.375.1.3 | NS | NS | [0.001] | [0.008] |
| 6.5 mMol KNO3 | EA2393.375.1.6 | 0.022 | 0.025 | NS | NS |
| 6.5 mMol KNO3 | EA2393.375.1.7 | NS | NS | NS | NS |
| 6.5 mMol KNO3 | EA2393.375.1.9 | NS | NS | NS | [0.016] |

Significant positive results have p-values less than or equal to 0.1. Significant negative results are in brackets. "NS" when difference not significant.

FIG. 17D Evaluation of Individual Gaspe Flint Derived Maize Lines Transformed with PHP30116

| Treatment | Event name | shoot dry weight | shoot fresh weight | shoot+ear dry weight | shoot+ear fresh weight |
|---|---|---|---|---|---|
| 1.0 mMol KNO3 | EA2393.375.1.1 | NS | NS | NS | NS |
| 1.0 mMol KNO3 | EA2393.375.1.11 | NS | NS | NS | NS |
| 1.0 mMol KNO3 | EA2393.375.1.3 | NS | 0.022 | NS | 0.036 |
| 1.0 mMol KNO3 | EA2393.375.1.6 | NS | NS | NS | NS |
| 1.0 mMol KNO3 | EA2393.375.1.7 | 0.016 | 0.028 | 0.056 | NS |
| 1.0 mMol KNO3 | EA2393.375.1.9 | NS | [0.006] | NS | NS |
| 6.5 mMol KNO3 | EA2393.375.1.1 | NS | NS | NS | NS |
| 6.5 mMol KNO3 | EA2393.375.1.11 | [0.039] | [0.053] | NS | NS |
| 6.5 mMol KNO3 | EA2393.375.1.3 | [0.001] | [0.002] | [0.029] | [0.045] |
| 6.5 mMol KNO3 | EA2393.375.1.6 | [0.054] | [0.098] | NS | NS |
| 6.5 mMol KNO3 | EA2393.375.1.7 | NS | NS | NS | NS |
| 6.5 mMol KNO3 | EA2393.375.1.9 | 0.036 | NS | NS | NS |

Significant positive results have p-values less than or equal to 0.1. Significant negative results are in brackets. "NS" when difference not significant.

FIG. 17E Evaluation of Individual Gaspe Flint Derived Maize Lines Transformed with PHP30116

| Treatment | Event name | stalk+ear diameter |
|---|---|---|
| 1.0 mMol KNO3 | EA2393.375.1.1 | NS |
| 1.0 mMol KNO3 | EA2393.375.1.11 | NS |
| 1.0 mMol KNO3 | EA2393.375.1.3 | [0.099] |
| 1.0 mMol KNO3 | EA2393.375.1.6 | [0.012] |
| 1.0 mMol KNO3 | EA2393.375.1.7 | NS |
| 1.0 mMol KNO3 | EA2393.375.1.9 | 0.014 |
| 6.5 mMol KNO3 | EA2393.375.1.1 | 0.044 |
| 6.5 mMol KNO3 | EA2393.375.1.11 | NS |
| 6.5 mMol KNO3 | EA2393.375.1.3 | NS |
| 6.5 mMol KNO3 | EA2393.375.1.6 | NS |
| 6.5 mMol KNO3 | EA2393.375.1.7 | NS |
| 6.5 mMol KNO3 | EA2393.375.1.9 | NS |

Significant positive results have p-values less than or equal to 0.1. Significant negative results are in brackets. "NS" when difference not significant.

FIG. 18 Summary Evaluation of Gaspe Flint Derived Maize Lines Transformed with PHP30116

| Treatment | Event name | % green_end exponential | % green harvest | % lightgreen_end exponential | % lightgreen_harvest | area_end exponential |
|---|---|---|---|---|---|---|
| 1.0 mMol KNO3 | All Events | NS | NS | 0.081 | NS | NS |
| 6.5 mMol KNO3 | All Events | [0.020] | [0.001] | NS | 0.004 | [0.088] |

| Treatment | Event name | area_harvest | days to emergence | ear diameter | ear dry weight | ear fresh weight |
|---|---|---|---|---|---|---|
| 1.0 mMol KNO3 | All Events | 0.036 | NS | NS | NS | NS |
| 6.5 mMol KNO3 | All Events | [0.006] | NS | NS | NS | NS |

| Treatment | Event name | maximum area | sgr - r2 > 0.9 | shoot dry weight | shoot fresh weight | shoot+ear dry weight |
|---|---|---|---|---|---|---|
| 1.0 mMol KNO3 | All Events | NS | NS | NS | 0.047 | NS |
| 6.5 mMol KNO3 | All Events | [0.013] | [0.003] | [0.015] | [0.030] | NS |

| Treatment | Event name | shoot+ear fresh weight | stalk+ear diameter |
|---|---|---|---|
| 1.0 mMol KNO3 | All Events | NS | [0.015] |
| 6.5 mMol KNO3 | All Events | NS | NS |

Significant positive results have p-values less than or equal to 0.1.
Significant negative results are in brackets.
"NS" when difference not significant.

SEQUENCE LISTING

```
<160> NUMBER OF SEQ ID NOS: 37

<210> SEQ ID NO 1
<211> LENGTH: 18491
<212> TYPE: DNA
<213> ORGANISM: Artificial Sequence
<220> FEATURE:
<223> OTHER INFORMATION: pHSbarENDs2 activation tagging vector

<400> SEQUENCE: 1
catgaatcaa acaaacatac acagcgactt attcacacga gctcaaatta caacggtata      60
```

```
tatcctgccg tcgacaacca tggtctagac aggatccccg ggtaccgagc tcgaatttgc    120
aggtcgactg cgtcatccct tacgtcagtg gagatatcac atcaatccac ttgctttgaa    180
gacgtggttg gaacgtcttc ttttccacg atgctcctcg tgggtggggg tccatctttg     240
ggaccactgt cggcagaggc atcttgaacg atagcctttc ctttatcgca atgatggcat    300
ttgtaggtgc caccttcctt ttctactgtc cttttgatga agtgacagat agctgggcaa    360
tggaatccga ggaggtttcc cgatattacc ctttgttgaa aagtctcaat tgcccttgg    420 tcttctgaga ctgttgcgtc atcccttacg tcagtggaga tatcacatca tccacttgc    480 tttgaagacg tggttggaac gtcttctttt tccacgatgc tcctcgtggg tggggtcca    540 tctttgggac cactgtcggc agaggcatct tgaacgatag cctttccttt atcgcaatga    600
tggcatttgt aggtgccacc ttccttttct actgtccttt tgatgaagtg acagatagct    660
gggcaatgga atccgaggag gtttcccgat attacccttt gttgaaaagt ctcagttaac    720
ccgcgatcct gcgtcatccc ttacgtcagt ggagatatca tcaatcca cttgctttga     780 agacgtggtt ggaacgtctt cttttccac gatgctcctc gtgggtgggg gtccatcttt    840
gggaccactg tcggcagagg catcttgaac gatagccttt cctttatcgc aatgatggca    900
tttgtaggtg ccaccttcct tttctactgt ccttttgatg aagtgacaga tagctgggca    960
atggaatccg aggaggtttc ccgatattac cctttgttga aaagtctcaa ttgcccttg    1020 gtcttctgag actgttgcgt catcccttac gtcagtggag atcacatc aatccacttg     1080 ctttgaagac gtggttggaa cgtcttcttt tccacgatg ctcctcgtgg gtggggtcc    1140 atctttggga ccactgtcgg cagaggcatc ttgaacgata gcctttcctt tatcgcaatg    1200
atggcatttg taggtccac cttccttttc tactgtcctt tgatgaagt gacagatagc    1260 tgggcaatgg aatccgagga ggtttcccga tattacccctt tgttgaaaag tctcagttaa    1320
cccgcaattc actggccgtc gtttacaac gtcgtgactg ggaaaaccct ggcgttaccc    1380
aacttaatcg ccttgcagca catcccccctt tcgccagctg gcgtaatagc gaagaggccc    1440
gcaccgatcg cccttcccaa cagttgcgca gcctgaatgg cgaatggatc gatccgtcga    1500
tcgaccaaag cggccatcgt gcctcccac tcctgcagtt cggggcatg gatgcgcgga    1560 tagccgctgc tggttttcctg gatgccgacg gatttgcact gccggtagaa ctccgcgagg    1620
tcgtccagcc tcaggcagca gctgaaccaa ctcgcgaggg gatcgagccc ctgctgagcc    1680
tcgacatgtt gtcgcaaaat tcgccctgga cccgcccaac gatttgtcgt cactgtcaag    1740
gtttgacctg cacttcattt ggggcccaca tacaccaaaa aaatgctgca taattctcgg    1800
ggcagcaagt cggttacccg ccgccgtgc tggaccgggt tgaatggtgc ccgtaacttt    1860
cggtagagcg gacggccaat actcaacttc aaggaatctc acccatgcgc gccggcgggg    1920
aaccggagtt cccttcagtg aacgttatta gttcgccgct cggtgtgtcg tagatactag    1980 cccctgggc ttttgaaat ttgaataaga tttatgtaat cagtctttta ggtttgaccg    2040
gttctgccgc ttttttaaa attggatttg taataataaa acgcaattgt ttgttattgt    2100
ggcgctctat catagatgtc gctataaacc tattcagcac aatatattgt tttcatttta    2160
atattgtaca tataagtagt agggtacaat cagtaaattg aacggagaat attattcata    2220
aaaatacgat agtaacgggt gatatattca ttagaatgaa ccgaaccgg cggtaaggat    2280 ctgagctaca catgctcagg tttttacaa cgtgcacaac agaattgaaa gcaaatatca    2340
tgcgatcata ggcgtctcgc atatctcatt aaagcagggg gtgggcgaag aactccagca    2400
tgagatcccc gcgctggagg atcatccagc cggcgtcccg gaaaacgatt ccgaagccca    2460
```

```
accttctcata gaaggcggcg gtggaatcga atctcgtga tggcaggttg ggcgtcgctt    2520
ggtcggtcat ttcgaacccc agagtcccgc tcagaagaac tcgtcaagaa ggcgatagaa    2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccggccac agtcgatgaa tccagaaaag cggccatttt ccaccatgat    2760
attcggcaag caggcatcgc catgggtcac gacgagatcc tcgccgtcgg catgccccc    2820
caattcactg gccgtcgttt tacaacgtcg tgactgggaa accctggcg ttacccaact    2880
taatcgcctt gcagcacatc cccctttcgc cagctggcgt aatagcgaag aggcccgcac    2940
cgatcgccct tcccaacagt tgcgcagcct gaatggcgaa tggcgcctga tgcggtattt    3000
tctccttacg catctgtgcg gtatttcaca ccgcatatgg tgcactctca gtacaatctg    3060
ctctgatgcc gcatagttaa gccagccccg acacccgcca cacccgctg acgcgccctg    3120
acgggcttgt ctgctcccgg catccgctta cagacaagct gtgaccgtct ccgggagctg    3180
catgtgtcag aggttttcac cgtcatcacc gaaacgcgcg agacgaaagg gcctcgtgat    3240
acgcctattt ttataggtta atgtcatgat aataatggtt tcttagacgt caggtggcac    3300
ttttcgggga atgtgcgcg gaaccccat ttgtttattt ttctaaatac attcaaatat    3360
gtatccgctc atgagacaat aaccctgata aatgcttcaa taatattgaa aaggaagag    3420
tatgagtatt caacatttcc gtgtcgccct tattccctt tttgcggcat tttgccttcc    3480
tgttttgct cacccagaaa cgctggtgaa agtaaaagat gctgaagatc agttgggtgc    3540
acgagtgggt tacatcgaac tggatctcaa cagcggtaag atccttgaga gttttcgccc    3600
cgaagaacgt tttccaatga tgagcacttt taaagttctg ctatgtggcg cggtattatc    3660
ccgtattgac gccgggcaag agcaactcgg tcgccgcata cactattctc agaatgactt    3720
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgcttttt gcacaacatg ggggatcatg taactcgcct    3900
tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt catttttaat ttaaaaggat ctaggtgaag atcctttttg ataatctcat    4380
gaccaaaatc ccttaacgtg agttttcgtt ccactgagcg tcagaccccg tagaaaagat    4440
caaaggatct tcttgagatc ctttttttct gcgcgtaatc tgctgcttgc aaacaaaaaa    4500
accaccgcta ccagcggtgg tttgtttgcc ggatcaagag ctaccaactc tttttccgaa    4560
ggtaactggc ttcagcagag cgcagatacc aaatactgtc cttctagtgt agccgtagtt    4620
aggccaccac ttcaagaact ctgtagcacc gcctacatac ctcgctctgc taatcctgtt    4680
accagtggct gctgccagtg gcgataagtc gtgtcttacc gggttggact caagacgata    4740
gttaccggat aaggcgcagc ggtcgggctg aacggggggt tcgtgcacac agcccagctt    4800
ggagcgaacg acctacaccg aactgagata cctacagcgt gagcattgag aaagcgccac    4860
```

```
gcttcccgaa gggagaaagg cggacaggta tccggtaagc ggcagggtcg gaacaggaga    4920
gcgcacgagg gagcttccag ggggaaacgc ctggtatctt tatagtcctg tcgggtttcg    4980
ccacctctga cttgagcgtc gattttgtgt atgctcgtca ggggggcgga gcctatggaa    5040
aaacgccagc aacgcggcct ttttacggtt cctggccttt tgctggcctt ttgctcacat    5100
gttctttcct gcgttatccc ctgattctgt ggataaccgt attaccgcct ttgagtgagc    5160
tgataccgct cgccgcagcc gaacgaccga gcgcagcgag tcagtgagcg aggaagcgga    5220
agagcgccca atacgcaaac cgcctctccc cgcgcgttgg ccgattcatt aatgcagctg    5280
gcacgacagg tttcccgact ggaaagcggg cagtgagcgc aacgcaatta atgtgagtta    5340
gctcactcat taggcacccc aggctttaca ctttatgctt ccggctcgta tgttgtgtgg    5400
aattgtgagc ggataacaat ttcacacagg aaacagctat gaccatgatt acgccaagct    5460
ttctaggggg ggggtaccga tctgagatcg gtaacgaaaa cgaacgggta gggatgaaaa    5520
cggtcggtaa cggtcggtaa aatacctcta ccgttttcat tttcatattt aacttgcggg    5580
acggaaacga aacgggata taccggtaac gaaaacgaac gggataaata cggtaatcga    5640
aaaccgatac gatccggtcg ggttaaagtc gaaatcggac gggaaccggt attttgttc    5700 ggtaaaatca cacatgaaaa catatattca aaacttaaaa acaaatataa aaaattgtaa    5760
acacaagtct taatgatcac tagtggcgcg cctaggagat ctcgagtagg gataacaggg    5820
taatacatag ataaaatcca tataaatctg gagcacacat agtttaatgt agcacataag    5880
tgataagtct tgggctcttg gctaacataa gaagccatat aagtctacta gcacacatga    5940
cacaatataa agtttaaaac acatattcat aatcacttgc tcacatctgg atcacttagc    6000
atgctacagc tagtgcaata ttagacactt tccaatattt ctcaaacttt tcactcattg    6060
caacggccat tctcctaatg acaaattttt catgaacaca ccattggtca atcaaatcct    6120
ttatctcaca gaaacctttg taaaataaat ttgcagtgga atattgagta ccagatagga    6180
gttcagtgag atcaaaaaac ttcttcaaac acttaaaaag agttaatgcc atcttccact    6240
cctcggcttt aggacaaatt gcatcgtacc tacaataatt gacatttgat taattgagaa    6300
tttataatga tgacatgtac aacaattgag acaaacatac ctgcgaggat cacttgtttt    6360
aagccgtgtt agtgcaggct tataatataa ggcatccctc aacatcaaat aggttgaatt    6420
ccatctagtt gagacatcat atgagatccc tttagattta tccaagtcac attcactagc    6480
acacttcatt agttcttccc actgcaaagg agaagatttt acagcaagaa caatcgcttt    6540
gattttctca attgttcctg caattacagc caagccatcc tttgcaacca agttcagtat    6600
gtgacaagca cacctcacat gaaagaaagc accatcacaa actagatttg aatcagtgtc    6660
ctgcaaatcc tcaattatat cgtgcacagc tacttcattt gcactagcat tatccaaaga    6720
caaggcaaac aatttttct caatgttcca cttaaccatg attgcagtga aggtttgtga     6780 taaccttttgg ccagtgtggc gcccttcaac atgaaaaaag ccaacaattc tttttggag    6840 acaccaatca tcatcaatcc aatggatggt gacacacatg tatgacttat tttgacaaga    6900
tgtccacata tccatagttg tactgaagcg agactgaaca tcttttagtt ttccatacaa    6960
cttttctttt tcttccaaat acaaatccat gatatatttt ctagcagtga cacgggactt    7020
tattggaaag tgagggcgca gagacttaac aaactcaaca aagtactcat gttctacaat    7080
attgaaagga tattcatgca tgattattgc caaatgaagc ttctttaggc taaccacttc    7140
atcgtactta taaggctcaa tgagatttat gtctttgcca tgatcctttt cacttttag    7200 acacaactga cctttaacta aactatgtga tgttctcaag tgatttcgaa atccgcttgt    7260
```

```
tccatgatga ccctcagccc tatacttagc cttgcaatta ggaaagttgc aatgtcccca    7320
tacctgaacg tatttctttc catcgacctc cacttcaatt tccttcttgg tgaaatgctg    7380
ccatacatcc gatgtgcact tctttgccct cttctgtggt gcttcttctt cgggttcagg    7440
ttgtggctgt ggttgtggtt ctggttgtgg ttgtggttgt ggttgtggtt catgaacaat    7500
agccatatca tcttgactcg gatctgtagc tgtaccattt gcattactac tgcttacact    7560
ctgaataaaa tgcctctcgg cctcagctgt tgatgatgat ggtgatgtgc ggccacatcc    7620
atgcccacgc gcacgtgcac gtacattctg aatccgacta aagaggctt cagcttttct     7680
tttcaacccct gttataaaca gattttcgt attattctac agtcaatatg atgcttccca    7740
atctacaacc aattagtaat gctaatgcta ttgctactgt ttttctaata tataccttga    7800
gcatatgcag agaatacgga atttgttttg cgagtagaag gcgctcttgt ggtagacatc    7860
aacttggcca atcttatggc tgagcctgag ggaggattat ttccaaccgg aggcgtcatc    7920
tgaggaatgg agtcgtagcc ggctagccga agtggagagc agagccctgg acagcaggtg    7980
ttcagcaatc agcttggtgc tgtactgctg tgacttgtga gcacctggac ggctggacag    8040
caatcagcag gtgttgcaga gcccctggac agcacacaaa tgacacaaca gcttggtgca    8100
atggtgctga cgtgctgtac tgctaagtgc tgtgagcctg tgagcagccg tggagacagg    8160
gagaccgcgg atggccggat gggcgagcgc cgagcagtgg aggtctggag accgctgac     8220
cgcagatggc ggatggcgga tgggcggacc gcggatgggc gagcagtgga gtggaggtct    8280
gggcggatgg gcggaccgcg gcgcggatgg gcgagtcgcg agcagtggag tggagggcgg    8340
accgtggatg gcggcgtctg cgtccggcgt gccgcgtcac ggccgtcacc gcgtgtggtg    8400
cctggtgcag cccagcggcc ggccggctgg gagacaggga gagtcggaga gagcaggcga    8460
gagcgagacg cgtcgccggc gtcggcgtgc ggctggcggc gtccggactc cggcgtgggc    8520
gcgtggcggc gtgtgaatgt gtgatgctgt tactcgtgtg gtgcctggcc gcctgggaga    8580
gaggcagagc agcgttcgct aggtatttct tacatgggct gggcctcagt ggttatggat    8640
gggagttgga gctggccata ttgcagtcat cccgaattag aaaatacggt aacgaaacgg    8700
gatcatcccg attaaaaacg ggatcccggt gaaacggtcg ggaaactagc tctaccgttt    8760
ccgtttccgt ttaccgtttt gtatatcccg ttttcgttcc gttttcgttt tttacctcgg    8820
gttcgaaatc gatcgggata aaactaacaa aatcggttat acgataacgg tcggtacggg    8880
attttcccat cctactttca tccctgagat tattgtcgtt tctttcgcag atcggtaccc    8940
cccccctaga gtcgacatcg atctagtaac atagatgaca ccgcgcgcga taatttatcc    9000
tagtttgcgc gctatatttt gttttctatc gcgtattaaa tgtataattg cgggactcta    9060
atcataaaaa cccatctcat aaataacgtc atgcattaca tgttaattat tacatgctta    9120
acgtaattca acagaaatta tatgataatc atcgcaagac cggcaacagg attcaatctt    9180
aagaaacttt attgccaaat gtttgaacga tctgcttcga cgcactcctt ctttaggtac    9240
ggactagatc tcggtgacgg gcaggaccgg acggggcggt accggcaggc tgaagtccag    9300
ctgccagaaa cccacgtcat gccagttccc gtgcttgaag ccggccgccc gcagcatgcc    9360
gcgggggca tatccgagcg cctcgtgcat gcgcacgctc gggtcgttgg gcagcccgat     9420
gacagcgacc acgctcttga agccctgtgc ctccaggac  ttcagcaggt gggtgtagag    9480
cgtggagccc agtcccgtcc gctggtggcg gggggagacg tacacggtcg actcggccgt    9540
ccagtcgtag gcgttgcgtg ccttccaggg gcccgcgtag gcgatgccgg cgacctcgcc    9600
gtccacctcg gcgacgagcc agggatagcg ctcccgcaga cggacgaggt cgtccgtcca    9660
```

```
ctcctgcggt tcctgcggct cggtacggaa gttgaccgtg cttgtctcga tgtagtggtt   9720
gacgatggtg cagaccgccg gcatgtccgc ctcggtggca cggcggatgt cggccgggcg   9780
tcgttctggg ctcatggatc tggattgaga gtgaatatga gactctaatt ggataccgag   9840
gggaatttat ggaacgtcag tggagcattt ttgacaagaa atatttgcta gctgatagtg   9900
accttaggcg acttttgaac gcgcaataat ggtttctgac gtatgtgctt agctcattaa   9960
actccagaaa cccgcggctg agtggctcct tcaatcgttg cggttctgtc agttccaaac  10020
gtaaaacggc ttgtcccgcg tcatcggcgg gggtcataac gtgactccct taattctccg  10080
ctcatgatcc ccgggtaccg agctcgaatt cggctgagt ggctccttca atcgttgcgg  10140
ttctgtcagt tccaaacgta aaacggcttg tcccgcgtca tcggcggggg tcataacgtg  10200
actcccttaa ttctccgctc atgatcttga tcccctgcgc catcagatcc ttggcggcaa  10260
gaaagccatc cagtttactt tgcagggctt cccaaccttg ccagagggcg cccagctgg   10320 caattccggt tcgcttgctg tatcgatatg gtggatttat cacaaatggg acccgccgcc  10380
gacagaggtg tgatgttagg ccaggacttt gaaaatttgc gcaactatcg tatagtggcc  10440
gacaaattga cgccgagttg acagactgcc tagcatttga gtgaattatg tgaggtaatg  10500
ggctacactg aattggtagc tcaaactgtc agtatttatg tatatgagtg tatattttcg  10560
cataatctca gaccaatctg aagatgaaat gggtatctgg gaatggcgaa atcaaggcat  10620
cgatcgtgaa gtttctcatc taagccccca tttggacgtg aatgtagaca cgtcgaaata  10680
aagatttccg aattagaata atttgtttat tgctttcgcc tataaatacg acggatcgta  10740
atttgtcgtt ttatcaaaat gtactttcat tttataataa cgctgcggac atctacattt  10800
ttgaattgaa aaaaaattgg taattactct ttcttttct ccatattgac catcatactc  10860
attgctgatc catgtagatt tcccggacat gaagccattt acaattgaat atatcctgcc  10920
gccgctgccg ctttgcaccc ggtggagctt gcatgttggt ttctacgcag aactgagccg  10980
gttaggcaga taatttccat tgagaactga gccatgtgca ccttccccc aacacggtga  11040 gcgacgggc aacggagtga tccacatggg acttttaaac atcatccgtc ggatggcgtt  11100
gcgagagaag cagtcgatcc gtgagatcag ccgacgcacc gggcaggcgc gcaacacgat  11160
cgcaaagtat ttgaacgcag gtacaatcga ccgacgttc accgtcaccc tggatgctgt  11220
aggcataggc ttggttatgc cggtactgcc gggcctcttg cgggatatcg tccattccga  11280
cagcatcgcc agtcactatg gcgtgctgct agcgctatat gcgttgatgc aatttctatg  11340
cgcacccgtt ctcggagcac tgtccgaccg ctttggccgc cgcccagtcc tgctcgcttc  11400
gctacttgga gccactatcg actacgcgat catggcgacc acaccgtcc tgtggtccaa  11460 cccctccgct gctatagtgc agtcggcttc tgacgttcag tgcagccgtc ttctgaaaac  11520
gacatgtcgc acaagtccta agttacgcga caggctgccg ccctgcccctt tcctggcgt   11580 tttcttgtcg cgtgttttag tcgcataaag tagaatactt gcgactagaa ccggagacat  11640
tacgccatga acaagagcgc cgccgctggc ctgctgggct atgcccgcgt cagcaccgac  11700
gaccaggact tgaccaacca acgggccgaa ctgcacgcgg ccggctgcac caagctgttt  11760
tccgagaaga tcaccggcac caggcgcgac cgcccggagc tggccaggat gcttgaccac  11820
ctacgccctg gcgacgttgt gacagtgacc aggctagacc gcctggcccg cagcacccgc  11880
gacctactgg acattgccga gcgcatccag gaggccggcg cgggcctgcg tagcctggca  11940
gagccgtggg ccgacaccac cacgccggcc ggccgcatgg tgttgaccgt gttcgccggc  12000
attgccgagt tcgagcgttc cctaatcatc gaccgcaccc ggagcgggcg cgaggccgcc  12060
```

-continued

```
aaggcccgag gcgtgaagtt tggcccccgc cctaccctca ccccggcaca gatcgcgcac   12120
gcccgcgagc tgatcgacca ggaaggccgc accgtgaaag aggcggctgc actgcttggc   12180
gtgcatcgct cgaccctgta ccgcgcactt gagcgcagcg aggaagtgac gcccaccgag   12240
gccaggcggc gcggtgcctt ccgtgaggac gcattgaccg aggccgacgc cctggcggcc   12300
gccgagaatg aacgccaaga ggaacaagca tgaaaccgca ccaggacggc caggacgaac   12360 cgttttcat taccgaagag atcgaggcgg agatgatcgc ggccgggtac gtgttcgagc   12420
cgcccgcgca cgtctcaacc gtgcggctgc atgaaatcct ggccggtttg tctgatgcca   12480
agctggcggc ctggccggcc agcttggccg ctgaagaaac cgagcgccgc cgtctaaaaa   12540
ggtgatgtgt atttgagtaa aacagcttgc gtcatgcggt cgctgcgtat atgatgcgat   12600
gagtaaataa acaaatacgc aagggaacgc atgaagttat cgctgtactt aaccagaaag   12660
gcgggtcagg caagacgacc atcgcaaccc atctagcccg cgccctgcaa ctcgccgggg   12720
ccgatgttct gttagtcgat tccgatcccc agggcagtgc ccgcgattgg gcggccgtgc   12780
gggaagatca accgctaacc gttgtcggca tcgaccgccc gacgattgac cgcgacgtga   12840
aggccatcgg ccgcgcgac ttcgtagtga tcgacggagc gccccaggcg gcggacttgg   12900
ctgtgtccgc gatcaaggca gccgacttcg tgctgattcc ggtgcagcca gcccttacg   12960 acatatgggc caccgccgac ctggtggagc tggttaagca gcgcattgag gtcacggatg   13020
gaaggctaca agcggccttt gtcgtgtcgc gggcgatcaa aggcacgcgc atcggcggtg   13080
aggttgccga ggcgctggcc gggtacgagc tgcccattct tgagtccgt atcacgcagc   13140 gcgtgagcta cccaggcact gccgccgccg gcacaaccgt tcttgaatca gaacccgagg   13200
gcgacgctgc ccgcgaggtc caggcgctgg ccgctgaaat taaatcaaaa ctcatttgag   13260
ttaatgaggt aaagagaaaa tgagcaaaag cacaaacacg ctaagtgccg gccgtccgag   13320
cgcacgcagc agcaaggctg caacgttggc cagcctggca gacacgccag ccatgaagcg   13380
ggtcaacttt cagttgccgg cggaggatca caccaagctg aagatgtacg cggtacgcca   13440
aggcaagacc attaccgagc tgctatctga atacatcgcg cagctaccag agtaaatgag   13500
caaatgaata aatgagtaga tgaattttag cggctaaagg aggcggcatg gaaaatcaag   13560
aacaaccagg caccgacgcc gtggaatgcc ccatgtgtgg aggaacgggc ggttggccag   13620
gcgtaagcgg ctgggttgtc tgccggccct gcaatggcac tggaaccccc aagcccgagg   13680
aatcggcgtg agcggtcgca aaccatccgg cccggtacaa atcggcgcgg cgctgggtga   13740
tgacctggtg gagaagttga aggccgcgca ggccgcccag cggcaacgca tcgaggcaga   13800
agcacgcccc ggtgaatcgt ggcaagcggc cgctgatcga atccgcaaag aatcccggca   13860
accgccggca gccggtgcgc cgtcgattag gaagccgccc aagggcgacg agcaaccaga   13920
ttttttcgtt ccgatgctct atgacgtggg cacccgcgat agtcgcagca tcatggacgt   13980
ggccgttttc cgtctgtcga agcgtgaccg acgagctggc gaggtgatcc gctacgagct   14040
tccagacggg cacgtagagg tttccgcagg gccggccggc atggccagtg tgtgggatta   14100
cgacctggta ctgatggcgg tttcccatct aaccgaatcc atgaaccgat accgggaagg   14160
gaagggagac aagcccggcc gcgtgttccg tccacacgtt gcggacgtac tcaagttctg   14220
ccggcgagcc gatggcggaa agcagaaaga cgacctggta gaaacctgca ttcggttaaa   14280
caccacgcac gttgccatgc agcgtacgaa gaaggccaag aacggccgcc tggtgacggt   14340
atccgagggt gaagccttga ttagccgcta caagatcgta aagagcgaaa ccgggcggcc   14400
ggagtacatc gagatcgagc tagctgattg gatgtaccgc gagatcacag aaggcaagaa   14460
```

```
cccggacgtg ctgacggttc accccgatta cttttttgatc gatcccggca tcggccgttt    14520
tctctaccgc ctggcacgcc gcgccgcagg caaggcagaa gccagatggt tgttcaagac    14580
gatctacgaa cgcagtggca gcgccggaga gttcaagaag ttctgtttca ccgtgcgcaa    14640
gctgatcggg tcaaatgacc tgccggagta cgatttgaag gaggaggcgg ggcaggctgg    14700
cccgatccta gtcatgcgct accgcaacct gatcgagggc gaagcatccg ccggttccta    14760
atgtacggag cagatgctag ggcaaattgc cctagcaggg gaaaaggtc gaaaaggtct     14820 cttttcctgtg gatagcacgt acattgggaa cccaaagccg tacattggga accggaaccc   14880
gtacattggg aacccaaagc cgtacattgg gaaccggtca cacatgtaag tgactgatat    14940
aaaagagaaa aaaggcgatt tttccgccta aaactcttta aaacttatta aaactcttaa    15000
aacccgcctg gcctgtgcat aactgtctgg ccagcgcaca gccgaagagc tgcaaaaagc    15060 gcctacccctt cggtcgctgc gctccctacg ccccgccgct tcgcgtcggc ctatcgcggc    15120
cgctggccgc tcaaaaatgg ctggcctacg gccaggcaat ctaccagggc gcggacaagc    15180
cgcgccgtcg ccactcgacc gccggcgccc acatcaaggc accctgcctc gcgcgtttcg    15240
gtgatgacgg tgaaaacctc tgacacatgc agctcccgga gacggtcaca gcttgtctgt    15300
aagcggatgc cgggagcaga caagcccgtc agggcgcgtc agcgggtgtt ggcgggtgtc    15360
ggggcgcagc catgacccag tcacgtagcg atagcggagt gtatactggc ttaactatgc    15420
ggcatcagag cagattgtac tgagagtgca ccatatgcgg tgtgaaatac cgcacagatg    15480
cgtaaggaga aaataccgca tcaggcgctc ttccgcttcc tcgctcactg actcgctgcg    15540
ctcggtcgtt cggctgcggc gagcggtatc agctcactca aaggcggtaa tacggttatc    15600
cacagaatca ggggataacg caggaaagaa catgtgagca aaaggccagc aaaaggccag    15660
gaaccgtaaa aaggccgcgt tgctggcgtt tttccatagg ctccgccccc ctgacgagca    15720
tcacaaaaat cgacgctcaa gtcagaggtg gcgaaacccg acaggactat aaagatacca    15780
ggcgtttccc cctggaagct ccctcgtgcg ctctcctgtt ccgaccctgc cgcttaccgg    15840
atacctgtcc gcctttctcc cttcgggaag cgtggcgctt tctcatagct cacgctgtag    15900
gtatctcagt tcggtgtagg tcgttcgctc caagctgggc tgtgtgcacg aaccccccgt    15960
tcagcccgac cgctgcgcct tatccggtaa ctatcgtctt gagtccaacc cggtaagaca    16020
cgacttatcg ccactggcag cagccactgg taacaggatt agcagagcga ggtatgtagg    16080
cggtgctaca gagttcttga agtggtggcc taactacggc tacactagaa ggacagtatt    16140
tggtatctgc gctctgctga agccagttac cttcggaaaa agagttggta gctcttgatc    16200
cggcaaacaa accaccgctg gtagcggtgg ttttttttgtt tgcaagcagc agattacgcg    16260
cagaaaaaaa ggatctcaag aagatccttt gatctttttct acgggggtctg acgctcagtg    16320 gaacgaaaac tcacgttaag ggattttggt catgagatta tcaaaaagga tcttcaccta    16380 gatccttta aattaaaaat gaagttttaa atcaatctaa agtatatatg agtaaacttg    16440
gtctgacagt taccaatgct taatcagtga ggcacctatc tcagcgatct gtctatttcg    16500
ttcatccata gttgcctgac tccccgtcgt gtagataact acgatacggg agggcttacc    16560
atctggcccc agtgctgcaa tgataccgcg agacccacgc tcaccggctc cagatttatc    16620
agcaataaac cagccagccg gaagggccga gcgcagaagt ggtcctgcaa ctttatccgc    16680
ctccatccag tctattaatt gttgccggga agctagagta agtagttcgc cagttaatag    16740
tttgcgcaac gttgttgcca ttgctacagg catcgtggtg tcacgctcgt cgtttggtat    16800
ggcttcattc agctccggtt cccaacgatc aaggcgagtt acatgatccc ccatgttgtg    16860
```

```
caaaaaagcg gttagctcct tcggtcctcc gatcgttgtc agaagtaagt tggccgcagt    16920
gttatcactc atggttatgg cagcactgca taattctctt actgtcatgc catccgtaag    16980
atgcttttct gtgactggtg agtactcaac caagtcattc tgagaatagt gtatgcggcg    17040
accgagttgc tcttgcccgg cgtcaacacg ggataatacc gcgccacata gcagaacttt    17100
aaaagtgctc atcattggaa aagacctgca ggggggggg ggaaagccac gttgtgtctc    17160 aaaatcctg atgttacatt gcacaagata aaaatatatc atcatgaaca ataaaactgt    17220
ctgcttacat aaacagtaat acaaggggtg ttatgagcca tattcaacgg gaaacgtctt    17280
gctcgaggcc gcgattaaat tccaacatgg atgctgattt atatgggtat aaatgggctc    17340
gcgataatgt cgggcaatca ggtgcgacaa tctatcgatt gtatgggaag cccgatgcgc    17400
cagagttgtt tctgaaacat ggcaaaggta gcgttgccaa tgatgttaca gatgagatgg    17460
tcagactaaa ctggctgacg gaatttatgc ctcttccgac catcaagcat tttatccgta    17520
ctcctgatga tgcatggtta ctcaccactg cgatccccgg aaaacagca ttccaggtat    17580 tagaagaata tcctgattca ggtgaaaata ttgttgatgc gctggcagtg ttcctgcgcc    17640
ggttgcattc gattcctgtt tgtaattgtc cttttaacag cgatcgcgta tttcgtctcg    17700
ctcaggcgca atcacgaatg aataacggtt tggttgatgc gagtgatttt gatgacgagc    17760
gtaatggctg gcctgttgaa caagtctgga aagaaatgca taagcttttg ccattctcac    17820
cggattcagt cgtcactcat ggtgatttct cacttgataa ccttatttt gacgagggga    17880 aattaatagg ttgtattgat gttggacgag tcggaatcgc agaccgatac caggatcttg    17940
ccatcctatg gaactgcctc ggtgagtttt ctccttcatt acagaaacgg ctttttcaaa    18000
aatatggtat tgataatcct gatatgaata aattgcagtt tcatttgatg ctcgatgagt    18060
ttttctaatc agaattggtt aattggttgt aacactggca gagcattacg ctgacttgac    18120
gggacggcgg ctttgttgaa taatcgaac ttttgctgag ttgaaggatc agatcacgca    18180
tcttcccgac aacgcagacc gttccgtggc aaagcaaaag ttcaaaatca ccaactggtc    18240
cacctacaac aaagctctca tcaaccgtgg ctccctcact ttctggctgg atgatggggc    18300
gattcaggcc tggtatgagt cagcaacacc ttcttcacga ggcagacctc agcgcccccc    18360
cccccctgca ggtcaattcg gtcgatatgg ctattacgaa gaaggctcgt gcgcggagtc    18420
ccgtgaactt tcccacgcaa caagtgaacc gcaccgggtt gccggaggc catttcgtta    18480 aaatgcgcag c                                                         18491
```

<210> SEQ ID NO 2
<211> LENGTH: 4291
<212> TYPE: DNA
<213> ORGANISM: Artificial Sequence
<220> FEATURE:
<223> OTHER INFORMATION: pDONRZeo construct

<400> SEQUENCE: 2

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
```

```
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacacattg atgagcaatg ctttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat taaatcataa aaagaaataa gaaaaagagg    960
tgcgagcctc ttttttgtgt gacaaaataa aaacatctac ctattcatat acgctagtgt   1020
catagtcctg aaaatcatct gcatcaagaa caatttcaca actcttatac tttttctctta  1080 caagtcgttc ggcttcatct ggattttcag cctctatact tactaaacgt gataaagttt   1140
ctgtaatttc tactgtatcg acctgcagac tggctgtgta agggagcc tgacatttat     1200 attccccaga acatcaggtt aatggcgttt ttgatgtcat tttcgcggtg gctgagatca   1260
gccacttctt ccccgataac ggagaccggc acactggcca tatcggtggt catcatgcgc   1320
cagctttcat ccccgatatg caccaccggg taaagttcac gggagacttt atctgacagc   1380
agacgtgcac tggccagggg gatcaccatc cgtcgcccgg gcgtgtcaat aatatcactc   1440
tgtacatcca caaacagacg ataacggctc tctcttttat aggtgtaaac cttaaactgc   1500
atttcaccag cccctgttct cgtcagcaaa agagccgttc atttcaataa accgggcgac   1560
ctcagccatc ccttcctgat tttccgcttt ccagcgttcg gcacgcagac gacgggcttc   1620
attctgcatg gttgtgctta ccagaccgga gatattgaca tcatatatgc cttgagcaac   1680
tgatagctgt cgctgtcaac tgtcactgta atacgctgct tcatagcata cctcttttttg  1740 acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct tgcgtataat   1980
atttgcccat ggtgaaaacg ggggcgaaga agttgtccat attggccacg tttaaatcaa   2040
aactggtgaa actcacccag ggattggctg agacgaaaaa catattctca ataaacccctt  2100 tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacggaa ttccggatga gcattcatca ggcgggcaag aatgtgaata aaggccggat   2340
aaaacttgtg cttattttc tttacggtct ttaaaaaggc cgtaatatcc agctgaacgg    2400
tctggttata ggtacattga gcaactgact gaaatgcctc aaaatgttct ttacgatgcc   2460
attgggatat atcaacggtg gtatatccag tgattttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640 gcttccggt atcaacaggg acaccaggat ttatttattc tgcgaagtga tcttccgtca    2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
```

-continued

| | |
|---|---|
| atgtagtctg ttttttatgc aaaatctaat ttaatatatt gatatttata tcattttacg | 2880 |
| tttctcgttc agctttcttg tacaaagttg gcattataag aaagcattgc ttatcaattt | 2940 |
| gttgcaacga acaggtcact atcagtcaaa ataaaatcat tatttgccat ccagctgata | 3000 |
| tcccctatag tgagtcgtat tacatggtca tagctgtttc ctggcagctc tggcccgtgt | 3060 |
| ctcaaaatct ctgatgttac attgcacaag ataaaataat atcatcatga tcagtcctgc | 3120 |
| tcctcggcca cgaagtgcac gcagttgccg gccgggtcgc gcagggcgaa ctcccgcccc | 3180 |
| cacggctgct cgccgatctc ggtcatggcc ggcccggagg cgtcccggaa gttcgtggac | 3240 |
| acgacctccg accactcggc gtacagctcg tccaggccgc gcacccacac ccaggccagg | 3300 |
| gtgttgtccg gcaccacctg gtcctggacc gcgctgatga acagggtcac gtcgtcccgg | 3360 |
| accacaccgg cgaagtcgtc ctccacgaag tcccgggaga acccgagccg gtcggtccag | 3420 |
| aactcgaccg ctccggcgac gtcgcgcgcg gtgagcaccg gaacggcact ggtcaacttg | 3480 |
| gccatggttt agttcctcac cttgtcgtat tatactatgc cgatatacta tgccgatgat | 3540 |
| taattgtcaa cacgtgctga tcatgaccaa aatcccttaa cgtgagttac gcgtcgttcc | 3600 |
| actgagcgtc agaccccgta gaaaagatca aaggatcttc ttgagatcct ttttttctgc | 3660 |
| gcgtaatctg ctgcttgcaa acaaaaaaac caccgctacc agcggtggtt tgtttgccgg | 3720 |
| atcaagagct accaactctt tttccgaagg taactggctt cagcagagcg cagataccaa | 3780 |
| atactgttct tctagtgtag ccgtagttag gccaccactt caagaactct gtagcaccgc | 3840 |
| ctacatacct cgctctgcta atcctgttac cagtggctgc tgccagtggc gataagtcgt | 3900 |
| gtcttaccgg gttggactca agacgatagt taccggataa ggcgcagcgg tcgggctgaa | 3960 |
| cggggggttc gtgcacacag cccagcttgg agcgaacgac ctacaccgaa ctgagatacc | 4020 |
| tacagcgtga gctatgagaa agcgccacgc ttcccgaagg gagaaaggcg gacaggtatc | 4080 |
| cggtaagcgg cagggtcgga acaggagagc gcacgaggga gcttccaggg ggaaacgcct | 4140 |
| ggtatcttta tagtcctgtc gggtttcgcc acctctgact tgagcgtcga tttttgtgat | 4200 |
| gctcgtcagg gggcggagc ctatggaaaa acgccagcaa cgcggccttt ttacggttcc | 4260 |
| tggccttttg ctggcctttt gctcacatgt t | 4291 |

<210> SEQ ID NO 3
<211> LENGTH: 4762
<212> TYPE: DNA
<213> ORGANISM: Artificial Sequence
<220> FEATURE:
<223> OTHER INFORMATION: pDONR221

<400> SEQUENCE: 3

| | |
|---|---|
| ctttcctgcg ttatccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt tcccagtcac gacgttgtaa | 540 |
| aacgacggcc agtcttaagc tcgggcccca ataatgatt ttattttgac tgatagtgac | 600 |

```
ctgttcgttg caacacattg atgagcaatg cttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt   780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat taaatcataa aaagaaataa gaaaagagg     960 tgcgagcctc tttttgtgt gacaaaataa aaacatctac ctattcatat acgctagtgt    1020
catagtcctg aaaatcatct gcatcaagaa caatttcaca actcttatac ttttctctta    1080
caagtcgttc ggcttcatct ggattttcag cctctatact tactaaacgt gataaagttt   1140
ctgtaatttc tactgtatcg acctgcagac tggctgtgta aagggagcc tgacatttat    1200 attccccaga acatcaggtt aatggcgttt ttgatgtcat tttcgcggtg gctgagatca   1260
gccacttctt ccccgataac ggagaccggc acactggcca tatcggtggt catcatgcgc   1320
cagctttcat ccccgatatg caccaccggg taaagttcac gggagacttt atctgacagc    1380
agacgtgcac tggccagggg gatcaccatc cgtcgcccgg gcgtgtcaat aatatcactc    1440
tgtacatcca caaacagacg ataacggctc tctcttttat aggtgtaaac cttaaactgc   1500
atttcaccag cccctgttct cgtcagcaaa agagccgttc atttcaataa accgggcgac    1560
ctcagccatc ccttcctgat tttccgcttt ccagcgttcg gcacgcagac gacgggcttc    1620
attctgcatg gttgtgctta ccagaccgga gatattgaca tcatatatgc cttgagcaac    1680
tgatagctgt cgctgtcaac tgtcactgta atacgctgct tcatagcata cctcttttg    1740 acatacttcg ggtatacata tcagtatata ttcttatacc gcaaaaatca gcgcgcaaat    1800
acgcatactg ttatctggct tttagtaagc cggatccacg cggcgtttac gccccgccct   1860
gccactcatc gcagtactgt tgtaattcat taagcattct gccgacatgg aagccatcac    1920
agacggcatg atgaacctga atcgccagcg gcatcagcac cttgtcgcct tgcgtataat    1980
atttgcccat ggtgaaaacg ggggcgaaga agttgtccat attggccacg tttaaatcaa    2040
aactggtgaa actcacccag ggattggctg agacgaaaaa catattctca ataaacccct    2100
tagggaaata ggccaggttt tcaccgtaac acgccacatc ttgcgaatat atgtgtagaa   2160
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280 ccatacgaa ttccggatga gcattcatca ggcgggcaag aatgtgaata aaggccggat    2340
aaaacttgtg cttattttc tttacggtct ttaaaaggc cgtaatatcc agctgaacgg    2400
tctggttata ggtacattga gcaactgact gaaatgcctc aaaatgttct ttacgatgcc    2460
attgggatat atcaacggtg gtatatccag tgatttttt ctccatttta gcttccttag    2520
ctcctgaaaa tctcgataac tcaaaaaata cgcccggtag tgatcttatt tcattatggt    2580
gaaagttgga acctcttacg tgccgatcaa cgtctcattt tcgccaaaag ttggcccagg    2640
gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atctaagtag ttgattcata gtgactggat atgttgtgtt ttacagtatt    2820
atgtagtctg ttttttatgc aaaatctaat ttaatatatt gatatttata tcattttacg    2880
tttctcgttc agctttcttg tacaaagttg gcattataag aaagcattgc ttatcaattt    2940
gttgcaacga acaggtcact atcagtcaaa ataaaatcat tatttgccat ccagctgata    3000
```

-continued

```
tcccctatag tgagtcgtat tacatggtca tagctgtttc ctggcagctc tggcccgtgt    3060
ctcaaaatct ctgatgttac attgcacaag ataaaataat atcatcatga acaataaaac    3120
tgtctgctta cataaacagt aatacaaggg gtgttatgag ccatattcaa cgggaaacgt    3180
cgaggccgcg attaaattcc aacatggatg ctgatttata tgggtataaa tgggctcgcg    3240
ataatgtcgg gcaatcaggt gcgacaatct atcgcttgta tgggaagccc gatgcgccag    3300
agttgtttct gaaacatggc aaaggtagcg ttgccaatga tgttacagat gagatggtca    3360
gactaaactg gctgacggaa tttatgcctc ttccgaccat caagcatttt atccgtactc    3420
ctgatgatgc atggttactc accactgcga tccccgaaaa acagcattc caggtattag     3480 aagaatatcc tgattcaggt gaaaatattg ttgatgcgct ggcagtgttc ctgcgccggt    3540
tgcattcgat tcctgtttgt aattgtcctt ttaacagcga tcgcgtattt cgtctcgctc    3600
aggcgcaatc acgaatgaat aacggtttgg ttgatgcgag tgattttgat gacgagcgta    3660
atggctggcc tgttgaacaa gtctggaaag aaatgcataa acttttgcca ttctcaccgg    3720
attcagtcgt cactcatggt gatttctcac ttgataacct tattttgac gaggggaaat     3780 taataggttg tattgatgtt ggacgagtcg aatcgcaga ccgataccag gatcttgcca     3840
tcctatggaa ctgcctcggt gagttttctc cttcattaca gaaacggctt tttcaaaaat    3900
atggtattga taatcctgat atgaataaat tgcagtttca tttgatgctc gatgagtttt    3960
tctaatcaga attggttaat tggttgtaac actggcagag cattacgctg acttgacggg    4020
acggcgcaag ctcatgacca aaatccctta acgtgagtta cgcgtcgttc cactgagcgt    4080 cagacccgt agaaaagatc aaaggatctt cttgagatcc ttttttctg cgcgtaatct      4140 gctgcttgca acaaaaaaa ccaccgctac cagcggtggt ttgtttgccg gatcaagagc     4200
taccaactct tttccgaag gtaactggct tcagcagagc gcagatacca aatactgttc     4260
ttctagtgta gccgtagtta ggccaccact tcaagaactc tgtagcaccg cctacatacc    4320
tcgctctgct aatcctgtta ccagtggctg ctgccagtgg cgataagtcg tgtcttaccg    4380
ggttggactc aagacgatag ttaccggata aggcgcagcg gtcgggctga acggggggtt    4440
cgtgcacaca gcccagcttg gagcgaacga cctacaccga actgagatac ctacagcgtg    4500
agctatgaga aagcgccacg cttcccgaag ggagaaaggc ggacaggtat ccggtaagcg    4560
gcagggtcgg aacaggagag cgcacgaggg agcttccagg gggaaacgcc tggtatcttt    4620
atagtcctgt cgggtttcgc cacctctgac ttgagcgtcg atttttgtga tgctcgtcag    4680
gggggcggag cctatggaaa aacgccagca acgcggcctt tttacggttc ctggccttt    4740 gctggccttt tgctcacatg tt                                             4762
```

<210> SEQ ID NO 4
<211> LENGTH: 16843
<212> TYPE: DNA
<213> ORGANISM: Artificial Sequence
<220> FEATURE:
<223> OTHER INFORMATION: pBC-yellow construct

<400> SEQUENCE: 4

```
ccgggctggt tgccctcgcc gctgggctgg cggccgtcta tggccctgca aacgcgccag     60
aaacgccgtc gaagccgtgt gcgagacacc gcggccgccg gcgttgtgga tacctcgcgg    120
aaaacttggc cctcactgac agatgagggg cggacgttga cacttgaggg gccgactcac    180
ccggcgcggc gttgacagat gaggggcagg ctcgatttcg gccggcgacg tggagctggc    240
cagcctcgca aatcggcgaa aacgcctgat tttacgcgag tttcccacag atgatgtgga    300
```

-continued

```
caagcctggg gataagtgcc ctgcggtatt gacacttgag gggcgcgact actgacagat    360
gaggggcgcg atccttgaca cttgaggggc agagtgctga cagatgaggg gcgcacctat    420
tgacatttga ggggctgtcc acaggcagaa atccagcat  ttgcaagggt tccgcccgt     480
tttttcggcca ccgctaacct gtcttttaac ctgcttttaa accaatattt ataaaccttg   540
tttttaacca gggctgcgcc ctgtgcgcgt gaccgcgcac gccgaagggg ggtgcccccc    600
cttctcgaac cctcccggcc cgctaacgcg ggcctccat  cccccagggg ctgcgcccc     660
tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcgggc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gacctttaca gaattactct atgaagcgcc atatttaaaa agctaccaag   1080
acgaagagga tgaagaggat gaggaggcag attgccttga atatattgac aatactgata   1140
agataaatata tcttttatat agaagatatc gccgtatgta aggatttcag ggggcaaggc   1200
ataggcagcg cgcttatcaa tatatctata gaatgggcaa agcataaaaa cttgcatgga   1260
ctaatgcttg aaacccagga caataacctt atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgatta   1680
gccccgacat agccccactg ttcgtccatt ccgcgcaga cgatgacgtc actgcccggc    1740
tgtatgcgcg aggttaccga ctgcggcctg agttttttaa gtgacgtaaa atcgtgttga   1800
ggccaacgcc cataatgcgg gctgttgccc ggcatccaac gccattcatg gccatatcaa   1860
tgattttctg gtgcgtaccg ggttgagaag cggtgtaagt gaactgcagt tgccatgttt   1920
tacggcagtg agagcagaga tagcgctgat gtccggcggt gcttttgccg ttacgcacca   1980
ccccgtcagt agctgaacag gagggacagc tgatagacac agaagccact ggagcacctc   2040
aaaaacacca tcatacacta aatcagtaag ttggcagcat cacccataat tgtggtttca   2100
aaatcggctc cgtcgatact atgttatacg ccaactttga aaacaacttt gaaaagctg    2160
ttttctggta tttaaggttt tagaatgcaa ggaacagtga attggagttc gtcttgttat   2220
aattagcttc ttggggtatc tttaaatact gtagaaaaga ggaaggaaat aataaatggc   2280
taaaatgaga atatcaccgg aattgaaaaa actgatcgaa aaataccgct gcgtaaaaga   2340
tacgaaagga atgtctcctg ctaaggtata taagctggtg ggagaaaatg aaaacctata   2400
tttaaaaatg acggacagcc ggtataaagg gaccacctat gatgtggaac gggaaaagga   2460
catgatgcta tggctggaag gaaagctgcc tgttccaaag gtcctgcact ttgaacggca   2520
tgatggctgg agcaatctgc tcatgagtga ggccgatggc gtcctttgct cggaagagta   2580
tgaagatgaa caaagccctg aaaagattat cgagctgtat gcggagtgca tcaggctctt   2640
tcactccatc gacatatcgg attgtcccta tacgaatagc ttagacagcc gcttagccga   2700
```

-continued

```
attggattac ttactgaata acgatctggc cgatgtggat tgcgaaaact gggaagaaga   2760
cactccattt aaagatccgc gcgagctgta tgattttta aagacggaaa agcccgaaga    2820
ggaacttgtc ttttcccacg gcgacctggg agacagcaac atctttgtga agatggcaa    2880
agtaagtggc tttattgatc ttgggagaag cggcagggcg acaagtggt atgacattgc    2940
cttctgcgtc cggtcgatca gggaggatat cggggaagaa cagtatgtcg agctattttt   3000
tgacttactg gggatcaagc ctgattggga gaaaataaaa tattatattt tactggatga   3060
attgttttag tacctagatg tggcgcaacg atgccggcga caagcaggag cgcaccgact   3120
tcttccgcat caagtgtttt ggctctcagg ccgaggccca cggcaagtat ttgggcaagg   3180
ggtcgctggt attcgtgcag ggcaagattc ggaataccaa gtacgagaag gacggccaga   3240
cggtctacgg gaccgacttc attgccgata aggtggatta tctggacacc aaggcaccag   3300
gcgggtcaaa tcaggaataa gggcacattg ccccggcgtg agtcgggca atcccgcaag    3360
gagggtgaat gaatcggacg tttgaccgga aggcatacag gcaagaactg atcgacgcgg   3420
ggttttccgc cgaggatgcc gaaaccatcg caagccgcac cgtcatgcgt gcgccccgcg   3480
aaaccttcca gtccgtcggc tcgatggtcc agcaagctac ggccaagatc gagcgcgaca   3540
gcgtgcaact ggctccccct gccctgcccg cgccatcggc cgccgtggag cgttcgcgtc   3600
gtctcgaaca ggaggcggca ggtttggcga agtcgatgac catcgacacg cgaggaacta   3660
tgacgaccaa gaagcgaaaa accgccggcg aggacctggc aaaacaggtc agcgaggcca   3720
agcaggccgc gttgctgaaa cacacgaagc agcagatcaa ggaaatgcag ctttccttgt   3780
tcgatattgc gccgtggccg gacacgatgc gagcgatgcc aaacgacacg gcccgctctg   3840
ccctgttcac cacgcgcaac aagaaaatcc gcgcgaggc gctgcaaaac aaggtcattt    3900
tccacgtcaa caaggacgtg aagatcacct acaccggcgt cgagctgcgg gccgacgatg   3960
acgaactggt gtggcagcag gtgttggagt acgcgaagcg caccctatc ggcgagccga    4020
tcaccttcac gttctacgag ctttgccagg acctgggctg gtcgatcaat ggccggtatt   4080
acacgaaggc cgaggaatgc ctgtcgcgcc tacaggcgac ggcgatgggc ttcacgtccg   4140
accgcgttgg gcacctggaa tcggtgtcgc tgctgcaccg cttccgcgtc ctggaccgtg   4200
gcaagaaaac gtcccgttgc caggtcctga tcgacgagga aatcgtcgtg ctgtttgctg   4260
gcgaccacta cacgaaattc atatgggaga agtaccgcaa gctgtcgccg acggcccgac   4320
ggatgttcga ctatttcagc tcgcaccggg agccgtaccc gctcaagctg gaaaccttcc   4380
gcctcatgtg cggatcggat tccacccgcg tgaagaagtg gcgcgagcag gtcggcgaag   4440
cctgcgaaga gttgcgaggc agcggcctgg tggaacacgc ctgggtcaat gatgacctgg   4500
tgcattgcaa acgctagggc cttgtggggt cagttccggc tgggggttca gcagccagcg   4560
ctttactggc atttcaggaa caagcgggca ctgctcgacg cacttgcttc gctcagtatc   4620
gctcgggacg cacggcgcgc tctacgaact gccgataaac agaggattaa aattgacaat   4680
tgtgattaag gctcagattc gacggcttgg agcggccgac gtgcaggatt ccgcgagat    4740
ccgattgtcg gccctgaaga aagctccaga gatgttcggg tccgtttacg agcacgagga   4800
gaaaaagccc atggaggcgt tcgctgaacg gttgcgagat gccgtggcat tcggcgccta   4860
catcgacggc gagatcattg gctgtcggt cttcaaacag gaggacggcc ccaaggacgc    4920
tcacaaggcg catctgtccg gcgttttcgt ggagcccgaa cagcgaggcc gagggtcgc    4980
cggtatgctg ctgcgggcgt tgccggcggg tttattgctc gtgatgatcg tccgacagat   5040
tccaacggga atctggtgga tgcgcatctt catcctcggc gcacttaata tttcgctatt   5100
```

-continued

```
ctggagcttg ttgtttattt cggtctaccg cctgccgggc ggggtcgcgg cgacggtagg      5160
cgctgtgcag ccgctgatgg tcgtgttcat ctctgccgct ctgctaggta gcccgatacg      5220
attgatggcg gtcctggggg ctatttgcgg aactgcgggc gtggcgctgt tggtgttgac      5280
accaaacgca gcgctagatc ctgtcggcgt cgcagcgggc ctggcggggg cggtttccat      5340
ggcgttcgga accgtgctga cccgcaagtg gcaacctccc gtgcctctgc tcacctttac      5400
cgcctggcaa ctggcggccg gaggacttct gctcgttcca gtagctttag tgtttgatcc      5460
gccaatcccg atgcctacag gaaccaatgt tctcggcctg gcgtggctcg gcctgatcgg      5520
agcgggttta acctacttcc tttggttccg ggggatctcg cgactcgaac ctacagttgt      5580
ttccttactg ggctttctca gccccagatc tggggtcgat cagccgggga tgcatcaggc      5640
cgacagtcgg aacttcgggt ccccgacctg taccattcgg tgagcaatgg ataggggagt      5700
tgatatcgtc aacgttcact tctaaagaaa tagcgccact cagcttcctc agcggcttta      5760
tccagcgatt tcctattatg tcggcatagt tctcaagatc gacagcctgt cacggttaag      5820
cgagaaatga ataagaaggc tgataattcg gatctctgcg agggagatga tatttgatca      5880
caggcagcaa cgctctgtca tcgttacaat caacatgcta ccctccgcga gatcatccgt      5940
gtttcaaacc cggcagctta gttgccgttc ttccgaatag catcggtaac atgagcaaag      6000
tctgccgcct tacaacggct ctcccgctga cgccgtcccg gactgatggg ctgcctgtat      6060
cgagtggtga ttttgtgccg agctgccggt cggggagctg ttggctggct ggtggcagga      6120
tatattgtgg tgtaaacaaa ttgacgctta gacaacttaa taacacattg cggacgtttt      6180
taatgtactg gggtggtttt tcttttcacc agtgagacgg gcaacagctg attgcccttc      6240
accgcctggc cctgagagag ttgcagcaag cggtccacgc tggtttgccc cagcaggcga      6300
aaatcctgtt tgatggtggt tccgaaatcg gcaaaatccc ttataaatca aagaatagc       6360 ccgagatagg gttgagtgtt gttccagttt ggaacaagag tccactatta agaacgtgg       6420 actccaacgt caaagggcga aaaccgtct atcagggcga tggcccacta cctgtatggc       6480
cgcattcgca aaacacacct agactagatt tgttttgcta acccaattga tattaattat      6540
atatgattaa tatttatatg tatatggatt tggttaatga aatgcatctg gttcatcaaa      6600
gaattataaa gacacgtgac attcatttag gataagaaat atggatgatc tctttctctt      6660
ttattcagat aactagtaat tacacataac acacaacttt gatgcccaca ttatagtgat      6720
tagcatgtca ctatgtgtgc atcctttat ttcatacatt aattaagttg gccaatccag       6780
aagatggaca agtctaggtt aaccatgtgg tacctacgcg ttcgaatatc catgggccgc      6840
ttcaggccag ggcgctgggg aaggcgatgg cgtgctcggt cagctgccac ttctggttct      6900
tggcgtcgct ccgtcctcc cgcagcagct tgtgctggat gaagtgccac tcgggcatct      6960
tgctgggcac gctcttggcc ttgtacacgg tgtcgaactg gcaccggtac cggccgccgt      7020
ccttcagcag caggtacatg ctcacgtcgc ccttcaggat gccctgctta ggcacgggca      7080
tgatcttctc gcagctggcc tcccagttgg tggtcatctt cttcatcacg ggccgtcgg       7140 cggggaagtt cacgccgttg aagatgctct tgtggtagat gcagttctcc ttcacgctca      7200
cggtgatgtc cacgttacag atgcacacgg cgccgtcctc gaacaggaag ctccggcccc      7260
aggtgtagcc ggcggggcag ctgttcttga agtagtccac gatgtcctgg gggtactcgg      7320
tgaagatccg gtcgccgtac ttgaagccgg cgctcaggat gtcctcgctg aagggcaggg      7380
ggccgccctc gatcacgcac aggttgatgg tctgcttgcc cttgaagggg tagccgatgc      7440
cctcgccggt gatcacgaac ttgtggccgt tcacgcagcc ctccatgtgg tacttcatgg      7500
```

```
tcatctcctc cttcaggccg tgcttgctgt gggccatggt ggcgaccggt gaattcgagc    7560
tcggtacccg gggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atcttttttt ttgcttttg gaactcatgt     7740
cggtagtata tcttttattt atttttcctt tttttcccct ttctttcaaa ctgatgtcgg    7800
tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920
cacatccttc tcattcgaat tgtatttctc cttaatcgtt ctaataggta tgatctttta    7980
ttttatacgt aaaattaaaa ttgaatgatg tcaagaacga aaattaattt gtatttacaa    8040
aggagctaaa tattgtttat tcctctactg gtagaagata aagaagtag atgaaataat      8100
gatcttacta gagaatattc ctcatttaca ctagtcaaat ggaaatcttg taaacttta     8160
caataattta tcctgaaaat atgaaaaat agaagaaaat gtttacctcc tctctcctct     8220
taattcacct acgatcggtg cgggcctctt cgctattacg ccagctggcg aaggggat      8280
gtgctgcaag gcgattaagt tgggtaacgc cagggttttc ccagtcacga cgttgtaaaa    8340
cgacggccag tgaattcgag ctcggtaccc ggggatcctc tagagtcgac ctgcaggcat    8400
gcaagcttgt tgaaacatcc ctgaagtgtc tcattttatt ttatttattc tttgctgata    8460
aaaaaataaa ataaagaag ctaagcacac ggtcaaccat tgctctactg ctaaagggt      8520
tatgtgtagt gttttactgc ataaattatg cagcaaacaa gacaactcaa attaaaaat     8580
ttcctttgct tgtttttttg ttgtctctga cttgactttc ttgtggaagt tggttgtata    8640
aggattggga cacaccattg tccttcttaa tttaatttta tttctttgct gataaaaaaa    8700
aaaaatttca tatagtgtta aataataatt tgttaaataa ccaaaaagtc aaatatgttt    8760
actctcgttt aaataattga gagtcgtcca gcaaggctaa acgattgtat agatttatga    8820
caatatttac ttttttatag ataaatgtta tattataata aatttatata catatattat    8880
atgttattta ttatttatta ttatttaaa tccttcaata ttttatcaaa ccaactcata     8940
atttttttt tatctgtaag aagcaataaa attaaataga cccactttaa ggatgatcca     9000
acctttatac agagtaagag agttcaaata gtacccttc atatacatat caactaaaat     9060
attagaaata tcatggatca aaccttataa agacattaaa taagtggata agtataatat    9120
ataaatgggt agtatataat atataaatgg atacaaactt ctctctttat aattgttatg    9180
tctccttaac atcctaatat aatacataag tgggtaatat ataatatata aatggagaca    9240
aacttcttcc attataattg ttatgtcttc ttaacactta tgtctcgttc acaatgctaa    9300
agttagaatt gtttagaaag tcttatagta cacatttgtt tttgtactat ttgaagcatt    9360
ccataagccg tcacgattca gatgattat aataataaga ggaaatttat catgaacaa      9420
taaggtgcat agatagagtg ttaatatatc ataacatcct ttgtttattc atagaagaag    9480
tgagatggag ctcagttatt atactgttac atggtcggat acaatattcc atgctctcca    9540
tgagctctta cacctacatg catttagtt catacttcat gcacgtggcc atcacagcta      9600
gctgcagcta catatttaca ttttacaaca ccaggagaac tgccctgtta gtgcataaca    9660
atcgagaagat ggccgtggct actcgagtta tcgaaccact ttgtacaaga aagctgaacg   9720
agaaacgtaa aatgatataa atatcaatat attaaattag attttgcata aaaaacagac    9780
tacataaatac tgtaaaacac aacatatcca gtcactatgg tcgacctgca gactggctgt   9840
gtataaggga gcctgacatt tatattcccc agaacatcag gttaatggcg tttttgatgt    9900
```

```
cattttcgcg gtggctgaga tcagccactt cttccccgat aacggagacc ggcacactgg    9960
ccatatcggt ggtcatcatg cgccagcttt catccccgat atgcaccacc gggtaaagtt   10020
cacgggagac tttatctgac agcagacgtg cactggccag ggggatcacc atccgtcgcc   10080
cgggcgtgtc aataatatca ctctgtacat ccacaaacag acgataacgg ctctctcttt   10140
tataggtgta aaccttaaac tgcatttcac cagtccctgt tctcgtcagc aaaagagccg   10200
ttcatttcaa taaccgggc gacctcagcc atcccttcct gattttccgc tttccagcgt    10260
tcggcacgca gacgacgggc ttcattctgc atggttgtgc ttaccagacc ggagatattg   10320
acatcatata tgccttgagc aactgatagc tgtcgctgtc aactgtcact gtaatacgct   10380
gcttcatagc acacctcttt ttgacatact tcgggtatac atatcagtat atattcttat   10440
accgcaaaaa tcagcgcgca aatacgcata ctgttatctg cttttagta agccggatcc    10500
tctagattac gccccgccct gccactcatc gcagtactgt tgtaattcat taagcattct   10560
gccgacatgg aagccatcac agacggcatg atgaacctga tcgccagcg gcatcagcac    10620
cttgtcgcct tgcgtataat atttgcccat ggtgaaaacg ggggcgaaga agttgtccat   10680
attggccacg tttaaatcaa aactggtgaa actcacccag ggattggctg agacgaaaaa   10740
catattctca ataaacccctt tagggaaata ggccaggttt tcaccgtaac acgccacatc   10800
ttgcgaatat atgtgtagaa actgccgaaa atcgtcgtgg tattcactcc agagcgatga   10860
aaacgtttca gtttgctcat ggaaaacggt gtaacaaggg tgaacactat cccatatcac   10920
cagctcaccg tctttcattg ccatacgaaa ttccggatga gcattcatca ggcgggcaag   10980
aatgtgaata aaggccggat aaaacttgtg cttatttttc tttacggtct ttaaaaaggc   11040
cgtaatatcc agctgaacgg tctggttata ggtacattga gcaactgact gaaatgcctc   11100
aaaatgttct ttacgatgcc attgggatat atcaacggtg gtatatccag tgatttttt    11160
ctccatttta gcttccttag ctcctgaaaa tctcgccgga tcctaactca aaatccacac   11220
attatacgag ccggaagcat aaagtgtaaa gcctggggtg cctaatgcgg ccgccatagt   11280
gactggatat gttgtgtttt acagtattat gtagtctgtt ttttatgcaa atctaatt    11340
aatatattga tatttatatc attttacgtt tctcgttcag ctttttgta caaacttgtt    11400
tgataaccgg tactagtgtg cacgtcgagc gtgtcctctc caaatgaaat gaacttcctt   11460
atatagagga agggtcttgc gaaggatagt gggattgtgc gtcatccctt acgtcagtgg   11520
agatgtcaca tcaatccact tgctttgaag acgtggttgg aacgtcttct ttttccacga   11580
tgctcctcgt gggtggggt ccatcttgg gaccactgtc ggcagaggca tcttgaatga    11640
tagcctttcc tttatcgcaa tgatggcatt tgtaggagcc accttccttt tctactgtcc   11700
tttcgatgaa gtgacagata gctgggcaat ggaatccgag gaggtttccc gaaattatcc   11760
tttgttgaaa agtctcaata gcccttggt cttctgagac tgtatctttg acattttgg    11820
agtagaccag agtgtcgtgc tccaccatgt tgacgaagat tttcttcttg tcattgagtc   11880
gtaaaagact ctgtatgaac tgttcgccag tcttcacggc gagttctgtt agatcctcga   11940
tttgaatctt agactccatg catggcctta gattcagtag gaactacctt tttagagact   12000
ccaatctcta ttacttgcct tggtttatga agcaagcctt gaatcgtcca tactggaata   12060
gtacttctga tcttgagaaa tatgtctttc tctgtgttct tgatgcaatt agtcctgaat   12120
cttttgactg catctttaac cttcttggga aggtatttga tctcctggag attgttactc   12180
gggtagatcg tcttgatgag acctgctgcg taggcctctc taaccatctg tgggtcagca   12240
ttctttctga aattgaagag gctaaccttc tcattatcag tggtgaacat agtgtcgtca   12300
```

```
ccttcacctt cgaacttcct tcctagatcg taaagataga ggaaatcgtc cattgtaatc   12360
tccggggcaa aggagatctc tttgggggct ggatcactgc tgggccttt ggttcctagc   12420 gtgagccagt gggcttttg ctttggtggg cttgttaggg ccttagcaaa gctcttgggc   12480
ttgagttgag cttctccttt ggggatgaag ttcaacctgt ctgtttgctg acttgttgtg   12540
tacgcgtcag ctgctgctct tgcctctgta atagtggcaa atttcttgtg tgcaactccg   12600
ggaacgccgt tgttgccgc ctttgtacaa ccccagtcat cgtatatacc ggcatgtgga   12660
ccgttataca caacgtagta gttgatatga gggtgttgaa tacccgattc tgctctgaga   12720
ggagcaactg tgctgttaag ctcagatttt tgtgggattg gaattggatc ctctagagca   12780
aagcttggcg taatcatggt catagctgtt tcctgtgtga aattgttatc cgctcacaat   12840
tccacacaac atacgagccg aagcataaa gtgtaaagcc tggggtgcct aatgagtgag   12900
ctaactcaca ttaattgcgt tgcgctcact gcccgctttc cagtcgggaa acctgtcgtg   12960
ccagctgcat taatgaatcg gccaacgcgc ggggagaggc ggtttgcgta ttgggccaaa   13020
gacaaaaggg cgacattcaa ccgattgagg gagggaaggt aaatattgac ggaaattatt   13080
cattaaaggt gaattatcac cgtcaccgac ttgagccatt tgggaattag agccagcaaa   13140
atcaccagta gcaccattac cattagcaag gccggaaacg tcaccaatga aaccatcatc   13200
tagtaacata gatgacaccg cgcgcgataa tttatcctag tttgcgcgct atattttgtt   13260
ttctatcgcg tattaaatgt ataattgcgg gactctaatc ataaaaaccc atctcataaa   13320
taacgtcatg cattacatgt taattattac atgcttaacg taattcaaca gaaattatat   13380
gataatcatc gcaagaccgg caacaggatt caatcttaag aaactttatt gccaaatgtt   13440
tgaacgatct gcttcgacgc actccttctt taggtacgga ctagatctcg gtgacgggca   13500
ggaccggacg gggcggtacc ggcaggctga agtccagctg ccagaaaccc acgtcatgcc   13560
agttcccgtg cttgaagccg gccgcccgca gcatgccgcg ggggcatat ccgagcgcct   13620 cgtgcatgcg cacgctcggg tcgttgggca gcccgatgac agcgaccacg ctcttgaagc   13680
cctgtgcctc cagggacttc agcaggtggg tgtagagcgt ggagcccagt cccgtccgct   13740
ggtggcgggg ggagacgtac acggtcgact cggccgtcca gtcgtaggcg ttgcgtgcct   13800
tccaggggcc cgcgtaggcg atgccggcga cctcgccgtc cacctcggcg acgagccagg   13860
gatagcgctc ccgcagacgg acgaggtcgt ccgtccactc ctgcggttcc tgcggctcgg   13920
tacggaagtt gaccgtgctt gtctcgatgt agtggttgac gatggtgcag accgccggca   13980
tgtccgcctc ggtggcacgg cggatgtcgg ccggcgtcg ttctgggctc atggatctgg   14040
attgagagtg aatatgagac tctaattgga taccgagggg aatttatgga acgtcagtgg   14100 agcattttg acaagaaata tttgctagct gatagtgacc ttaggcgact tttgaacgcg   14160
caataatggt ttctgacgta tgtgcttagc tcattaaact ccagaaaccc gcggctgagt   14220
ggctccttca acgttgcggt tctgtcagtt ccaaacgtaa aacggcttgt cccgcgtcat   14280 cggcggggt cataacgtga ctcccttaat tctccgctca tgatcagatt gtcgtttccc   14340
gccttcagtt taaactatca gtgtttgaca ggatatattg gcgggtaaac ctaagagaaa   14400
agagcgttta ttagaataat cggatattta aaagggcgtg aaaaggttta tccgttcgtc   14460
catttgtatg tgcatgccaa ccacagggtt ccccagatct ggcgccggcc agcgagacga   14520
gcaagattgg ccgccgcccg aaacgatccg acagcgcgcc cagcacaggt gcgcaggcaa   14580
attgcaccaa cgcatacagc gccagcagaa tgccatagtg ggcggtgacg tcgttcgagt   14640
gaaccagatc gcgcaggagg cccggcagca ccggcataat caggccgatg ccgacagcgt   14700
```

```
cgagcgcgac agtgctcaga attacgatca ggggtatgtt gggtttcacg tctggcctcc  14760
ggaccagcct ccgctggtcc gattgaacgc gcggattctt tatcactgat aagttggtgg  14820
acatattatg tttatcagtg ataaagtgtc aagcatgaca aagttgcagc cgaatacagt  14880
gatccgtgcc gccctggacc tgttgaacga ggtcggcgta gacggtctga cgacacgcaa  14940
actggcggaa cggttggggg ttcagcagcc ggcgctttac tggcacttca ggaacaagcg  15000
ggcgctgctc gacgcactgg ccgaagccat gctggcggag aatcatacgc attcggtgcc  15060
gagagccgac gacgactggc gctcatttct gatcgggaat gcccgcagct caggcaggc   15120
gctgctcgcc taccgcgatg gcgcgcgcat ccatgccggc acgcgaccgg cgcaccgca   15180
gatggaaacg gccgacgcgc agcttcgctt cctctgcgag gcgggttttt cggccgggga  15240
cgccgtcaat gcgctgatga caatcagcta cttcactgtt ggggccgtgc ttgaggagca  15300
ggccggcgac agcgatgccg gcgagcgcgg cggcaccgtt gaacaggctc cgctctcgcc  15360
gctgttgcgg gccgcgatag acgccttcga cgaagccggt ccggacgcag cgttcgagca  15420
gggactcgcg gtgattgtcg atggattggc gaaaaggagg ctcgttgtca ggaacgttga  15480
aggaccgaga aagggtgacg attgatcagg accgctgccg gagcgcaacc cactcactac  15540
agcagagcca tgtagacaac atcccctccc cctttccacc gcgtcagacg cccgtagcag  15600
cccgctacgg gcttttttcat gccctgccct agcgtccaag cctcacggcc gcgctcggcc  15660
tctctggcgg ccttctggcg ctcttccgct tcctgctca ctgactcgct gcgctcggtc   15720
gttcggctgc ggcgagcggt atcagctcac tcaaaggcgg taatacggtt atccacagaa  15780
tcaggggata acgcaggaaa gaacatgtga gcaaaaggcc agcaaaaggc caggaaccgt  15840
aaaaaggccg cgttgctggc gttttttccat aggctccgcc cccctgacga gcatcacaaa  15900
aatcgacgct caagtcagag gtggcgaaac ccgacaggac tataaagata ccaggcgttt  15960
cccccttggaa gctccctcgt gcgctctcct gttccgaccc tgccgcttac cggatacctg  16020
tccgcctttc tcccttcggg aagcgtggcg ctttccgct gcataaccct gcttcggggt   16080
cattatagcg atttttttcgg tatatccatc cttttcgca cgatatacag gattttgcca  16140
aagggttcgt gtagactttc cttggtgtat ccaacgcgt cagccgggca ggataggtga   16200
agtaggccca cccgcgagcg ggtgttcctt cttcactgtc ccttattcgc acctggcggt  16260
gctcaacggg aatcctgctc tgcgaggctg gccggctacc gccggcgtaa cagatgaggg  16320
caagcggatg gctgatgaaa ccaagccaac caggaagggc agcccaccta tcaaggtgta  16380
ctgccttcca gacgaacgaa gagcgattga ggaaaaggcg gcggcggccg gcatgagcct  16440
gtcggcctac ctgctggccg tcggccaggg ctacaaaatc acgggcgtcg tggactatga  16500
gcacgtccgc gagctggccc gcatcaatgg cgacctgggc cgcctgggcg gcctgctgaa  16560
actctggctc accgacgacc cgcgcacggc gcggttcggt gatgccacga tcctcgccct  16620
gctggcgaag atcgaagaga agcaggacga gcttggcaag gtcatgatgg gcgtggtccg  16680
cccgagggca gagccatgac tttttttagcc gctaaaacgg ccgggggtg cgcgtgattg   16740
ccaagcacgt ccccatgcgc tccatcaaga agagcgactt cgcggagctg gtgaagtaca  16800
tcaccgacga gcaaggcaag accgagcgcc tttgcgacgc tca                    16843
```

<210> SEQ ID NO 5
<211> LENGTH: 9142
<212> TYPE: DNA
<213> ORGANISM: Artificial Sequence
<220> FEATURE:
<223> OTHER INFORMATION: PHP27840 construct

<400> SEQUENCE: 5

```
ctagttatct gaataaaaga gaaagagatc atccatattt cttatcctaa atgaatgtca      60
cgtgtcttta taattctttg atgaaccaga tgcatttcat taaccaaatc catatacata     120
taaatattaa tcatatataa ttaatatcaa ttgggttagc aaaacaaatc tagtctaggt     180
gtgttttgcg aattcgatat caagcttgat gggtaccggc gcgcccgatc atccggatat     240
agttcctcct ttcagcaaaa aaccccctcaa gacccgttta gaggcccaa ggggttatgc     300
tagttattgc tcagcggtgg cagcagccaa ctcagcttcc tttcgggctt tgttagcagc     360
cggatcgatc caagctgtac ctcactattc ctttgccctc ggacgagtgc tggggcgtcg     420
gtttccacta tcggcgagta cttctacaca gccatcggtc cagacggccg cgcttctgcg     480
ggcgatttgt gtacgcccga cagtcccggc tccggatcgg acgattgcgt cgcatcgacc     540
ctgcgcccaa gctgcatcat cgaaattgcc gtcaaccaag ctctgataga gttggtcaag     600
accaatgcgg agcatatacg cccggagccg cggcgatcct gcaagctccg gatgcctccg     660
ctcgaagtag cgcgtctgct gctccataca agccaaccac ggcctccaga agaagatgtt     720
ggcgacctcg tattgggaat ccccgaacat cgcctcgctc cagtcaatga ccgctgttat     780
gcggccattg tccgtcagga cattgttgga gccgaaatcc gcgtgcacga ggtgccggac     840
ttcggggcag cctccggccc aaagcatcag ctcatcgaga gcctgcgcga cggacgcact     900
gacggtgtcg tccatcacag tttgccagtg atacacatgg ggatcagcaa tcgcgcatat     960
gaaatcacgc catgtagtgt attgaccgat tccttgcggt ccgaatgggc cgaacccgct    1020
cgtctggcta agatcggccg cagcgatcgc atccatagcc tccgcgaccg gctgcagaac    1080
agcgggcagt tcggtttcag gcaggtcttg caacgtgaca ccctgtgcac ggcgggagat    1140
gcaataggtc aggctctcgc tgaattcccc aatgtcaagc acttccggaa tcgggagcgc    1200
ggccgatgca aagtgccgat aaacataacg atctttgtag aaaccatcgg cgcagctatt    1260
tacccgcagg acatatccac gccctcctac atcgaagctg aaagcacgag attcttcgcc    1320
ctccagagag ctgcatcaggt cggagacgct gtcgaacttt tcgatcagaa acttctcgac    1380
agacgtcgcg gtgagttcag gcttttccat gggtatatct ccttcttaaa gttaaacaaa    1440
attatttcta gagggaaacc gttgtggtct ccctatagtg agtcgtatta atttcgcggg    1500
atcgagatct gatcaacctg cattaatgaa tcggccaacg cgcggggaga gcggtttgc    1560
gtattgggcg ctcttccgct tcctcgctca ctgactcgct gcgctcggtc gttcggctgc    1620
ggcgagcggt atcagctcac tcaaaggcgg taatacggtt atccacagaa tcaggggata    1680
acgcaggaaa gaacatgtga gcaaaaggcc agcaaaggc caggaaccgt aaaaaggccg    1740
cgttgctggc gttttccat aggctccgcc ccctgacga gcatcacaaa aatcgacgct    1800
caagtcagag gtggcgaaac ccgacaggac tataaagata ccaggcgttt cccctggaa    1860
gctccctcgt gcgctctcct gttccgaccc tgccgcttac cggatacctg tccgcctttc    1920
tcccttcggg aagcgtggcg ctttctcaat gctcacgctg taggtatctc agttcggtgt    1980
aggtcgttcg ctccaagctg ggctgtgtgc acgaaccccc cgttcagccc gaccgctgcg    2040
ccttatccgg taactatcgt cttgagtcca acccggtaag acacgactta tcgccactgg    2100
cagcagccac tggtaacagg attagcagag cgaggtatgt aggcggtgct acagagttct    2160
tgaagtggtg gcctaactac ggctacacta gaaggacagt atttggtatc tgcgctctgc    2220
tgaagccagt taccttcgga aaaagagttg gtagctcttg atccggcaaa caaaccaccg    2280
ctggtagcgg tggttttttt gtttgcaagc agcagattac gcgcagaaaa aaaggatctc    2340
```

```
aagaagatcc tttgatcttt tctacggggt ctgacgctca gtggaacgaa aactcacgtt    2400
aagggatttt ggtcatgaca ttaacctata aaaataggcg tatcacgagg cccttcgtc     2460 tcgcgcgttt cggtgatgac ggtgaaaacc tctgacacat gcagctcccg gagacggtca    2520
cagcttgtct gtaagcggat gccgggagca gacaagcccg tcagggcgcg tcagcgggtg    2580
ttggcgggtg tcgggctgg cttaactatg cggcatcaga gcagattgta ctgagagtgc     2640
accatatgga catattgtcg ttagaacgcg gctacaatta atacataacc ttatgtatca    2700
tacacatacg atttaggtga cactatagaa cggcgcgcca agctgggtct agaactagaa    2760
acgtgatgcc acttgttatt gaagtcgatt acagcatcta ttctgtttta ctatttataa    2820
ctttgccatt tctgactttt gaaaactatc tctggatttc ggtatcgctt tgtgaagatc    2880
gagcaaaaga gacgttttgt ggacgcaatg gtccaaatcc gttctacatg aacaaattgg    2940
tcacaatttc cactaaaagt aaataaatgg caagttaaaa aaggaatatg cattttactg    3000
attgcctagg tgagctccaa gagaagttga atctacacgt ctaccaaccg ctaaaaaaag    3060
aaaaacattg aatatgtaac ctgattccat tagcttttga cttcttcaac agattctcta    3120
cttagatttc taacagaaat attattacta gcacatcatt ttcagtctca ctacagcaaa    3180
aaatccaacg gcacaataca gacaacagga gatatcagac tacagagata gatagatgct    3240
actgcatgta gtaagttaaa taaaaggaaa ataaaatgtc ttgctaccaa aactactaca    3300
gactatgatg ctcaccacag gccaaatcct gcaactagga cagcattatc ttatatatat    3360
tgtacaaaac aagcatcaag gaacatttgg tctaggcaat cagtacctcg ttctaccatc    3420
accctcagtt atcacatcct tgaaggatcc attactggga atcatcggca acacatgctc    3480
ctgatggggc acaatgacat caagaaggta ggggccaggg gtgtccaaca ttctctgaat    3540
tgccgctcta agctcttcct tcttcgtcac tcgcgctgcc ggtatccac aagcatcagc     3600 aaacttgagc atgttgga atatctcgct ctcgctagac ggatctccaa gataggtgtg      3660
agctctattg gacttgtaga acctatcctc caactgaacc accataccca aatgctgatt    3720
gttcaacaac aatatcttaa ctgggagatt ctccactctt atagtggcca actcctgaac    3780
attcatgatg aaactaccat ccccatcaat gtcaaccaca acagcccag ggttagcaac     3840 agcagcacca atagccgcag gcaatccaaa acccatggct ccaagacccc ctgaggtcaa    3900
ccactgcctc ggtctcttgt acttgtaaaa ctgcgcagcc cacatttgat gctgcccaac    3960
cccagtacta acaatagcat ctccattagt caactcatca agaacctcga tagcatgctg    4020
cggagaaatc gcgtcctgga atgtcttgta acccaatgga aacttgtgtt tctgcacatt    4080
aatctcttct ctccaacctc caagatcaaa cttaccctcc actcctttct cctccaaaat    4140
catattaatt cccttcaagg ccaacttcaa atccgcgcaa accgacacgt gcgcctgctt    4200
gttcttccca atctcggcag aatcaatatc aatgtgaaca atcttagccc tactagcaaa    4260
agcctcaagc ttcccagtaa cacggtcatc aaaccttacc ccaaaggcaa gcaacaaatc    4320
actattgtca acagcatagt tagcataaac agtaccatgc atacccagca tctgaaggga    4380
atattcatca ccaataggaa aagttccaag acccattaaa gtgctagcaa cgggaatacc    4440
agtgagttca acaaagcgcc tcaattcagc actggaattc aaactgccac cgccgacgta    4500
gagaacgggc ttttgggcct ccatgatgag tctgacaatg tgttccaatt gggcctcggc    4560 gggggggcctg gcagcctgg cgaggtaacc ggggaggtta acgggctcgt cccaattagg    4620
cacggcgagt tgctgctgaa cgtctttggg aatgtcgatg aggaccggac cggggcggcc    4680
ggaggtggcg acgaagaaag cctcggcgac gacgcggggg atgtcgtcga cgtcgaggat    4740
```

```
gaggtagttg tgcttcgtga tggatctgct cacctccacg atcggggttt cttggaaggc   4800
gtcggtgccg atcatccggc gggcgacctg gccggtgatg gcgacgactg ggacgctgtc   4860
cattaaagcg tcggcgaggc cgctcacgag gttggtggcg ccggggccgg aggtggcaat   4920
gcagacgccg gggaggccgg aggaacgcgc gtagccttcg gcggcgaaga cgccgccctg   4980
ctcgtggcgc gggagcacgt tgcggatggc ggcggagcgc gtgagcgcct ggtggatctc   5040
catcgacgca ccgccggggt acgcgaacac cgtcgtcacg ccctgcctct ccagcgcctc   5100
cacaaggatg tccgcgccct tgcgaggttc gccggaggcg aaccgtgaca cgaagggctc   5160
cgtggtcggc gcttccttgg tgaagggcgc cgccgtgggg ggtttggaga tggaacattt   5220
gattttgaga gcgtggttgg gtttggtgag ggtttgatga gagagaggga gggtggatct   5280
agtaatgcgt ttggggaagg tggggtgtga agaggaagaa gagaatcggg tggttctgga   5340
agcggtggcc gccattgtgt tgtgtggcat ggttatactt caaaaactgc acaacaagcc   5400
tagagttagt acctaaacag taaatttaca acagagagca aagacacatg caaaaatttc   5460
agccataaaa aaagttataa tagaatttaa agcaaaagtt tcattttta aacatatata   5520 caaacaaact ggatttgaag gaagggatta attcccctgc tcaaagtttg aattcctatt   5580
gtgacctata ctcgaataaa attgaagcct aaggaatgta tgagaaacaa gaaaacaaaa   5640
caaaactaca gacaaacaag tacaattaca aaattcgcta aaattctgta atcaccaaac   5700
cccatctcag tcagcacaag gcccaaggtt tattttgaaa taaaaaaaaa gtgattttat   5760
ttctcataag ctaaagaaa gaaaggcaat tatgaaatga tttcgactag atctgaaagt   5820
caaacgcgta ttccgcagat attaaagaaa gagtagagtt tcacatggat cctagatgga   5880
cccagttgag gaaaaagcaa ggcaaagcaa accagaagtg caagatccga aattgaacca   5940
cggaatctag gatttggtag agggagaaga aaagtacctt gagaggtaga agagaagaga   6000
agagcagaga gatatatgaa cgagtgtgtc ttggtctcaa ctctgaagcg atacgagttt   6060
agaggggagc attgagttcc aatttatagg gaaaccgggt ggcaggggtg agttaatgac   6120
ggaaaagccc ctaagtaacg agattggatt gtgggttaga ttcaaccgtt tgcatccgcg   6180
gcttagattg gggaagtcag agtgaatctc aaccgttgac tgagttgaaa attgaatgta   6240
gcaaccaatt gagccaaccc cagcctttgc cctttgattt tgatttgttt gttgcatact   6300
ttttatttgt cttctggttc tgactctctt tctctcgttt caatgccagg ttgcctactc   6360
ccacaccact cacaagaaga ttctactgtt agtattaaat attttttaat gtattaaatg   6420
atgaatgctt ttgtaaacag aacaagacta tgtctaataa gtgtcttgca acattttta   6480 agaaattaaa aaaaatatat ttattatcaa aatcaaatgt atgaaaaatc atgaataata   6540
taattttata catttttta aaaatctttt taatttctta attaatatct aaaaataat   6600 gattaatatt taacccaaaa taattagtat gattggtaag aagatatcc atgttatgtt   6660 tggatgtgag tttgatctag agcaaagctt actagagtcg acctgcagcc cctccaccgc   6720
ggtggcggcc gctctagaga tccgtcaaca tggtggagca cgacactctc gtctactcca   6780
agaatatcaa agatacagtc tcagaagacc aaagggctat tgagactttt caacaaaggg   6840
taatatcggg aaacctcctc ggattccatt gcccagctat ctgtcacttc atcaaaagga   6900
cagtagaaaa ggaaggtggc acctacaaat gccatcattg cgataaagga aaggctatcg   6960
ttcaagatgc ctctgccgac agtggtccca agatggaccc cacccacg aggagcatcg   7020 tggaaaaaga agacgttcca accacgtctt caaagcaagt ggattgatgt gatgatccta   7080
tgcgtatggt atgacgtgtg ttcaagatga tgacttcaaa cctacctatg acgtatggta   7140
```

-continued

```
tgacgtgtgt cgactgatga cttagatcca ctcgagcggc tataaatacg tacctacgca   7200
ccctgcgcta ccatccctag agctgcagct tatttttaca acaattacca acaacaacaa   7260
acaacaaaca acattacaat tactatttac aattacagtc gacccatcaa caagtttgta   7320
caaaaaagct gaacgagaaa cgtaaaatga tataaatatc aatatattaa attagatttt   7380
gcataaaaaa cagactacat aatactgtaa aacacaacat atccagtcat attggcggcc   7440
gcattaggca ccccaggctt tacactttat gcttccggct cgtataatgt gtggattttg   7500
agttaggatc cgtcgagatt ttcaggagct aaggaagcta aaatggagaa aaaaatcact   7560
ggatatacca ccgttgatat atcccaatgg catcgtaaag aacattttga ggcatttcag   7620
tcagttgctc aatgtaccta taaccagacc gttcagctgg atattacggc cttttttaaag  7680 accgtaaaga aaaataagca caagttttat ccggccttta ttcacattct tgcccgcctg   7740
atgaatgctc atccggaatt ccgtatggca atgaaagacg gtgagctggt gatatgggat   7800
agtgttcacc cttgttacac cgttttccat gagcaaactg aaacgttttc atcgctctgg   7860
agtgaatacc acgacgattt ccggcagttt ctacacatat attcgcaaga tgtggcgtgt   7920
tacggtgaaa acctggccta tttccctaaa gggtttattg agaatatgtt tttcgtctca   7980
gccaatccct gggtgagttt caccagtttt gatttaaacg tggccaatat ggacaacttc   8040 ttcgccccg tttttcaccat gggcaaatat tatacgcaag cgacaaggt gctgatgccg   8100 ctggcgattc aggttcatca tgccgtttgt gatggcttcc atgtcggcag aatgcttaat   8160
gaattacaac agtactgcga tgagtggcag ggcggggcgt aaagatctgg atccggctta   8220
ctaaaagcca gataacagta tgcgtatttg cgcgctgatt tttgcggtat aagaatatat   8280
actgatatgt atacccgaag tatgtcaaaa agaggtatgc tatgaagcag cgtattacag   8340
tgacagttga cagcgacagc tatcagttgc tcaaggcata tatgatgtca atatctccgg   8400
tctggtaagc acaaccatgc agaatgaagc ccgtcgtctg cgtgccgaac gctggaaagc   8460
ggaaaatcag gaagggatgg ctgaggtcgc ccggtttatt gaaatgaacg gctcttttgc   8520
tgacgagaac aggggctggt gaaatgcagt ttaaggttta cacctataaa agagagagcc   8580
gttatcgtct gtttgtggat gtacagagtg atattattga cacgcccggg cgacggatgg   8640
tgatccccct ggccagtgca cgtctgctgt cagataaagt ctcccgtgaa ctttacccgg   8700
tggtgcatat cggggatgaa agctggcgca tgatgaccac cgatatggcc agtgtgccgg   8760
tctccgttat cggggaagaa gtggctgatc tcagccaccg cgaaaatgac atcaaaaacg   8820
ccattaacct gatgttctgg ggaatataaa tgtcaggctc ccttatacac agccagtctg   8880
caggtcgacc atagtgactg gatatgttgt gttttacagt attatgtagt ctgttttta    8940 tgcaaaatct aatttaatat attgatattt atatcatttt acgtttctcg ttcagctttc   9000
ttgtacaaag tggttgataa cctagacttg tccatcttct ggattggcca acttaattaa   9060
tgtatgaaat aaaaggatgc acacatagtg acatgctaat cactataatg tgggcatcaa   9120
agttgtgtgt tatgtgtaat ta                                            9142
```

<210> SEQ ID NO 6  
<211> LENGTH: 49911  
<212> TYPE: DNA  
<213> ORGANISM: Artificial Sequence  
<220> FEATURE:  
<223> OTHER INFORMATION: PHP23236 construct

<400> SEQUENCE: 6

```
gtgcagcgtg acccggtcgt gcccctctct agagataatg agcattgcat gtctaagtta     60
```

```
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg ttttataga ctaattttt tagtacatct attttattct attttagcct    420
ctaaattaag aaaactaaaa ctctatttta gttttttat ttaataattt agatataaaa    480
tagaataaaa taagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcacggca gctacggggg attccttcc caccgctcct    840 tcgctttccc ttcctcgccc gccgtaataa atagacaccc cctccacacc ctctttcccc    900
aacctcgtgt tgttcggagc gcacacacac acaaccagat ctcccccaaa tccacccgtc    960
ggcacctccg cttcaaggta cgccgctcgt cctccccccc ccccctctc taccttctct    1020 agatcggcgt tccggtccat ggttagggcc cggtagttct acttctgttc atgtttgtgt    1080
tagatccgtg tttgtgttag atccgtgctg ctagcgttcg tacacggatg cgacctgtac    1140
gtcagacacg ttctgattgc taacttgcca gtgtttctct ttggggaatc ctgggatggc    1200
tctagccgtt ccgcagacgg gatcgatttc atgattttt ttgtttcgtt gcatagggtt    1260
tggtttgccc ttttccttta tttcaatata tgccgtgcac ttgtttgtcg ggtcatcttt    1320
tcatgctttt ttttgtcttg gttgtgatga tgtggtctgg ttgggcggtc gttctagatc    1380
ggagtagaat tctgtttcaa actacctggt ggatttatta attttggatc tgtatgtgtg    1440
tgccatacat attcatagtt acgaattgaa gatgatggat ggaaatatcg atctaggata    1500
ggtatacatg ttgatgcggg ttttactgat gcatatacag agatgctttt tgttcgcttg    1560
gttgtgatga tgtggtgtgg ttgggcggtc gttcattcgt tctagatcgg agtagaatac    1620
tgtttcaaac tacctggtgt atttattaat tttggaactg tatgtgtgtg tcatacatct    1680
tcatagttac gagtttaaga tggatggaaa tatcgatcta ggataggtat acatgttgat    1740
gtgggtttta ctgatgcata tacatgatgg catatgcagc atctattcat atgctctaac    1800
cttgagtacc tatctattat aataaacaag tatgttttat aattattttg atcttgatat    1860
acttggatga tggcatatgc agcagctata tgtggatttt tttagccctg ccttcatacg    1920
ctatttattt gcttggtact gtttcttttg tcgatgctca ccctgttgtt tggtgttact    1980
tctgcaggtc gactctagag gatccacaag tttgtacaaa aaagctgaac gagaaacgta    2040
aaatgatata aatatcaata tattaaatta gattttgcat aaaaaacaga ctacataata    2100
ctgtaaaaca caacatatcc agtcactatg gcggccgcat taggcacccc aggctttaca    2160
ctttatgctt ccggctcgta atgtgtgg attttgagtt aggatttaaa tacgcgttga    2220
tccggcttac taaagccag ataacagtat gcgtatttgc gcgctgattt ttgcggtata    2280
agaatatata ctgatatgta tacccgaagt atgtcaaaaa gaggtatgct atgaagcagc    2340
gtattacagt gacagttgac agcgacagct atcagttgct caaggcatat atgatgtcaa    2400
tatctccggt ctggtaagca caaccatgca gaatgaagcc cgtcgtctgc gtgccgaacg    2460
```

```
ctggaaagcg gaaaatcagg aagggatggc tgaggtcgcc cggtttattg aaatgaacgg    2520 ctctttttgct gacgagaaca gggggctggtg aaatgcagtt taaggtttac acctataaaa   2580
gagagagccg ttatcgtctg tttgtggatg tacagagtga tatcattgac acgcccggtc    2640
gacggatggt gatcccctg gccagtgcac gtctgctgtc agataaagtc tcccgtgaac    2700
tttacccggt ggtgcatatc ggggatgaaa gctggcgcat gatgaccacc gatatggcca   2760
gtgtgccggt ctccgttatc ggggaagaag tggctgatct cagccaccgc gaaaatgaca   2820
tcaaaaacgc cattaacctg atgttctggg aatataaat gtcaggctcc cttatacaca    2880
gccagtctgc aggtcgacca tagtgactgg atatgttgtg ttttacagta ttatgtagtc   2940
tgttttttat gcaaaatcta atttaatata ttgatattta tcatttta cgtttctcgt    3000 tcagcttct tgtacaaagt ggtgttaacc tagacttgtc catcttctgg attggccaac    3060
ttaattaatg tatgaaataa aaggatgcac acatagtgac atgctaatca ctataatgtg   3120
ggcatcaaag ttgtgtgtta tgtgtaatta ctagttatct gaataaaaga gaaagagatc   3180
atccatattt cttatcctaa atgaatgtca cgtgtcttta taattctttg atgaaccaga   3240
tgcatttcat taaccaaatc catatacata taaatattaa tcatatataa ttaatatcaa   3300
ttgggttagc aaaacaaatc tagtctaggt gtgttttgcg aattgcggcc gccaccgcgg   3360
tggagctcga attccggtcc gggtcacctt tgtccaccaa gatggaactg cggccgctca   3420
ttaattaagt caggcgcgcc tctagttgaa gacacgttca tgtcttcatc gtaagaagac   3480
actcagtagt cttcggccag aatggccatc tggattcagc aggcctagaa ggccatttaa   3540
atcctgagga tctggtcttc ctaaggaccc gggatatcgg accgattaaa ctttaattcg   3600
gtccgaagct tgcatgcctg cagtgcagcg tgacccggtc gtgcccctct ctagagataa   3660
tgagcattgc atgtctaagt tataaaaaat taccacatat ttttttgtc acacttgttt    3720 gaagtgcagt ttatctatct ttatacatat atttaaactt tactctacga ataatataat   3780
ctatagtact acaataatat cagtgtttta gagaatcata taaatgaaca gttagacatg   3840
gtctaaagga caattgagta ttttgacaac aggactctac agttttatct ttttagtgtg   3900
catgtgttct ccttttttttt tgcaaatagc ttcacctata taatacttca tccatttat    3960 tagtacatcc atttagggtt tagggttaat ggttttttata gactaatttt tttagtacat   4020
ctattttatt ctattttagc ctctaaatta agaaaactaa aactctatt tagttttttt    4080 atttaataat ttagatataa aatagaataa aataaagtga ctaaaaatta aacaaatacc   4140
ctttaagaaa ttaaaaaaac taaggaaaca ttttcttgt ttcgagtaga taatgccagc    4200
ctgttaaacg ccgtcgacga gtctaacgga caccaaccag cgaaccagca gcgtcgcgtc   4260
gggccaagcg aagcagacgg cacggcatct ctgtcgctgc ctctggaccc ctctcgagag   4320
ttccgctcca ccgttggact tgctccgctg tcggcatcca gaaattgcgt ggcggagcgg   4380
cagacgtgag ccggcacggc aggcggcctc ctcctcctct cacggcaccg gcagctacgg   4440
gggattcctt tcccaccgct ccttcgcttt cccttcctcg cccgccgtaa taaatagaca   4500 cccctccac accctctttc cccaacctcg tgttgttcgg agcgcacaca cacacaacca   4560
gatctccccc aaatccaccc gtcggcacct ccgcttcaag gtacgccgct cgtcctcccc   4620
cccccccctc tctaccttct ctagatcggc gttccggtcc atgcatggtt agggcccggt   4680
agttctactt ctgttcatgt ttgtgttaga tccgtgtttg tgttagatcc gtgctgctag   4740
cgttcgtaca cggatgcgac ctgtacgtca gacacgttct gattgctaac ttgccagtgt   4800
ttctctttgg ggaatcctgg gatggctcta gccgttccgc agacgggatc gatttcatga   4860
```

```
tttttttttgt ttcgttgcat agggtttggt ttgcccttt  cctttatttc aatatatgcc    4920
gtgcacttgt ttgtcgggtc atcttttcat gctttttttt gtcttggttg tgatgatgtg    4980
gtctggttgg gcggtcgttc tagatcggag tagaattctg tttcaaacta cctggtggat    5040
ttattaattt tggatctgta tgtgtgtgcc atacatattc atagttacga attgaagatg    5100
atggatggaa atatcgatct aggataggta tacatgttga tgcgggtttt actgatgcat    5160
atacagagat gcttttgtt cgcttggttg tgatgatgtg gtgtggttgg gcggtcgttc    5220
attcgttcta gatcggagta gaatactgtt tcaaactacc tggtgtattt attaattttg    5280
gaactgtatg tgtgtgtcat acatcttcat agttacgagt ttaagatgga tggaaatatc    5340
gatctaggat aggtatacat gttgatgtgg gttttactga tgcatataca tgatggcata    5400
tgcagcatct attcatatgc tctaaccttg agtacctatc tattataata aacaagtatg    5460
ttttataatt attttgatct tgatatactt ggatgatggc atatgcagca gctatatgtg    5520
gatttttta gccctgcctt catacgctat ttatttgctt ggtactgttt cttttgtcga    5580
tgctcaccct gttgtttggt gttacttctg caggtcgact ttaacttagc ctaggatcca    5640
cacgacacca tgtccccga gcgccgcccc gtcgagatcc gccggccac cgccgccgac    5700
atggccgccg tgtgcgacat cgtgaaccac tacatcgaga cctccaccgt gaacttccgc    5760
accgagccgc agaccccgca ggagtggatc gacgacctgg agcgcctcca ggaccgctac    5820
ccgtggctcg tggccgaggt ggagggcgtg gtggccggca tcgcctacgc cggcccgtgg    5880
aaggcccgca acgcctacga ctggaccgtg gagtccaccg tgtacgtgtc ccaccgccac    5940
cagcgcctcg gcctcggctc cacctctac acccacctcc tcaagagcat ggaggcccag    6000
ggcttcaagt ccgtggtggc cgtgatcggc ctccccgaacg accgtccgt gcgcctccac    6060
gaggccctcg gctacaccgc ccgcggcacc ctccgcgccg ccggctacaa gcacggcggc    6120
tggcacgacg tcggcttctg gcagcgcgac ttcgagctgc cggccccgcc gcgcccggtg    6180
cgcccggtga cgcagatctg agtcgaaacc tagacttgtc catcttctgg attggccaac    6240
ttaattaatg tatgaaataa aaggatgcac acatagtgac atgctaatca ctataatgtg    6300
ggcatcaaag ttgtgtgtta tgtgtaatta ctagttatct gaataaaaga gaaagagatc    6360
atccatattt cttatcctaa atgaatgtca cgtgtcttta taattctttg atgaaccaga    6420
tgcatttcat taaccaaatc catatacata taaatattaa tcatatataa ttaatatcaa    6480
ttgggttagc aaaacaaatc tagtctaggt gtgttttgcg aattgcggcc gccaccgcgg    6540
tggagctcga attcattccg attaatcgtg gcctcttgct cttcaggatg aagagctatg    6600
tttaaacgtg caagcgctac tagacaattc agtacattaa aaacgtccgc aatgtgttat    6660
taagttgtct aagcgtcaat ttggtttaca ccacaatata tcctgccacc agccagccaa    6720
cagctccccg accggcagct cggcacaaaa tcaccactcg ataccaggcag cccatcagtc    6780
cgggacggc tcagcgggag agccgttgta aggcggcaga ctttgctcat gttaccgatg    6840
ctattcggaa gaacggcaac taagctgccg ggtttgaaac acggatgatc tcgcggaggg    6900
tagcatgttg attgtaacga tgacagagcg ttgctgcctg tgatcaaata tcatctccct    6960
cgcagagatc cgaattatca gccttcttat tcatttctcg cttaaccgtg acaggctgtc    7020
gatcttgaga actatgccga cataatagga aatcgctgga taaagccgct gaggaagctg    7080
agtggcgcta tttctttaga agtgaacgtt gacgatcgtc gaccgtaccc cgatgaatta    7140
attcggacgt acgttctgaa cacagctgga tacttacttg ggcgattgtc atacatgaca    7200
tcaacaatgt acccgtttgt gtaaccgtct cttggaggtt cgtatgacac tagtggttcc    7260
```

```
cctcagcttg cgactagatg ttgaggccta acattttatt agagagcagg ctagttgctt   7320
agatacatga tcttcaggcc gttatctgtc agggcaagcg aaaattggcc atttatgacg   7380
accaatgccc cgcagaagct cccatctttg ccgccataga cgccgcgccc ccttttgggg   7440
gtgtagaaca tccttttgcc agatgtggaa aagaagttcg ttgtcccatt gttggcaatg   7500
acgtagtagc cggcgaaagt gcgagaccca tttgcgctat atataagcct acgatttccg   7560
ttgcgactat tgtcgtaatt ggatgaacta ttatcgtagt tgctctcaga gttgtcgtaa   7620
tttgatggac tattgtcgta attgcttatg gagttgtcgt agttgcttgg agaaatgtcg   7680
tagttggatg gggagtagtc atagggaaga cgagcttcat ccactaaaac aattggcagg   7740
tcagcaagtg cctgccccga tgccatcgca agtacgaggc ttagaaccac cttcaacaga   7800
tcgcgcatag tcttccccag ctctctaacg cttgagttaa gccgcgccgc gaagcggcgt   7860
cggcttgaac gaattgttag acattatttg ccgactacct tggtgatctc gcctttcacg   7920
tagtgaacaa attcttccaa ctgatctgcg cgcgaggcca agcgatcttc ttgtccaaga   7980
taagcctgcc tagcttcaag tatgacgggc tgatactggg ccggcaggcg ctccattgcc   8040
cagtcggcag cgacatcctt cggcgcgatt ttgccggtta ctgcgctgta ccaaatgcgg   8100
gacaacgtaa gcactacatt tcgctcatcg ccagcccagt cgggcggcga gttccatagc   8160
gttaaggttt catttagcgc ctcaaataga tcctgttcag gaaccggatc aaagagttcc   8220
tccgccgctg gacctaccaa ggcaacgcta tgttctcttg cttttgtcag caagatagcc   8280
agatcaatgt cgatcgtggc tggctcgaag atacctgcaa gaatgtcatt gcgctgccat   8340
tctccaaatt gcagttcgcg cttagctgga taacgccacg gaatgatgtc gtcgtgcaca   8400
acaatggtga cttctacagc gcggagaatc tcgctctctc caggggaagc cgaagtttcc   8460
aaaaggtcgt tgatcaaagc tcgccgcgtt gtttcatcaa gccttacagt caccgtaacc   8520
agcaaatcaa tatcactgtg tggcttcagg ccgccatcca ctgcggagcc gtacaaatgt   8580
acggccagca acgtcggttc gagatggcgc tcgatgacgc caactacctc tgatagttga   8640
gtcgatactt cggcgatcac cgcttccctc atgatgttta actcctgaat taagccgcgc   8700
cgcgaagcgg tgtcggcttg aatgaattgt taggcgtcat cctgtgctcc cgagaaccag   8760
taccagtaca tcgctgtttc gttcgagact tgaggtctag ttttatacgt gaacaggtca   8820
atgccgccga gagtaaagcc acattttgcg tacaaattgc aggcaggtac attgttcgtt   8880
tgtgtctcta atcgtatgcc aaggagctgt ctgcttagtg cccactttt cgcaaattcg   8940 atgagactgt gcgcgactcc tttgcctcgg tgcgtgtgcg acacaacaat gtgttcgata   9000
gaggctagat cgttccatgt tgagttgagt tcaatcttcc cgacaagctc ttggtcgatg   9060
aatgcgccat agcaagcaga gtcttcatca gagtcatcat ccgagatgta atccttccgg   9120
taggggctca cacttctggt agatagttca aagccttggt cggataggtg cacatcgaac   9180
acttcacgaa caatgaaatg gttctcagca tccaatgttt ccgccacctg ctcagggatc   9240
accgaaatct tcatatgacg cctaacgcct ggcacagcgg atcgcaaacc tggcgcggct   9300
tttggcacaa aaggcgtgac aggtttgcga atccgttgct gccacttgtt aaccctttg   9360 ccagatttgg taactataat ttatgttaga ggcgaagtct gggtaaaaa ctggcctaaa   9420 attgctgggg atttcaggaa agtaaacatc accttccggc tcgatgtcta ttgtagatat   9480
atgtagtgta tctacttgat cgggggatct gctgcctcgc gcgtttcggt gatgacggtg   9540
aaaacctctg acacatgcag ctcccggaga cggtcacagc ttgtctgtaa gcggatgccg   9600
ggagcagaca agcccgtcag ggcgcgtcag cgggtgttgg cgggtgtcgg ggcgcagcca   9660
```

-continued

```
tgacccagtc acgtagcgat agcggagtgt atactggctt aactatgcgg catcagagca    9720
gattgtactg agagtgcacc atatgcggtg tgaaataccg cacagatgcg taaggagaaa    9780
ataccgcatc aggcgctctt ccgcttcctc gctcactgac tcgctgcgct cggtcgttcg    9840
gctgcggcga gcggtatcag ctcactcaaa ggcggtaata cggttatcca cagaatcagg    9900
ggataacgca ggaaagaaca tgtgagcaaa aggccagcaa aaggccagga accgtaaaaa    9960
ggccgcgttg ctggcgtttt tccataggct ccgcccccct gacgagcatc acaaaaatcg   10020
acgctcaagt cagaggtggc gaaacccgac aggactataa agataccagg cgtttccccc   10080
tggaagctcc ctcgtgcgct ctcctgttcc gaccctgccg cttaccggat acctgtccgc   10140
ctttctccct tcgggaagcg tggcgctttc tcatagctca cgctgtaggt atctcagttc   10200
ggtgtaggtc gttcgctcca agctgggctg tgtgcacgaa ccccccgttc agcccgaccg   10260
ctgcgcctta tccggtaact atcgtcttga gtccaacccg gtaagacacg acttatcgcc   10320
actggcagca gccactggta acaggattag cagagcgagg tatgtaggcg gtgctacaga   10380
gttcttgaag tggtggccta actacggcta cactagaagg acagtatttg gtatctgcgc   10440
tctgctgaag ccagttacct tcggaaaaag agttggtagc tcttgatccg gcaaacaaac   10500
caccgctggt agcggtggtt tttttgtttg caagcagcag attacgcgca gaaaaaaagg   10560
atctcaagaa gatcctttga tcttttctac ggggtctgac gctcagtgga acgaaaactc   10620
acgttaaggg attttggtca tgagattatc aaaaaggatc ttcacctaga tccttttaaa   10680
ttaaaaatga agttttaaat caatctaaag tatatatgag taaacttggt ctgacagtta   10740
ccaatgctta atcagtgagg cacctatctc agcgatctgt ctatttcgtt catccatagt   10800
tgcctgactc cccgtcgtgt agataactac gatacgggag ggcttaccat ctggccccag   10860
tgctgcaatg ataccgcgag acccacgctc accggctcca gatttatcag caataaacca   10920
gccagccgga agggccgagc gcagaagtgg tcctgcaact ttatccgcct ccatccagtc   10980
tattaattgt tgccgggaag ctagagtaag tagttcgcca gttaatagtt tgcgcaacgt   11040
tgttgccatt gctgcagggg ggggggggg gggggacttc cattgttcat tccacggaca   11100
aaaacagaga aaggaaacga cagaggccaa aaagcctcgc tttcagcacc tgtcgtttcc   11160
tttcttttca gagggtattt taaataaaaa cattaagtta tgacgaagaa gaacggaaac   11220
gccttaaacc ggaaaatttt cataaatagc gaaaacccgc gaggtcgccg ccccgtaacc   11280
tacctgtcgg atcaccggaa aggacccgta aagtgataat gattatcatc tacatatcac   11340
aacgtgcgtg gaggccatca aaccacgtca aataatcaat tatgacgcag gtatcgtatt   11400
aattgatctg catcaactta acgtaaaaac aacttcagac aatacaaatc agcgacactg   11460
aatacggggc aacctcatgt cccccccccc ccccccctg caggcatcgt ggtgtcacgc   11520
tcgtcgtttg gtatggcttc attcagctcc ggttcccaac gatcaaggcg agttacatga   11580
tcccccatgt tgtgcaaaaa agcggttagc tccttcggtc ctccgatcgt tgtcagaagt   11640
aagttggccg cagtgttatc actcatggtt atggcagcac tgcataattc tcttactgtc   11700
atgccatccg taagatgctt ttctgtgact ggtgagtact caaccaagtc attctgagaa   11760
tagtgtatgc ggcgaccgag ttgctcttgc ccggcgtcaa cacgggataa taccgcgcca   11820
catagcagaa ctttaaaagt gctcatcatt ggaaaacgtt cttcggggcg aaaactctca   11880
aggatcttac cgctgttgag atccagttcg atgtaaccca ctcgtgcacc caactgatct   11940
tcagcatctt ttactttcac cagcgtttct gggtgagcaa aaacaggaag gcaaaatgcc   12000
gcaaaaaagg gaataagggc gacacggaaa tgttgaatac tcatactctt ccttttcaa   12060
```

```
tattattgaa gcatttatca gggttattgt ctcatgagcg gatacatatt tgaatgtatt    12120
tagaaaaata aacaaatagg ggttccgcgc acatttcccc gaaaagtgcc acctgacgtc    12180
taagaaacca ttattatcat gacattaacc tataaaaata ggcgtatcac gaggcccttt    12240
cgtcttcaag aattcggagc ttttgccatt ctcaccggat tcagtcgtca ctcatggtga    12300
tttctcactt gataaccta tttttgacga ggggaaatta ataggttgta ttgatgttgg    12360
acgagtcgga atcgcagacc gataccagga tcttgccatc ctatggaact gcctcggtga    12420
gttttctcct tcattacaga aacggctttt tcaaaaatat ggtattgata atcctgatat    12480
gaataaattg cagtttcatt tgatgctcga tgagttttc taatcagaat tggttaattg    12540
gttgtaacac tggcagagca ttacgctgac ttgacgggac ggcggctttg ttgaataaat    12600
cgaacttttg ctgagttgaa ggatcagatc acgcatcttc ccgacaacgc agaccgttcc    12660
gtggcaaagc aaaagttcaa aatcaccaac tggtccacct acaacaaagc tctcatcaac    12720
cgtggctccc tcactttctg gctggatgat ggggcgattc aggcctggta tgagtcagca    12780
acaccttctt cacgaggcag acctcagcgc cagaaggccg ccagagaggc cgagcgcggc    12840
cgtgaggctt ggacgctagg gcagggcatg aaaaagcccg tagcgggctg ctacgggcgt    12900
ctgacgcggt ggaaagggg aggggatgtt gtctacatgg ctctgctgta gtgagtgggt    12960
tgcgctccgg cagcggtcct gatcaatcgt cacccttct cggtccttca acgttcctga    13020
caacgagcct ccttttcgcc aatccatcga caatcaccgc gagtccctgc tcgaacgctg    13080
cgtccggacc ggcttcgtcg aaggcgtcta tcgcggcccg caacagcggc gagagcggag    13140
cctgttcaac ggtgccgccg cgctcgccgg catcgctgtc gccggcctgc tcctcaagca    13200 cggcccccaac agtgaagtag ctgattgtca tcagcgcatt gacggcgtcc ccggccgaaa    13260
aacccgcctc gcagaggaag cgaagctgcg cgtcggccgt ttccatctgc ggtgcgcccg    13320
gtcgcgtgcc ggcatggatg cgcgcgccat cgcggtaggc gagcagcgcc tgcctgaagc    13380
tgcgggcatt cccgatcaga aatgagcgcc agtcgtcgtc ggctctcggc accgaatgcg    13440
tatgattctc cgccagcatg gcttcggcca gtgcgtcgag cagcgcccgc ttgttcctga    13500
agtgccagta aagcgccggc tgctgaaccc ccaaccgttc cgccagtttg cgtgtcgtca    13560
gaccgtctac gccgacctcg ttcaacaggt ccagggcggc acggatcact gtattcggct    13620
gcaactttgt catgcttgac actttatcac tgataaacat aatatgtcca ccaacttatc    13680
agtgataaag aatccgcgcg ttcaatcgga ccagcggagg ctggtccgga ggccagacgt    13740
gaaacccaac atacccctga tcgtaattct gagcactgtc gcgctcgacg ctgtcggcat    13800
cggcctgatt atgccggtgc tgccgggcct cctgcgcgat ctggttcact cgaacgacgt    13860
caccgcccac tatggcattc tgctggcgct gtatgcgttg gtgcaatttg cctgcgcacc    13920
tgtgctgggc gcgctgtcgg atcgtttcgg gcggcggcca atcttgctcg tctcgctggc    13980
cggcgccact gtcgactacg ccatcatggc gacagcgcct ttccttggg ttctctatat    14040 cgggcggatc gtggccggca tcaccggggc gactggggcg gtagccggcg cttatattgc    14100
cgatatcact gatggcgatg agcgcgcgcg gcacttcggc ttcatgagcg cctgtttcgg    14160
gttcgggatg gtcgcgggac ctgtgctcgg tgggctgatg ggcggtttct cccccacgc    14220 tccgttcttc gccgcggcag ccttgaacgg cctcaatttc ctgacgggct gttcctttt    14280 gccggagtcg cacaaaggcg aacgccggcc gttacgccgg gaggctctca acccgctcgc    14340
ttcgttccgg tgggcccggg gcatgaccgt cgtcgccgcc ctgatggcgg tcttcttcat    14400
catgcaactt gtcggacagg tgccggccgc gctttgggtc attttcggcg aggatcgctt    14460
```

```
tcactgggac gcgaccacga tcggcatttc gcttgccgca tttggcattc tgcattcact   14520
cgcccaggca atgatcaccg gccctgtagc cgcccggctc ggcgaaaggc gggcactcat   14580
gctcggaatg attgccgacg gcacaggcta catcctgctt gccttcgcga cacggggatg   14640
gatgcgttc ccgatcatgg tcctgcttgc ttcgggtggc atcggaatgc cggcgctgca   14700
agcaatgttg tccaggcagg tggatgagga acgtcagggg cagctgcaag gctcactggc   14760
ggcgctcacc agcctgacct cgatcgtcgg acccctcctc ttcacggcga tctatgcggc   14820
ttctataaca acgtggaacg ggtgggcatg gattgcaggc gctgccctct acttgctctg   14880
cctgccggcg ctgcgtcgcg ggcttttggag cggcgcaggg caacgagccg atcgctgatc   14940
gtggaaacga taggcctatg ccatgcgggt caaggcgact tccggcaagc tatacgcgcc   15000
ctaggagtgc ggttggaacg ttggcccagc cagatactcc cgatcacgag caggacgccg   15060
atgatttgaa gcgcactcag cgtctgatcc aagaacaacc atcctagcaa cacggcggtc   15120
cccgggctga gaaagcccag taaggaaaca actgtaggtt cgagtcgcga gatcccccgg   15180
aaccaaagga agtaggttaa acccgctccg atcaggccga gccacgccag gccgagaaca   15240
ttggttcctg taggcatcgg gattggcgga tcaaacacta aagctactgg aacgagcaga   15300
agtcctccgg ccgccagttg ccaggcggta aaggtgagca gaggcacggg aggttgccac   15360
ttgcgggtca gcacggttcc gaacgccatg gaaaccgccc ccgccaggcc cgctgcgacg   15420
ccgacaggat ctagcgctgc gtttggtgtc aacaccaaca gcgccacgcc cgcagttccg   15480
caaatagccc ccaggaccgc catcaatcgt atcgggctac ctagcagagc ggcagagatg   15540
aacacgacca tcagcggctg cacagcgcct accgtcgccg cgaccccgcc cggcaggcgg   15600
tagaccgaaa taaacaacaa gctccagaat agcgaaatat taagtgcgcc gaggatgaag   15660
atgcgcatcc accagattcc cgttggaatc tgtcggacga tcatcacgag caataaaccc   15720
gccggcaacg cccgcagcag cataccggcg acccctcggc ctcgctgttc gggctccacg   15780
aaaacgccgg acagatgcgc cttgtgagcg tccttgggg cgtcctcctg tttgaagacc   15840
gacagcccaa tgatctcgcc gtcgatgtag gcgccgaatg ccacggcatc tcgcaaccgt   15900
tcagcgaacg cctccatggg cttttttctcc tcgtgctcgt aaacggaccc gaacatctct   15960
ggagctttct tcagggccga caatcggatc tcgcggaaat cctgcacgtc ggccgctcca   16020
agccgtcgaa tctgagcctt aatcacaatt gtcaattta atcctctgtt tatcggcagt   16080
tcgtagagcg cgccgtgcgt cccgagcgat actgagcgaa gcaagtgcgt cgagcagtgc   16140
ccgcttgttc ctgaaatgcc agtaaagcgc tggctgctga accccagcc ggaactgacc   16200
ccacaaggcc ctagcgtttg caatgcacca ggtcatcatt gacccaggcg tgttccacca   16260
ggccgctgcc tcgcaactct tcgcaggctt cgccgacctg ctcgcgccac ttcttcacgc   16320
gggtggaatc cgatccgcac atgaggcgga aggtttccag cttgagcggg tacggctccc   16380
ggtgcgagct gaaatagtcg aacatccgtc gggccgtcgg cgacagcttg cggtacttct   16440
cccatatgaa tttcgtgtag tggtcgccag caaacagcac gacgatttcc tcgtcgatca   16500
ggacctggca acgggacgtt ttcttgccac ggtccaggac gcggaagcgg tgcagcagcg   16560
acaccgattc caggtgccca acgcggtcgg acgtgaagcc catcgccgtc gcctgtaggc   16620
gcgacaggca ttcctcggcc ttcgtgtaat accggccatt gatcgaccag cccaggtcct   16680
ggcaaagctc gtagaacgtg aaggtgatcg gctcgccgat aggggtgcgc ttcgcgtact   16740
ccaacacctg ctgccacacc agttcgtcat cgtcggcccg cagctcgacg ccggtgtagg   16800
tgatcttcac gtccttgttg acgtggaaaa tgaccttgtt ttgcagcgcc tcgcgcggga   16860
```

```
ttttcttgtt gcgcgtggtg aacagggcag agcgggccgt gtcgtttggc atcgctcgca   16920
tcgtgtccgg ccacggcgca atatcgaaca aggaaagctg catttccttg atctgctgct   16980
tcgtgtgttt cagcaacgcg gcctgcttgg cctcgctgac ctgttttgcc aggtcctcgc   17040
cggcggtttt tcgcttcttg gtcgtcatag ttcctcgcgt gtcgatggtc atcgacttcg   17100
ccaaacctgc cgcctcctgt tcgagacgac gcgaacgctc cacggcggcc gatggcgcgg   17160
gcagggcagg gggagccagt tgcacgctgt cgcgctcgat cttggccgta gcttgctgga   17220
ccatcgagcc gacggactgg aaggtttcgc ggggcgcacg catgacggtg cggcttgcga   17280
tggtttcggc atcctcggcg gaaaaccccg cgtcgatcag ttcttgcctg tatgccttcc   17340
ggtcaaacgt ccgattcatt caccctcctt gcgggattgc cccgactcac gccggggcaa   17400
tgtgccctta ttcctgattt gacccgcctg gtgccttggt gtccagataa tccaccttat   17460
cggcaatgaa gtcggtcccg tagaccgtct ggccgtcctt ctcgtacttg gtattccgaa   17520
tcttgccctg cacgaatacc agcgacccct tgcccaaata cttgccgtgg gcctcggcct   17580
gagagccaaa acacttgatg cggaagaagt cggtgcgctc ctgcttgtcg ccggcatcgt   17640
tgcgccactc ttcattaacc gctatatcga aaattgcttg cggcttgtta gaattgccat   17700
gacgtacctc ggtgtcacgg gtaagattac cgataaactg gaactgatta tggctcatat   17760
cgaaagtctc cttgagaaag gagactctag tttagctaaa cattggttcc gctgtcaaga   17820
actttagcgg ctaaaatttt gcgggccgcg accaaaggtg cgaggggcgg cttccgctgt   17880
gtacaaccag atatttttca ccaacatcct tcgtctgctc gatgagcggg gcatgacgaa   17940
acatgagctg tcggagaggg caggggtttc aatttcgttt ttatcagact taaccaacgg   18000
taaggccaac ccctcgttga aggtgatgga ggccattgcc gacgccctgg aaactcccct   18060
acctcttctc ctggagtcca ccgaccttga ccgcgaggca ctcgcggaga ttgcgggtca   18120
tcctttcaag agcagcgtgc cgcccggata cgaacgcatc agtgtggttt tgccgtcaca   18180
taaggcgttt atcgtaaaga aatggggcga cgacacccga aaaaagctgc gtggaaggct   18240
ctgacgccaa gggttagggc ttgcacttcc ttctttagcc gctaaaacgg ccccttctct   18300
gcgggccgtc ggctcgcgca tcatatcgac atcctcaacg gaagccgtgc cgcgaatggc   18360
atcgggcggg tgcgctttga cagttgtttt ctatcagaac ccctacgtcg tgcggttcga   18420
ttagctgttt gtcttgcagg ctaaacactt tcggtatatc gtttgcctgt gcgataatgt   18480
tgctaatgat ttgttgcgta ggggttactg aaaagtgagc gggaaagaag agtttcagac   18540
catcaaggag cgggccaagc gcaagctgga acgcgacatg ggtgcggacc tgttggccgc   18600
gctcaacgac ccgaaaaccg ttgaagtcat gctcaacgcg gacggcaagg tgtggcacga   18660
acgccttggc gagccgatgc ggtacatctg cgacatgcgg cccagccagt cgcaggcgat   18720
tatagaaacg gtggccggat ccacggcaa agaggtcacg cggcattcgc ccatcctgga   18780
aggcgagttc cccttggatg gcagccgctt tgccggccaa ttgccgccgg tcgtggccgc   18840
gccaaccttt gcgatccgca agcgcgcggt cgccatcttc acgctggaac agtacgtcga   18900
ggcgggcatc atgacccgcg agcaatacga ggtcattaaa agcgccgtcg cggcgcatcg   18960
aaacatcctc gtcattggcg gtactggctc gggcaagacc acgctcgtca acgcgatcat   19020
caatgaaatg gtcgccttca acccgtctga gcgcgtcgtc atcatcgagg acaccggcga   19080
aatccagtgc gccgcagaga acgccgtcca ataccacacc agcatcgacg tctcgatgac   19140
gctgctgctc aagacaacgc tgcgtatgcg ccccgaccgc atcctggtcg gtgaggtacg   19200
tggccccgaa gcccttgatc tgttgatggc ctggaacacc gggcatgaag gaggtgccgc   19260
```

```
caccctgcac gcaaacaacc ccaaagcggg cctgagccgg ctcgccatgc ttatcagcat   19320
gcacccggat tcaccgaaac ccattgagcc gctgattggc gaggcggttc atgtggtcgt   19380
ccatatcgcc aggacccta gcggccgtcg agtgcaagaa attctcgaag ttcttggtta    19440
cgagaacggc cagtacatca ccaaaaccct gtaaggagta tttccaatga caacggctgt   19500
tccgttccgt ctgaccatga atcgcggcat tttgttctac cttgccgtgt tcttcgttct   19560
cgctctcgcg ttatccgcgc atccggcgat ggcctcggaa ggcaccggcg gcagcttgcc   19620
atatgagagc tggctgacga acctgcgcaa ctccgtaacc ggcccggtgg ccttcgcgct   19680
gtccatcatc ggcatcgtcg tcgcggcgg cgtgctgatc ttcggcggcg aactcaacgc    19740
cttcttccga accctgatct tcctggttct ggtgatggcg ctgctggtcg gcgcgcagaa   19800
cgtgatgagc accttcttcg gtcgtggtgc cgaaatcgcg ccctcggca acggggcgct    19860
gcaccaggtg caagtcgcgg cggcggatgc cgtgcgtgcg gtagcggctg gacggctcgc   19920
ctaatcatgg ctctgcgcac gatccccatc cgtcgcgcag gcaaccgaga aaacctgttc   19980
atgggtggtg atcgtgaact ggtgatgttc tcgggcctga tggcgtttgc gctgattttc   20040
agcgcccaag agctgcgggc caccgtggtc ggtctgatcc tgtggttcgg ggcgctctat   20100
gcgttccgaa tcatggcgaa ggccgatccg aagatgcggt tcgtgtacct cgtcaccgc    20160
cggtacaagc cgtattaccc ggcccgctcg accccgttcc gcgagaacac caatagccaa   20220
gggaagcaat accgatgatc caagcaattg cgattgcaat cgcgggcctc ggcgcgcttc   20280
tgttgttcat cctctttgcc cgcatccgcg cggtcgatgc cgaactgaaa ctgaaaaagc   20340
atcgttccaa ggacgccggc ctggccgatc tgctcaacta cgccgctgtc gtcgatgacg   20400
gcgtaatcgt gggcaagaac ggcagcttta tggctgcctg gctgtacaag ggcgatgaca   20460
acgcaagcag caccgaccag cagcgcgaag tagtgtccgc ccgcatcaac caggccctcg   20520
cgggcctggg aagtgggtgg atgatccatg tggacgccgt gcggcgtcct gctccgaact   20580
acgcggagcg gggcctgtcg gcgttccctg accgtctgac ggcagcgatt gaagaagagc   20640
gctcggtctt gccttgctcg tcggtgatgt acttcaccag ctccgcgaag tcgctcttct   20700
tgatggagcg catgggacg tgcttggcaa tcacgcgcac ccccggccg ttttagcggc     20760
taaaaagtc atggctctgc cctcgggcgg accacgccca tcatgacctt gccaagctcg    20820
tcctgcttct cttcgatctt cgccagcagg gcgaggatcg tggcatcacc gaaccgcgcc   20880
gtgcgcgggt cgtcggtgag ccagagtttc agcaggccgc ccaggcggcc caggtcgcca   20940
ttgatgcggg ccagctcgcg gacgtgctca tagtccacga cgcccgtgat tttgtagccc   21000
tggccgacgg ccagcaggta ggccgacagg ctcatgccgg ccgccgccgc ctttcctca    21060
atcgctcttc gttcgtctgg aaggcagtac accttgatag gtgggctgcc cttcctggtt   21120
ggcttggttt catcagccat ccgcttgccc tcatctgtta cgccggcggt agccggccag   21180
cctcgcagag caggattccc gttgagcacc gccaggtgcg aataagggac agtgaagaag   21240
gaacacccgc tcgcgggtgg gcctacttca cctatcctgc ccggctgacg ccgttggata   21300
caccaaggaa agtctacacg aacccttttgg caaaatcctg tatatcgtgc gaaaaggat   21360
ggatataccg aaaaaatcgc tataatgacc ccgaagcagg gttatgcagc ggaaaagcgc   21420
tgcttccctg ctgttttgtg gaatatctac cgactggaaa caggcaaatg caggaaatta   21480
ctgaactgag gggacaggcg agagacgatg ccaaagagct acaccgacga gctggccgag   21540
tgggttgaat cccgcgcggc caagaagcgc cggcgtgatg aggctgcggt tgcgttcctg   21600
gcggtgaggg cggatgtcga ggcggcgtta gcgtccggct atgcgctcgt caccatttgg   21660
```

```
gagcacatgc gggaaacggg gaaggtcaag ttctcctacg agacgttccg ctcgcacgcc   21720
aggcggcaca tcaaggccaa gcccgccgat gtgcccgcac cgcaggccaa ggctgcggaa   21780
cccgcgccgg cacccaagac gccggagcca cggcggccga agcagggggg caaggctgaa   21840
aagccggccc ccgctgcggc cccgaccggc ttcaccttca acccaacacc ggacaaaaag   21900
gatctactgt aatggcgaaa attcacatgg ttttgcaggg caagggcggg gtcggcaagt   21960
cggccatcgc cgcgatcatt gcgcagtaca agatggacaa ggggcagaca cccttgtgca   22020
tcgacaccga cccggtgaac gcgacgttcg agggctacaa ggccctgaac gtccgccggc   22080
tgaacatcat ggccggcgac gaaattaact cgcgcaactt cgacaccctg gtcgagctga   22140
ttgcgccgac caaggatgac gtggtgatcg acaacggtgc cagctcgttc gtgcctctgt   22200
cgcattacct catcagcaac caggtgccgg ctctgctgca agaaatgggg catgagctgg   22260
tcatccatac cgtcgtcacc ggcggccagg ctctcctgga cacggtgagc ggcttcgccc   22320
agctcgccag ccagttcccg gccgaagcgc ttttcgtggt ctggctgaac ccgtattggg   22380
ggcctatcga gcatgagggc aagagctttg agcagatgaa ggcgtacacg gccaacaagg   22440
cccgcgtgtc gtccatcatc cagattccgg ccctcaagga agaaacctac ggccgcgatt   22500
tcagcgacat gctgcaagag cggctgacgt tcgaccaggc gctggccgat gaatcgctca   22560
cgatcatgac gcggcaacgc ctcaagatcg tgcggcgcgg cctgtttgaa cagctcgacg   22620
cggcggccgt gctatgagcg accagattga agagctgatc cgggagattg cggccaagca   22680
cggcatcgcc gtcggccgcg acgacccggt gctgatcctg cataccatca cgcccggct   22740 catggccgac agtgcggcca agcaagagga aatccttgcc gcgttcaagg aagagctgga   22800
agggatcgcc catcgttggg gcgaggacgc caaggccaaa gcggagcgga tgctgaacgc   22860
ggccctggcg gccagcaagg acgcaatggc gaaggtaatg aaggacagcg ccgcgcaggc   22920
ggccgaagcg atccgcaggg aaatcgacga cggccttggc cgccagctcg cggccaaggt   22980
cgcggacgcg cggcgcgtgg cgatgatgaa catgatcgcc ggcggcatgg tgttgttcgc   23040
ggccgccctg gtggtgtggg cctcgttatg aatcgcagag gcgcagatga aaaagcccgg   23100
cgttgccggg cttttgtttt gcgttagctg ggcttgtttg acaggccaa gctctgactg   23160 cgcccgcgct cgcgctcctg ggcctgtttc ttctcctgct cctgcttgcg catcagggcc   23220
tggtgccgtc gggctgcttc acgcatcgaa tcccagtcgc cggccagctc gggatgctcc   23280
gcgcgcatct tgcgcgtcgc cagttcctcg atcttgggcg cgtgaatgcc catgccttcc   23340
ttgatttcgc gcaccatgtc cagccgcgtg tgcagggtct gcaagcgggc ttgctgttgg   23400
gcctgctgct gctgccaggc ggcctttgta cgcggcaggg acagcaagcc gggggcattg   23460
gactgtagct gctgcaaacg cgcctgctga cggtctacga gctgttctag gcggtcctcg   23520
atgcgctcca cctggtcatg ctttgcctgc acgtagagcg caagggtctg ctggtaggtc   23580
tgctcgatgg gcgcggattc taagagggcc tgctgttccg tctcggcctc ctgggccgcc   23640
tgtagcaaat cctcgccgct gttgccgctg gactgcttta ctgccgggga ctgctgttgc   23700
cctgctcgcg ccgtcgtcgc agttcggctt gcccccactc gattgactgc ttcatttcga   23760
gccgcagcga tgcgatctcg gattgcgtca acggacgggg cagcgcggag gtgtccggct   23820
tctccttggg tgagtcggtc gatgccatag ccaaaggttt ccttccaaaa tgcgtccatt   23880
gctggaccgt gtttctcatt gatgcccgca agcatcttcg gcttgaccgc caggtcaagc   23940
gcgccttcat gggcggtcat gacggacgcc gccatgacct tgccgccgtt gttctcgatg   24000
tagccgcgta atgaggcaat ggtgccgccc atcgtcagcg tgtcatcgac aacgatgtac   24060
```

```
ttctggccgg ggatcacctc cccctcgaaa gtcgggttga acgccaggcg atgatctgaa    24120
ccggctccgg ttcgggcgac cttctcccgc tgcacaatgt ccgtttcgac ctcaaggcca    24180
aggcggtcgg ccagaacgac cgccatcatg gccggaatct tgttgttccc cgccgcctcg    24240
acggcgagga ctgaacgat gcggggcttg tcgtcgccga tcagcgtctt gagctgggca     24300
acagtgtcgt ccgaaatcag gcgctcgacc aaattaagcg ccgcttccgc gtcgccctgc    24360
ttcgcagcct ggtattcagg ctcgttggtc aaagaaccaa ggtcgccgtt gcgaaccacc    24420
ttcgggaagt ctccccacgg tgcgcgctcg gctctgctgt agctgctcaa gacgcctccc    24480
tttttagccg ctaaaactct aacgagtgcg cccgcgactc aacttgacgc tttcggcact    24540
tacctgtgcc ttgccacttg cgtcataggt gatgcttttc gcactcccga tttcaggtac    24600
tttatcgaaa tctgaccggg cgtgcattac aaagttcttc cccacctgtt ggtaaatgct    24660
gccgctatct gcgtggacga tgctgccgtc gtggcgctgc gacttatcgg ccttttgggc    24720
catatagatg ttgtaaatgc caggtttcag ggccccggct ttatctacct tctggttcgt    24780
ccatgcgcct tggttctcgg tctggacaat tctttgccca ttcatgacca ggaggcggtg    24840
tttcattggg tgactcctga cggttgcctc tggtgttaaa cgtgtcctgg tcgcttgccg    24900
gctaaaaaaa agccgacctc ggcagttcga ggccggcttt ccctagagcc gggcgcgtca    24960
aggttgttcc atctatttta gtgaactgcg ttcgatttat cagttacttt cctcccgctt    25020
tgtgtttcct cccactcgtt tccgcgtcta gccgaccct caacatagcg gcctcttctt     25080
gggctgcctt tgcctcttgc cgcgcttcgt cacgctcggc ttgcaccgtc gtaaagcgct    25140
cggcctgcct ggccgcctct tgcgccgcca acttcctttg ctcctggtgg gcctcggcgt    25200
cggcctgcgc cttcgctttc accgctgcca actccgtgcg caaactctcc gcttcgcgcc    25260
tggtggcgtc gcgctcgccg cgaagcgcct gcatttcctg gttggccgcg tccagggtct    25320
tgcggctctc ttctttgaat gcgcgggcgt cctggtgagc gtagtccagc tcggcgcgca    25380
gctcctgcgc tcgacgctcc acctcgtcgg cccgctgcgt cgccagcgcg gccgctgct    25440 cggctcctgc cagggcggtg cgtgcttcgg ccagggcttg ccgctggcgt gcggccagct    25500
cggccgcctc ggcggcctgc tgctctagca atgtaacgcg cgcctgggct tcttccagct    25560
cgcgggcctg cgcctcgaag gcgtcggcca gctcccgcg cacggcttcc aactcgttgc     25620
gctcacgatc ccagccggct tgcgctgcct gcaacgattc attggcaagg gcctgggcgg    25680
cttgccagag ggcggccacg gcctggttgc cggcctgctg caccgcgtcc ggcacctgga    25740
ctgccagcgg ggcggcctgc gccgtgcgct ggcgtcgcca ttcgcgcatg ccggcgctgg    25800
cgtcgttcat gttgacgcgg gcggccttac gcactgcatc cacggtcggg aagttctccc    25860
ggtcgccttg ctcgaacagc tcgtccgcag ccgcaaaaat gcggtcgcgc gtctctttgt    25920
tcagttccat gttggctccg gtaattggta agaataataa tactcttacc taccttatca    25980
gcgcaagagt ttagctgaac agttctcgac ttaacggcag gttttttagc ggctgaaggg    26040
caggcaaaaa aagccccgca cggtcggcgg gggcaaaggg tcagcgggaa ggggattagc    26100
gggcgtcggg cttcttcatg cgtcgggcc gcgcttcttg ggatggagca cgacgaagcg     26160
cgcacgcgca tcgtcctcgg ccctatcggc ccgcgtcgcg gtcaggaact tgtcgcgcgc    26220
taggtcctcc ctggtgggca ccaggggcat gaactcggcc tgctcgatgt aggtccactc    26280
catgaccgca tcgcagtcga ggccgcgttc cttcaccgtc tcttgcaggt cgcggtacgc    26340 ccgtcgttg agcggctggt aacgggccaa ttggtcgtaa atggctgtcg gccatgagcg     26400
gcctttcctg ttgagccagc agccgacgac gaagccggca atgcaggccc ctggcacaac    26460
```

```
caggccgacg ccgggggcag gggatggcag cagctcgcca accaggaacc ccgccgcgat   26520
gatgccgatg ccggtcaacc agcccttgaa actatccggc cccgaaacac ccctgcgcat   26580
tgcctggatg ctgcgccgga tagcttgcaa catcaggagc cgtttctttt gttcgtcagt   26640
catggtccgc cctcaccagt tgttcgtatc ggtgtcggac gaactgaaat cgcaagagct   26700
gccggtatcg gtccagccgc tgtccgtgtc gctgctgccg aagcacggcg aggggtccgc   26760
gaacgccgca gacggcgtat ccggccgcag cgcatcgccc agcatggccc cggtcagcga   26820
gccgccggcc aggtagccca gcatggtgct gttggtcgcc ccggccacca gggccgacgt   26880
gacgaaatcg ccgtcattcc ctctggattg ttcgctgctc ggcggggcag tgcgccgcgc   26940
cggcggcgtc gtggatggct cgggttggct ggcctgcgac ggccggcgaa aggtgcgcag   27000
cagctcgtta tcgaccggct gcggcgtcgg ggccgccgcc ttgcgctgcg gtcggtgttc   27060
cttcttcggc tcgcgcagct tgaacagcat gatcgcggaa accagcagca acgccgcgcc   27120
tacgcctccc gcgatgtaga acagcatcgg attcattctt cggtcctcct tgtagcggaa   27180
ccgttgtctg tgcggcgcgg gtggcccgcg ccgctgtctt tggggatcag ccctcgatga   27240
gcgcgaccag tttcacgtcg gcaaggttcg cctcgaactc ctggccgtcg tcctcgtact   27300
tcaaccaggc atagccttcc gccggcggcc gacggttgag gataaggcgg gcagggcgct   27360
cgtcgtgctc gacctggacg atggcctttt tcagcttgtc cgggtccggc tccttcgcgc   27420
cctttccctt ggcgtcctta ccgtcctggt cgccgtcctc gccgtcctgg ccgtcgccgg   27480
cctccgcgtc acgctcggca tcagtctggc cgttgaaggc atcgacggtg ttgggatcgc   27540
ggcccttctc gtccaggaac tcgcgcagca gcttgaccgt gccgcgcgtg atttcctggg   27600
tgtcgtcgtc aagccacgcc tcgacttcct ccgggcgctt cttgaaggcc gtcaccagct   27660
cgttcaccac ggtcacgtcg cgcacgcggc cggtgttgaa cgcatcggcg atcttctccg   27720
gcaggtccag cagcgtgacg tgctgggtga tgaacgccgg cgacttgccg atttccttgg   27780
cgatatcgcc tttcttcttg cccttcgcca gctcgcggcc aatgaagtcg gcaatttcgc   27840
gcggggtcag ctcgttgcgt tgcaggttct cgataacctg gtcggcttcg ttgtagtcgt   27900
tgtcgatgaa cgccgggatg gacttcttgc cggcccactt cgagccacgg tagcggcggg   27960
cgccgtgatt gatgatatag cggcccggct gctcctggtt ctcgcgcacc gaaatgggtg   28020 acttcaccccc gcgctctttg atcgtggcac cgatttccgc gatgctctcc ggggaaaagc   28080
cggggttgtc ggccgtccgc ggctgatgcg gatcttcgtc gatcaggtcc aggtccagct   28140
cgatagggcc ggaaccgccc tgagacgccg caggagcgtc caggaggctc gacaggtcgc   28200
cgatgctatc caaccccagg ccggacggct gcgccgcgcc tgcggcttcc tgagcggccg   28260
cagcggtgtt tttcttggtg gtcttggctt gagccgcagt cattgggaaa tctccatctt   28320
cgtgaacacg taatcagcca gggcgcgaac ctctttcgat gccttgcgcg cggccgtttt   28380
cttgatcttc cagaccggca caccggatgc gagggcatcg gcgatgctgc tgcgcaggcc   28440
aacggtggcc ggaatcatca tcttggggta cgcggccagc agctcggctt ggtggcgcgc   28500
gtggcgcgga ttccgcgcat cgaccttgct gggcaccatg ccaaggaatt gcagcttggc   28560
gttcttctgg cgcacgttcg caatggtcgt gaccatcttc ttgatgccct ggatgctgta   28620
cgcctcaagc tcgatggggg acagcacata gtcggccgcg aagagggcgg ccgccaggcc   28680
gacgccaagg gtcggggccg tgtcgatcag gcacacgtcg aagccttggt tcgccagggc   28740
cttgatgttc gccccgaaca gctcgcgggc gtcgtccagc gacagccgtt cggcgttcgc   28800
cagtaccggg ttggactcga tgagggcgag gcgcgcggcc tggccgtcgc cggctgcggg   28860
```

```
tgcggtttcg gtccagccgc cggcagggac agcgccgaac agcttgcttg catgcaggcc    28920
ggtagcaaag tccttgagcg tgtaggacgc attgccctgg gggtccaggt cgatcacggc    28980
aacccgcaag ccgcgctcga aaaagtcgaa ggcaagatgc acaagggtcg aagtcttgcc    29040
gacgccgcct ttctggttgg ccgtgaccaa agttttcatc gtttggtttc ctgttttttc    29100
ttggcgtccg cttcccactt ccggacgatg tacgcctgat gttccggcag aaccgccgtt    29160
acccgcgcgt acccctcggg caagttcttg tcctcgaacg cggcccacac gcgatgcacc    29220
gcttgcgaca ctgcgcccct ggtcagtccc agcgacgttg cgaacgtcgc ctgtggcttc    29280
ccatcgacta agacgccccg cgctatctcg atggtctgct gccccacttc agcccctgg     29340 atcgcctcct ggaactggct ttcggtaagc cgtttcttca tggataacac ccataatttg    29400
ctccgcgcct tggttgaaca tagcggtgac agccgccagc acatgagaga agtttagcta    29460
aacatttctc gcacgtcaac acctttagcc gctaaaactc gtccttggcg taacaaaaca    29520
aaagcccgga aaccgggctt tcgtctcttg ccgcttatgg ctctgcaccc ggctccatca    29580
ccaacaggtc gcgcacgcgc ttcactcggt tgcggatcga cactgccagc ccaacaaagc    29640
cggttgccgc cgccgccagg atcgcgccga tgatgccggc cacaccggcc atcgcccacc    29700
aggtcgccgc cttccggttc cattcctgct ggtactgctt cgcaatgctg gacctcggct    29760
caccataggc tgaccgctcg atggcgtatg ccgcttctcc ccttggcgta aaacccagcg    29820
ccgcaggcgg cattgccatg ctgcccgccg cttccccgac cacgacgcgc gcaccaggct    29880
tgcggtccag accttcggcc acggcgagct gcgcaaggac ataatcagcc gccgacttgg    29940
ctccacgcgc ctcgatcagc tcttgcactc gcgcgaaatc cttggcctcc acggccgcca    30000
tgaatcgcgc acgcggcgaa ggctccgcag ggccggcgtc gtgatcgccg ccagaaatgc    30060
ccttcaccaa gttcgacgac acgaaaatca tgctgacggc tatcaccatc atgcagacgg    30120
atcgcacgaa cccgctgaat tgaacacgag cacggcaccc gcgaccacta tgccaagaat    30180
gcccaaggta aaaattgccg gccccgccat gaagtccgtg aatgccccga cggccgaagt    30240
gaagggcagg ccgccaccca ggccgccgcc ctcactgccc ggcacctggt cgctgaatgt    30300
cgatgccagc acctgcggca cgtcaatgct tccgggcgtc gcgctcgggc tgatcgccca    30360
tcccgttact gccccgatcc cggcaatggc aaggactgcc agcgctgcca ttttttgggt    30420
gaggccgttc gcggccgagg ggcgcagccc tgggggggat gggaggcccg cgttagcggg    30480
ccgggagggt tcgagaaggg ggggcacccc ccttcggcgt gcgcggtcac gcgcacaggg    30540
cgcagccctg gttaaaaaca aggtttataa atattggttt aaaagcaggt taaaagacag    30600
gttagcggtg gccgaaaaac gggcggaaac ccttgcaaat gctggatttt ctgcctgtgg    30660
acagcccctc aaatgtcaat aggtgcgccc ctcatctgtc agcactctgc ccctcaagtg    30720
tcaaggatcg cgcccctcat ctgtcagtag tcgcgcccct caagtgtcaa taccgcaggg    30780
cacttatccc caggcttgtc cacatcatct gtgggaaact cgcgtaaaat caggcgtttt    30840
cgccgatttg cgaggctggc cagctccacg tcgccggccg aaatcgagcc tgcccctcat    30900
ctgtcaacgc cgcgccgggt gagtcggccc ctcaagtgtc aacgtccgcc cctcatctgt    30960
cagtgagggc caagtttttcc gcgaggtatc cacaacgccg gcggccgcgg tgtctcgcac    31020
acggcttcga cggcgtttct ggcgcgtttg caggggccata gacggccgcc agcccagcgg    31080
cgagggcaac cagcccggtg agcgtcggaa aggcgctgga agccccgtag cgacgcggag    31140
aggggcgaga caagccaagg gcgcaggctc gatgcgcagc acgacatagc cggttctcgc    31200
aaggacgaga atttccctgc ggtgcccctc aagtgtcaat gaaagtttcc aacgcgagcc    31260
```

```
attcgcgaga gccttgagtc cacgctagat gagagctttg ttgtaggtgg accagttggt    31320
gattttgaac ttttgctttg ccacggaacg gtctgcgttg tcgggaagat gcgtgatctg    31380
atccttcaac tcagcaaaag ttcgatttat tcaacaaagc cacgttgtgt ctcaaaatct    31440
ctgatgttac attgcacaag ataaaaatat atcatcatga acaataaaac tgtctgctta    31500
cataaacagt aatacaaggg gtgttatgag ccatattcaa cgggaaacgt cttgctcgac    31560
tctagagctc gttcctcgag gaacggtacc tgcggggaag cttacaataa tgtgtgttgt    31620
taagtcttgt tgcctgtcat cgtctgactg actttcgtca taaatcccgg cctccgtaac    31680
ccagctttgg gcaagctcac ggatttgatc cggcggaacg ggaatatcga gatgccgggc    31740
tgaacgctgc agttccagct ttccctttcg ggacaggtac tccagctgat tgattatctg    31800
ctgaagggtc ttggttccac ctcctggcac aatgcgaatg attacttgag cgcgatcggg    31860
catccaattt tctcccgtca ggtgcgtggt caagtgctac aaggcacctt tcagtaacga    31920
gcgaccgtcg atccgtcgcc gggatacgga caaaatggag cgcagtagtc catcgagggc    31980
ggcgaaagcc tcgccaaaag caatacgttc atctcgcaca gcctccagat ccgatcgagg    32040
gtcttcggcg taggcagata gaagcatgga tacattgctt gagagtattc cgatggactg    32100
aagtatggct tccatctttt ctcgtgtgtc tgcatctatt tcgagaaagc ccccgatgcg    32160
gcgcaccgca acgcgaattg ccatactatc cgaaagtccc agcaggcgcg cttgatagga    32220
aaaggtttca tactcggccg atcgcagacg ggcactcacg accttgaacc cttcaacttt    32280
cagggatcga tgctggttga tggtagtctc actcgacgtg gctctggtgt gttttgacat    32340
agcttcctcc aaagaaagcg gaaggtctgg atactccagc acgaaatgtg cccgggtaga    32400
cggatggaag tctagccctg ctcaatatga aatcaacagt acatttacag tcaatactga    32460
atatacttgc tacatttgca attgtcttat aacgaatgtg aaataaaaat agtgtaacaa    32520
cgcttttact catcgataat cacaaaaaca tttatacgaa caaaaataca aatgcactcc    32580
ggtttcacag dataggcggg atcagaatat gcaacttttg acgttttgtt ctttcaaagg    32640
gggtgctggc aaaaccaccg cactcatggg cctttgcgct gctttggcaa atgacggtaa    32700
acgagtggcc ctctttgatg ccgacgaaaa ccggcctctg acgcgatgga gagaaaacgc    32760
cttacaaagc agtactggga tcctcgctgt gaagtctatt ccgccgacga aatgccccct    32820
cttgaagcag cctatgaaaa tgccgagctc gaaggatttg attatgcgtt ggccgatacg    32880
cgtggcggct cgagcgagct caacaacaca atcatcgcta gctcaaacct gcttctgatc    32940
cccaccatgc taacgccgct cgacatcgat gaggcactat ctacctaccg ctacgtcatc    33000
gagctgctgt tgagtgaaaa tttggcaatt cctacagctg ttttgcgcca acgcgtcccg    33060
gtcggccgat tgcaacatc gcaacgcagg atgtcagaga cgctagagag ccttccagtt    33120
gtaccgtctc ccatgcatga aagagatgca tttgccgcga tgaaagaacg cggcatgttg    33180
catcttacat tactaaacac gggaactgat ccgacgatgc gcctcataga gaggaatctt    33240
cggattgcga tggaggaagt cgtggtcatt tcgaaactga tcagcaaaat cttggaggct    33300
tgaagatggc aattcgcaag cccgcattgt cggtcggcga agcacggcgg cttgctggtg    33360
ctcgacccga gatccaccat cccaaccccga cacttgttcc ccagaagctg gacctccagc    33420
acttgcctga aaaagccgac gagaaagacc agcaacgtga gcctctcgtc gccgatcaca    33480
tttacagtcc cgatcgacaa cttaagctaa ctgtggatgc ccttagtcca cctccgtccc    33540
cgaaaaagct ccaggttttt ctttcagcgc gaccgcccgc gcctcaagtg tcgaaaacat    33600
atgacaacct cgttcggcaa tacagtccct cgaagtcgct acaaatgatt ttaaggcgcg    33660
```

```
cgttggacga tttcgaaagc atgctggcag atggatcatt tcgcgtggcc ccgaaaagtt   33720
atccgatccc ttcaactaca gaaaaatccg ttctcgttca gacctcacgc atgttcccgg   33780
ttgcgttgct cgaggtcgct cgaagtcatt ttgatccgtt ggggttggag accgctcgag   33840
ctttcggcca caagctggct accgccgcgc tcgcgtcatt ctttgctgga gagaagccat   33900
cgagcaattg gtgaagaggg acctatcgga accctcacc aaatattgag tgtaggtttg    33960
aggccgctgg ccgcgtcctc agtcaccttt tgagccagat aattaagagc caatgcaat    34020 tggctcaggc tgccatcgtc ccccgtgcg aaacctgcac gtccgcgtca agaaataac     34080 cggcacctct tgctgttttt atcagttgag ggcttgacgg atccgcctca gtttgcggc    34140 gcagccgcaa aatgagaaca tctatactcc tgtcgtaaac ctcctcgtcg cgtactcgac   34200
tggcaatgag aagttgctcg cgcgatagaa cgtcgcgggg tttctctaaa acgcgagga    34260 gaagattgaa ctcacctgcc gtaagtttca cctcaccgcc agcttcggac atcaagcgac   34320
gttgcctgag attaagtgtc cagtcagtaa aacaaaaaga ccgtcggtct ttggagcgga   34380
caacgttggg gcgcacgcgc aaggcaaccc gaatgcgtgc aagaaactct ctcgtactaa   34440
acggcttagc gataaaatca cttgctccta gctcgagtgc aacaacttta tccgtctcct   34500
caaggcggtc gccactgata attatgattg gaatatcaga cttttgccgcc agatttcgaa   34560 cgatctcaag cccatcttca cgacctaaat ttagatcaac aaccacgaca tcgaccgtcg   34620
cggaagagag tactctagtg aactgggtgc tgtcggctac cgcggtcact ttgaaggcgt   34680
ggatcgtaag gtattcgata ataagatgcc gcatagcgac atcgtcatcg ataagaagaa   34740 cgtgttttcaa cggctcacct ttcaatctaa aatctgaacc cttgttcaca gcgcttgaga  34800
aattttcacg tgaaggatgt acaatcatct ccagctaaat gggcagttcg tcagaattgc   34860
ggctgaccgc ggatgacgaa aatgcgaacc aagtatttca attttatgac aaaagttctc   34920
aatcgttgtt acaagtgaaa cgcttcgagg ttacagctac tattgattaa ggagatcgcc   34980
tatggtctcg ccccggcgtc gtgcgtccgc cgcgagccag atctcgccta cttcataaac   35040
gtcctcatag gcacggaatg gaatgatgac atcgatcgcc gtagagagca tgtcaatcag   35100
tgtgcgatct tccaagctag caccttgggc gctacttttg acaagggaaa acagtttctt   35160
gaatccttgg attggattcg cgccgtgtat tgttgaaatc gatcccggat gtcccgagac   35220
gacttcactc agataagccc atgctgcatc gtcgcgcatc tcgccaagca atatccggtc   35280
cggccgcata cgcagacttg cttggagcaa gtgctcggcg ctcacagcac ccagcccagc   35340
accgttcttg gagtagagta gtctaacatg attatcgtgt ggaatgacga gttcgagcgt   35400
atcttctatg gtgattagcc tttcctgggg ggggatggcg ctgatcaagg tcttgctcat   35460
tgttgtcttg ccgcttccgg tagggccaca tagcaacatc gtcagtcggc tgacgacgca   35520
tgcgtgcaga aacgcttcca aatccccgtt gtcaaaatgc tgaaggatag cttcatcatc   35580
ctgattttgg cgtttccttc gtgtctgcca ctggttccac ctcgaagcat cataacggga   35640
ggagacttct ttaagaccag aaacacgcga gcttggccgt cgaatggtca agctgacggt   35700
gcccgaggga acgtcggcg gcagacagat ttgtagtcgt tcaccaccag gaagttcagt   35760
ggcgcagagg gggttacgtg gtccgacatc ctgctttctc agcgcgcccg ctaaaatagc   35820
gatatcttca agatcatcat aagagacggg caaaggcatc ttggtaaaaa tgccggcttg   35880
gcgcacaaat gcctctccag gtcgattgat cgcaatttct tcagtcttcg ggtcatcgag   35940
ccattccaaa atcggcttca gaagaaagcg tagttgcgga tccacttcca tttcaatgt    36000 atcctatctc taagcggaaa tttgaattca ttaagagcgg cggttcctcc cccgcgtggc   36060
```

```
gccgccagtc aggcggagct ggtaaacacc aaagaaatcg aggtcccgtg ctacgaaaat   36120
ggaaacggtg tcaccctgat tcttcttcag ggttggcggt atgttgatgg ttgccttaag   36180
ggctgtctca gttgtctgct caccgttatt ttgaaagctg ttgaagctca tcccgccacc   36240
cgagctgccg gcgtaggtgc tagctgcctg gaaggcgcct tgaacaacac tcaagagcat   36300
agctccgcta aaacgctgcc agaagtggct gtcgaccgag cccggcaatc ctgagcgacc   36360
gagttcgtcc gcgcttggcg atgttaacga gatcatcgca tggtcaggtg tctcggcgcg   36420
atcccacaac acaaaaacgc gcccatctcc ctgttgcaag ccacgctgta tttcgccaac   36480
aacggtggtg ccacgatcaa gaagcacgat attgttcgtt gttccacgaa tatcctgagg   36540
caagacacac tttacatagc ctgccaaatt tgtgtcgatt gcggtttgca agatgcacgg   36600
aattattgtc ccttgcgtta ccataaaatc ggggtgcggc aagagcgtgg cgctgctggg   36660
ctgcagctcg gtgggtttca tacgtatcga caaatcgttc tcgccggaca cttcgccatt   36720
cggcaaggag ttgtcgtcac gcttgccttc ttgtcttcgg cccgtgtcgc cctgaatggc   36780
gcgtttgctg accccttgat cgccgctgct atatgcaaaa atcggtgttt cttccggccg   36840
tggctcatgc cgctccggtt cgcccctcgg cggtagagga gcagcaggct gaacagcctc   36900
ttgaaccgct ggaggatccg gcggcacctc aatcggagct ggatgaaatg gcttggtgtt   36960
tgttgcgatc aaagttgacg gcgatgcgtt ctcattcacc ttcttttggc gcccacctag   37020
ccaaatgagg cttaatgata acgcgagaac gacacctccg acgatcaatt tctgagaccc   37080
cgaaagacgc cggcgatgtt tgtcggagac cagggatcca gatgcatcaa cctcatgtgc   37140
cgcttgctga ctatcgttat tcatcccttc gcccccttca ggacgcgttt cacatcgggc   37200
ctcaccgtgc ccgtttgcgg cctttggcca acgggatcgt aagcggtgtt ccagatacat   37260
agtactgtgt ggccatccct cagacgccaa cctcgggaaa ccgaagaaat ctcgacatcg   37320
ctccctttaa ctgaatagtt ggcaacagct tccttgccat caggattgat ggtgtagatg   37380
gagggtatgc gtacattgcc cggaaagtgg aataccgtcg taaatccatt gtcgaagact   37440
tcgagtggca acagcgaacg atcgccttgg gcgacgtagt gccaattact gtccgccgca   37500
ccaagggctg tgacaggctg atccaataaa ttctcagctt tccgttgata ttgtgcttcc   37560
gcgtgtagtc tgtccacaac agccttctgt tgtgcctccc ttcgccgagc cgccgcatcg   37620
tcggcggggt aggcgaattg gacgctgtaa tagagatcgg gctgctcttt atcgaggtgg   37680
gacagagtct tggaacttat actgaaaaca taacggcgca tcccggagtc gcttgcggtt   37740
agcacgatta ctggctgagg cgtgaggacc tggcttgcct tgaaaaatag ataatttccc   37800
cgcggtaggg ctgctagatc tttgctattt gaaacggcaa ccgctgtcac cgtttcgttc   37860
gtggcgaatg ttacgaccaa agtagctcca accgccgtcg agaggcgcac cacttgatcg   37920
ggattgtaag ccaaataacg catgcgcgga tctagcttgc ccgccattgg agtgtcttca   37980
gcctccgcac cagtcgcagc ggcaaataaa catgctaaaa tgaaaagtgc ttttctgatc   38040
atggttcgct gtggcctacg tttgaaacgg tatcttccga tgtctgatag gaggtgacaa   38100
ccagacctgc cgggttggtt agtctcaatc tgccgggcaa gctggtcacc tttttcgtagc  38160 gaactgtcgc ggtccacgta ctcaccacag gcattttgcc gtcaacgacg agggtccttt   38220
tatagcgaat ttgctgcgtg cttggagtta catcatttga agcgatgtgc tcgacctcca   38280
ccctgccgcg tttgccaaga atgacttgag gcgaactggg attgggatag ttgaagaatt   38340
gctggtaatc ctgcgcact gttggggcac tgaagttcga taccaggtcg taggcgtact    38400
gagcggtgtc ggcatcataa ctctcgcgca ggcgaacgta ctcccacaat gaggcgttaa   38460
```

```
cgacggcctc ctcttgagtt gcaggcaatc gcgagacaga cacctcgctg tcaacggtgc   38520
cgtccggccg tatccataga tatacgggca caagcctgct caacggcacc attgtggcta   38580
tagcgaacgc ttgagcaaca tttcccaaaa tcgcgatagc tgcgacagct gcaatgagtt   38640
tggagagacg tcgcgccgat ttcgctcgcg cggtttgaaa ggcttctact tccttatagt   38700
gctcggcaag gctttcgcgc gccactagca tggcatattc aggccccgtc atagcgtcca   38760
cccgaattgc cgagctgaag atctgacgga gtaggctgcc atcgcccac attcagcggg    38820 aagatcgggc ctttgcagct cgctaatgtg tcgtttgtct ggcagccgct caaagcgaca   38880
actaggcaca gcaggcaata cttcatgaa ttctccattg aggcgaattt ttgcgcgacc    38940
tagcctcgct caacctgagc gaagcgacgg tacaagctgc tggcagattg ggttgcgccg   39000
ctccagtaac tgcctccaat gttgccgcg atcgccggca aagcgacaat gagcgcatcc    39060
cctgtcagaa aaacatatc gagttcgtaa agaccaatga tcttggccgc ggtcgtaccg    39120
gcgaaggtga ttacaccaag cataagggtg agcgcagtcg cttcggttag gatgacgatc   39180
gttgccacga ggtttaagag gagaagcaag agaccgtagg tgataagttg cccgatccac   39240
ttagctgcga tgtcccgcgt gcgatcaaaa atatatccga cgaggatcag aggcccgatc   39300
gcgagaagca ctttcgtgag aattccaacg gcgtcgtaaa ctccgaaggc agaccagagc   39360
gtgccgtaaa ggacccactg tgcccccttgg aaagcaagga tgtcctggtc gttcatcgga  39420
ccgatttcgg atgcgatttt ctgaaaaacg gcctgggtca cggcgaacat tgtatccaac   39480
tgtgccggaa cagtctgcag aggcaagccg gttacactaa actgctgaac aaagtttggg   39540
accgtctttt cgaagatgga aaccacatag tcttggtagt tagcctgccc aacaattaga   39600
gcaacaacga tggtgaccgt gatcacccga gtgataccgc tacgggtatc gacttcgccg   39660
cgtatgacta aaatacccctg aacaataatc caaagagtga cacaggcgat caatggcgca  39720
ctcaccgcct cctggatagt ctcaagcatc gagtccaagc ctgtcgtgaa ggctacatcg   39780
aagatcgtat gaatggccgt aaacggcgcc ggaatcgtga aattcatcga ttggacctga   39840
acttgactgg tttgtcgcat aatgttggat aaaatgagct cgcattcggc gaggatgcgg   39900
gcggatgaac aaatcgccca gccttagggg agggcaccaa agatgacagc ggtcttttga   39960
tgctccttgc gttgagcggc cgcctcttcc gcctcgtgaa ggccggcctg cgcggtagtc   40020
atcgttaata ggcttgtcgc ctgtacattt tgaatcattg cgtcatggat ctgcttgaga   40080
agcaaaccat tggtcacggt tgcctgcatg atattgcgag atcgggaaag ctgagcagac   40140
gtatcagcat tcgccgtcaa gcgtttgtcc atcgtttcca gattgtcagc cgcaatgcca   40200
gcgctgtttg cggaaccggt gatctgcgat cgcaacaggt ccgcttcagc atcactaccc   40260
acgactgcac gatctgtatc gctggtgatc gcacgtgccg tggtcgacat ggcattcgc    40320 ggcgaaaaca tttcattgtc taggtccttc gtcgaaggat actgattttt ctggttgagc   40380
gaagtcagta gtccagtaac gccgtaggcc gacgtcaaca tcgtaaccat cgctatagtc   40440
tgagtgagat tctccgcagt cgcgagcgca gtcgcgagcg tctcagcctc cgttgccggg   40500
tcgctaacaa caaactgcgc ccgcgcgggc tgaatatata gaaagctgca ggtcaaaact   40560
gttgcaataa gttgcgtcgt cttcatcgtt tcctacctta tcaatcttct gcctcgtggt   40620
gacgggccat gaattcgctg agccagccag atgagttgcc ttcttgtgcc tcgcgtagtc   40680
gagttgcaaa gcgcaccgtg ttggcacgcc ccgaaagcac ggcgacatat tcacgcatat   40740
cccgcagatc aaattcgcag atgacgcttc cactttctcg tttaagaaga aacttacggc   40800
tgccgaccgt catgtcttca cggatcgcct gaaattcctt ttcggtacat ttcagtccat   40860
```

```
cgacataagc cgatcgatct gcggttggtg atggatagaa aatcttcgtc atacattgcg    40920
caaccaagct ggctcctagc ggcgattcca gaacatgctc tggttgctgc gttgccagta    40980
ttagcatccc gttgtttttt cgaacggtca ggaggaattt gtcgacgaca gtcgaaaatt    41040
tagggtttaa caaataggcg cgaaactcat cgcagctcat cacaaaacgg cggccgtcga    41100
tcatggctcc aatccgatgc aggagatatg ctgcagcggg agcgcatact tcctcgtatt    41160
cgagaagatg cgtcatgtcg aagccggtaa tcgacggatc taactttact tcgtcaactt    41220
cgccgtcaaa tgcccagcca agcgcatggc cccggcacca gcgttggagc gcgctcctg    41280 cgccttcggc gggcccatgc aacaaaaatt cacgtaaccc cgcgattgaa cgcatttgtg    41340
gatcaaacga gagctgacga tggataccac ggaccagacg gcggttctct tccggagaaa    41400 tcccacccccg accatcactc tcgatgagag ccacgatcca ttcgcgcaga aaatcgtgtg    41460
aggctgctgt gttttctagg ccacgcaacg gcgccaaccc gctgggtgtg cctctgtgaa    41520
gtgccaaata tgttcctcct gtggcgcgaa ccagcaattc gccacccccgg tccttgtcaa    41580 agaacacgac cgtacctgca cggtcgacca tgctctgttc gagcatggct agaacaaaca    41640
tcatgagcgt cgtcttaccc ctcccgatag gcccgaatat tgccgtcatg ccaacatcgt    41700
gctcatgcgg gatatagtcg aaaggcgttc cgccattggt acgaaatcgg gcaatcgcgt    41760
tgccccagtg gcctgagctg gcgccctctg gaaagttttc gaaagagaca aaccctgcga    41820
aattgcgtga agtgattgcg ccagggcgtg tgcgccactt aaaattcccc ggcaattggg    41880
accaataggc cgcttccata ccaatacctt cttggacaac cacggcacct gcatccgcca    41940
ttcgtgtccg agcccgcgcg cccctgtccc caagactatt gagatcgtct gcatagacgc    42000
aaaggctcaa atgatgtgag cccataacga attcgttgct cgcaagtgcg tcctcagcct    42060
cggataattt gccgatttga gtcacggctt tatcgccgga actcagcatc tggctcgatt    42120
tgaggctaag tttcgcgtgc gcttgcgggc gagtcaggaa cgaaaaactc tgcgtgagaa    42180
caagtggaaa atcgagggat agcagcgcgt tgagcatgcc cggccgtgtt tttgcagggt    42240
attcgcgaaa cgaatagatg gatccaacgt aactgtcttt tggcgttctg atctcgagtc    42300
ctcgcttgcc gcaaatgact ctgtcggtat aaatcgaagc gccagtgag ccgctgacga    42360 ccggaaccgg tgtgaaccga ccagtcatga tcaaccgtag cgcttcgcca atttcggtga    42420
agagcacacc ctgcttctcg cggatgccaa gacgatgcag gccatacgct taagagagc    42480 cagcgacaac atgccaaaga tcttccatgt tcctgatctg gcccgtgaga tcgttttccc    42540
tttttccgct tagcttggtg aacctcctct ttaccttccc taaagccgcc tgtgggtaga    42600
caatcaacgt aaggaagtgt tcattgcgga ggagttggcc ggagagcacg cgctgttcaa    42660
aagcttcgtt caggctagcg gcgaaaacac tacggaagtg tcgcggcgcc gatgatggca    42720
cgtcggcatg acgtacgagg tgagcatata ttgacacatg atcatcagcg atattgcgca    42780
acagcgtgtt gaacgcacga caacgcgcat tgcgcatttc agtttcctca agctcgaatg    42840
caacgccatc aattctcgca atggtcatga tcgatccgtc ttcaagaagg acgatatggt    42900
cgctgaggtg gccaatataa gggagataga tctcaccgga tctttcggtc gttccactcg    42960
cgccgagcat cacaccattc ctctccctcg tgggggaacc ctaattggat ttgggctaac    43020
agtagcgccc cccaaactg cactatcaat gcttcttccc gcggtccgca aaaatagcag    43080
gacgacgctc gccgcattgt agtctcgctc cacgatgagc cgggctgcaa accataacgg    43140
cacgagaacg acttcgtaga gcgggttctg aacgataacg atgacaaagc cggcgaacat    43200
catgaataac cctgccaatg tcagtggcac cccaagaaac aatgcgggcc gtgtggctgc    43260
```

```
gaggtaaagg gtcgattctt ccaaacgatc agccatcaac taccgccagt gagcgtttgg   43320
ccgaggaagc tcgccccaaa catgataaca atgccgccga cgacgccggc aaccagccca   43380
agcgaagccc gcccgaacat ccaggagatc ccgatagcga caatgccgag aacagcgagt   43440
gactggccga acgaccaag gataaacgtg catatattgt taaccattgt ggcggggtca    43500
gtgccgccac ccgcagattg cgctgcggcg ggtccggatg aggaaatgct ccatgcaatt   43560
gcaccgcaca agcttggggc gcagctcgat atcacgcgca tcatcgcatt cgagagcgag   43620
aggcgattta gatgtaaacg gtatctctca aagcatcgca tcaatgcgca cctccttagt   43680
ataagtcgaa taagacttga ttgtcgtctg cggatttgcc gttgtcctgg tgtggcggtg   43740
gcggagcgat taaccgcca gcgccatcct cctgcgagcg gcgctgatat gaccccaaa    43800 catcccacgt ctcttcggat tttagcgcct cgtgatcgtc ttttggaggc tcgattaacg   43860
cgggcaccag cgattgagca gctgtttcaa ctttttcgcac gtagccgttt gcaaaaccgc  43920
cgatgaaatt accggtgttg taagcggaga tcgcccgacg aagcgcaaat tgcttctcgt   43980
caatcgtttc gccgcctgca taacgacttt tcagcatgtt tgcagcggca gataatgatg   44040
tgcacgcctg gagcgcaccg tcaggtgtca gaccgagcat agaaaaattt cgagagttta   44100
tttgcatgag gccaacatcc agcgaatgcc gtgcatcgag acggtgcctg acgacttggg   44160
ttgcttggct gtgatcttgc cagtgaagcg tttcgccggt cgtgttgtca tgaatcgcta   44220
aaggatcaaa gcgactctcc accttagcta tcgccgcaag cgtagatgtc gcaactgatg   44280
gggcacactt gcgagcaaca tggtcaaact cagcagatga gagtggcgtg gcaaggctcg   44340
acgaacagaa ggagaccatc aaggcaagag aaagcgaccc cgatctctta agcataccctt  44400 atctccttag ctcgcaacta acaccgcctc tcccgttgga agaagtgcgt tgttttatgt   44460
tgaagattat cgggagggtc ggttactcga aaattttcaa ttgcttcttt atgatttcaa   44520
ttgaagcgag aaacctcgcc cggcgtcttg gaacgcaaca tggaccgaga accgcgcatc   44580
catgactaag caaccggatc gacctattca ggccgcagtt ggtcaggtca ggctcagaac   44640
gaaaatgctc ggcgaggtta cgctgtctgt aaacccattc gatgaacggg aagcttcctt   44700
ccgattgctc ttggcaggaa tattggccca tgcctgcttg cgcttttgcaa atgctcttat   44760 cgcgttggta tcatatgcct tgtccgccag cagaaacgca ctctaagcga ttatttgtaa   44820
aaatgtttcg gtcatgcggc ggtcatgggc ttgacccgct gtcagcgcaa gacggatcgg   44880
tcaaccgtcg gcatcgacaa cagcgtgaat cttggtggtc aaaccgccac gggaacgtcc   44940
catacagcca tcgtcttgat cccgctgttt cccgtcgccg catgttggtg gacgcggaca   45000
caggaactgt caatcatgac gacattctat cgaaagcctt ggaaatcaca ctcagaatat   45060
gatcccagac gtctgcctca cgccatcgta caaagcgatt gtagcaggtt gtacaggaac   45120
cgtatcgatc aggaacgtct gcccagggcg ggcccgtccg gaagcgccac aagatgacat   45180
tgatcacccg cgtcaacgcg cggcacgcga cgcggcttat ttgggaacaa aggactgaac   45240
aacagtccat tcgaaatcgg tgacatcaaa gcggggacgg gttatcagtg gcctccaagt   45300
caagcctcaa tgaatcaaaa tcagaccgat ttgcaaacct gatttatgag tgtgcggcct   45360
aaatgatgaa atcgtccttc tagatcgcct ccgtggtgta gcaacacctc gcagtatcgc   45420
cgtgctgacc ttggccaggg aattgactgg caagggtgct ttcacatgac cgctcttttg   45480
gccgcgatag atgatttcgt tgctgctttg ggcacgtaga aggagagaag tcatatcgga   45540
gaaattcctc ctggcgcgag agcctgctct atcgcgacgg catcccactg tcgggaacag   45600
accggatcat tcacgaggcg aaagtcgtca acacatgcgt tataggcatc ttcccttgaa   45660
```

```
ggatgatctt gttgctgcca atctggaggt gcggcagccg caggcagatg cgatctcagc   45720
gcaacttgcg gcaaaacatc tcactcacct gaaaaccact agcgagtctc gcgatcgagac  45780 gaaggccttt tacttaacga cacaatatcc gatgtctgca tcacaggcgt cgctatccca   45840
gtcaatacta aagcggtgca ggaactaaag attactgatg acttaggcgt gccacgaggc   45900
ctgagacgac gcgcgtagac agttttttga aatcattatc aaagtgatgg cctccgctga   45960
agcctatcac ctctgcgccg gtctgtcgga gagatgggca agcattatta cggtcttcgc   46020
gcccgtacat gcattggacg attgcagggt caatggatct gagatcatcc agaggattgc   46080
cgcccttacc ttccgtttcg agttggagcc agccccctaaa tgagacgaca tagtcgactt  46140
gatgtgacaa tgccaagaga gagatttgct taacccgatt tttttgctca agcgtaagcc   46200
tattgaagct gccggcatg acgtccgcgc cgaaagaata tcctacaagt aaaacattct    46260
gcacaccgaa atgcttggtg tagacatcga ttatgtgacc aagatcctta gcagtttcgc   46320
ttggggaccg ctccgaccag aaataccgaa gtgaactgac gccaatgaca ggaatccctt   46380
ccgtctgcag ataggtacca tcgatagatc tgctgcctcg cgcgtttcgg tgatgacggt   46440
gaaaacctct gacacatgca gctcccggag acggtcacag cttgtctgta agcggatgcc   46500
gggagcagac aagcccgtca gggcgcgtca gcgggtgttg gcgggtgtcg gggcgcagcc   46560
atgacccagt cacgtagcga tagcggagtg tatactggct taactatgcg gcatcagagc   46620
agattgtact gagagtgcac catatgcggt gtgaaatacc gcacagatgc gtaaggagaa   46680
aataccgcat caggcgctct tccgcttcct cgctcactga ctcgctgcgc tcggtcgttc   46740
ggctgcggcg agcggtatca gctcactcaa aggcggtaat acggttatcc acagaatcag   46800
gggataacgc aggaaagaac atgtgagcaa aaggccagca aaaggccagg aaccgtaaaa   46860
aggccgcgtt gctggcgttt ttccataggc tccgccccc tgacgagcat cacaaaaatc     46920
gacgctcaag tcagaggtgg cgaaacccga caggactata agataccag gcgtttcccc     46980 ctggaagctc cctcgtgcgc tctcctgttc cgaccctgcc gcttaccgga tacctgtccg     47040 ccttctccc ttcgggaagc gtggcgcttt ctcatagctc acgctgtagg tatctcagtt      47100
cggtgtaggt cgttcgctcc aagctgggct gtgtgcacga acccccgtt cagcccgacc     47160 gctgcgcctt atccggtaac tatcgtcttg agtccaaccc ggtaagacac gacttatcgc     47220
cactggcagc agccactggt aacaggatta gcagagcgag gtatgtaggc ggtgctacag    47280
agttcttgaa gtggtggcct aactacggct acactagaag gacagtattt ggtatctgcg    47340
ctctgctgaa gccagttacc ttcggaaaaa gagttggtag ctcttgatcc ggcaaacaaa    47400
ccaccgctgg tagcggtggt ttttttgttt gcaagcagca gattacgcgc agaaaaaaag    47460
gatctcaaga agatcctttg atcttttcta cggggtctga cgctcagtgg aacgaaaact    47520
cacgttaagg gattttggtc atgagattat caaaaggat cttcacctag atcctttaa      47580 attaaaatg aagtttaaaaa tcaatctaaa gtatatatga gtaaacttgg tctgacagtt    47640
accaatgctt aatcagtgag gcacctatct cagcgatctg tctatttcgt tcatccatag    47700
ttgcctgact cccccgtcgtg tagataacta cgatacggga gggcttacca tctggcccca   47760
gtgctgcaat gataccgcga gacccacgct caccggctcc agatttatca gcaataaacc    47820
agccagccgg aagggccgag cgcagaagtg gtcctgcaac tttatccgcc tccatccagt    47880
ctattaattg ttgccgggaa gctagagtaa gtagttcgcc agttaatagt ttgcgcaacg    47940
ttgttgccat tgctgcaggg ggggggggg gggggacttt ccattgttca ttccacggac    48000
aaaaacagag aaaggaaacg acagaggcca aaaagcctcg ctttcagcac ctgtcgtttc   48060
```

```
ctttctttc  agagggtatt  ttaaataaaa  acattaagtt  atgacgaaga  agaacggaaa    48120
cgccttaaac  cggaaaattt  tcataaatag  cgaaaacccg  cgaggtcgcc  gccccgtagt    48180
cggatcaccg  gaaaggaccc  gtaaagtgat  aatgattatc  atctacatat  cacaacgtgc    48240
gtggaggcca  tcaaaccacg  tcaaataatc  aattatgacg  caggtatcgt  attaattgat    48300
ctgcatcaac  ttaacgtaaa  aacaacttca  gacaatacaa  atcagcgaca  ctgaatacgg    48360
ggcaacctca  tgtcccccc   ccccccccc   ctgcaggcat  cgtggtgtca  cgctcgtcgt    48420
ttggtatggc  ttcattcagc  tccggttccc  aacgatcaag  gcgagttaca  tgatccccca    48480
tgttgtgcaa  aaaagcggtt  agctccttcg  gtcctccgat  cgttgtcaga  agtaagttgg    48540
ccgcagtgtt  atcactcatg  gttatggcag  cactgcataa  ttctcttact  gtcatgccat    48600
ccgtaagatg  ctttctgtg   actggtgagt  actcaaccaa  gtcattctga  aatagtgta    48660
tgcggcgacc  gagttgctct  tgcccggcgt  caacacggga  taataccgcg  ccacatagca    48720
gaactttaaa  agtgctcatc  attggaaaac  gttcttcggg  gcgaaaactc  tcaaggatct    48780
taccgctgtt  gagatccagt  tcgatgtaac  ccactcgtgc  acccaactga  tcttcagcat    48840
cttttacttt  caccagcgtt  tctgggtgag  caaaaacagg  aaggcaaaat  gccgcaaaaa    48900
agggaataag  ggcgacacgg  aaatgttgaa  tactcatact  cttccttttt  caatattatt    48960
gaagcattta  tcagggttat  tgtctcatga  gcggatacat  atttgaatgt  atttagaaaa    49020
ataaacaaat  aggggttccg  cgcacatttc  cccgaaaagt  gccacctgac  gtctaagaaa    49080
ccattattat  catgacatta  acctataaaa  ataggcgtat  cacgaggccc  tttcgtcttc    49140
aagaattggt  cgacgatctt  gctgcgttcg  gatattttcg  tggagttccc  gccacagacc    49200
cggattgaag  gcgagatcca  gcaactcgcg  ccagatcatc  ctgtgacgga  actttggcgc    49260
gtgatgactg  gccaggacgt  cggccgaaag  agcgacaagc  agatcacgct  tttcgacagc    49320
gtcggatttg  cgatcgagga  ttttcggcg   ctgcgctacg  tccgcgaccg  cgttgaggga    49380
tcaagccaca  gcagcccact  cgaccttcta  gccgacccag  acgagccaag  ggatcttttt    49440
ggaatgctgc  tccgtcgtca  ggcttttccga cgtttgggtg  gttgaacaga  agtcattatc    49500
gtacggaatg  ccaagcactc  ccgaggggaa  ccctgtggtt  ggcatgcaca  tacaaatgga    49560
cgaacggata  aaccttttca  cgccctttta  aatatccgtt  attctaataa  acgctctttt    49620
ctcttaggtt  tacccgccaa  tatatcctgt  caaacactga  tagtttaaac  tgaaggcggg    49680
aaacgacaat  ctgatcatga  gcggagaatt  aagggagtca  cgttatgacc  cccgccgatg    49740
acgcgggaca  agccgtttta  cgtttggaac  tgacagaacc  gcaacgttga  aggagccact    49800
cagcaagctg  gtacgattgt  aatacgactc  actatagggc  gaattgagcg  ctgtttaaac    49860
gctcttcaac  tggaagagcg  gttacccgga  ccgaagcttg  catgcctgca  g              49911
```

<210> SEQ ID NO 7
<211> LENGTH: 36909
<212> TYPE: DNA
<213> ORGANISM: Artificial Sequence
<220> FEATURE:
<223> OTHER INFORMATION: PHP10523 construct

<400> SEQUENCE: 7

```
tctagagctc  gttcctcgag  gcctcgaggc  ctcgaggaac  ggtacctgcg  gggaagctta      60
caataatgtg  tgttgttaag  tcttgttgcc  tgtcatcgtc  tgactgactt  tcgtcataaa     120
tcccggcctc  cgtaacccag  cttttgggcaa gctcacggat  ttgatccggc  ggaacgggaa     180
tatcgagatg  ccgggctgaa  cgctgcagtt  ccagcttttcc  ctttcgggac  aggtactcca     240
```

-continued

```
gctgattgat tatctgctga agggtcttgg ttccacctcc tggcacaatg cgaatgatta    300
cttgagcgcg atcgggcatc caattttctc ccgtcaggtg cgtggtcaag tgctacaagg    360
cacctttcag taacgagcga ccgtcgatcc gtcgccggga tacggacaaa atggagcgca    420
gtagtccatc gagggcggcg aaagcctcgc caaaagcaat acgttcatct cgcacagcct    480
ccagatccga tcgagggtct tcggcgtagg cagatagaag catggataca ttgcttgaga    540
gtattccgat ggactgaagt atggcttcca tcttttctcg tgtgtctgca tctatttcga    600
gaaagccccc gatgcggcgc accgcaacgc gaattgccat actatccgaa agtcccagca    660
ggcgcgcttg ataggaaaag gtttcatact cggccgatcg cagacgggca ctcacgacct    720
tgaacccttc aactttcagg gatcgatgct ggttgatggt agtctcactc gacgtggctc    780
tggtgtgttt tgacatagct tcctccaaag aaagcggaag gtctggatac tccagcacga    840
aatgtgcccg ggtagacgga tggaagtcta gccctgctca atatgaaatc aacagtacat    900
ttacagtcaa tactgaatat acttgctaca tttgcaattg tcttataacg aatgtgaaat    960
aaaaatagtg taacaacgct tttactcatc gataatcaca aaaacattta tacgaacaaa    1020
aatacaaatg cactccggtt tcacaggata ggcgggatca gaatatgcaa cttttgacgt    1080
tttgttcttt caaggggggt gctggcaaaa ccaccgcact catgggcctt tgcgctgctt    1140
tggcaaatga cggtaaacga gtggccctct tgatgccga cgaaaaccgg cctctgacgc    1200
gatggagaga aaacgcctta caaagcagta ctgggatcct cgctgtgaag tctattccgc    1260
cgacgaaatg cccccttcttg aagcagccta tgaaaatgcc gagctcgaag gatttgatta    1320
tgcgttggcc gatacgcgtg gcggctcgag cgagctcaac aacacaatca tcgctagctc    1380
aaacctgctt ctgatcccca ccatgctaac gccgctcgac atcgatgagg cactatctac    1440
ctaccgctac gtcatcgagc tgctgttgag tgaaaatttg gcaattccta cagctgtttt    1500
gcgccaacgc gtcccggtcg gccgattgac aacatcgcaa gcaggatgt cagagacgct    1560 agagagcctt ccagttgtac cgtctcccat gcatgaaaga gatgcatttg ccgcgatgaa    1620
agaacgcggc atgttgcatc ttacattact aaacacggga actgatccga cgatgcgcct    1680
catagagagg aatcttcgga ttgcgatgga ggaagtcgtg gtcatttcga aactgatcag    1740
caaaatcttg gaggcttgaa gatggcaatt cgcaagcccg cattgtcggt cggcgaagca    1800
cggcggcttg ctggtgctcg acccgagatc caccatccca acccgacact tgttccccag    1860
aagctggacc tccagcactt gcctgaaaaa gccgacgaga aagaccagca acgtgagcct    1920
ctcgtcgccg atcacattta cagtcccgat cgacaactta agctaactgt ggatgccctt    1980
agtccacctc cgtccccgaa aaagctccag gttttttcttt cagcgcgacc gccgcgcct    2040 caagtgtcga aaacatatga caacctcgtt cggcaataca gtccctcgaa gtcgctacaa    2100 atgatttttaa ggcgcgcgtt ggacgatttc gaaagcatgc tggcagatgg atcatttcgc    2160
gtggccccga aaagttatcc gatcccttca actacagaaa aatccgttct cgttcagacc    2220
tcacgcatgt tcccggttgc gttgctcgag gtcgctcgaa gtcattttga tccgttgggg    2280
ttggagaccg ctcgagcttt cggccacaag ctggctaccg ccgcgctcgc gtcattctt    2340 gctggagaga agccatcgag caattggtga agagggacct atcggaaccc ctcaccaaat    2400
attgagtgta ggtttgaggc cgctggccgc gtcctcagtc accttttgag ccagataatt    2460
aagagccaaa tgcaattggc tcaggctgcc atcgtccccc cgtgcgaaac ctgcacgtcc    2520
gcgtcaaaga aataaccggc acctcttgct gttttttatca gttgagggct tgacggatcc    2580
gcctcaagtt tgcggcgcag ccgcaaaatg agaacatcta tactcctgtc gtaaacctcc    2640
```

-continued

```
tcgtcgcgta ctcgactggc aatgagaagt tgctcgcgcg atagaacgtc gcggggtttc   2700
tctaaaaacg cgaggagaag attgaactca cctgccgtaa gtttcacctc accgccagct   2760
tcggacatca agcgacgttg cctgagatta agtgtccagt cagtaaaaca aaaagaccgt   2820
cggtctttgg agcggacaac gttggggcgc acgcgcaagg caacccgaat gcgtgcaaga   2880
aactctctcg tactaaacgg cttagcgata aaatcacttg ctcctagctc gagtgcaaca   2940
actttatccg tctcctcaag gcggtcgcca ctgataatta tgattggaat atcagacttt   3000
gccgccagat ttcgaacgat ctcaagccca tcttcacgac ctaaatttag atcaacaacc   3060
acgacatcga ccgtcgcgga agagagtact ctagtgaact gggtgctgtc ggctaccgcg   3120
gtcactttga aggcgtggat cgtaaggtat tcgataataa gatgccgcat agcgacatcg   3180
tcatcgataa aagaacgtg tttcaacggc tcacctttca atctaaaatc tgaacccttg    3240
ttcacagcgc ttgagaaatt ttcacgtgaa ggatgtacaa tcatctccag ctaaatgggc   3300
agttcgtcag aattgcggct gaccgcggat gacgaaaatg cgaaccaagt atttcaattt   3360
tatgacaaaa gttctcaatc gttgttacaa gtgaaacgct tcgaggttac agctactatt   3420
gattaaggag atcgcctatg gtctcgcccc ggcgtcgtgc gtccgccgcg agccagatct   3480
cgcctacttc ataaacgtcc tcataggcac ggaatggaat gatgacatcg atcgccgtag   3540
agagcatgtc aatcagtgtg cgatcttcca agctagcacc ttgggcgcta cttttgacaa   3600
gggaaaacag tttcttgaat ccttggattg gattcgcgcc gtgtattgtt gaaatcgatc   3660
ccggatgtcc cgagacgact tcactcagat aagcccatgc tgcatcgtcg cgcatctcgc   3720
caagcaatat ccggtccggc cgcatacgca gacttgcttg gagcaagtgc tcggcgctca   3780
cagcacccag cccagcaccg ttcttggagt agagtagtct aacatgatta tcgtgtggaa   3840
tgacgagttc gagcgtatct tctatggtga ttagcctttc ctggggggg atggcgctga   3900 tcaaggtctt gctcattgtt gtcttgccgc ttccggtagg gccacatagc aacatcgtca   3960
gtcggctgac gacgcatgcg tgcagaaacg cttccaaatc cccgttgtca aaatgctgaa   4020
ggatagcttc atcatcctga ttttggcgtt tccttcgtgt ctgccactgg ttccacctcg   4080
aagcatcata acgggaggag acttctttaa gaccagaaac acgcgagctt ggccgtcgaa   4140
tggtcaagct gacggtgccc gagggaacgg tcggcggcag acagatttgt agtcgttcac   4200
caccaggaag ttcagtggcg cagaggggggt tacgtggtcc gacatcctgc tttctcagcg   4260
cgcccgctaa aatagcgata tcttcaagat catcataaga gacgggcaaa ggcatcttgg   4320
taaaaatgcc ggcttggcgc acaaatgcct ctccaggtcg attgatcgca atttcttcag   4380
tcttcgggtc atcgagccat tccaaaatcg gcttcagaag aaagcgtagt gcggatcca   4440 cttccatttta caatgtatcc tatctctaag cggaaatttg aattcattaa gagcggcggt   4500 tcctccccg cgtggcgccg ccagtcaggc ggagctggta acaccaaag aaatcgaggt    4560 cccgtgctac gaaaatggaa acggtgtcac cctgattctt cttcagggtt ggcggtatgt   4620
tgatggttgc cttaagggct gtctcagttg tctgctcacc gttatttttga aagctgttga   4680 agctcatccc gccaccccgag ctgccggcgt aggtgctagc tgcctggaag gcgccttgaa   4740
caacactcaa gagcatagct ccgctaaaac gctgccagaa gtggctgtcg accgagcccg   4800
gcaatcctga gcgaccgagt tcgtccgcgc ttggcgatgt taacgagatc atcgcatggt   4860
caggtgtctc ggcgcgatcc cacaacacaa aaacgcgccc atctccctgt tgcaagccac   4920
gctgtatttc gccaacaacg gtggtgccac gatcaagaag cacgatattg ttcgttgttc   4980
cacgaatatc ctgaggcaag acacactttta catagcctgc caaatttgtg tcgattgcgg   5040
```

```
tttgcaagat gcacggaatt attgtccctt gcgttaccat aaaatcgggg tgcggcaaga    5100
gcgtggcgct gctgggctgc agctcggtgg gtttcatacg tatcgacaaa tcgttctcgc    5160
cggacacttc gccattcggc aaggagttgt cgtcacgctt gccttcttgt cttcggcccg    5220
tgtcgccctg aatggcgcgt ttgctgaccc cttgatcgcc gctgctatat gcaaaaatcg    5280
gtgtttcttc cggccgtggc tcatgccgct ccggttcgcc cctcggcggt agaggagcag    5340
caggctgaac agcctcttga accgctggag gatccggcgg cacctcaatc ggagctggat    5400
gaaatggctt ggtgtttgtt gcgatcaaag ttgacggcga tgcgttctca ttcaccttct    5460
tttggcgccc acctagccaa atgaggctta atgataacgc gagaacgaca cctccgacga    5520
tcaatttctg agaccccgaa agacgccggc gatgtttgtc ggagaccagg atccagatg     5580
catcaacctc atgtgccgct tgctgactat cgttattcat cccttcgccc ccttcaggac    5640
gcgtttcaca tcgggcctca ccgtgcccgt ttgcggcctt tggccaacgg gatcgtaagc    5700
ggtgttccag atacatagta ctgtgtggcc atccctcaga cgccaacctc gggaaaccga    5760
agaaatctcg acatcgctcc ctttaactga atagttggca acagcttcct tgccatcagg    5820
attgatggta tagatggagg gtatgcgtac attgcccgga aagtggaata ccgtcgtaaa    5880
tccattgtcg aagacttcga gtggcaacag cgaacgatcg ccttgggcga cgtagtgcca    5940
attactgtcc gccgcaccaa gggctgtgac aggctgatcc aataaattct cagctttccg    6000
ttgatattgt gcttccgcgt gtagtctgtc cacaacagcc ttctgttgtg cctcccttcg    6060
ccgagccgcc gcatcgtcgg cggggtaggc gaattggacg ctgtaataga gatcgggctg    6120
ctctttatcg aggtgggaca gagtcttgga acttatactg aaaacataac ggcgcatccc    6180
ggagtcgctt gcggttagca cgattactgg ctgaggcgtg aggacctggc ttgccttgaa    6240
aaatagataa tttccccgcg gtagggctgc tagatctttg ctatttgaaa cggcaaccgc    6300
tgtcaccgtt tcgttcgtgg cgaatgttac gaccaaagta gctccaaccg ccgtcgagag    6360
gcgcaccact tgatcgggat tgtaagccaa ataacgcatg cgcggatcta gcttgcccgc    6420
cattggagtg tcttcagcct ccgcaccagt cgcagcggca aataaacatg ctaaaatgaa    6480
aagtgctttt ctgatcatgg ttcgctgtgg cctacgtttg aaacggtatc ttccgatgtc    6540
tgataggagg tgacaaccag acctgccggg ttggttagtc tcaatctgcc gggcaagctg    6600
gtcacctttt cgtagcgaac tgtcgcggtc cacgtactca ccacaggcat tttgccgtca    6660
acgacgaggg tccttttata gcgaatttgc tgcgtgcttg gagttacatc atttgaagcg    6720
atgtgctcga cctccaccct gccgcgtttg ccaagaatga cttgaggcga actgggattg    6780
ggatagttga agaattgctg gtaatcctgg cgcactgttg gggcactgaa gttcgatacc    6840
aggtcgtagg cgtactgagc ggtgtcggca tcataactct cgcgcaggcg aacgtactcc    6900
cacaatgagg cgttaacgac ggcctcctct tgagttgcag gcaatcgcga gacagacacc    6960
tcgctgtcaa cggtgccgtc cggccgtatc catagatata cgggcacaag cctgctcaac    7020
ggcaccattg tggctatagc gaacgcttga gcaacatttc ccaaaatcgc gatagctgcg    7080
acagctgcaa tgagtttgga gagacgtcgc gccgatttcg ctcgcgcggt ttgaaaggct    7140
tctacttcct tatagtgctc ggcaaggctt tcgcgcgcca ctagcatggc atattcaggc    7200
cccgtcatag cgtccacccg aattgccgag ctgaagatct gacggagtag gctgccatcg    7260
ccccacattc agcgggaaga tcgggccttt gcagctcgct aatgtgtcgt ttgtctggca    7320
gccgctcaaa gcgacaacta ggcacagcag gcaatacttc atagaattct ccattgaggc    7380
gaattttgc gcgacctagc ctcgctcaac ctgagcgaag cgacggtaca agctgctggc    7440
```

```
agattgggtt gcgccgctcc agtaactgcc tccaatgttg ccggcgatcg ccggcaaagc    7500
gacaatgagc gcatcccctg tcagaaaaaa catatcgagt tcgtaaagac caatgatctt    7560
ggccgcggtc gtaccggcga aggtgattac accaagcata agggtgagcg cagtcgcttc    7620
ggttaggatg acgatcgttg ccacgaggtt aagaggaga agcaagagac cgtaggtgat    7680
aagttgcccg atccacttag ctgcgatgtc ccgcgtgcga tcaaaatat atccgacgag    7740 gatcagaggc ccgatcgcga gaagcacttt cgtgagaatt ccaacggcgt cgtaaactcc    7800
gaaggcagac cagagcgtgc cgtaaaggac ccactgtgcc ccttggaaag caaggatgtc    7860
ctggtcgttc atcggaccga tttcggatgc gattttctga aaaacggcct gggtcacggc    7920
gaacattgta tccaactgtg ccggaacagt ctgcagaggc aagccggtta cactaaactg    7980
ctgaacaaag tttgggaccg tcttttcgaa gatggaaacc acatagtctt ggtagttagc    8040
ctgcccaaca attagagcaa caacgatggt gaccgtgatc acccgagtga taccgctacg    8100
ggtatcgact tcgccgcgta tgactaaaat accctgaaca ataatccaaa gagtgacaca    8160
ggcgatcaat ggcgcactca ccgcctcctg gatagtctca agcatcgagt ccaagcctgt    8220
cgtgaaggct acatcgaaga tcgtatgaat ggccgtaaac ggcgccggaa tcgtgaaatt    8280
catcgattgg acctgaactt gactggtttg tcgcataatg ttggataaaa tgagctcgca    8340
ttcggcgagg atgcgggcgg atgaacaaat cgcccagcct taggggaggg caccaaagat    8400
gacagcggtc ttttgatgct ccttgcgttg agcggccgcc tcttccgcct cgtgaaggcc    8460
ggcctgcgcg gtagtcatcg ttaataggct tgtcgcctgt acattttgaa tcattgcgtc    8520
atggatctgc ttgagaagca aaccattggt cacggttgcc tgcatgatat tgcgagatcg    8580
ggaaagctga gcagacgtat cagcattcgc cgtcaagcgt tgtccatcg tttccagatt    8640 gtcagccgca atgccagcgc tgtttgcgga accggtgatc tgcgatcgca acaggtccgc    8700
ttcagcatca ctacccacga ctgcacgatc tgtatcgctg gtgatcgcac gtgccgtggt    8760
cgacattggc attcgcggcg aaaacatttc attgtctagg tccttcgtcg aaggatactg    8820
atttttctgg ttgagcgaag tcagtagtcc agtaacgccg taggccgacg tcaacatcgt    8880
aaccatcgct atagtctgag tgagattctc cgcagtcgcg agcgcagtcg cgagcgtctc    8940
agcctccgtt gccgggtcgc taacaacaaa ctgcgcccgc gcgggctgaa tatatagaaa    9000
gctgcaggtc aaaactgttg caataagttg cgtcgtcttc atcgtttcct accttatcaa    9060
tcttctgcct cgtggtgacg ggccatgaat tcgctgagcc agccagatga gttgccttct    9120
tgtgcctcgc gtagtcgagt tgcaaagcgc accgtgttgg cacgccccga aagcacggcg    9180
acatattcac gcatatcccg cagatcaaat tcgcagatga cgcttccact ttctcgttta    9240
agaagaaact tacggctgcc gaccgtcatg tcttcacgga tcgcctgaaa ttccttttcg    9300
gtacatttca gtccatcgac ataagccgat cgatctgcgg ttggtgatgg atagaaaatc    9360
ttcgtcatac attgcgcaac caagctggct cctagcggcg attccagaac atgctctggt    9420
tgctgcgttg ccagtattag catcccgttg ttttttcgaa cggtcaggag gaatttgtcg    9480
acgacagtcg aaaatttagg gtttaacaaa taggcgcgaa actcatcgca gctcatcaca    9540
aaacggcggc cgtcgatcat ggctccaatc cgatgcagga gatatgctgc agcgggagcg    9600
catacttcct cgtattcgag aagatgcgtc atgtcgaagc cggtaatcga cggatctaac    9660
tttacttcgt caacttcgcc gtcaaatgcc cagccaagcg catggccccg gcaccagcgt    9720
tggagccgcg ctcctgcgcc ttcggcgggc ccatgcaaca aaaattcacg taaccccgcg    9780
attgaacgca tttgtggatc aaacgagagc tgacgatgga taccacggac cagacggcgg    9840
```

-continued

```
ttctcttccg gagaaatccc accccgacca tcactctcga tgagagccac gatccattcg    9900
cgcagaaaat cgtgtgaggc tgctgtgttt tctaggccac gcaacggcgc caacccgctg    9960
ggtgtgcctc tgtgaagtgc caaatatgtt cctcctgtgg cgcgaaccag caattcgcca   10020
ccccggtcct tgtcaaagaa cacgaccgta cctgcacggt cgaccatgct ctgttcgagc   10080
atggctagaa caaacatcat gagcgtcgtc ttacccctcc cgataggccc gaatattgcc   10140
gtcatgccaa catcgtgctc atgcgggata tagtcgaaag gcgttccgcc attggtacga   10200
aatcgggcaa tcgcgttgcc ccagtggcct gagctggcgc cctctggaaa gttttcgaaa   10260
gagacaaacc ctgcgaaatt gcgtgaagtg attgcgccag ggcgtgtgcg ccacttaaaa   10320
ttccccggca attgggacca ataggccgct ccataccaa taccttcttg acaaccacg    10380
gcacctgcat ccgccattcg tgtccgagcc cgcgcgcccc tgtccccaag actattgaga   10440
tcgtctgcat agacgcaaag gctcaaatga tgtgagccca taacgaattc gttgctcgca   10500
agtgcgtcct cagcctcgga taatttgccg atttgagtca cggctttatc gccggaactc   10560
agcatctggc tcgatttgag gctaagtttc gcgtgcgctt gcgggcgagt caggaacgaa   10620
aaactctgcg tgagaacaag tggaaaatcg agggatagca gcgcgttgag catgcccggc   10680
cgtgtttttg cagggtattc gcgaaacgaa tagatggatc caacgtaact gtcttttggc   10740
gttctgatct cgagtcctcg cttgccgcaa atgactctgt cggtataaat cgaagcgccg   10800
agtgagccgc tgacgaccgg aaccggtgtg aaccgaccag tcatgatcaa ccgtagcgct   10860
tcgccaattt cggtgaagag cacaccctgc ttctcgcgga tgccaagacg atgcaggcca   10920
tacgctttaa gagagccagc gacaacatgc caaagatctt ccatgttcct gatctggccc   10980
gtgagatcgt tttcccttt tccgcttagc ttggtgaacc tcctctttac cttccctaaa   11040
gccgcctgtg ggtagacaat caacgtaagg aagtgttcat tgcggaggag ttggccggag   11100
agcacgcgct gttcaaaagc ttcgttcagg ctagcggcga aaacactacg gaagtgtcgc   11160
ggcgccgatg atggcacgtc ggcatgacgt acgaggtgag catatattga cacatgatca   11220
tcagcgatat tgcgcaacag cgtgttgaac gcacgacaac gcgcattgcg catttcagtt   11280
tcctcaagct cgaatgcaac gccatcaatt ctcgcaatgg tcatgatcga tccgtcttca   11340
agaaggacga tatggtcgct gaggtggcca atataaggga gatagatctc accggatctt   11400
tcggtcgttc cactcgcgcc gagcatcaca ccattcctct ccctcgtggg ggaaccctaa   11460
ttggatttgg gctaacagta gcgcccccc aaactgcact atcaatgctt cttccgcgg    11520
tccgcaaaaa tagcaggacg acgctcgccg cattgtagtc tcgctccacg atgagccggg   11580
ctgcaaacca taacggcacg agaacgactt cgtagagcgg gttctgaacg ataacgatga   11640
caaagccggc gaacatcatg aataaccctg ccaatgtcag tggcaccca agaaacaatg    11700
cgggccgtgt ggctgcgagg taaagggtcg attcttccaa acgatcagcc atcaactacc   11760
gccagtgagc gtttggccga ggaagctcgc cccaaacatg ataacaatgc cgccgacgac   11820
gccggcaacc agcccaagcg aagcccgccc gaacatccag gagatcccga tagcgacaat   11880
gccgagaaca gcgagtgact ggccgaacgg accaaggata acgtgcata tattgttaac    11940
cattgtggcg gggtcagtgc cgccacccgc agattgcgct gcggcgggtc cggatgagga   12000
aatgctccat gcaattgcac cgcacaagct tggggcgcag ctcgatatca cgcgcatcat   12060
cgcattcgag agcgagaggc gatttagatg taaacggtat ctctcaaagc atcgcatcaa   12120
tgcgcacctc cttagtataa gtcgaataag acttgattgt cgtctgcgga tttgccgttg   12180
tcctggtgtg gcggtggcgg agcgattaaa ccgccagcgc catcctcctg cgagcggcgc   12240
```

```
tgatatgacc cccaaacatc ccacgtctct tcggatttta gcgcctcgtg atcgtctttt    12300
ggaggctcga ttaacgcggg caccagcgat tgagcagctg tttcaacttt tcgcacgtag    12360
ccgtttgcaa aaccgccgat gaaattaccg gtgttgtaag cggagatcgc ccgacgaagc    12420
gcaaattgct tctcgtcaat cgtttcgccg cctgcataac gacttttcag catgtttgca    12480
gcggcagata atgatgtgca cgcctggagc gcaccgtcag gtgtcagacc gagcatagaa    12540
aaatttcgag agtttatttg catgaggcca acatccagcg aatgccgtgc atcgagacgg    12600
tgcctgacga cttgggttgc ttggctgtga tcttgccagt gaagcgtttc gccggtcgtg    12660
ttgtcatgaa tcgctaaagg atcaaagcga ctctccacct tagctatcgc cgcaagcgta    12720
gatgtcgcaa ctgatggggc acacttgcga gcaacatggt caaactcagc agatgagagt    12780
ggcgtggcaa ggctcgacga acagaaggag accatcaagg caagagaaag cgaccccgat    12840
ctcttaagca taccttatct ccttagctcg caactaacac cgcctctccc gttggaagaa    12900
gtgcgttgtt ttatgttgaa gattatcggg agggtcggtt actcgaaaat tttcaattgc    12960
ttctttatga tttcaattga agcgagaaac ctcgcccggc gtcttggaac gcaacatgga    13020
ccgagaaccg cgcatccatg actaagcaac cggatcgacc tattcaggcc gcagttggtc    13080
aggtcaggct cagaacgaaa atgctcggcg aggttacgct gtctgtaaac ccattcgatg    13140
aacgggaagc ttccttccga ttgctcttgg caggaatatt ggcccatgcc tgcttgcgct    13200
ttgcaaatgc tcttatcgcg ttggtatcat atgccttgtc cgccagcaga aacgcactct    13260
aagcgattat ttgtaaaaat gtttcggtca tgcggcggtc atgggcttga cccgctgtca    13320
gcgcaagacg gatcggtcaa ccgtcggcat cgacaacagc gtgaatcttg gtggtcaaac    13380
cgccacggga acgtcccata cagccatcgt cttgatcccg ctgtttcccg tcgccgcatg    13440
ttggtggacg cggacacagg aactgtcaat catgacgaca ttctatcgaa agccttggaa    13500
atcacactca gaatatgatc ccagacgtct gcctcacgcc atcgtacaaa gcgattgtag    13560
caggttgtac aggaaccgta tcgatcagga acgtctgccc agggcgggcc cgtccggaag    13620
cgccacaaga tgacattgat cacccgcgtc aacgcgcggc acgcgacgcg gcttatttgg    13680
gaacaaagga ctgaacaaca gtccattcga aatcggtgac atcaaagcgg ggacgggtta    13740
tcagtggcct ccaagtcaag cctcaatgaa tcaaaatcag accgatttgc aaacctgatt    13800
tatgagtgtg cggcctaaat gatgaaatcg tccttctaga tcgcctccgt ggtgtagcaa    13860
cacctcgcag tatcgccgtg ctgaccttgg ccagggaatt gactggcaag ggtgctttca    13920
catgaccgct cttttggccg cgatagatga tttcgttgct gctttgggca cgtagaagga    13980
gagaagtcat atcggagaaa ttcctcctgg cgcgagagcc tgctctatcg cgacggcatc    14040
ccactgtcgg gaacagaccg gatcattcac gaggcgaaag tcgtcaacac atgcgttata    14100
ggcatcttcc cttgaaggat gatcttgttg ctgccaatct ggaggtgcgg cagccgcagg    14160
cagatgcgat ctcagcgcaa cttgcggcaa aacatctcac tcacctgaaa accactagcg    14220
agtctcgcga tcagacgaag gccttttact taacgacaca atatccgatg tctgcatcac    14280
aggcgtcgct atcccagtca atactaaagc ggtgcaggaa ctaaagatta ctgatgactt    14340
aggcgtgcca cgaggcctga gacgacgcgc gtagacagtt ttttgaaatc attatcaaag    14400
tgatggcctc cgctgaagcc tatcacctct gcgccggtct gtcggagaga tgggcaagca    14460
ttattacggt cttcgcgccc gtacatgcat tggacgattg cagggtcaat ggatctgaga    14520
tcatccagag gattgccgcc cttaccttcc gtttcgagtt ggagccagcc cctaaatgag    14580
acgacatagt cgacttgatg tgacaatgcc aagagagaga tttgcttaac ccgattttt     14640
```

```
tgctcaagcg taagcctatt gaagcttgcc ggcatgacgt ccgcgccgaa agaatatcct   14700
acaagtaaaa cattctgcac accgaaatgc ttggtgtaga catcgattat gtgaccaaga   14760
tccttagcag tttcgcttgg ggaccgctcc gaccagaaat accgaagtga actgacgcca   14820
atgacaggaa tcccttccgt ctgcagatag gtaccatcga tagatctgct gcctcgcgcg   14880
tttcggtgat gacggtgaaa acctctgaca catgcagctc ccggagacgg tcacagcttg   14940
tctgtaagcg gatgccggga gcagacaagc ccgtcagggc gcgtcagcgg gtgttggcgg   15000 gtgtcgggc gcagccatga cccagtcacg tagcgatagc ggagtgtata ctggcttaac    15060
tatgcggcat cagagcagat tgtactgaga gtgcaccata tgcggtgtga aataccgcac   15120
agatgcgtaa ggagaaaata ccgcatcagg cgctcttccg cttcctcgct cactgactcg   15180
ctgcgctcgg tcgttcggct gcggcgagcg gtatcagctc actcaaaggc ggtaatacgg   15240
ttatccacag aatcagggga taacgcagga agaacatgt gagcaaaagg ccagcaaaag    15300
gccaggaacc gtaaaaaggc cgcgttgctg gcgtttttcc ataggctccg ccccctgac    15360 gagcatcaca aaaatcgacg ctcaagtcag aggtggcgaa acccgacagg actataaaga   15420
taccaggcgt ttcccctgg aagctccctc gtgcgctctc ctgttccgac cctgccgctt    15480
accggatacc tgtccgcctt tctccctcg ggaagcgtgg cgctttctca tagctcacgc    15540
tgtaggtatc tcagttcggt gtaggtcgtt cgctccaagc tgggctgtgt gcacgaaccc   15600
cccgttcagc ccgaccgctg cgccttatcc ggtaactatc gtcttgagtc aacccggta    15660 agacacgact tatcgccact ggcagcagcc actggtaaca ggattagcag agcgaggtat   15720
gtaggcggtg ctacagagtt cttgaagtgg tggcctaact acggctacac tagaaggaca   15780
gtatttggta tctgcgctct gctgaagcca gttaccttcg gaaaaagagt ggtagctct    15840 tgatccggca acaaaccac cgctggtagc ggtggttttt ttgtttgcaa gcagcagatt    15900
acgcgcagaa aaaaggatc tcaagaagat cctttgatct tttctacggg gtctgacgct    15960
cagtggaacg aaaactcacg ttaagggatt ttggtcatga gattatcaaa aaggatcttc   16020
acctagatcc ttttaaatta aaaatgaagt tttaaatcaa tctaaagtat atatgagtaa   16080
acttggtctg acagttacca atgcttaatc agtgaggcac ctatctcagc gatctgtcta   16140
tttcgttcat ccatagttgc ctgactcccc gtcgtgtaga taactacgat acgggagggc   16200
ttaccatctg gccccagtgc tgcaatgata ccgcgagacc cacgctcacc ggctccagat   16260
ttatcagcaa taaaccagcc agccggaagg gccgagcgca gaagtggtcc tgcaactta    16320 tccgcctcca tccagtctat taattgttgc cgggaagcta gagtaagtag ttcgccagtt   16380
aatagtttgc gcaacgttgt tgccattgct gcagggggg ggggggggg gttccattgt     16440 tcattccacg gacaaaaaca gagaaaggaa acgacagagg ccaaaaagct cgctttcagc   16500
acctgtcgtt tccttctctt tcagagggta ttttaaataa aaacattaag ttatgacgaa   16560
gaagaacgga aacgccttaa accggaaaat tttcataaat agcgaaaacc cgcgaggtcg   16620
ccgccccgta acctgtcgga tcaccggaaa ggacccgtaa agtgataatg attatcatct   16680
acatatcaca acgtgcgtgg aggccatcaa accacgtcaa ataatcaatt atgacgcagg   16740
tatcgtatta attgatctgc atcaacttaa cgtaaaaaca acttcagaca atacaaatca   16800
gcgacactga atacggggca acctcatgtc cccccccccc ccccccctgc aggcatcgtg   16860
gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
```

```
cttactgtca tgccatccgt aagatgcttt tctgtgactg gtgagtactc aaccaagtca   17100
ttctgagaat agtgtatgcg gcgaccgagt tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa acaggaagg    17340 caaaatgccg caaaaaggg aataagggcg cacggaaat gttgaatact catactcttc     17400 cttttcaat attattgaag catttatcag ggttattgtc tcatgagcgg atacatattt    17460
gaatgtattt agaaaaataa acaaataggg gttccgcgca catttccccg aaaagtgcca   17520
cctgacgtct aagaaaccat tattatcatg acattaacct ataaaaatag gcgtatcacg   17580 aggcccttc gtcttcaaga attcggagct tttgccattc tcaccggatt cagtcgtcac    17640
tcatggtgat ttctcacttg ataaccttat ttttgacgag gggaaattaa taggttgtat   17700
tgatgttgga cgagtcggaa tcgcagaccg ataccaggat cttgccatcc tatggaactg   17760
cctcggtgag ttttctcctt cattacagaa acggctttt caaaaatatg gtattgataa    17820
tcctgatatg aataaattgc agtttcattt gatgctcgat gagttttctt aatcagaatt   17880
ggttaattgg ttgtaacact ggcagagcat tacgctgact tgacgggacg gcggctttgt   17940
tgaataaatc gaacttttgc tgagttgaag gatcagatca cgcatcttcc cgacaacgca   18000
gaccgttccg tggcaaagca aaagttcaaa atcaccaact ggtccaccta caacaaagct   18060
ctcatcaacc gtggctccct cactttctgg ctggatgatg gggcgattca ggcctggtat   18120
gagtcagcaa caccttcttc acgaggcaga cctcagcgcc agaaggccgc cagagaggcc   18180
gagcgcggcc gtgaggcttg gacgctaggg cagggcatga aaagcccgt agcgggctgc    18240 tacgggcgtc tgacgcggtg gaaaggggga ggggatgttg tctacatggc tctgctgtag   18300
tgagtgggtt gcgctccggc agcggtcctg atcaatcgtc acctttctc ggtccttcaa    18360 cgttcctgac aacgagcctc cttttcgcca atccatcgac aatcaccgcg agtccctgct   18420
cgaacgctgc gtccggaccg gcttcgtcga aggcgtctat cgcggcccgc aacagcggcg   18480
agagcggagc ctgttcaacg gtgccgccgc gctcgccggc atcgctgtcg ccggcctgct   18540
cctcaagcac ggccccaaca gtgaagtagc tgattgtcat cagcgcattg acggcgtccc   18600
cggccgaaaa accgcctcg cagaggaagc gaagctgcgc gtcggccgtt tccatctgcg    18660
gtgcgcccgg tcgcgtgccg gcatggatgc gcgcgccatc gcggtaggcg agcagcgcct   18720
gcctgaagct gcgggcattc ccgatcagaa atgagcgcca gtcgtcgtcg gctctcggca   18780
ccgaatgcgt atgattctcc gccagcatgg cttcggccag tgcgtcgagc agcgcccgct   18840
tgttcctgaa gtgccagtaa agcgccggct gctgaacccc caaccgttcc gccagtttgc   18900
gtgtcgtcag accgtctacg ccgacctcgt tcaacaggtc cagggcggca cggatcactg   18960
tattcggctg caactttgtc atgcttgaca ctttatcact gataaacata atatgtccac   19020
caacttatca gtgataaaga atccgcgcgt tcaatcggac cagcggaggc tggtccggag   19080
gccagacgtg aaacccaaca taccctgat cgtaattctg agcactgtcg cgctcgacgc    19140
tgtcggcatc ggcctgatta tgccggtgct gccgggcctc ctgcgcgatc tggttcactc   19200
gaacgacgtc accgcccact atggcattct gctggcgctg tatgcgttgg tgcaatttgc   19260
ctgcgcacct gtgctgggcg cgctgtcgga tcgtttcggg cggcggccaa tcttgctcgt   19320
ctcgctggcc ggcgccactg tcgactacgc catcatggcg acagcgcctt tcctttgggt   19380
tctctatatc gggcggatcg tggccggcat caccggggcg actggggcgg tagccggcgc   19440
```

```
ttatattgcc gatatcactg atggcgatga gcgcgcgcgg cacttcggct tcatgagcgc   19500
ctgtttcggg ttcgggatgg tcgcgggacc tgtgctcggt gggctgatgg gcggtttctc   19560
cccccacgct ccgttcttcg ccgcggcagc cttgaacggc ctcaatttcc tgacgggctg   19620
tttccttttg ccggagtcgc acaaaggcga acgccggccg ttacgccggg aggctctcaa   19680
cccgctcgct tcgttccggt gggcccgggg catgaccgtc gtcgccgccc tgatggcggt   19740
cttcttcatc atgcaacttg tcggacaggt gccggccgcg cttgggtca ttttcggcga   19800
ggatcgcttt cactgggacg cgaccacgat cggcatttcg cttgccgcat ttggcattct   19860
gcattcactc gcccaggcaa tgatcaccgg ccctgtagcc gcccggctcg gcgaaaggcg   19920
ggcactcatg ctcggaatga ttgccgacgg cacaggctac atcctgcttg ccttcgcgac   19980
acggggatgg atggcgttcc cgatcatggt cctgcttgct tcgggtggca tcggaatgcc   20040
ggcgctgcaa gcaatgttgt ccaggcaggt ggatgaggaa cgtcaggggc agctgcaagg   20100
ctcactggcg gcgctcacca gcctgacctc gatcgtcgga cccctcctct tcacggcgat   20160
ctatgcggct tctataacaa cgtggaacgg gtgggcatgg attgcaggcg ctgccctcta   20220
cttgctctgc ctgccggcgc tgcgtcgcgg gctttggagc ggcgcagggc aacgagccga   20280
tcgctgatcg tggaaacgat aggcctatgc catgcgggtc aaggcgactt ccggcaagct   20340
atacgcgccc taggagtgcg gttggaacgt tgcccagcc agatactccc gatcacgagc   20400
aggacgccga tgatttgaag cgcactcagc gtctgatcca agaacaacca tcctagcaac   20460
acggcggtcc ccgggctgag aaagcccagt aaggaaacaa ctgtaggttc gagtcgcgag   20520
atcccccgga accaaaggaa gtaggttaaa cccgctccga tcaggccgag ccacgccagg   20580
ccgagaacat tggttcctgt aggcatcggg attggcggat caaacactaa agctactgga   20640
acgagcagaa gtcctccggc cgccagttgc caggcggtaa aggtgagcag aggcacggga   20700
ggttgccact tgcgggtcag cacggttccg aacgccatgg aaaccgcccc cgccaggccc   20760
gctgcgacgc cgacaggatc tagcgctgcg tttggtgtca acaccaacag cgccacgccc   20820
gcagttccgc aaatagcccc caggaccgcc atcaatcgta tcgggctacc tagcagagcg   20880
gcagagatga acacgaccat cagcggctgc acagcgccta ccgtcgccgc gaccccgccc   20940
ggcaggcggt agaccgaaat aaacaacaag ctccagaata gcgaaatatt aagtgcgccg   21000
aggatgaaga tgcgcatcca ccagattccc gttggaatct gtcggacgat catcacgagc   21060
aataaacccg ccggcaacgc ccgcagcagc ataccggcga ccctcggcc tcgctgttcg   21120
ggctccacga aaacgccgga cagatgcgcc ttgtgagcgt ccttgggcc gtcctcctgt   21180
ttgaagaccg acagcccaat gatctcgccg tcgatgtagg cgccgaatgc cacggcatct   21240
cgcaaccgtt cagcgaacgc ctccatgggc tttttctcct cgtgctcgta acggacccg   21300
aacatctctg gagctttctt cagggccgac aatcggatct cgcggaaatc ctgcacgtcg   21360
gccgctccaa gccgtcgaat ctgagcctta atcacaattg tcaattttaa tcctctgttt   21420
atcggcagtt cgtagagcgc gccgtgcgtc ccgagcgata ctgagcgaag caagtgcgtc   21480
gagcagtgcc cgcttgttcc tgaaatgcca gtaaagcgct ggctgctgaa cccccagccg   21540
gaactgaccc cacaaggccc tagcgtttgc aatgcaccag gtcatcattg acccaggcgt   21600
gttccaccag gccgctgcct cgcaactctt cgcaggcttc gccgacctgc tcgcgccact   21660
tcttcacgcg ggtggaatcc gatccgcaca tgaggcggaa ggtttccagc ttgagcgggt   21720
acggctcccg gtgcgagctg aaatagtcga acatccgtcg ggccgtcggc gacagcttgc   21780
ggtacttctc ccatatgaat ttcgtgtagt ggtcgccagc aaacagcacg acgatttcct   21840
```

```
cgtcgatcag gacctggcaa cgggacgttt tcttgccacg gtccaggacg cggaagcggt   21900
gcagcagcga caccgattcc aggtgcccaa cgcggtcgga cgtgaagccc atcgccgtcg   21960
cctgtaggcg cgacaggcat tcctcggcct tcgtgtaata ccggccattg atcgaccagc   22020
ccaggtcctg gcaaagctcg tagaacgtga aggtgatcgg ctcgccgata ggggtgcgct   22080
tcgcgtactc caacacctgc tgccacacca gttcgtcatc gtcggcccgc agctcgacgc   22140
cggtgtaggt gatcttcacg tccttgttga cgtggaaaat gaccttgttt tgcagcgcct   22200
cgcgcgggat tttcttgttg cgcgtggtga acagggcaga gcgggccgtg tcgtttggca   22260
tcgctcgcat cgtgtccggc cacggcgcaa tatcgaacaa ggaaagctgc atttccttga   22320
tctgctgctt cgtgtgtttc agcaacgcgg cctgcttggc ctcgctgacc tgttttgcca   22380
ggtcctcgcc ggcggttttt cgcttcttgg tcgtcatagt tcctcgcgtg tcgatggtca   22440
tcgacttcgc caaacctgcc gcctcctgtt cgagacgacg cgaacgctcc acggcggccg   22500
atggcgcggg cagggcaggg ggagccagtt gcacgctgtc gcgctcgatc ttggccgtag   22560
cttgctggac catcgagccg acggactgga aggtttcgcg gggcgcacgc atgacggtgc   22620
ggcttgcgat ggtttcggca tcctcggcgg aaaaccccgc gtcgatcagt tcttgcctgt   22680
atgccttccg gtcaaacgtc cgattcattc accctccttg cgggattgcc ccgactcacg   22740
ccggggcaat gtgcccttat tcctgatttg acccgcctgg tgccttggtg tccagataat   22800
ccaccttatc ggcaatgaag tcggtcccgt agaccgtctg gccgtccttc tcgtacttgg   22860
tattccgaat cttgccctgc acgaatacca gcgaccccct tgcccaaatac ttgccgtggg   22920 cctcggcctg agagccaaaa cacttgatgc ggaagaagtc ggtgcgctcc tgcttgtcgc   22980
cggcatcgtt gcgccactct tcattaaccg ctatatcgaa aattgcttgc ggcttgttag   23040
aattgccatg acgtacctcg gtgtcacggg taagattacc gataaactgg aactgattat   23100
ggctcatatc gaaagtctcc ttgagaaagg agactctagt ttagctaaac attggttccg   23160
ctgtcaagaa ctttagcggc taaaattttg cgggccgcga ccaaaggtgc gaggggcggc   23220
ttccgctgtg tacaaccaga tattttcac caacatcctt cgtctgctcg atgagcgggg   23280
catgacgaaa catgagctgt cggagagggc aggggtttca atttcgtttt tatcagactt   23340
aaccaacggt aaggccaacc cctcgttgaa ggtgatggag gccattgccg acgccctgga   23400
aactccccta cctcttctcc tggagtccac cgacctcgac cgcgaggcac tcgcggagat   23460
tgcgggtcat cctttcaaga gcagcgtgcc gcccggatac gaacgcatca gtgtggtttt   23520
gccgtcacat aaggcgttta tcgtaaagaa atggggcgac gacacccgaa aaaagctgcg   23580
tggaaggctc tgacgccaag ggttagggct tgcacttcct tctttagccg ctaaaacggc   23640
cccttctctg cgggccgtcg gctcgcgcat catatcgaca tcctcaacgg aagccgtgcc   23700
gcgaatggca tcgggcgggt gcgctttgac agttgttttc tatcagaacc cctacgtcgt   23760
gcggttcgat tagctgtttg tcttgcaggc taaacacttt cggtatatcg tttgcctgtg   23820
cgataatgtt gctaatgatt tgttgcgtag gggttactga aaagtgagcg ggaaagaaga   23880
gtttcagacc atcaaggagc gggccaagcg caagctggaa cgcgacatgg gtgcggacct   23940
gttggccgcg ctcaacgacc cgaaaaccgt tgaagtcatg ctcaacgcgg acggcaaggt   24000
gtggcacgaa cgccttggcg agccgatgcg gtacatctgc gacatgcggc ccagccagtc   24060
gcaggcgatt atagaaacgg tggccggatt ccacggcaaa gaggtcacgc ggcattcgcc   24120
catcctggaa ggcgagttcc ccttggatgg cagccgcttt gccggccaat tgccgccggt   24180
cgtggccgcg ccaaccttttg cgatccgcaa gcgcgcggtc gccatcttca cgctggaaca   24240
```

```
gtacgtcgag gcgggcatca tgacccgcga gcaatacgag gtcattaaaa gcgccgtcgc   24300
ggcgcatcga aacatcctcg tcattggcgg tactggctcg gcaagacca cgctcgtcaa    24360 cgcgatcatc aatgaaatgg tcgccttcaa cccgtctgag cgcgtcgtca tcatcgagga   24420
caccggcgaa atccagtgcg ccgcagagaa cgccgtccaa taccacacca gcatcgacgt   24480
ctcgatgacg ctgctgctca agacaacgct gcgtatgcgc cccgaccgca tcctggtcgg   24540
tgaggtacgt ggccccgaag cccttgatct gttgatggcc tggaacaccg gcatgaagg    24600 aggtgccgcc accctgcacg caaacaaccc caaagcgggc ctgagccggc tcgccatgct   24660
tatcagcatg cacccggatt caccgaaacc cattgagccg ctgattggcg aggcggttca   24720
tgtggtcgtc catatcgcca ggaccccctag cggccgtcga gtgcaagaaa ttctcgaagt   24780
tcttggttac gagaacggcc agtacatcac caaaaccctg taaggagtat ttccaatgac   24840
aacggctgtt ccgttccgtc tgaccatgaa tcgcggcatt ttgttctacc ttgccgtgtt   24900
cttcgttctc gctctcgcgt tatccgcgca tccggcgatg gcctcggaag caccggcgg    24960 cagcttgcca tatgagagct ggctgacgaa cctgcgcaac tccgtaaccg gcccggtggc   25020
cttcgcgctg tccatcatcg gcatcgtcgt cgccggcggc gtgctgatct tcggcggcga   25080
actcaacgcc ttcttccgaa ccctgatctt cctggttctg gtgatggcgc tgctggtcgg   25140
cgcgcagaac gtgatgagca ccttcttcgg tcgtggtgcc gaaatcgcgg ccctcggcaa   25200
cggggcgctg caccaggtgc aagtcgcggc ggcggatgcc gtgcgtgcgg tagcggctgg   25260
acggctcgcc taatcatggc tctgcgcacg atccccatcc gtcgcgcagg caaccgagaa   25320
aacctgttca tgggtggtga tcgtgaactg gtgatgttct cgggcctgat ggcgtttgcg   25380
ctgattttca gcgcccaaga gctgcgggcc accgtggtcg gtctgatcct gtggttcggg   25440
gcgctctatg cgttccgaat catggcgaag gccgatccga agatgcggtt cgtgtacctg   25500
cgtcaccgcc ggtacaagcc gtattacccg gcccgctcga ccccgttccg cgagaacacc   25560
aatagccaag ggaagcaata ccgatgatcc aagcaattgc gattgcaatc gcgggcctcg   25620
gcgcgcttct gttgttcatc ctctttgccc gcatccgcgc ggtcgatgcc gaactgaaac   25680
tgaaaaagca tcgttccaag gacgccggcc tggccgatct gctcaactac gccgctgtcg   25740
tcgatgacgg cgtaatcgtg ggcaagaacg gcagctttat ggctgcctgg ctgtacaagg   25800
gcgatgacaa cgcaagcagc accgaccagc agcgcgaagt agtgtccgcc cgcatcaacc   25860
aggccctcgc gggcctggga agtgggtgga tgatccatgt ggacgccgtg cggcgtcctg   25920
ctccgaacta cgcggagcgg ggcctgtcgg cgttccctga ccgtctgacg gcagcgattg   25980
aagaagagcg ctcggtcttg ccttgctcgt cggtgatgta cttcaccagc tccgcgaagt   26040
cgctcttctt gatggagcgc atggggacgt gcttggcaat cacgcgcacc cccggccgt    26100 tttagcggct aaaaaagtca tggctctgcc ctcgggcgga ccacgcccat catgaccttg   26160
ccaagctcgt cctgcttctc ttcgatcttc gccagcaggg cgaggatcgt ggcatcaccg   26220
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
ttgtagccct ggccgacggc cagcaggtag gccgacaggc tcatgccggc cgccgccgcc   26400 tttcctcaa tcgctcttcg ttcgtctgga aggcagtaca ccttgatagg tgggctgccc    26460
ttcctggttg gcttggtttc atcagccatc cgcttgccct catctgttac gccggcggta   26520
gccggccagc ctcgcagagc aggattcccg ttgagcaccg ccaggtgcga ataagggaca   26580
gtgaagaagg aacacccgct cgcgggtggg cctacttcac ctatcctgcc cggctgacgc   26640
```

```
cgttggatac accaaggaaa gtctacacga acccctttggc aaaatcctgt atatcgtgcg   26700
aaaaaggatg gatataccga aaaaatcgct ataatgaccc cgaagcaggg ttatgcagcg   26760
gaaaagcgct gcttccctgc tgttttgtgg aatatctacc gactggaaac aggcaaatgc   26820
aggaaattac tgaactgagg ggacaggcga gagacgatgc caaagagcta caccgacgag   26880
ctggccgagt gggttgaatc ccgcgcggcc aagaagcgcc ggcgtgatga ggctgcggtt   26940
gcgttcctgg cggtgagggc ggatgtcgag gcggcgttag cgtccggcta tgcgctcgtc   27000
accatttggg agcacatgcg ggaaacgggg aaggtcaagt tctcctacga gacgttccgc   27060
tcgcacgcca ggcggcacat caaggccaag cccgccgatg tgcccgcacc gcaggccaag   27120
gctgcggaac ccgcgccggc acccaagacg ccggagccac ggcggccgaa gcaggggggc   27180
aaggctgaaa agccggcccc cgctgcggcc ccgaccggct tcaccttcaa cccaacaccg   27240
gacaaaaagg atctactgta atggcgaaaa ttcacatggt tttgcagggc aagggcgggg   27300
tcggcaagtc ggccatcgcc gcgatcattg cgcagtacaa gatggacaag gggcagacac   27360
ccttgtgcat cgacaccgac ccggtgaacg cgacgttcga gggctacaag gccctgaacg   27420
tccgccggct gaacatcatg gccggcgacg aaattaactc gcgcaacttc gacaccctgg   27480
tcgagctgat tgcgccgacc aaggatgacg tggtgatcga caacggtgcc agctcgttcg   27540
tgcctctgtc gcattacctc atcagcaacc aggtgccggc tctgctgcaa gaaatggggc   27600
atgagctggt catccatacc gtcgtcaccg gcggccaggc tctcctggac acggtgagcg   27660
gcttcgccca gctcgccagc cagttcccgg ccgaagcgct tttcgtggtc tggctgaacc   27720
cgtattgggg gcctatcgag catgagggca agagctttga gcagatgaag gcgtacacgg   27780
ccaacaaggc ccgcgtgtcg tccatcatcc agattccggc cctcaaggaa gaaacctacg   27840
gccgcgattt cagcgacatg ctgcaagagc ggctgacgtt cgaccaggcg ctggccgatg   27900
aatcgctcac gatcatgacg cggcaacgcc tcaagatcgt gcggcgcggc ctgtttgaac   27960
agctcgacgc ggcggccgtg ctatgagcga ccagattgaa gagctgatcc gggagattgc   28020
ggccaagcac ggcatcgccg tcggccgcga cgacccggtg ctgatcctgc ataccatcaa   28080
cgcccggctc atggccgaca gtgcggccaa gcaagaggaa atccttgccg cgttcaagga   28140
agagctggaa gggatcgccc atcgttgggg cgaggacgcc aaggccaaag cggagcggat   28200
gctgaacgcg gccctggcgg ccagcaagga cgcaatggcg aaggtaatga aggacagcgc   28260
cgcgcaggcg gccgaagcga tccgcaggga aatcgacgac ggccttggcc gccagctcgc   28320
ggccaaggtc gcggacgcgc ggcgcgtggc gatgatgaac atgatcgccg gcggcatggt   28380
gttgttcgcg gccgccctgg tggtgtgggc ctcgttatga atcgcagagg cgcagatgaa   28440
aaagcccggc gttgccgggc tttgtttttg cgttagctgg gcttgtttga caggcccaag   28500
ctctgactgc gcccgcgctc gcgctcctgg gcctgtttct tctcctgctc ctgcttgcgc   28560
atcagggcct ggtgccgtcg ggctgcttca cgcatcgaat cccagtcgcc ggccagctcg   28620
ggatgctccg cgcgcatctt gcgcgtcgcc agttcctcga tcttgggcgc gtgaatgccc   28680
atgccttcct tgatttcgcg caccatgtcc agccgcgtgt gcagggtctg caagcgggct   28740
tgctgttggg cctgctgctg ctgccaggcg gcctttgtac gcggcaggga cagcaagccg   28800
ggggcattgg actgtagctg ctgcaaacgc ggcctgctgac ggtctacgag ctgttctagg   28860
cggtcctcga tgcgctccac ctggtcatgc tttgcctgca cgtagagcgc aagggtctgc   28920
tggtaggtct gctcgatggg cgcggattct aagagggcct gctgttccgt tcggcctcc   28980
tgggccgcct gtagcaaatc ctcgccgctg ttgccgctgg actgctttac tgccggggac   29040
```

```
tgctgttgcc ctgctcgcgc cgtcgtcgca gttcggcttg cccccactcg attgactgct  29100
tcatttcgag ccgcagcgat gcgatctcgg attgcgtcaa cggacggggc agcgcggagg  29160
tgtccggctt ctccttgggt gagtcggtcg atgccatagc caaaggtttc cttccaaaat  29220
gcgtccattg ctggaccgtg tttctcattg atgcccgcaa gcatcttcgg cttgaccgcc  29280
aggtcaagcg cgccttcatg ggcggtcatg acggacgccg ccatgacctt gccgccgttg  29340
ttctcgatgt agccgcgtaa tgaggcaatg gtgccgccca tcgtcagcgt gtcatcgaca  29400
acgatgtact tctggccggg gatcacctcc ccctcgaaag tcgggttgaa cgccaggcga  29460
tgatctgaac cggctccggt tcgggcgacc ttctcccgct gcacaatgtc cgtttcgacc  29520
tcaaggccaa ggcggtcggc cagaacgacc gccatcatgg ccggaatctt gttgttcccc  29580
gccgcctcga cggcgaggac tggaacgatg cggggcttgt cgtcgccgat cagcgtcttg  29640
agctgggcaa cagtgtcgtc cgaaatcagg cgctcgacca aattaagcgc cgcttccgcg  29700
tcgccctgct tcgcagcctg gtattcaggc tcgttggtca agaaccaag gtcgccgttg  29760
cgaaccacct tcgggaagtc tccccacggt gcgcgctcgg ctctgctgta gctgctcaag  29820
acgcctccct ttttagccgc taaaactcta cgagtgcgc ccgcgactca acttgacgct  29880
ttcggcactt acctgtgcct tgccacttgc gtcataggtg atgcttttcg cactcccgat  29940
ttcaggtact ttatcgaaat ctgaccgggc gtgcattaca aagttcttcc ccacctgttg  30000
gtaaatgctg ccgctatctg cgtggacgat gctgccgtcg tggcgctgcg acttatcggc  30060
cttttgggcc atatagatgt tgtaaatgcc aggtttcagg gccccggctt tatctacctt  30120
ctggttcgtc catgcgcctt ggttctcggt ctggacaatt ctttgcccat tcatgaccag  30180
gaggcggtgt ttcattgggt gactcctgac ggttgcctct ggtgttaaac gtgtcctggt  30240
cgcttgccgg ctaaaaaaaa gccgacctcg gcagttcgag gccggctttc cctagagccg  30300
ggcgcgtcaa ggttgttcca tctatttag tgaactgcgt tcgatttatc agttactttc  30360
ctcccgcttt gtgtttcctc ccactcgttt ccgcgtctag ccgacccctc aacatagcgg  30420
cctcttcttg ggctgccttt gcctcttgcc gcgcttcgtc acgctcggct tgcaccgtcg  30480
taaagcgctc ggcctgcctg gccgcctctt gcgccgccaa cttcctttgc tcctggtggg  30540
cctcggcgtc ggcctgcgcc ttcgcttttca ccgctgccaa ctccgtgcgc aaactctccg  30600
cttcgcgcct ggtggcgtcg cgctcgccgc gaagcgcctg catttcctgg ttggccgcgt  30660
ccagggtctt gcggctctct tctttgaatg cgcgggcgtc ctggtgagcg tagtccagct  30720
cggcgcgcag ctcctgcgct cgacgctcca cctcgtcggc ccgctgcgtc gccagcgcgg  30780
cccgctgctc ggctcctgcc agggcggtgc gtgcttcggc cagggcttgc cgctggcgtg  30840
cggccagctc ggccgcctcg gcggcctgct gctctagcaa tgtaacgcgc gcctgggctt  30900
cttccagctc gcgggcctgc gcctcgaagg cgtcggccag ctccccgcgc acggcttcca  30960
actcgttgcg ctcacgatcc cagccggctt gcgctgcctg caacgattca ttggcaaggg  31020
cctgggcggc ttgccagagg gcggccacgg cctggttgcc ggcctgctgc accgcgtccg  31080
gcacctggac tgccagcggg gcggcctgcg ccgtgcgctg gcgtcgccat cgcgcatgc  31140
cggcgctggc gtcgttcatg ttgacgcggg cggccttacg cactgcatcc acggtcggga  31200
agttctcccg gtcgccttgc tcgaacagct cgtccgcagc cgcaaaaatg cggtcgcgcg  31260
tctctttgtt cagttccatg ttggctccgg taattggtaa gaataataat actcttacct  31320
accttatcag cgcaagagtt tagctgaaca gttctcgact taacggcagg ttttttagcg  31380
gctgaagggc aggcaaaaaa agccccgcac ggtcggcggg ggcaaagggt cagcgggaag  31440
```

```
gggattagcg ggcgtcgggc ttcttcatgc gtcggggccg cgcttcttgg gatggagcac    31500
gacgaagcgc gcacgcgcat cgtcctcggc cctatcggcc cgcgtcgcgg tcaggaactt    31560
gtcgcgcgct aggtcctccc tggtgggcac caggggcatg aactcggcct gctcgatgta    31620
ggtccactcc atgaccgcat cgcagtcgag gccgcgttcc ttcaccgtct cttgcaggtc    31680
gcggtacgcc cgctcgttga gcggctggta acgggccaat tggtcgtaaa tggctgtcgg    31740
ccatgagcgg cctttcctgt tgagccagca gccgacgacg aagccggcaa tgcaggcccc    31800
tggcacaacc aggccgacgc cgggggcagg ggatggcagc agctcgccaa ccaggaaccc    31860
cgccgcgatg atgccgatgc cggtcaacca gcccttgaaa ctatccggcc ccgaaacacc    31920
cctgcgcatt gcctggatgc tgcgccggat agcttgcaac atcaggagcc gtttcttttg    31980
ttcgtcagtc atggtccgcc ctcaccagtt gttcgtatcg gtgtcggacg aactgaaatc    32040
gcaagagctg ccggtatcgg tccagccgct gtccgtgtcg ctgctgccga agcacggcga    32100
ggggtccgcg aacgccgcag acggcgtatc cggccgcagc gcatcgccca gcatggcccc    32160
ggtcagcgag ccgccggcca ggtagcccag catggtgctg ttggtcgccc cggccaccag    32220
ggccgacgtg acgaaatcgc cgtcattccc tctggattgt tcgctgctcg gcggggcagt    32280
gcgccgcgcc ggcggcgtcg tggatggctc gggttggctg gcctgcgacg gccggcgaaa    32340
ggtgcgcagc agctcgttat cgaccggctg cggcgtcggg gccgccgcct tgcgctgcgg    32400
tcggtgttcc ttcttcggct cgcgcagctt gaacagcatg atcgcggaaa ccagcagcaa    32460
cgccgcgcct acgcctcccg cgatgtagaa cagcatcgga ttcattcttc ggtcctcctt    32520
gtagcggaac cgttgtctgt gcggcgcggg tggcccgcgc cgctgtcttt ggggatcagc    32580
cctcgatgag cgcgaccagt ttcacgtcgg caaggttcgc ctcgaactcc tggccgtcgt    32640
cctcgtactt caaccaggca tagccttccg ccggcggccg acggttgagg ataaggcggg    32700
cagggcgctc gtcgtgctcg acctggacga tggcctttt cagcttgtcc gggtccggct    32760
ccttcgcgcc ctttccttg gcgtccttac cgtcctggtc gccgtcctcg ccgtcctggc    32820
cgtcgccggc ctccgcgtca cgctcggcat cagtctggcc gttgaaggca tcgacggtgt    32880
tgggatcgcg gcccttctcg tccaggaact cgcgcagcag cttgaccgtg ccgcgcgtga    32940
tttcctgggt gtcgtcgtca agccacgcct cgacttcctc cgggcgcttc ttgaaggccg    33000
tcaccagctc gttcaccacg gtcacgtcgc gcacgcggcc ggtgttgaac gcatcggcga    33060
tcttctccgg caggtccagc agcgtgacgt gctgggtgat gaacgccggc gacttgccga    33120
tttccttggc gatatcgcct ttcttcttgc ccttcgccag ctcgcggcca atgaagtcgg    33180
caatttcgcg cggggtcagc tcgttgcgtt gcaggttctc gataacctgg tcggcttcgt    33240
tgtagtcgtt gtcgatgaac gccgggatgg acttcttgcc ggcccacttc gagccacggt    33300
agcggcgggc gccgtgattg atgatatagc ggcccggctg ctcctggttc tcgcgcaccg    33360
aaatgggtga cttcaccccg cgctctttga tcgtggcacc gatttccgcg atgctctccg    33420
gggaaaagcc ggggttgtcg gccgtccgcg gctgatgcgg atcttcgtcg atcaggtcca    33480
ggtccagctc gatagggccg gaaccgcct gagacgccgc aggagcgtcc aggaggctcg    33540
acaggtcgcc gatgctatcc aaccccaggc cggacggctg cgccgcgcct gcggcttcct    33600
gagcggccgc agcggtgttt ttcttggtgg tcttggcttg agccgcagtc attgggaaat    33660
ctccatcttc gtgaacacgt aatcagccag ggcgcgaacc tctttcgatg ccttgcgcgc    33720
ggccgttttc ttgatcttcc agaccggcac accggatgcg agggcatcgg cgatgctgct    33780
gcgcaggcca acggtggccg gaatcatcat cttggggtac gcggccagca gctcggcttg    33840
```

```
gtggcgcgcg tggcgcggat tccgcgcatc gaccttgctg ggcaccatgc caaggaattg   33900
cagcttggcg ttcttctggc gcacgttcgc aatggtcgtg accatcttct tgatgccctg   33960
gatgctgtac gcctcaagct cgatggggga cagcacatag tcggccgcga agagggcggc   34020
cgccaggccg acgccaaggg tcgggccgt gtcgatcagg cacacgtcga agccttggtt   34080
cgccagggcc ttgatgttcg ccccgaacag ctcgcgggcg tcgtccagcg acagccgttc   34140
ggcgttcgca agtaccgggt tggactcgat gagggcgagg cgcgcggcct ggccgtcgcc   34200
ggctgcgggt gcggtttcgg tccagccgcc ggcagggaca gcgccgaaca gcttgcttgc   34260
atgcaggccg gtagcaaagt ccttgagcgt gtaggacgca ttccctgggg ggtccaggtc   34320
gatcacggca acccgcaagc gcgctcgaa aaagtcgaag gcaagatgca caagggtcga   34380
agtcttgccg acgccgcctt tctgttggc cgtgaccaaa gttttcatcg tttggtttcc   34440
tgttttttct tggcgtccgc ttcccacttc cggacgatgt acgcctgatg ttccggcaga   34500
accgccgtta cccgcgcgta cccctcgggc aagttcttgt cctcgaacgc ggcccacacg   34560
cgatgcaccg cttgcgacac tgcgccctg gtcagtccca gcgacgttgc gaacgtcgcc   34620
tgtggcttcc catcgactaa gacgccccgc gctatctcga tggtctgctg ccccacttcc   34680
agcccctgga tcgcctcctg gaactggctt tcggtaagcc gtttcttcat ggataacacc   34740
cataatttgc tccgcgcctt ggttgaacat agcggtgaca gccgccagca catgagagaa   34800
gtttagctaa acatttctcg cacgtcaaca cctttagccg ctaaaactcg tccttggcgt   34860
aacaaaacaa aagcccggaa accgggcttt cgtctcttgc cgcttatggc tctgcacccg   34920
gctccatcac caacaggtcg cgcacgcgct tcactcggtt gcggatcgac actgccagcc   34980
caacaaagcc ggttgccgcc gccgccagga tcgcgccgat gatgccggcc acaccggcca   35040
tcgcccacca ggtcgccgcc ttccggttcc attcctgctg gtactgcttc gcaatgctgg   35100
acctcggctc accataggct gaccgctcga tggcgtatgc cgcttctccc cttggcgtaa   35160
aacccagcgc cgcaggcggc attgccatgc tgcccgccgc tttcccgacc acgacgcgcg   35220
caccaggctt gcggtccaga ccttcggcca cggcgagctg cgcaaggaca taatcagccg   35280
ccgacttggc tccacgcgcc tcgatcagct cttgcactcg cgcgaaatcc ttggcctcca   35340
cggccgccat gaatcgcgca cgcggcgaag gctccgcagg gccggcgtcg tgatcgccgc   35400
cgagaatgcc cttcaccaag ttcgacgaca cgaaaatcat gctgacggct atcaccatca   35460
tgcagacgga tcgcacgaac ccgctgaatt gaacacgagc acggcacccg cgaccactat   35520
gccaagaatg cccaaggtaa aaattgccgg ccccgccatg aagtccgtga atgccccgac   35580
ggccgaagtg aagggcaggc cgccacccag gccgccgccc tcactgcccg gcacctggtc   35640
gctgaatgtc gatgccagca cctgcggcac gtcaatgctt ccgggcgtcg cgctcgggct   35700
gatcgcccat cccgttactg ccccgatccc ggcaatggca aggactgcca gcgctgccat   35760
ttttggggtg aggccgttcg cggccgaggg gcgcagcccc tgggggatg ggaggccgc   35820 gttagcgggc cggagggtt cgagaagggg gggcaccccc cttcggcgtg cgcggtcacg   35880
cgcacagggc gcagccctgg ttaaaaacaa ggtttataaa tattggttta aaagcaggtt   35940
aaaagacagg ttagcggtgg ccgaaaaacg ggcggaaacc cttgcaaatg ctggattttc   36000
tgcctgtgga cagcccctca aatgtcaata gtgtcgcccc tcatctgtca gcactctgcc   36060
cctcaagtgt caaggatcgc gcccctcatc tgtcagtagt cgcgcccctc aagtgtcaat   36120
accgcagggc acttatcccc aggcttgtcc acatcatctg tgggaaactc gcgtaaaatc   36180
aggcgttttc gccgatttgc gaggctggcc agctccacgt cgccgccga aatcgagcct   36240
```

```
gccectcatc tgtcaacgcc gcgccgggtg agtcggcccc tcaagtgtca acgtccgccc    36300
ctcatctgtc agtgagggcc aagttttccg cgaggtatcc acaacgccgg cggccgcggt    36360
gtctcgcaca cggcttcgac ggcgtttctg gcgcgtttgc agggccatag acggccgcca    36420
gcccagcggc gagggcaacc agcccggtga gcgtcggaaa ggcgctggaa gccccgtagc    36480
gacgcggaga ggggcgagac aagccaaggg cgcaggctcg atgcgcagca cgacatagcc    36540
ggttctcgca aggacgagaa tttccctgcg gtgcccctca agtgtcaatg aaagtttcca    36600
acgcgagcca ttcgcgagag ccttgagtcc acgctagatg agagctttgt tgtaggtgga    36660
ccagttggtg attttgaact tttgctttgc cacggaacgg tctgcgttgt cgggaagatg    36720
cgtgatctga tccttcaact cagcaaaagt tcgatttatt caacaaagcc acgttgtgtc    36780
tcaaaatctc tgatgttaca ttgcacaaga taaaaatata tcatcatgaa caataaaact    36840
gtctgcttac ataaacagta atacaagggg tgttatgagc catattcaac gggaaacgtc    36900
ttgctcgac                                                           36909
```

<210> SEQ ID NO 8
<211> LENGTH: 13019
<212> TYPE: DNA
<213> ORGANISM: Artificial Sequence
<220> FEATURE:
<223> OTHER INFORMATION: PHP23235 construct

<400> SEQUENCE: 8

```
gttacccgga ccgaagctta gcccgggcat gcctgcagtg cagcgtgacc cggtcgtgcc      60
cctctctaga gataatgagc attgcatgtc taagttataa aaaattacca catattttt     120 ttgtcacact tgtttgaagt gcagtttatc tatctttata catatattta aactttactc    180
tacgaataat ataatctata gtactacaat aatatcagtg ttttagagaa tcatataaat    240
gaacagttag acatggtcta aaggacaatt gagtattttg acaacaggac tctacagttt    300
tatcttttta gtgtgcatgt gttctccttt ttttttgcaa atagcttcac ctatataata    360
cttcatccat tttattagta catccattta gggtttaggg ttaatggttt ttatagacta    420 attttttag tacatctatt ttattctatt ttagcctcta aattaagaaa actaaaactc    480
tattttagtt tttttattta ataatttaga tataaaatag aataaaataa agtgactaaa    540
aattaaacaa atacccttta agaaattaaa aaaactaagg aaacatttt cttgtttcga    600 gtagataatg ccagcctgtt aaacgccgtc gacgagtcta acggacacca accagcgaac    660
cagcagcgtc gcgtcgggcc aagcgaagca acggcacgg catctctgtc gctgcctctg    720 gaccctctc gagagttccg ctccaccgtt ggacttgctc cgctgtcggc atccagaaat    780
tgcgtggcgg agcggcagac gtgagccggc acggcaggcg gcctcctcct cctctcacgg    840
cacggcagct acggggggatt cctttcccac cgctccttcg cttccccttc ctcgcccgcc    900
gtaataaata gacaccccct ccacaccctc ttttcccaac ctcgtgttgt tcggagcgca    960
cacacacaca accagatctc ccccaaatcc acccgtcggc acctccgctt caaggtacgc   1020
cgctcgtcct ccccccccc ccctctctac cttctctaga tcggcgttcc ggtccatggt   1080
tagggcccgg tagttctact tctgttcatg tttgtgttag atccgtgttt gtgttagatc   1140
cgtgctgcta gcgttcgtac acggatgcga cctgtacgtc agacacgttc tgattgctaa   1200
cttgccagtg tttctctttg gggaatcctg ggatggctct agccgttccg cagacgggat   1260
cgatttcatg attttttttg tttcgttgca taggggtttgg tttgcccttt ccttttattt   1320
caatatatgc cgtgcacttg tttgtcgggt catcttttca tgcttttttt tgtcttggtt   1380
```

```
gtgatgatgt ggtctggttg ggcggtcgtt ctagatcgga gtagaattct gtttcaaact    1440
acctggtgga tttattaatt ttggatctgt atgtgtgtgc catacatatt catagttacg    1500
aattgaagat gatggatgga aatatcgatc taggataggt atacatgttg atgcgggttt    1560
tactgatgca tatacagaga tgcttttgt tcgcttggtt gtgatgatgt ggtgtggttg     1620
ggcggtcgtt cattcgttct agatcggagt agaatactgt ttcaaactac ctggtgtatt    1680
tattaatttt ggaactgtat gtgtgtgtca tacatcttca tagttacgag tttaagatgg    1740
atggaaatat cgatctagga taggtataca tgttgatgtg ggttttactg atgcatatac    1800
atgatggcat atgcagcatc tattcatatg ctctaacctt gagtacctat ctattataat    1860
aaacaagtat gttttataat tattttgatc ttgatatact tggatgatgg catatgcagc    1920
agctatatgt ggatttttt agccctgcct tcatacgcta tttatttgct tggtactgtt     1980
tcttttgtcg atgctcaccc tgttgtttgg tgttacttct gcaggtcgac tctagaggat    2040
ccacaagttt gtacaaaaaa gctgaacgag aaacgtaaaa tgatataaat atcaatatat    2100
taaattagat tttgcataaa aaacagacta cataatactg taaaacacaa catatccagt    2160
cactatggcg gccgcattag gcaccccagg ctttacactt tatgcttccg gctcgtataa    2220
tgtgtggatt ttgagttagg atttaaatac gcgttgatcc ggcttactaa aagccagata    2280
acagtatgcg tatttgcgcg ctgattttg cggtataaga atatatactg atatgtatac     2340
ccgaagtatg tcaaaagag gtatgctatg aagcagcgta ttacagtgac agttgacagc     2400
gacagctatc agttgctcaa ggcatatatg atgtcaatat ctccggtctg gtaagcacaa    2460
ccatgcagaa tgaagcccgt cgtctgcgtg ccgaacgctg gaaagcggaa aatcaggaag    2520
ggatggctga ggtcgcccgg tttattgaaa tgaacggctc ttttgctgac gagaacaggg    2580
gctggtgaaa tgcagtttaa ggtttacacc tataaaagag agagccgtta tcgtctgttt    2640
gtggatgtac agagtgatat cattgacacg cccggtcgac ggatggtgat cccctggcc    2700 agtgcacgtc tgctgtcaga taaagtctcc cgtgaacttt acccggtggt gcatatcggg    2760
gatgaaagct ggcgcatgat gaccaccgat atggccagtg tgccggtctc cgttatcggg    2820
gaagaagtgg ctgatctcag ccaccgcgaa aatgacatca aaaacgccat taacctgatg    2880
ttctggggaa tataaatgtc aggctcccctt atacacagcc agtctgcagg tcgaccatag    2940
tgactggata tgttgtgttt tacagtatta tgtagtctgt tttttatgca aaatctaatt    3000
taatatattg atatttatat cattttacgt ttctcgttca gctttcttgt acaaagtggt    3060
gttaacctag acttgtccat cttctggatt ggccaactta attaatgtat gaaataaaag    3120
gatgcacaca tagtgacatg ctaatcacta taatgtgggc atcaaagttg tgtgttatgt    3180
gtaattacta gttatctgaa taaaagagaa agagatcatc catatttctt atcctaaatg    3240
aatgtcacgt gtctttataa ttctttgatg aaccagatgc atttcattaa ccaaatccat    3300
atacatataa atattaatca tatataatta atatcaattg ggttagcaaa acaaatctag    3360
tctaggtgtg ttttgcgaat tgcggccgcc accgcggtgg agctcgaatt ccggtccggg    3420
tcacctttgt ccaccaagat ggaactgcgg ccgctcatta ttaagtcag gcgcgcctct    3480 agttgaagac acgttcatgt cttcatcgta agaagacact cagtagtctt cggccagaat    3540
ggccatctgg attcagcagg cctagaaggc catttaaatc ctgaggatct ggtcttccta    3600
aggacccggg atatcggacc gattaaactt taattcggtc cgaagcttgc atgcctgcag    3660
tgcagcgtga cccggtcgtg cccctctcta gagataatga gcattgcatg tctaagttat    3720
aaaaaattac cacatatttt ttttgtcaca cttgtttgaa gtgcagttta tctatcttta    3780
```

-continued

| | |
|---|---|
| tacatatatt taaactttac tctacgaata atataatcta tagtactaca ataatatcag | 3840 |
| tgttttagag aatcatataa atgaacagtt agacatggtc taaaggacaa ttgagtattt | 3900 |
| tgacaacagg actctacagt tttatctttt tagtgtgcat gtgttctcct ttttttttgc | 3960 |
| aaatagcttc acctatataa tacttcatcc attttattag tacatccatt tagggtttag | 4020 |
| ggttaatggt ttttatagac taattttttt agtacatcta ttttattcta ttttagcctc | 4080 |
| taaattaaga aaactaaaac tctatttag ttttttatt taataattta gatataaaat | 4140 |
| agaataaaat aaagtgacta aaaattaaac aaatacccctt taagaaatta aaaaaactaa | 4200 |
| ggaaacattt ttcttgtttc gagtagataa tgccagcctg ttaaacgccg tcgacgagtc | 4260 |
| taacggacac caaccagcga accagcagcg tcgcgtcggg ccaagcgaag cagacggcac | 4320 |
| ggcatctctg tcgctgcctc tggacccctc tcgagagttc cgctccaccg ttggacttgc | 4380 |
| tccgctgtcg gcatccagaa attgcgtggc ggagcggcag acgtgagccg gcacggcagg | 4440 |
| cggcctcctc ctcctctcac ggcaccggca gctacggggg attcctttcc caccgctcct | 4500 |
| tcgctttccc ttcctcgccc gccgtaataa atagacaccc cctccacacc ctctttcccc | 4560 |
| aacctcgtgt tgttcggagc gcacacacac acaaccagat ctcccccaaa tccacccgtc | 4620 |
| ggcacctccg cttcaaggta cgccgctcgt cctccccccc cccctctct accttctcta | 4680 |
| gatcggcgtt ccggtccatg catggttagg gcccggtagt tctacttctg ttcatgtttg | 4740 |
| tgttagatcc gtgtttgtgt tagatccgtg ctgctagcgt tcgtacacgg atgcgacctg | 4800 |
| tacgtcagac acgttctgat tgctaacttg ccagtgtttc tctttggga atcctgggat | 4860 |
| ggctctagcc gttccgcaga cgggatcgat ttcatgattt ttttttgtttc gttgcatagg | 4920 |
| gtttggtttg cccttttcct ttatttcaat atatgccgtg cacttgtttg tcgggtcatc | 4980 |
| ttttcatgct ttttttgtc ttggttgtga tgatgtggtc tggttgggcg gtcgttctag | 5040 |
| atcggagtag aattctgttt caaactacct ggtggattta ttaattttgg atctgtatgt | 5100 |
| gtgtgccata catattcata gttacgaatt gaagatgatg gatggaaata tcgatctagg | 5160 |
| ataggtatac atgttgatgc gggttttact gatgcatata cagagatgct ttttgttcgc | 5220 |
| ttggttgtga tgatgtggtg tggttgggcg gtcgttcatt cgttctagat cggagtagaa | 5280 |
| tactgtttca aactacctgg tgtatttatt aattttggaa ctgtatgtgt gtgtcataca | 5340 |
| tcttcatagt tacgagttta agatggatgg aaatatcgat ctaggatagg tatacatgtt | 5400 |
| gatgtgggtt ttactgatgc atatacatga tggcatatgc agcatctatt catatgctct | 5460 |
| aaccttgagt acctatctat tataataaac aagtatgttt tataattatt ttgatcttga | 5520 |
| tatacttgga tgatggcata tgcagcagct atatgtggat ttttttagcc ctgccttcat | 5580 |
| acgctattta tttgcttggt actgtttctt ttgtcgatgc tcaccctgtt gtttggtgtt | 5640 |
| acttctgcag gtcgacttta acttagccta ggatccacac gacaccatgt cccccgagcg | 5700 |
| ccgccccgtc gagatccgcc cggccaccgc cgccgacatg gccgccgtgt gcgacatcgt | 5760 |
| gaaccactac atcgagacct ccaccgtgaa cttccgcacc gagccgcaga ccccgcagga | 5820 |
| gtggatcgac gacctggagc gcctccagga ccgctacccg tggctcgtgg ccgaggtgga | 5880 |
| gggcgtggtg gccggcatcg cctacgccgg cccgtggaag gcccgcaacg cctacgactg | 5940 |
| gaccgtggag tccaccgtgt acgtgtccca ccgccaccag cgcctcggcc tcggctccac | 6000 |
| cctctacacc cacctcctca agagcatgga ggcccagggc ttcaagtccg tggtggccgt | 6060 |
| gatcggcctc ccgaacgacc cgtccgtgcg cctccacgag gccctcggct acaccgcccg | 6120 |
| cggcacccctc cgcgccgccg gctacaagca cggcggctgg cacgacgtcg gcttctggca | 6180 |

```
gcgcgacttc gagctgccgg ccccgccgcg cccggtgcgc ccggtgacgc agatctgagt   6240
cgaaacctag acttgtccat cttctggatt ggccaactta attaatgtat gaaataaaag   6300
gatgcacaca tagtgacatg ctaatcacta taatgtgggc atcaaagttg tgtgttatgt   6360
gtaattacta gttatctgaa taaaagagaa agagatcatc catatttctt atcctaaatg   6420
aatgtcacgt gtcttttataa ttctttgatg aaccagatgc atttcattaa ccaaatccat   6480
atacatataa atattaatca tatataatta atatcaattg ggttagcaaa acaaatctag   6540
tctaggtgtg ttttgcgaat tgcggccgcc accgcggtgg agctcgaatt cattccgatt   6600
aatcgtggcc tcttgctctt caggatgaag agctatgttt aaacgtgcaa gcgctactag   6660
acaattcagt acattaaaaa cgtccgcaat gtgttattaa gttgtctaag cgtcaatttg   6720
tttacaccac aatatatcct gccaccagcc agccaacagc tccccgaccg gcagctcggc   6780
acaaaatcac cactcgatac aggcagccca tcagtccggg acggcgtcag cgggagagcc   6840
gttgtaaggc ggcagacttt gctcatgtta ccgatgctat tcggaagaac ggcaactaag   6900
ctgccgggtt tgaaacacgg atgatctcgc ggagggtagc atgttgattg taacgatgac   6960
agagcgttgc tgcctgtgat caaatatcat ctccctcgca gagatccgaa ttatcagcct   7020
tcttattcat ttctcgctta accgtgacag gctgtcgatc ttgagaacta tgccgacata   7080
ataggaaatc gctggataaa gccgctgagg aagctgagtg gcgctatttc tttagaagtg   7140
aacgttgacg atcgtcgacc gtaccccgat gaattaattc ggacgtacgt tctgaacaca   7200
gctggatact tacttgggcg attgtcatac atgacatcaa caatgtaccc gtttgtgtaa   7260
ccgtctcttg gaggttcgta tgacactagt ggttcccctc agcttgcgac tagatgttga   7320
ggcctaacat tttattagag agcaggctag ttgcttagat acatgatctt caggccgtta   7380
tctgtcaggg caagcgaaaa ttggccattt atgacgacca atgccccgca gaagctccca   7440
tctttgccgc catagacgcc gcgccccct tttggggtgt agaacatcct tttgccagat   7500
gtggaaaaga agttcgttgt cccattgttg gcaatgacgt agtagccggc gaaagtgcga   7560
gacccatttg cgctatatat aagcctacga tttccgttgc gactattgtc gtaattggat   7620
gaactattat cgtagttgct ctcagagttg tcgtaatttg atggactatt gtcgtaattg   7680
cttatggagt tgtcgtagtt gcttggagaa atgtcgtagt tggatgggga gtagtcatag   7740
ggaagacgag cttcatccac taaaacaatt ggcaggtcag caagtgcctg ccccgatgcc   7800
atcgcaagta cgaggcttag aaccaccttc aacagatcgc gcatagtctt ccccagctct   7860
ctaacgcttg agttaagccg cgccgcgaag cggcgtcggc ttgaacgaat tgttagacat   7920
tatttgccga ctaccttggt gatctcgcct ttcacgtagt gaacaaattc ttccaactga   7980
tctgcgcgcg aggccaagcg atcttcttgt ccaagataag cctgcctagc ttcaagtatg   8040
acgggctgat actgggccgg caggcgctcc attgcccagt cggcagcgac atccttcggc   8100
gcgattttgc cggttactgc gctgtaccaa atgcgggaca acgtaagcac tacatttcgc   8160
tcatcgccag cccagtcggg cggcgagttc catagcgtta aggtttcatt tagcgcctca   8220
aatagatcct gttcaggaac cggatcaaag agttcctccg ccgctggacc taccaaggca   8280
acgctatgtt ctcttgcttt tgtcagcaag atagccagat caatgtcgat cgtggctggc   8340
tcgaagatac ctgcaagaat gtcattgcgc tgccattctc caaattgcag ttcgcgctta   8400
gctggataac gccacggaat gatgtcgtcg tgcacaacaa tggtgacttc tacagcgcgg   8460
agaatctcgc tctctccagg ggaagccgaa gtttccaaaa ggtcgttgat caaagctcgc   8520
cgcgttgttt catcaagcct tacagtcacc gtaaccagca aatcaatatc actgtgtggc   8580
```

```
ttcaggccgc catccactgc ggagccgtac aaatgtacgg ccagcaacgt cggttcgaga   8640
tggcgctcga tgacgccaac tacctctgat agttgagtcg atacttcggc gatcaccgct   8700
tccctcatga tgtttaactc ctgaattaag ccgcgccgcg aagcggtgtc ggcttgaatg   8760
aattgttagg cgtcatcctg tgctcccgag aaccagtacc agtacatcgc tgtttcgttc   8820
gagacttgag gtctagtttt atacgtgaac aggtcaatgc cgccgagagt aaagccacat   8880
tttgcgtaca aattgcaggc aggtacattg ttcgtttgtg tctctaatcg tatgccaagg   8940
agctgtctgc ttagtgccca ctttttcgca aattcgatga gactgtgcgc gactcctttg   9000
cctcggtgcg tgtgcgacac aacaatgtgt tcgatagagg ctagatcgtt ccatgttgag   9060
ttgagttcaa tcttcccgac aagctcttgg tcgatgaatg cgccatagca agcagagtct   9120
tcatcagagt catcatccga gatgtaatcc ttccggtagg ggctcacact tctggtagat   9180
agttcaaagc cttggtcgga taggtgcaca tcgaacactt cacgaacaat gaaatggttc   9240
tcagcatcca atgtttccgc cacctgctca gggatcaccg aaatcttcat atgacgccta   9300
acgcctggca cagcggatcg caaacctggc gcggcttttg gcacaaaagg cgtgacaggt   9360
ttgcgaatcc gttgctgcca cttgttaacc cttttgccag atttggtaac tataattat   9420
gttagaggcg aagtcttggg taaaaactgg cctaaaattg ctggggattt caggaaagta   9480
aacatcacct tccggctcga tgtctattgt agatatatgt agtgtatcta cttgatcggg   9540
ggatctgctg cctcgcgcgt ttcggtgatg acggtgaaaa cctctgacac atgcagctcc   9600
cggagacggt cacagcttgt ctgtaagcgg atgccgggag cagacaagcc cgtcagggcg   9660
cgtcagcggg tgttggcggg tgtcggggcg cagccatgac ccagtcacgt agcgatagcg   9720
gagtgtatac tggcttaact atgcggcatc agagcagatt gtactgagag tgcaccatat   9780
gcggtgtgaa ataccgcaca gatgcgtaag gagaaaatac cgcatcaggc gctcttccgc   9840
ttcctcgctc actgactcgc tgcgctcggt cgttcggctg cggcgagcgg tatcagctca   9900
ctcaaaggcg gtaatacggt tatccacaga atcagggga acgcaggaa agaacatgtg   9960
agcaaaaggc cagcaaaagg ccaggaaccg taaaaaggcc gcgttgctgg cgtttttcca  10020
taggctccgc ccccctgacg agcatcacaa aaatcgacgc tcaagtcaga ggtggcgaaa  10080
cccgacagga ctataaagat accaggcgtt tccccctgga agctccctcg tgcgctctcc  10140
tgttccgacc ctgccgctta ccggatacct gtccgccttt ctcccttcgg gaagcgtggc  10200
gctttctcat agctcacgct gtaggtatct cagttcggtg taggtcgttc gctccaagct  10260
gggctgtgtg cacgaacccc ccgttcagcc cgaccgctgc gccttatccg gtaactatcg  10320
tcttgagtcc aacccggtaa gacacgactt atcgccactg gcagcagcca ctggtaacag  10380
gattagcaga gcgaggtatg taggcggtgc tacagagttc ttgaagtggt ggcctaacta  10440
cggctacact agaaggacag tatttggtat ctgcgctctg ctgaagccag ttaccttcgg  10500
aaaaagagtt ggtagctctt gatccggcaa acaaaccacc gctggtagcg gtggtttttt  10560
tgtttgcaag cagcagatta cgcgcagaaa aaaaggatct caagaagatc ctttgatctt  10620
ttctacgggg tctgacgctc agtggaacga aaactcacgt taagggattt tggtcatgag  10680
attatcaaaa aggatcttca cctagatcct tttaaattaa aaatgaagtt ttaaatcaat  10740
ctaaagtata tatgagtaaa cttggtctga cagttaccaa tgcttaatca gtgaggcacc  10800
tatctcagcg atctgtctat ttcgttcatc catagttgcc tgactccccg tcgtgtagat  10860
aactacgata cgggagggct taccatctgg ccccagtgct gcaatgatac cgcgagaccc  10920
acgctcaccg gctccagatt tatcagcaat aaaccagcca gccggaaggg ccgagcgcag  10980
```

```
aagtggtcct gcaactttat ccgcctccat ccagtctatt aattgttgcc gggaagctag     11040
agtaagtagt tcgccagtta atagtttgcg caacgttgtt gccattgctg cagggggggg     11100
gggggggggg gacttccatt gttcattcca cggacaaaaa cagagaaagg aaacgacaga     11160
ggccaaaaag cctcgctttc agcacctgtc gtttcctttc ttttcagagg gtattttaaa     11220
taaaaacatt aagttatgac gaagaagaac ggaaacgcct taaaccggaa aattttcata     11280
aatagcgaaa acccgcgagg tcgccgcccc gtaacctgtc ggatcaccgg aaaggacccg     11340
taaagtgata atgattatca tctacatatc acaacgtgcg tggaggccat caaaccacgt     11400
caaataatca attatgacgc aggtatcgta ttaattgatc tgcatcaact taacgtaaaa     11460
acaacttcag acaatacaaa tcagcgacac tgaatacggg gcaacctcat gtcccccccc     11520
cccccccccc tgcaggcatc gtggtgtcac gctcgtcgtt tggtatggct tcattcagct     11580
ccggttccca acgatcaagg cgagttacat gatcccccat gttgtgcaaa aaagcggtta     11640
gctccttcgg tcctccgatc gttgtcagaa gtaagttggc cgcagtgtta tcactcatgg     11700
ttatggcagc actgcataat tctcttactg tcatgccatc cgtaagatgc ttttctgtga     11760
ctggtgagta ctcaaccaag tcattctgag aatagtgtat gcggcgaccg agttgctctt     11820
gcccggcgtc aacacgggat aataccgcgc cacatagcag aactttaaaa gtgctcatca     11880
ttggaaaacg ttcttcgggg cgaaaactct caaggatctt accgctgttg agatccagtt     11940
cgatgtaacc cactcgtgca cccaactgat cttcagcatc ttttactttc accagcgttt     12000
ctgggtgagc aaaaacagga aggcaaaatg ccgcaaaaaa gggaataagg gcgacacgga     12060
aatgttgaat actcatactc ttcctttttc aatattattg aagcatttat cagggttatt     12120
gtctcatgag cggatacata tttgaatgta tttagaaaaa taaacaaata ggggttccgc     12180
gcacatttcc ccgaaaagtg ccacctgacg tctaagaaac cattattatc atgacattaa     12240
cctataaaaa taggcgtatc acgaggccct ttcgtcttca agaattggtc gacgatcttg     12300
ctgcgttcgg atattttcgt ggagttcccg ccacagaccc ggattgaagg cgagatccag     12360
caactcgcgc cagatcatcc tgtgacggaa ctttggcgcg tgatgactgg ccaggacgtc     12420
ggccgaaaga gcgacaagca gatcacgctt ttcgacagcg tcggatttgc gatcgaggat     12480
ttttcggcgc tgcgctacgt ccgcgaccgc gttgagggat caagccacag cagcccactc     12540
gaccttctag ccgacccaga cgagccaagg gatcttttg gaatgctgct ccgtcgtcag     12600
gctttccgac gtttgggtgg ttgaacagaa gtcattatcg tacggaatgc caagcactcc     12660 cgagggaac cctgtggttg gcatgcacat acaaatggac gaacggataa accttttcac     12720
gcccttttaa atatccgtta ttctaataaa cgctcttttc tcttaggttt acccgccaat     12780
atatcctgtc aaacactgat agtttaaact gaaggcggga aacgacaatc tgatcatgag     12840
cggagaatta agggagtcac gttatgaccc ccgccgatga cgcgggacaa gccgtttac     12900 gtttggaact gacagaaccg caacgttgaa ggagccactc agcaagctgg tacgattgta     12960
atacgactca ctatagggcg aattgagcgc tgtttaaacg ctcttcaact ggaagagcg     13019
```

<210> SEQ ID NO 9
<211> LENGTH: 2991
<212> TYPE: DNA
<213> ORGANISM: Artificial Sequence
<220> FEATURE:
<223> OTHER INFORMATION: PHP20234 construct

<400> SEQUENCE: 9

```
ctttcctgcg ttatcccctg attctgtgga taaccgtatt accgcctttg agtgagctga        60
```

```
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa     540 aacgacggcc agtcttaagc tcgggccctg cagctctaga gctcgaattc tacaggtcac    600
taataccatc taagtagttg gttcatagtg actgcatatg ttgtgtttta cagtattatg    660
tagtctgttt tttatgcaaa atctaattta atatattgat atttatatca ttttacgttt    720
ctcgttcaac tttcttgtac aaagtggccg ttaacggatc cagacttgtc catcttctgg    780
attggccaac ttaattaatg tatgaaataa aaggatgcac acatagtgac atgctaatca    840
ctataatgtg ggcatcaaag ttgtgtgtta tgtgtaatta ctagttatct gaataaaaga    900
gaaagagatc atccatattt cttatcctaa atgaatgtca cgtgtcttta taattctttg    960
atgaaccaga tgcatttcat taaccaaatc catatacata taaatattaa tcatatataa   1020
ttaatatcaa ttgggttagc aaaacaaatc tagtctaggt gtgttttgcg aattgcggca   1080
agcttgcggc cgccccgggc aactttatta tacaaagttg gcattataaa aaagcattgc   1140
ttatcaattt gttgcaacga acaggtcact atcagtcaaa ataaaatcat tatttggagc   1200
tccatggtag cgttaacgcg gccgcgatat cccctatagt gagtcgtatt acatggtcat   1260
agctgtttcc tggcagctct ggcccgtgtc tcaaaatctc tgatgttaca ttgcacaaga   1320
taaaaatata tcatcatgaa caataaaact gtctgcttac ataaacagta atacaagggg   1380
tgttatgagc catattcaac gggaaacgtc gaggccgcga ttaaattcca acatggatgc   1440
tgatttatat gggtataaat gggctcgcga taatgtcggg caatcaggtg cgacaatcta   1500
tcgcttgtat gggaagcccg atgcgccaga gttgtttctg aaacatggca aaggtagcgt   1560
tgccaatgat gttacagatg agatggtcag actaaactgg ctgacggaat ttatgcctct   1620
tccgaccatc aagcatttta tccgtactcc tgatgatgca tggttactca ccactgcgat   1680
ccccggaaaa acagcattcc aggtattaga agaatatcct gattcaggtg aaaatattgt   1740
tgatgcgctg gcagtgttcc tgcgccggtt gcattcgatt cctgtttgta attgtccttt   1800
taacagcgat cgcgtatttc gtctcgctca ggcgcaatca cgaatgaata cggtttggt    1860 tgatgcgagt gattttgatg acgagcgtaa tggctggcct gttgaacaag tctggaaaga   1920
aatgcataaa cttttgccat tctcaccgga ttcagtcgtc actcatggtg atttctcact   1980
tgataacctt attttgacg aggggaaatt aataggttgt attgatgttg gacgagtcgg    2040
aatcgcagac cgataccagg atcttgccat cctatggaac tgcctcggtg agttttctcc   2100
ttcattacag aaacggcttt ttcaaaaata tggtattgat aatcctgata tgaataaatt   2160
gcagtttcat ttgatgctcg atgagttttt ctaatcagaa ttggttaatt ggttgtaaca   2220
ctggcagagc attacgctga cttgacggga cggcgcaagc tcatgaccaa atcccttaa    2280 cgtgagttac gcgtcgttcc actgagcgtc agacccgta gaaagatca aggatcttc      2340 ttgagatcct ttttttctgc gcgtaatctg ctgcttgcaa acaaaaaaac caccgctacc   2400
agcggtggtt tgtttgccgg atcaagagct accaactctt tttccgaagg taactggctt   2460
```

-continued

| | |
|---|---|
| cagcagagcg cagataccaa atactgtcct tctagtgtag ccgtagttag gccaccactt | 2520 |
| caagaactct gtagcaccgc ctacatacct cgctctgcta atcctgttac cagtggctgc | 2580 |
| tgccagtggc gataagtcgt gtcttaccgg gttggactca agacgatagt taccggataa | 2640 |
| ggcgcagcgg tcgggctgaa cggggggttc gtgcacacag cccagcttgg agcgaacgac | 2700 |
| ctacaccgaa ctgagatacc tacagcgtga gcattgagaa agcgccacgc ttcccgaagg | 2760 |
| gagaaaggcg gacaggtatc cggtaagcgg cagggtcgga acaggagagc gcacgaggga | 2820 |
| gcttccaggg ggaaacgcct ggtatcttta tagtcctgtc gggtttcgcc acctctgact | 2880 |
| tgagcgtcga ttttttgtgat gctcgtcagg ggggcggagc ctatggaaaa acgccagcaa | 2940 |
| cgcggccttt ttacggttcc tggccttttg ctggccttttt gctcacatgt t | 2991 |

<210> SEQ ID NO 10
<211> LENGTH: 13278
<212> TYPE: DNA
<213> ORGANISM: Artificial Sequence
<220> FEATURE:
<223> OTHER INFORMATION: PHP22655 construct (destination vector)

<400> SEQUENCE: 10

| | |
|---|---|
| aagctggtac gattgtaata cgactcacta tagggcgaat tgagcgctgt ttaaacgctc | 60 |
| ttcaactgga agagcggtta ccagagctgg tcacctttgt ccaccaagat ggaactgcgg | 120 |
| ccgctcatta attaagtcag gcgcgcctct agttgaagac acgttcatgt cttcatcgta | 180 |
| agaagacact cagtagtctt cggccagaat ggcccggacc gaagctggcc gctctagaac | 240 |
| tagtggatct cgatgtgtag tctacgagaa gggttaaccg tctcttcgtg agaataaccg | 300 |
| tggcctaaaa ataagccgat gaggataaat aaaatgtggt ggtacagtac ttcaagaggt | 360 |
| ttactcatca agaggatgct tttccgatga gctctagtag tacatcggac ctcacatacc | 420 |
| tccattgtgg tgaaatattt tgtgctcatt tagtgatggg taaattttgt ttatgtcact | 480 |
| ctaggttttg acatttcagt tttgccactc ttaggttttg acaaataatt tccattccgc | 540 |
| ggcaaaagca aaacaatttt attttacttt taccactctt agctttcaca atgtatcaca | 600 |
| aatgccactc tagaaattct gtttatgcca cagaatgtga aaaaaacac tcacttattt | 660 |
| gaagccaagg tgttcatggc atggaaatgt gacataaagt aacgttcgtg tataagaaaa | 720 |
| aattgtactc ctcgtaacaa gagacggaaa catcatgaga caatcgcgtt tggaaggctt | 780 |
| tgcatcacct ttggatgatg cgcatgaatg gagtcgtctg cttgctagcc ttcgcctacc | 840 |
| gcccactgag tccgggcggc aactaccatc ggcgaacgac ccagctgacc tctaccgacc | 900 |
| ggacttgaat gcgctaccct cgtcagcgac gatggccgcg tacgctggcg acgtgccccc | 960 |
| gcatgcatgg cggcacatgg cgagctcaga ccgtgcgtgg ctggctacaa atacgtaccc | 1020 |
| cgtgagtgcc ctagctagaa acttacacct gcaactgcga gagcgagcgt gtgagtgtag | 1080 |
| ccgagtagat ccccggtcg ccaccatggc ctcctccgag aacgtcatca ccgagttcat | 1140 |
| gcgcttcaag gtgcgcatgg agggcaccgt gaacggccac gagttcgaga tcgagggcga | 1200 |
| gggcgagggc cgcccctacg agggccacaa caccgtgaag ctgaaggtga ccaagggcgg | 1260 |
| cccctgccc ttcgcctggg acatcctgtc ccccagttc cagtacggct ccaaggtgta | 1320 |
| cgtgaagcac cccgccgaca tccccgacta caagaagctg tccttccccg agggcttcaa | 1380 |
| gtgggagcgc gtgatgaact tcgaggacgg cggcgtggcg accgtgaccc aggactcctc | 1440 |
| cctgcaggac ggctgcttca tctacaaggt gaagttcatc ggcgtgaact tcccctccga | 1500 |
| cggccccgtg atgcagaaga gaccatgggg ctgggaggcc tccaccgagc gcctgtaccc | 1560 |

```
ccgcgacggc gtgctgaagg gcgagaccca caaggccctg aagctgaagg acggcggcca    1620
ctacctggtg gagttcaagt ccatctacat ggccaagaag cccgtgcagc tgcccggcta    1680
ctactacgtg gacgccaagc tggacatcac ctcccacaac gaggactaca ccatcgtgga    1740
gcagtacgag cgcaccgagg ccgccacca cctgttcctg tagcggccca tggatattcg     1800
aacgcgtagg taccacatgg ttaacctaga cttgtccatc ttctggattg ccaacttaa    1860 ttaatgtatg aaataaaagg atgcacacat agtgacatgc taatcactat aatgtgggca    1920
tcaaagttgt gtgttatgtg taattactag ttatctgaat aaaagagaaa gagatcatcc    1980
atatttctta tcctaaatga atgtcacgtg tctttataat tctttgatga accagatgca    2040
tttcattaac caaatccata tacatataaa tattaatcat ataaattaa tatcaattgg    2100 gttagcaaaa caaatctagt ctaggtgtgt tttgcgaatg cggccgccac cgcggtggag    2160
ctcgaattcc ggtccgggcc tagaaggcca tttaaatcct gaggatctgg tcttcctaag    2220
gacccgggat atcgctatca actttgtata gaaaagttga acgagaaacg taaaatgata    2280
taaatatcaa tatattaaat tagattttgc ataaaaaaca gactacataa tactgtaaaa    2340
cacaacatat ccagtcacta tggtcgacct gcagactggc tgtgtataag ggagcctgac    2400
atttatattc cccagaacat caggttaatg gcgttttga tgtcattttc gcggtggctg     2460
agatcagcca cttcttcccc gataacggag accggcacac tggccatatc ggtggtcatc    2520
atgcgccagc tttcatcccc gatatgcacc accgggtaaa gttcacgggg actttatct    2580 gacagcagac gtgcactggc caggggatc ccatccgtc gcccgggcgt gtcaataata    2640
tcactctgta catccacaaa cagacgataa cggctctctc ttttataggt gtaaaccta    2700 aactgcattt caccagcccc tgttctcgtc ggcaaaagag ccgttcattt caataaaccg    2760
ggcgacctca gccatccctt cctgattttc cgctttccag cgttcggcac gcagacgacg    2820
ggcttcattc tgcatggttg tgcttaccga accggagata ttgacatcat atatgccttg    2880
agcaactgat agctgtcgct gtcaactgtc actgtaatac gctgcttcat agcatacctc    2940
tttttgacat acttcgggta tacatatcag tatatattct tataccgcaa aaatcagcgc    3000
gcaaatacgc atactgttat ctggcttta gtaagccgga tcctctagat tacgccccgc    3060
ctgccactca tcgcagtact gttgtaattc attaagcatt ctgccgacat ggaagccatc    3120
acaaacggca tgatgaacct gaatcgccag cggcatcagc accttgtcgc cttgcgtata    3180
atatttgccc atggtgaaaa cggggggcgaa gaagttgtcc atattggcca cgtttaaatc    3240
aaaactggtg aaactcaccc agggattggc tgagacgaaa aacatattct caataaaccc    3300
tttagggaaa taggccaggt tttcaccgta acacgccaca tcttgcgaat atatgtgtag    3360
aaactgccgg aaatcgtcgt ggtattcact ccagagcgat gaaaacgttt cagtttgctc    3420
atggaaaacg gtgtaacaag ggtgaacact atcccatatc accagctcac cgtctttcat    3480
tgccatacga aattccggat gagcattcat caggcgggca agaatgtgaa taaaggccgg    3540
ataaaacttg tgcttatttt tctttacggt ctttaaaaag gccgtaatat ccagctgaac    3600
ggtctggtta taggtacatt gagcaactga ctgaaatgcc tcaaaatgtt ctttacgatg    3660
ccattgggat atatcaacgg tggtatatcc agtgattttt ttctccattt tagcttcctt    3720
agctcctgaa aatctcgacg gatcctaact caaaatccac acattatacg agccggaagc    3780
ataaagtgta aagcctgggg tgcctaatg cggccgccat agtgactgga tatgttgtgt    3840
tttacagtat tatgtagtct gttttttatg caaaatctaa tttaatatat tgatatttat    3900
atcattttac gtttctcgtt caactttatt atacaaagtt gatagatatc ggaccgatta    3960
```

```
aactttaatt cggtccgaag cttgcatgcc tgcagtgcag cgtgacccgg tcgtgcccct   4020
ctctagagat aatgagcatt gcatgtctaa gttataaaaa attaccacat atttttttg    4080 tcacacttgt ttgaagtgca gtttatctat ctttatacat atatttaaac tttactctac   4140
gaataatata atctatagta ctacaataat atcagtgttt tagagaatca tataaatgaa   4200
cagttagaca tggtctaaag gacaattgag tattttgaca acaggactct acagttttat   4260 cttttagtg tgcatgtgtt ctcctttttt tttgcaaata gcttcaccta tataatactt    4320
catccatttt attagtacat ccatttaggg tttagggtta atggttttta tagactaatt   4380
tttttagtac atctatttta ttctatttta gcctctaaat taagaaaact aaaactctat   4440
tttagttttt ttatttaata atttagatat aaaatagaat aaaataaagt gactaaaaat   4500
taaacaaata cccctttaaga aattaaaaaa actaaggaaa cattttttctt gtttcgagta  4560 gataatgcca gcctgttaaa cgccgtcgac gagtctaacg gacaccaacc agcgaaccag   4620
cagcgtcgcg tcgggccaag cgaagcagac ggcacggcat ctctgtcgct gcctctggac   4680
ccctctcgag agttccgctc caccgttgga cttgctccgc tgtcggcatc cagaaattgc   4740
gtggcggagc ggcagacgtg agccggcacg gcaggcggcc tcctcctcct ctcacggcac   4800
cggcagctac gggggattcc tttcccaccg ctccttcgct ttcccttcct cgcccgccgt   4860
aataaataga cacccctcc acaccctctt tccccaacct cgtgttgttc ggagcgcaca    4920
cacacacaac cagatctccc ccaaatccac ccgtcggcac ctccgcttca aggtacgccg   4980
ctcgtcctcc cccccccccc tctctacctt ctctagatcg gcgttccggt ccatgcatgg   5040
ttagggcccg gtagttctac ttctgttcat gtttgtgtta gatccgtgtt tgtgttagat   5100
ccgtgctgct agcgttcgta cacggatgcg acctgtacgt cagacacgtt ctgattgcta   5160
acttgccagt gtttctcttt ggggaatcct gggatggctc tagccgttcc gcagacggga   5220
tcgatttcat gatttttttt gtttcgttgc atagggtttg gtttgccctt ttcctttatt   5280
tcaatatatg ccgtgcactt gtttgtcggg tcatcttttc atgcttttt ttgtcttggt    5340 tgtgatgatg tggtctggtt gggcggtcgt tctagatcgg agtagaattc tgtttcaaac   5400
tacctggtgg atttattaat tttggatctg tatgtgtgtg ccatacatat tcatagttac   5460
gaattgaaga tgatggatgg aaatatcgat ctaggatagg tatacatgtt gatgcgggtt   5520
ttactgatgc atatacagag atgcttttg ttcgcttggt tgtgatgatg tggtgtggtt    5580
gggcggtcgt tcattcgttc tagatcggag tagaatactg tttcaaacta cctggtgtat   5640
ttattaattt tggaactgta tgtgtgtgtc atacatcttc atagttacga gtttaagatg   5700
gatggaaata tcgatctagg ataggtatac atgttgatgt gggttttact gatgcatata   5760
catgatggca tatgcagcat ctattcatat gctctaacct tgagtaccta tctattataa   5820
taaacaagta tgttttataa ttattttgat cttgatatac ttggatgatg gcatatgcag   5880
cagctatatg tggatttttt tagccctgcc ttcatacgct atttatttgc ttggtactgt   5940 ttctttgtc gatgctcacc ctgttgtttg gtgttacttc tgcaggtcga ctttaactta    6000
gcctaggatc cacacgacac catgtcccce gagcgccgcc ccgtcgagat ccgcccggcc   6060
accgccgccg acatggccgc cgtgtgcgac atcgtgaacc actacatcga gacctccacc  6120
gtgaacttcc gcaccgagcc gcagacccg caggagtgga tcgacgacct ggagcgcctc    6180
caggaccgct acccgtggct cgtggccgag gtggagggcg tggtggccgg catcgcctac   6240
gccggcccgt ggaaggcccg caacgcctac gactggaccg tggagtccac cgtgtacgtg   6300
tcccaccgcc accagcgcct cggcctcggc tccaccctct acacccacct cctcaagagc   6360
```

```
atggaggccc agggcttcaa gtccgtggtg gccgtgatcg gcctcccgaa cgacccgtcc    6420
gtgcgcctcc acgaggccct cggctacacc gcccgcggca ccctccgcgc cgccggctac    6480
aagcacggcg gctggcacga cgtcggcttc tggcagcgcg acttcgagct gccggccccg    6540
ccgcgcccgg tgcgcccggt gacgcagatc tgagtcgaaa cctagacttg tccatcttct    6600
ggattggcca acttaattaa tgtatgaaat aaaaggatgc acacatagtg acatgctaat    6660
cactataatg tgggcatcaa agttgtgtgt tatgtgtaat tactagttat ctgaataaaa    6720
gagaaagaga tcatccatat ttcttatcct aaatgaatgt cacgtgtctt tataattctt    6780
tgatgaacca gatgcatttc attaaccaaa tccatataca tataaatatt aatcatatat    6840
aattaatatc aattgggtta gcaaaacaaa tctagtctag gtgtgttttg cgaattgcgg    6900
ccgccaccgc ggtggagctc gaattcattc cgattaatcg tggcctcttg ctcttcagga    6960
tgaagagcta tgtttaaacg tgcaagcgct actagacaat tcagtacatt aaaaacgtcc    7020
gcaatgtgtt attaagttgt ctaagcgtca atttgtttac accacaatat atcctgccac    7080
cagccagcca acagctcccc gaccggcagc tcggcacaaa atcaccactc gatacaggca    7140
gcccatcagt ccgggacggc gtcagcggga gagccgttgt aaggcggcag actttgctca    7200
tgttaccgat gctattcgga agaacggcaa ctaagctgcc gggtttgaaa cacggatgat    7260
ctcgcggagg gtagcatgtt gattgtaacg atgacagagc gttgctgcct gtgatcaaat    7320
atcatctccc tcgcagagat ccgaattatc agccttctta ttcatttctc gcttaaccgt    7380
gacaggctgt cgatcttgag aactatgccg acataatagg aaatcgctgg ataaagccgc    7440
tgaggaagct gagtggcgct atttctttag aagtgaacgt tgacgatcgt cgaccgtacc    7500
ccgatgaatt aattcggacg tacgttctga acacagctgg atacttactt gggcgattgt    7560
catacatgac atcaacaatg tacccgtttg tgtaaccgtc tcttggaggt tcgtatgaca    7620
ctagtggttc ccctcagctt gcgactagat gttgaggcct aacattttat tagagagcag    7680
gctagttgct tagatacatg atcttcaggc cgttatctgt cagggcaagc gaaaattggc    7740
catttatgac gaccaatgcc ccgcagaagc tcccatcttt gccgccatag acgccgcgcc    7800
ccccttttgg ggtgtagaac atccttttgc cagatgtgga aaagaagttc gttgtcccat    7860
tgttggcaat gacgtagtag ccggcgaaag tgcgagaccc atttgcgcta tatataagcc    7920
tacgattttcc gttgcgacta ttgtcgtaat tggatgaact attatcgtag ttgctctcag    7980
agttgtcgta atttgatgga ctattgtcgt aattgcttat ggagttgtcg tagttgcttg    8040
gagaaatgtc gtagttggat ggggagtagt catagggaag acgagcttca tccactaaaa    8100
caattggcag gtcagcaagt gcctgccccg atgccatcgc aagtacgagg cttagaacca    8160
ccttcaacag atcgcgcata gtcttcccca gctctctaac gcttgagtta agccgcgccg    8220
cgaagcggcg tcggcttgaa cgaattgtta gacattattt gccgactacc ttggtgatct    8280
cgcctttcac gtagtgaaca aattcttcca actgatctgc gcgcgaggcc aagcgatctt    8340
cttgtccaag ataagcctgc ctagcttcaa gtatgacggg ctgatactgg gccggcaggc    8400
gctccattgc ccagtcggca gcgacatcct tcggcgcgat tttgccggtt actgcgctgt    8460
accaaatgcg ggacaacgta agcactacat ttcgctcatc gccagcccag tcgggcggcg    8520
agttccatag cgttaaggtt tcatttagcg cctcaaatag atcctgttca ggaaccggat    8580
caaagagttc ctccgccgct ggacctacca aggcaacgct atgttctctt gcttttgtca    8640
gcaagatagc cagatcaatg tcgatcgtgg ctggctcgaa gatacctgca agaatgtcat    8700
tgcgctgcca ttctccaaat tgcagttcgc gcttagctgg ataacgccac ggaatgatgt    8760
```

-continued

```
cgtcgtgcac aacaatggtg acttctacag cgcggagaat ctcgctctct ccaggggaag    8820
ccgaagtttc caaaaggtcg ttgatcaaag ctcgccgcgt tgtttcatca agccttacag    8880
tcaccgtaac cagcaaatca atatcactgt gtggcttcag gccgccatcc actgcggagc    8940
cgtacaaatg tacggccagc aacgtcggtt cgagatggcg ctcgatgacg ccaactacct    9000
ctgatagttg agtcgatact tcggcgatca ccgcttccct catgatgttt aactcctgaa    9060
ttaagccgcg ccgcgaagcg gtgtcggctt gaatgaattg ttaggcgtca tcctgtgctc    9120
ccgagaacca gtaccagtac atcgctgttt cgttcgagac ttgaggtcta gttttatacg    9180
tgaacaggtc aatgccgccg agagtaaagc cacattttgc gtacaaattg caggcaggta    9240
cattgttcgt ttgtgtctct aatcgtatgc caaggagctg tctgcttagt gcccacttt    9300
tcgcaaattc gatgagactg tgcgcgactc ctttgcctcg gtgcgtgtgc gacacaacaa    9360
tgtgttcgat agaggctaga tcgttccatg ttgagttgag ttcaatcttc ccgacaagct    9420
cttggtcgat gaatgcgcca tagcaagcag agtcttcatc agagtcatca tccgagatgt    9480
aatccttccg gtagggggctc acacttctgg tagatagttc aaagccttgg tcggataggt    9540
gcacatcgaa cacttcacga acaatgaaat ggttctcagc atccaatgtt ccgccacct    9600
gctcagggat caccgaaatc ttcatatgac gcctaacgcc tggcacagcg gatcgcaaac    9660
ctggcgcggc ttttggcaca aaaggcgtga caggtttgcg aatccgttgc tgccacttgt    9720
taacccttt gccagatttg gtaactataa tttatgttag aggcgaagtc ttgggtaaaa    9780
actggcctaa aattgctggg gatttcagga aagtaaacat caccttccgg ctcgatgtct    9840
attgtagata tatgtagtgt atctacttga tcgggggatc tgctgcctcg cgcgtttcgg    9900
tgatgacggt gaaaacctct gacacatgca gctcccggag acggtcacag cttgtctgta    9960
agcggatgcc gggagcagac aagcccgtca gggcgcgtca gcgggtgttg gcgggtgtcg   10020
gggcgcagcc atgacccagt cacgtagcga tagcggagtg tatactggct taactatgcg   10080
gcatcagagc agattgtact gagagtgcac catatgcggt gtgaaatacc gcacagatgc   10140
gtaaggagaa ataccgcat caggcgctct ccgcttcct cgctcactga ctcgctgcgc   10200
tcggtcgttc ggctgcggcg agcggtatca gctcactcaa aggcggtaat acggttatcc   10260
acagaatcag gggataacgc aggaaagaac atgtgagcaa aaggccagca aaaggccagg   10320
aaccgtaaaa aggccgcgtt gctggcgttt ttccataggc tccgcccccc tgacgagcat   10380
cacaaaaatc gacgctcaag tcagaggtgg cgaaacccga caggactata aagataccag   10440
gcgtttcccc ctggaagctc cctcgtgcgc tctcctgttc cgaccctgcc gcttaccgga   10500
tacctgtccg cctttctccc ttcgggaagc gtggcgcttt ctcatagctc acgctgtagg   10560
tatctcagtt cggtgtaggt cgttcgctcc aagctgggct gtgtgcacga accccccgtt   10620
cagcccgacc gctgcgcctt atccggtaac tatcgtcttg agtccaaccc ggtaagacac   10680
gacttatcgc cactggcagc agccactggt aacaggatta gcagagcgag gtatgtaggc   10740
ggtgctacag agttcttgaa gtggtggcct aactacggct acactagaag gacagtattt   10800
ggtatctgcg ctctgctgaa gccagttacc ttcggaaaaa gagttggtag ctcttgatcc   10860
ggcaaacaaa ccaccgctgg tagcggtggt ttttttgttt gcaagcagca gattacgcgc   10920
agaaaaaaag gatctcaaga agatcctttg atcttttcta cggggtctga cgctcagtgg   10980
aacgaaaact cacgttaagg gattttggtc atgagattat caaaaaggat cttcacctag   11040
atcctttaa attaaaaatg aagttttaaa tcaatctaaa gtatatatga gtaaacttgg   11100
tctgacagtt accaatgctt aatcagtgag gcacctatct cagcgatctg tctatttcgt   11160
```

```
tcatccatag ttgcctgact ccccgtcgtg tagataacta cgatacggga gggcttacca    11220
tctggcccca gtgctgcaat gataccgcga gacccacgct caccggctcc agatttatca    11280
gcaataaacc agccagccgg aagggccgag cgcagaagtg gtcctgcaac tttatccgcc    11340
tccatccagt ctattaattg ttgccgggaa gctagagtaa gtagttcgcc agttaatagt    11400
ttgcgcaacg ttgttgccat tgctgcaggg gggggggggg gggggacttc ccattgttca    11460
ttccacggac aaaaacagag aaaggaaacg acagaggcca aaaagcctcg ctttcagcac    11520
ctgtcgtttc ctttcttttc agagggtatt taaataaaa acattaagtt atgacgaaga     11580
agaacggaaa cgccttaaac cggaaaattt tcataaatag cgaaacccg cgaggtcgcc     11640 gcccccgtaac ctgtcggatc accggaaagg acccgtaaag tgataatgat tatcatctac   11700
atatcacaac gtgcgtggag gccatcaaac cacgtcaaat aatcaattat gacgcaggta    11760
tcgtattaat tgatctgcat caacttaacg taaaaacaac ttcagacaat acaaatcagc    11820
gacactgaat acgggcaac ctcatgtccc cccccccccc cccctgcag gcatcgtggt      11880 gtcacgctcg tcgtttggta tggcttcatt cagctccggt tcccaacgat caaggcgagt    11940
tacatgatcc cccatgttgt gcaaaaaagc ggttagctcc ttcggtcctc cgatcgttgt    12000
cagaagtaag ttggccgcag tgttatcact catggttatg gcagcactgc ataattctct    12060
tactgtcatg ccatccgtaa gatgctttc tgtgactggt gagtactcaa ccaagtcatt     12120
ctgagaatag tgtatgcggc gaccgagttg ctcttgcccg gcgtcaacac gggataatac    12180
cgcgccacat agcagaactt taaaagtgct catcattgga aaacgttctt cggggcgaaa    12240
actctcaagg atcttaccgc tgttgagatc cagttcgatg taacccactc gtgcacccaa    12300
ctgatcttca gcatctttta ctttcaccag cgtttctggg tgagcaaaaa caggaaggca    12360
aaatgccgca aaaaagggaa taaggcgac acggaaatgt tgaatactca tactcttcct    12420
ttttcaatat tattgaagca tttatcaggg ttattgtctc atgagcggat acatatttga    12480
atgtatttag aaaaataaac aaataggggt tccgcgcaca tttccccgaa aagtgccacc    12540
tgacgtctaa gaaaccatta ttatcatgac attaacctat aaaaataggc gtatcacgag    12600
gccctttcgt cttcaagaat tggtcgacga tcttgctgcg ttcggatatt ttcgtggagt    12660
tcccgccaca gacccggatt gaaggcgaga tccagcaact cgcgccagat catcctgtga    12720
cggaactttg gcgcgtgatg actggccagg acgtcggccg aaagagcgac aagcagatca    12780
cgcttttcga cagcgtcgga tttgcgatcg aggattttc ggcgctgcgc tacgtccgcg     12840
accgcgttga gggatcaagc cacagcagcc cactcgacct tctagccgac ccagacgagc    12900
caagggatct ttttggaatg ctgctccgtc gtcaggcttt ccgacgtttg ggtggttgaa    12960
cagaagtcat tatcgtacgg aatgccaagc actcccgagg ggaaccctgt ggttggcatg    13020
cacatacaaa tggacgaacg gataaacctt ttcacgccct tttaaatatc cgttattcta    13080
ataaacgctc ttttctctta ggtttacccg ccaatatatc ctgtcaaaca ctgatagttt    13140
aaactgaagg cgggaaacga caatctgatc atgagcggag aattaaggga gtcacgttat    13200 gaccccccgcc gatgacgcgg gacaagccgt tttacgtttg gaactgacag aaccgcaacg    13260
ttgaaggagc cactcagc                                                   13278
```

<210> SEQ ID NO 11
<211> LENGTH: 50
<212> TYPE: DNA
<213> ORGANISM: Artificial Sequence
<220> FEATURE:
<223> OTHER INFORMATION: poly-linker

```
<400> SEQUENCE: 11
gatcactagt ggcgcgccta ggagatctcg agtagggata acagggtaat              50

<210> SEQ ID NO 12
<211> LENGTH: 25
<212> TYPE: DNA
<213> ORGANISM: Artificial Sequence
<220> FEATURE:
<223> OTHER INFORMATION: attB1 seqeunce

<400> SEQUENCE: 12
acaagtttgt acaaaaaagc aggct                                         25

<210> SEQ ID NO 13
<211> LENGTH: 25
<212> TYPE: DNA
<213> ORGANISM: Artificial Sequence
<220> FEATURE:
<223> OTHER INFORMATION: attB2 sequence

<400> SEQUENCE: 13
accactttgt acaagaaagc tgggt                                         25

<210> SEQ ID NO 14
<211> LENGTH: 4778
<212> TYPE: DNA
<213> ORGANISM: Artificial Sequence
<220> FEATURE:
<223> OTHER INFORMATION: PHP23112 construct

<400> SEQUENCE: 14
gaaaggccca gtcttccgac tgagcctttc gttttatttg atgcctggca gttccctact   60
ctcgcgttaa cgctagcatg gatgttttcc cagtcacgac gttgtaaaac gacggccagt   120
cttaagctcg ggcccgcgtt aacgctacca tggagctcca ataatgatt ttattttgac    180 tgatagtgac ctgttcgttg caacaaattg ataagcaatg cttttttata atgccaactt   240
tgtatagaaa agttgggccg aattcgagct cggtacggcc agaatggccc ggaccgggtt   300
accgaattcg agctcggtac cctgggatca gcttgcatgc ctgcagtgca gcgtgacccg   360
gtcgtgcccc tctctagaga taatgagcat tgcatgtcta agttataaaa aattaccaca   420 tattttttt gtcacacttg tttgaagtgc agtttatcta tctttataca tatatttaaa   480
ctttactcta cgaataatat aatctatagt actacaataa tatcagtgtt ttagagaatc   540
atataaatga acagttagac atggtctaaa ggacaattga gtattttgac aacaggactc   600
tacagtttta tcttttttagt gtgcatgtgt tctccttttt ttttgcaaat agcttcacct   660
atataatact tcatccattt tattagtaca tccatttagg gtttagggtt aatggttttt   720
atagactaat tttttagta catctatttt attctatttt agcctctaaa ttaagaaaac   780
taaaactcta tttagttttt tttatttaat aatttagata taaatagaa taaaataaag    840 tgactaaaaa ttaaacaaat acccctttaag aaattaaaaa aactaaggaa acattttct    900 tgtttcgagt agataatgcc agcctgttaa acgccgtcga cgagtctaac ggacaccaac   960
cagcgaacca gcagcgtcgc gtcgggccaa gcgaagcaga cggcacggca tctctgtcgc   1020
tgcctctgga cccctctcga gagttccgct ccaccgttgg acttgctccg ctgtcggcat   1080
ccagaaattg cgtggcggag cggcagacgt gagccggcac ggcaggcggc ctcctcctcc   1140
tctcacggca ccggcagcta cggggggattc ctttcccacc gctccttcgc tttcccttcc   1200
tcgcccgccg taataaatag acaccccctc cacaccctct ttccccaacc tcgtgttgtt   1260
```

```
cggagcgcac acacacacaa ccagatctcc cccaaatcca cccgtcggca cctccgcttc    1320
aaggtacgcc gctcgtcctc cccccccccc ctctctacct tctctagatc ggcgttccgg    1380
tccatgcatg gttagggccc ggtagttcta cttctgttca tgtttgtgtt agatccgtgt    1440
ttgtgttaga tccgtgctgc tagcgttcgt acacggatgc gacctgtacg tcagacacgt    1500
tctgattgct aacttgccag tgtttctctt tggggaatcc tgggatggct ctagccgttc    1560
cgcagacggg atcgatttca tgattttttt tgtttcgttg catagggttt ggtttgccct    1620
tttcctttat ttcaatatat gccgtgcact tgtttgtcgg gtcatctttt catgcttttt    1680
tttgtcttgg ttgtgatgat gtggtctggt tgggcggtcg ttctagatcg gagtagaatt    1740
ctgtttcaaa ctacctggtg gatttattaa ttttggatct gtatgtgtgt gccatacata    1800
ttcatagtta cgaattgaag atgatggatg gaaatatcga tctaggatag gtatacatgt    1860
tgatgcgggt tttactgatg catatacaga gatgcttttt gttcgcttgg ttgtgatgat    1920
gtggtgtggt tgggcggtcg ttcattcgtt ctagatcgga gtagaatact gtttcaaact    1980
acctggtgta tttattaatt ttggaactgt atgtgtgtgt catacatctt catagttacg    2040
agtttaagat ggatggaaat atcgatctag gataggtata catgttgatg tgggttttac    2100
tgatgcatat acatgatggc atatgcagca tctattcata tgctctaacc ttgagtacct    2160
atctattata ataaacaagt atgttttata attattttga tcttgatata cttggatgat    2220
ggcatatgca gcagctatat gtggattttt ttagccctgc cttcatacgc tatttatttg    2280
cttggtactg tttcttttgt cgatgctcac cctgttgttt ggtgttactt ctgcaggtcg    2340
actctagagg atcagcttgg tcacccggtc cgggcctaga aggccagctt caagtttgta    2400
caaaaaagtt gaacgagaaa cgtaaaatga tataaatatc aatatattaa attagatttt    2460
gcataaaaaa cagactacat aatactgtaa aacacaacat atgcagtcac tatgaatcaa    2520
ctacttagat ggtattagtg acctgtagaa ttcgagctct agagctgcag gcggccgcg    2580 atatccccta tagtgagtcg tattacatgg tcatagctgt ttcctggcag ctctggcccg    2640
tgtctcaaaa tctctgatgt tacattgcac aagataaaaa tatatcatca tgaacaataa    2700
aactgtctgc ttacataaac agtaatacaa ggggtgttat gagccatatt caacgggaaa    2760
cgtcgaggcc gcgattaaat tccaacatgg atgctgattt atatgggtat aaatgggctc    2820
gcgataatgt cgggcaatca ggtgcgacaa tctatcgctt gtatgggaag cccgatgcgc    2880
cagagttgtt tctgaaacat ggcaaaggta gcgttgccaa tgatgttaca gatgagatgg    2940
tcagactaaa ctggctgacg gaatttatgc ctcttccgac catcaagcat tttatccgta    3000
ctcctgatga tgcatggtta ctcaccactg cgatccccgg aaaaacagca ttccaggtat    3060
tagaagaata tcctgattca ggtgaaaata ttgttgatgc gctggcagtg ttcctgcgcc    3120
ggttgcattc gattcctgtt tgtaattgtc cttttaacag cgatcgcgta tttcgtctcg    3180
ctcaggcgca atcacgaatg aataacggtt tggttgatgc gagtgatttt gatgacgagc    3240
gtaatggctg gcctgttgaa caagtctgga agaaatgca taaacttttg ccattctcac    3300
cggattcagt cgtcactcat ggtgatttct cacttgataa ccttattttt gacgagggga    3360
aattaatagg ttgtattgat gttggacgag tcggaatcgc agaccgatac caggatcttg    3420
ccatcctatg gaactgcctc ggtgagtttt ctccttcatt acagaaacgg ctttttcaaa    3480
aatatggtat tgataatcct gatatgaata aattgcagtt tcatttgatg ctcgatgagt    3540
ttttctaatc agaattggtt aattggttgt aacactggca gagcattacg ctgacttgac    3600
gggacggcgc aagctcatga ccaaaatccc ttaacgtgag ttacgcgtcg ttccactgag    3660
```

```
cgtcagaccc cgtagaaaag atcaaaggat cttcttgaga tcctttttt ctgcgcgtaa    3720 tctgctgctt gcaaacaaaa aaaccaccgc taccagcggt ggtttgtttg ccggatcaag    3780
agctaccaac tcttttccg aaggtaactg gcttcagcag agcgcagata ccaaatactg    3840
tccttctagt gtagccgtag ttaggccacc acttcaagaa ctctgtagca ccgcctacat    3900
acctcgctct gctaatcctg ttaccagtgg ctgctgccag tggcgataag tcgtgtctta    3960
ccgggttgga ctcaagacga tagttaccgg ataaggcgca gcggtcgggc tgaacggggg    4020
gttcgtgcac acagcccagc ttggagcgaa cgacctacac cgaactgaga tacctacagc    4080
gtgagcattg agaaagcgcc acgcttcccg aagggagaaa ggcggacagg tatccggtaa    4140
gcggcagggt cggaacagga gagcgcacga gggagcttcc agggggaaac gcctggtatc    4200
tttatagtcc tgtcgggttt cgccacctct gacttgagcg tcgatttttg tgatgctcgt    4260
caggggggcg gagcctatgg aaaaacgcca gcaacgcggc cttttacgg ttcctggcct    4320 tttgctggcc ttttgctcac atgttctttc ctgcgttatc ccctgattct gtggataacc    4380
gtattaccgc ctttgagtga gctgataccg ctcgccgcag ccgaacgacc gagcgcagcg    4440
agtcagtgag cgaggaagcg gaagagcgcc caatacgcaa accgcctctc cccgcgcgtt    4500
ggccgattca ttaatgcagc tggcacgaca ggtttcccga ctggaaagcg ggcagtgagc    4560
gcaacgcaat taatacgcgt accgctagcc aggaagagtt tgtagaaacg caaaaggcc    4620 atccgtcagg atggccttct gcttagtttg atgcctggca gtttatggcg ggcgtcctgc    4680
ccgccaccct ccgggccgtt gcttcacaac gttcaaatcc gctcccggcg gatttgtcct    4740
actcaggaga gcgttcaccg acaaacaaca gataaaac                           4778

<210> SEQ ID NO 15
<211> LENGTH: 54
<212> TYPE: DNA
<213> ORGANISM: Artificial Sequence
<220> FEATURE:
<223> OTHER INFORMATION: forward primer VC062

<400> SEQUENCE: 15
ttaaacaagt tgtacaaaaa aagcaggctg caattaaccc tcactaaagg gaac          54

<210> SEQ ID NO 16
<211> LENGTH: 53
<212> TYPE: DNA
<213> ORGANISM: Artificial Sequence
<220> FEATURE:
<223> OTHER INFORMATION: reverse primer VC063

<400> SEQUENCE: 16
ttaaaccact tgtacaaga aagctgggtg cgtaatacga ctcactatag ggc            53

<210> SEQ ID NO 17
<211> LENGTH: 1216
<212> TYPE: DNA
<213> ORGANISM: Zea mays

<400> SEQUENCE: 17
cgcagcccgc ccctctctct ctctctctcg gttcctgcgc acgcacacac gcacgtttcc     60
agttcgaccg agccagagcc ccgcccgg cagtttccat tcgctgtcgc gctcctcctc      120
ctcctcctgc acatcccctc cccccgaatt cgagccggag gaccgaagag tagatctgcg    180
ccgggcgacc agaggatggc cgtcaactgg gagctgcagg gctgctgcca ccgcgaccag    240
aggatcttca tcgccgccgt tggagtctcc accgtcgtca tcctcctcct ctggaggacg    300
```

-continued

```
ttcctgctca cgccgttcaa gctcatcacc gtcttcctcc acgagaccag ccacgcgctc    360
gcctgcaagc tcacctgcgg cgatgtagaa ggcatgcagg tccatgcgaa tgagggtggc    420
gttactcaaa ctcggggtgg catatattgg ataatcttgc ccgctggata tctgggttca    480
tcatttgggg aatggtgtt catacttgca tccacaaatc tcctcactac aagaattgca    540
gcgggttgtt tcatacttgc actgtttatt gtccttttg ttgcagacaa ttggtttctt    600
cgctggctct gccttggatt cattgtattc attgctgttg tttgggtcat acaagaattt    660
acatctttcc atattctgaa atatgtgatc ttattcatag gtgtgatgaa cagcttattt    720
tcagtttatg atatttatga cgacttgata tcccgaagag ttaatacaag tgatgctgag    780
aagtttgctg aaatatgccc ttgcccttgc aatggttttg catgggtgt tatatgggga    840 ttcatctcgt ttatcttcct ctgcgcttca atataccttg gactggtcat attgtcttga    900
gggttccaac ctcgcgcacg ccgttttgat ctgacaacca actctggttg ctttttcca    960 gagttctcct tgctctagat tttgggttca aacttacatt gttctggcgg ctgtacagta    1020
tacatgtagg gtaaacatgt acatccatcg tggagttaat tcggcgggga ttgttcatgt    1080
gattcttcga ttttagcggt tctatagata ccattgctca tttatggtct gtagcctcat    1140
tgctcatttg accaatttga aatcgtattc agaaacgcca aaaaaaaaa aaaaaaaaa    1200 aaaaaaaaaa aaaag                                                    1216
```

<210> SEQ ID NO 18
<211> LENGTH: 234
<212> TYPE: PRT
<213> ORGANISM: Zea mays

<400> SEQUENCE: 18

```
Met Ala Val Asn Trp Glu Leu Gln Gly Cys Cys His Arg Asp Gln Arg
1               5                   10                  15

Ile Phe Ile Ala Ala Val Gly Val Ser Thr Val Val Ile Leu Leu Leu
                20                  25                  30

Trp Arg Thr Phe Leu Leu Thr Pro Phe Lys Leu Ile Thr Val Phe Leu
            35                  40                  45

His Glu Thr Ser His Ala Leu Ala Cys Lys Leu Thr Cys Gly Asp Val
        50                  55                  60

Glu Gly Met Gln Val His Ala Asn Glu Gly Gly Val Thr Gln Thr Arg
65                  70                  75                  80

Gly Gly Ile Tyr Trp Ile Ile Leu Pro Ala Gly Tyr Leu Gly Ser Ser
                85                  90                  95

Phe Trp Gly Met Val Phe Ile Leu Ala Ser Thr Asn Leu Leu Thr Thr
                100                 105                 110

Arg Ile Ala Ala Gly Cys Phe Ile Leu Ala Leu Phe Ile Val Leu Phe
            115                 120                 125

Val Ala Asp Asn Trp Phe Leu Arg Trp Leu Cys Leu Gly Phe Ile Val
        130                 135                 140

Phe Ile Ala Val Val Trp Val Ile Gln Glu Phe Thr Ser Phe His Ile
145                 150                 155                 160

Leu Lys Tyr Val Ile Leu Phe Ile Gly Val Met Asn Ser Leu Phe Ser
                165                 170                 175

Val Tyr Asp Ile Tyr Asp Asp Leu Ile Ser Arg Arg Val Asn Thr Ser
            180                 185                 190

Asp Ala Glu Lys Phe Ala Glu Ile Cys Pro Cys Pro Cys Asn Gly Phe
        195                 200                 205

Ala Trp Gly Val Ile Trp Gly Phe Ile Ser Phe Ile Phe Leu Cys Ala
```

```
                210                 215                 220
Ser Ile Tyr Leu Gly Leu Val Ile Leu Ser
225                 230
```

<210> SEQ ID NO 19
<211> LENGTH: 877
<212> TYPE: DNA
<213> ORGANISM: Zea mays

<400> SEQUENCE: 19

```
agagccccgc cgggcagttt ccgttcgctg ttgcgatcca cctcctgcct gcacatcccc    60
tcccccgagt tcgagccgga gggccgaaga gtagatctgc ggcggcggcc agaggatggc   120
cgtcaactgg gagctgcggg gctgctgcga ccacgaccag aggatcttca tcgccgccgt   180
cggcgtctcc accgtcgtca tcctcctcct ctggaggacg ttcctgctca cgccgttcaa   240
gctcatcacc gtcttcctcc acgagaccag ccacgcgctt gcctgcaagc tcacttgcgg   300
cgatgtagaa ggcatgcagg tccatgcgaa tgagggtggc gttactcaaa cccggggtgg   360
catatattgg ataatcttgc cgctggata tctgggttca tcattttggg gaatggtctt    420
catacttgca tccacaaatc tcctcactac aagaattgca gcgggttgtt tcatacttgc   480
attgtttatt gttcttttg ttgcagaaaa ttggtttctt cgctggctct gccttggatt    540
cattgtgttc attgctgttg tttgggtcat acaagaattt acatctttcc atgttctgaa   600
atatgtgatc ttattcatag gtgtgatgaa cagcttattt tcagtttacg atatttatga   660
tgacttgata tcccgaagag ttaacacaag tgatgctgaa aagtttgctg aaatctgccc   720
ttgcccctgc aatggttttg catggggtgt tatatgggga ttcatctcgt ttatctttct   780
ctgcgcttca ataccttg gactggtcat attgtcttga gggttcgcca ttttgatctg     840
acaatcgact ctggttggct ttttcgaagc ttcgttg                            877
```

<210> SEQ ID NO 20
<211> LENGTH: 234
<212> TYPE: PRT
<213> ORGANISM: Zea mays

<400> SEQUENCE: 20

```
Met Ala Val Asn Trp Glu Leu Arg Gly Cys Cys Asp His Asp Gln Arg
1               5                   10                  15

Ile Phe Ile Ala Ala Val Gly Val Ser Thr Val Ile Leu Leu Leu
                20                  25                  30

Trp Arg Thr Phe Leu Leu Thr Pro Phe Lys Leu Ile Thr Val Phe Leu
            35                  40                  45

His Glu Thr Ser His Ala Leu Ala Cys Lys Leu Thr Cys Gly Asp Val
        50                  55                  60

Glu Gly Met Gln Val His Ala Asn Glu Gly Gly Val Thr Gln Thr Arg
65                  70                  75                  80

Gly Gly Ile Tyr Trp Ile Ile Leu Pro Ala Gly Tyr Leu Gly Ser Ser
                85                  90                  95

Phe Trp Gly Met Val Phe Ile Leu Ala Ser Thr Asn Leu Leu Thr Thr
            100                 105                 110

Arg Ile Ala Ala Gly Cys Phe Ile Leu Ala Leu Phe Ile Val Leu Phe
        115                 120                 125

Val Ala Glu Asn Trp Phe Leu Arg Trp Leu Cys Leu Gly Phe Ile Val
    130                 135                 140

Phe Ile Ala Val Val Trp Val Ile Gln Glu Phe Thr Ser Phe His Val
145                 150                 155                 160
```

```
Leu Lys Tyr Val Ile Leu Phe Ile Gly Val Met Asn Ser Leu Phe Ser
                165                 170                 175

Val Tyr Asp Ile Tyr Asp Asp Leu Ile Ser Arg Arg Val Asn Thr Ser
            180                 185                 190

Asp Ala Glu Lys Phe Ala Glu Ile Cys Pro Cys Pro Cys Asn Gly Phe
        195                 200                 205

Ala Trp Gly Val Ile Trp Gly Phe Ile Ser Phe Ile Phe Leu Cys Ala
    210                 215                 220

Ser Ile Tyr Leu Gly Leu Val Ile Leu Ser
225                 230

<210> SEQ ID NO 21
<211> LENGTH: 1114
<212> TYPE: DNA
<213> ORGANISM: Glycine max

<400> SEQUENCE: 21
gtttctttga ttctctctcc tacacccacc aaaccaaaaa cgcttccttt aatcagaaga      60
ttcagaacaa aacccatcac caccattcaa caaagtttaa tccttttcac ttcaattcat     120
cattgccttt tcgtttaagc acaaaagcta tgccgaactg ggagctcagg aactgttgtg     180
accacgacca gaaggtcttc attgcttgtg ttgctgcctt caccgttgta atcctcgtgc     240
tatggaggac ctttctactt acaccttta  agctcatcac cgtgtttctg catgaagcaa     300
gtcatgccat tgcttgctgg ctcacttgtg gcaaggtgga gggaattcag gttcatgcaa     360
atgagggtgg ggtaacccag actcgtggtg gcatatactg ggtgatcctg cctgctggat     420
atctcggttc atcattttgg ggaatggctt tgatacttgc gtccacaaat cttctcactg     480
caaaaattgc tgctggttgc tttattgctg ctttaattgt tgtgctcttt ctcgcaaaaa     540 attggacccct ccgaggactc tgtattggat ttattgtttt tattgctgta atttggcttc     600
tgcaagagaa acaacagtc cacgttcttc gctatgtgat tctctttatt ggtgtgatga     660
acagtttgtt ttcagtttat gatatttacg atgatttaat atctcggaga gtccactcta     720
gtgatgctga aaagtttgca gaagtttgcc catgcccttg taatggtttt ggatggggag     780
ttatttgggg aatgatatca tttgcatttc tttgcgcatc tttgtacctt ggcttggtca     840
tattatcagg ttgagaatgt tgtatccaag cggtttggta ctgcaaagag cttgacccttt    900 ctcttttgat gatttgtatt tttcttctaa tttttttcta tctgctggga gtttgctctc     960
tcaatgttac tcccatgcct tcattctttg cagcctatta tgggttgctt gatacatgat    1020 tgctttttgta tagaaactta gttccatgta ttgagttatt tgggcagatt tacatttagt    1080
gaaaaaaaaa aaaaaaaaaa aaaaaaaaaa aaaa                                 1114

<210> SEQ ID NO 22
<211> LENGTH: 234
<212> TYPE: PRT
<213> ORGANISM: Glycine max

<400> SEQUENCE: 22

Met Pro Asn Trp Glu Leu Arg Asn Cys Cys Asp His Asp Gln Lys Val
1               5                   10                  15

Phe Ile Ala Cys Val Ala Ala Phe Thr Val Val Ile Leu Val Leu Trp
            20                  25                  30

Arg Thr Phe Leu Leu Thr Pro Phe Lys Leu Ile Thr Val Phe Leu His
        35                  40                  45

Glu Ala Ser His Ala Ile Ala Cys Trp Leu Thr Cys Gly Lys Val Glu
```

```
                 50                  55                  60
Gly Ile Gln Val His Ala Asn Glu Gly Val Thr Gln Thr Arg Gly
 65                  70                  75                  80

Gly Ile Tyr Trp Val Ile Leu Pro Ala Gly Tyr Leu Gly Ser Ser Phe
                 85                  90                  95

Trp Gly Met Ala Leu Ile Leu Ala Ser Thr Asn Leu Leu Thr Ala Lys
                100                 105                 110

Ile Ala Ala Gly Cys Phe Ile Ala Ala Leu Ile Val Val Leu Phe Leu
                115                 120                 125

Ala Lys Asn Trp Thr Leu Arg Gly Leu Cys Ile Gly Phe Ile Val Phe
130                 135                 140

Ile Ala Val Ile Trp Leu Leu Gln Glu Lys Thr Thr Val His Val Leu
145                 150                 155                 160

Arg Tyr Val Ile Leu Phe Ile Gly Val Met Asn Ser Leu Phe Ser Val
                165                 170                 175

Tyr Asp Ile Tyr Asp Asp Leu Ile Ser Arg Arg Val His Ser Ser Asp
                180                 185                 190

Ala Glu Lys Phe Ala Glu Val Cys Pro Cys Pro Cys Asn Gly Phe Gly
                195                 200                 205

Trp Gly Val Ile Trp Gly Met Ile Ser Phe Ala Phe Leu Cys Ala Ser
    210                 215                 220

Leu Tyr Leu Gly Leu Val Ile Leu Ser Gly
225                 230

<210> SEQ ID NO 23
<211> LENGTH: 1261
<212> TYPE: DNA
<213> ORGANISM: Glycine max

<400> SEQUENCE: 23
ctcctacacc caccaaacca aaacgcttcc ttaatcataa gattcagaac aaaacccatc     60
accaccattc attaaagttc aatccttttc actttaattc atcattgccg tttcgtttaa    120
gcacaaaagc tatgccgaac tgggagctca ggaactgttg tgaccatgac cagaagatct    180
tcattgcttg tgttgctgcc ttcaccgttg taatcctcgt gctatggagg accttctac    240
ttacaccttt taagctcatc actgtgtttc tgcatgaagc gagtcatgcc attgcttgct    300
ggctcacttg tggcaaggtg gagggaattc aggttcatgc aaatgagggt ggggtaaccc    360
agactcgtgg tggcatatac tgggtgatct gcctgctgg atatcttggt tcatcatttt    420
ggggaatggt tttgatactt gcgtccacaa atcttctcac tgcaaaaatt gctgctggtt    480
gcttcattgc tgctctaatt gttgtgctat tccttgcaaa aaattggacc ctccgaggac    540
tctgtattgg atttattgtt tttattgctg taatttggct tctgcaagag aaaacaactg    600
tccatgttct tcgctatgtc attctcttta ttggtgtgat gaacagtttg ttttcagttt    660
atgatattta tgatgattta atatctcgga gagtccactc tagtgatgct gaaaagtttg    720
cagaagtttg cccatgccct tgtaatggtt ttggatgggg agttattgg ggaatgatat    780
catttgcatt tctttgcgca tctttgtacc ttggcttggt catattatca ggttgagaaa    840
gttgtatttg gtactgcaaa gaaattgacc ctttctcttt tgagggtttg cattttgtt    900
ctaatttttt ctttctgctg ggagtttgct ctctcaatgt tactcccatg ccttcattct    960
ttgcagccta ttcgggttg cttgatacat gattgctttt gtatagaaaa cttagttcca   1020
tgtattgaat tattggggc cgattttacag ttagtgaaat acatgtgagt atttcaatag   1080
ataggttgcc tttggcactt gcagctatta ttctcccttt ttttcccctcc aaatttttca  1140
```

-continued

```
tgtctatgta aaagcataca actgggctgg tttaggggta ttcgagacct taagtgcaaa    1200
acgttgtggc atcttaataa tataaaatac attgtacaaa aaaaaaaaaa aaaaaaaaaa    1260
a                                                                    1261
```

<210> SEQ ID NO 24
<211> LENGTH: 234
<212> TYPE: PRT
<213> ORGANISM: Glycine max

<400> SEQUENCE: 24

```
Met Pro Asn Trp Glu Leu Arg Asn Cys Cys Asp His Asp Gln Lys Ile
1               5                   10                  15

Phe Ile Ala Cys Val Ala Ala Phe Thr Val Val Ile Leu Val Leu Trp
            20                  25                  30

Arg Thr Phe Leu Leu Thr Pro Phe Lys Leu Ile Thr Val Phe Leu His
        35                  40                  45

Glu Ala Ser His Ala Ile Ala Cys Trp Leu Thr Cys Gly Lys Val Glu
    50                  55                  60

Gly Ile Gln Val His Ala Asn Glu Gly Val Thr Gln Thr Arg Gly
65                  70                  75                  80

Gly Ile Tyr Trp Val Ile Leu Pro Ala Gly Tyr Leu Gly Ser Ser Phe
                85                  90                  95

Trp Gly Met Val Leu Ile Leu Ala Ser Thr Asn Leu Leu Thr Ala Lys
            100                 105                 110

Ile Ala Ala Gly Cys Phe Ile Ala Ala Leu Ile Val Val Leu Phe Leu
        115                 120                 125

Ala Lys Asn Trp Thr Leu Arg Gly Leu Cys Ile Gly Phe Ile Val Phe
    130                 135                 140

Ile Ala Val Ile Trp Leu Leu Gln Glu Lys Thr Thr Val His Val Leu
145                 150                 155                 160

Arg Tyr Val Ile Leu Phe Ile Gly Val Met Asn Ser Leu Phe Ser Val
                165                 170                 175

Tyr Asp Ile Tyr Asp Asp Leu Ile Ser Arg Arg Val His Ser Ser Asp
            180                 185                 190

Ala Glu Lys Phe Ala Glu Val Cys Pro Cys Pro Cys Asn Gly Phe Gly
        195                 200                 205

Trp Gly Val Ile Trp Gly Met Ile Ser Phe Ala Phe Leu Cys Ala Ser
    210                 215                 220

Leu Tyr Leu Gly Leu Val Ile Leu Ser Gly
225                 230
```

<210> SEQ ID NO 25
<211> LENGTH: 1018
<212> TYPE: DNA
<213> ORGANISM: Helianthus sp.

<400> SEQUENCE: 25

```
aaaagccacc tcattctctc tctctctctc taacaatcat attttcaaac ttcttcgagg     60
agttgaagag agagaacgca acagtcactg atgacgtcac ctaattggga gctcaagaat    120
tgctgcgatc gcgaccagaa attctttctc gctaccgtcg gcatctattc tctcgtcatt    180
ctcgcgttat ggaggacatt tctgcttaca ccattcaagc ttatcacagt ctttcttcat    240
gaagctagcc atgcaatcgc ttgtaagctc acatgtggag aggtcatggg catggaggtt    300
catgccaatg agggtggggt gacgcagaca cgcggtggag tatattggtt aatattgcca    360
```

```
gccggatatc tcggttcatc gttttgggga atgcttttga tcctggcatc tactgacctt    420
ttaactgcga gaattgctgc cggatgttta gcagccgcct tgcttatcgt gctcttcatt    480
gccaaaaatt ggactcttcg aggactctgc attggattca tcgtattcct tgctattgtt    540
tggctactgc aagaaaaaac cacagtccgt atccttcgtt acgtcattct attcatcggt    600
gtcatgaaca gcttgttttc ggtttatgat atttatgatg atttaatttc ccggcgagtt    660
aattctagtg acgctgaaaa gtttgccgaa atttgtcctt gcccgtgtaa tggtgttgct    720
tggggagtca tatggggaat gatatccttc acttttctca gtgcttcagt ttacctggga    780
cttgtaatct tgtcatgaga ttcatggact ttgaacttca ttcatgggc tgtcttgatg     840 tgatctgatt atttactgca ctaacttta gtttcattct tttgacccct ggttgggtta    900
catacatatt gttgctttgt gtgcatacag tttcagtgta gcaaaaatt attttgtact    960 tttttgtgg atatgcaaat tcaaatctag agtttcaaaa aaaaaaaaaaa aaaaaaaaa    1018
```

<210> SEQ ID NO 26
<211> LENGTH: 235
<212> TYPE: PRT
<213> ORGANISM: Helianthus sp.

<400> SEQUENCE: 26

```
Met Thr Ser Pro Asn Trp Glu Leu Lys Asn Cys Cys Asp Arg Asp Gln
1               5                   10                  15

Lys Phe Phe Leu Ala Thr Val Gly Ile Tyr Ser Leu Val Ile Leu Ala
            20                  25                  30

Leu Trp Arg Thr Phe Leu Leu Thr Pro Phe Lys Leu Ile Thr Val Phe
        35                  40                  45

Leu His Glu Ala Ser His Ala Ile Ala Cys Lys Leu Thr Cys Gly Glu
    50                  55                  60

Val Met Gly Met Glu Val His Ala Asn Glu Gly Val Thr Gln Thr
65                  70                  75                  80

Arg Gly Gly Val Tyr Trp Leu Ile Leu Pro Ala Gly Tyr Leu Gly Ser
                85                  90                  95

Ser Phe Trp Gly Met Leu Leu Ile Leu Ala Ser Thr Asp Leu Leu Thr
            100                 105                 110

Ala Arg Ile Ala Ala Gly Cys Leu Ala Ala Ala Leu Leu Ile Val Leu
        115                 120                 125

Phe Ile Ala Lys Asn Trp Thr Leu Arg Gly Leu Cys Ile Gly Phe Ile
    130                 135                 140

Val Phe Leu Ala Ile Val Trp Leu Leu Gln Glu Lys Thr Thr Val Arg
145                 150                 155                 160

Ile Leu Arg Tyr Val Ile Leu Phe Ile Gly Val Met Asn Ser Leu Phe
                165                 170                 175

Ser Val Tyr Asp Ile Tyr Asp Asp Leu Ile Ser Arg Arg Val Asn Ser
            180                 185                 190

Ser Asp Ala Glu Lys Phe Ala Glu Ile Cys Pro Cys Pro Cys Asn Gly
        195                 200                 205

Val Ala Trp Gly Val Ile Trp Gly Met Ile Ser Phe Thr Phe Leu Ser
    210                 215                 220

Ala Ser Val Tyr Leu Gly Leu Val Ile Leu Ser
225                 230                 235
```

<210> SEQ ID NO 27
<211> LENGTH: 1144
<212> TYPE: DNA
<213> ORGANISM: Helianthus sp.

<400> SEQUENCE: 27

```
gccgaattttt ctcagaatat ttgtaaaata ttcattgacc cctggcttcc ataaataaat      60
catgcccatt tcttctctag atcccaaccc acctcataat ttccttaaat cccactcatt     120
tcccatcaat ctttattctt tctagagata aacatggcta attgggagct cagagactgt     180
tgtaatcatg atcagttgct gtttcttatc actctggctt tctgtgtcat tgtcattctt     240
gcgctatgga ggacaatagt gctttaccac ttcaagcttg tcactatttt tcttcatgaa     300
gccagtcatg ctgttgcttg caaacttaca tgtggccatg tggaaggaat gcaattttt      360
gccgatgaag gtggaatgac ccaaacacgc ggcggtgtat attggtttat attaccagct     420
ggatatttag gatcctcatt ttgggggatg gttttgatac tggcgtcgac aaatcttata     480
gctgcaagag ttgctgctgg atgttagca gctgccttga ttattgtgct ttttgtggct      540
aaaaattgga cgcttcgcgg gctttgcata ggatttattg tggtccttgc tgtggtttgg     600
attttgcaag aaacaacaaa agttcgaatt cttcggtaca tcataatgtt cattggtgtg     660
atgaacagtg tgttttctat ctatgatata tacggtgatc taatatccag acaggttcac     720
actagtgatg ctgagaagtt cgcagaagta tgtccttgtc cgtgtaatgg tgtcgggtgg     780
ggtgtcatat ggggtcttat atctctcatt tttctcggta tagctacata ctttggtctt     840
gtgatcttgt ctcaagtata actggtcata atttaatgca cagatagttg atgattgaag     900
ctgagagcaa catatgcaat atacattttt ggtataatct tgaatatcta taagggtcg      960
gctgattgta tttttatata aaatggtat agttaattct tttgtcaaat aaaagacttt    1020
ttgtttgact gcatgaaaga gttgataata gtagagttct tggttttatg gttaaaaaaa    1080
aaaaaaaaaa aaaaaaaaa aaaaaaaaaa aaaaaaaaaa aaaaaaaaaa aaaaaaaaaa    1140
aaaa                                                                  1144
```

<210> SEQ ID NO 28
<211> LENGTH: 235
<212> TYPE: PRT
<213> ORGANISM: Helianthus sp.

<400> SEQUENCE: 28

```
Met Ala Asn Trp Glu Leu Arg Asp Cys Cys Asn His Asp Gln Leu Leu
1               5                   10                  15

Phe Leu Ile Thr Leu Ala Phe Cys Val Ile Val Leu Ala Leu Trp
            20                  25                  30

Arg Thr Ile Val Leu Leu Pro Phe Lys Leu Val Thr Ile Phe Leu His
        35                  40                  45

Glu Ala Ser His Ala Val Ala Cys Lys Leu Thr Cys Gly His Val Glu
    50                  55                  60

Gly Met Gln Ile Phe Ala Asp Glu Gly Gly Met Thr Gln Thr Arg Gly
65                  70                  75                  80

Gly Val Tyr Trp Phe Ile Leu Pro Ala Gly Tyr Leu Gly Ser Ser Phe
                85                  90                  95

Trp Gly Met Val Leu Ile Leu Ala Ser Thr Asn Leu Ile Ala Ala Arg
            100                 105                 110

Val Ala Ala Gly Cys Leu Ala Ala Ala Leu Ile Ile Val Leu Phe Val
        115                 120                 125

Ala Lys Asn Trp Thr Leu Arg Gly Leu Cys Ile Gly Phe Ile Val Val
    130                 135                 140

Leu Ala Val Val Trp Ile Leu Gln Glu Thr Thr Lys Val Arg Ile Leu
145                 150                 155                 160
```

```
Arg Tyr Ile Ile Met Phe Ile Gly Val Met Asn Ser Val Phe Ser Ile
            165                 170                 175

Tyr Asp Ile Tyr Gly Asp Leu Ile Ser Arg Gln Val His Thr Ser Asp
            180                 185                 190

Ala Glu Lys Phe Ala Glu Val Cys Pro Cys Pro Cys Asn Gly Val Gly
            195                 200                 205

Trp Gly Val Ile Trp Gly Leu Ile Ser Leu Ile Phe Leu Gly Ile Ala
            210                 215                 220

Thr Tyr Phe Gly Leu Val Ile Leu Ser Gln Val
225                 230                 235

<210> SEQ ID NO 29
<211> LENGTH: 1305
<212> TYPE: DNA
<213> ORGANISM: Oryza sativa

<400> SEQUENCE: 29
gcagagctta caccagttcg aacggtttca atttcctcgt gttttcctgc ctcctcctcc       60
tcctcctcgt cctcttctcc cccatttcc cttgagggcg cagcagatct gcggcgagga      120
acgacgagga tggtgaaggt gaactgggag ctgcagggat gctgcgaccg cgaccagaag      180
atcttcatag ccgccgtcgg cgtctccacc gtcgtcatcc tcctcgtgag cacaccctcc      240
ctagctccgt ccttctccct gctttgcttg gtttggttgt gttgtgttgc ttctgaatcg      300
ggttcgttgt gtgtgggggg tttgggtttt gctctgcct ttggattgca gctgtggagg       360
acgttcctgc tcacgccctt caaactcatc accgtcttcc tccacgagac cagccacgcc      420
ctcgcctgca agctcacctg cggagatgta agttgagggc atgcaggtcc atcctaatga      480
gggcggtgtt actcaaactc ggggcggcat atattggata tcttgcctg ctggatatct       540
gggttcatca ttttggggaa tggtcttcat actggcttcc acaaatctcc tcactactag      600
aattgcagcg ggttgcttca ttcttgcatt aatcgttgtt cttttgttg ctaaaaattg       660
gtttcttcgc tggctctgca ttggtttcat cgtattcctt gctgttgttt ggtcattca       720
agaattcaca aaattccata gtctcaagta tgtaatttta ttcataggtg tgatgaatag      780
cttgttttca gtctacgata tctatgatga cttgatatca cgaagagttc attcaagtga      840
tgctgagaaa tttgctgaaa tctgcccatg tccttgcaat ggttgtgcat ggggtgtcat      900
atggggcttc atctcgttta tctttctttg cgcatcaata taccttggac tggttatatt      960
gtcttgagga ttccaatctt ccatatacca ttttgatatg agaaccaagt caagctgtgc     1020
tctcctgtat ttgcattgct ctggatgttg gctccagctt gtattgatct catgtgtcat     1080
gagttgtaga aagttcatac aaacggcaat cgatttatgc caattggagt tgatgggata     1140
gggattagtc attcgattct tccatttagt gcttctgtag atagcattct gcttatagtt     1200
catcttcata gctgattagc tgtcatttta gtactatctc atctcttgaa ttgttactat     1260
tcatcaacat atagaaattt actcgacaaa aaaaaaaaaa aaaaa                     1305

<210> SEQ ID NO 30
<211> LENGTH: 168
<212> TYPE: PRT
<213> ORGANISM: Oryza sativa

<400> SEQUENCE: 30

Met Gln Val His Pro Asn Glu Gly Gly Val Thr Gln Thr Arg Gly Gly
1               5                   10                  15

Ile Tyr Trp Ile Ile Leu Pro Ala Gly Tyr Leu Gly Ser Ser Phe Trp
```

```
                      20                  25                  30
Gly Met Val Phe Ile Leu Ala Ser Thr Asn Leu Leu Thr Thr Arg Ile
            35                  40                  45

Ala Ala Gly Cys Phe Ile Leu Ala Leu Ile Val Val Leu Phe Val Ala
        50                  55                  60

Lys Asn Trp Phe Leu Arg Trp Leu Cys Ile Gly Phe Ile Val Phe Leu
65                  70                  75                  80

Ala Val Val Trp Val Ile Gln Glu Phe Thr Lys Phe His Ser Leu Lys
                85                  90                  95

Tyr Val Ile Leu Phe Ile Gly Val Met Asn Ser Leu Phe Ser Val Tyr
            100                 105                 110

Asp Ile Tyr Asp Asp Leu Ile Ser Arg Arg Val His Ser Ser Asp Ala
            115                 120                 125

Glu Lys Phe Ala Glu Ile Cys Pro Cys Pro Cys Asn Gly Cys Ala Trp
            130                 135                 140

Gly Val Ile Trp Gly Phe Ile Ser Phe Ile Phe Leu Cys Ala Ser Ile
145                 150                 155                 160

Tyr Leu Gly Leu Val Ile Leu Ser
                165

<210> SEQ ID NO 31
<211> LENGTH: 1084
<212> TYPE: DNA
<213> ORGANISM: Arabidopsis thaliana

<400> SEQUENCE: 31
ttcgtccatt tttccctctt ttcttttct  ctttctttct cccaatcact cttcagattc      60
cggggaagag aaaagagaga agaaagaaa  gattcaatct ttattagccg gagatggatt     120
cgccaaactg ggaactccgt ggttgttgta accggaatca aaatactttc ctcatcacca     180
tcggagtctt caccgtagtt atccttctgc tatggaggac atttctattg actccattta     240
aactcattac ggtgtttttg cacgaagcta gtcatgccgt tgcttgcaag cttacatgtg     300
gagatgtaga ggggatggag gtgaatgcaa atgaaggggg ttcgaccaca acacgtggtg     360
gcatttattg gttgatctta cctgctggct atcttggctc atcattttgg ggaatggcat     420
tgattcttgc atctaccaat ctgcttacag caagaatagc tgctgctggt cttggtcttg     480
ctttattcat cgttctcttc attgccaaaa actggacgct tcgagggctt tgtataggtt     540
tcatagtttt cctcgctgtc atatgggttc tacaagagtt aactacagtc aaaattctcc     600
gttatgtcat tctgttttatt ggtgtgatga atagcttatt ctcagtttac gatatctatg     660
atgatttgat atctcggagg gtccattcga gcgatgctga aagttcgca gagatctgtc     720 cttgctgtac cggttgtggc tggggtgtca tctggggaat gatatcattt gcgtttcttt     780
gtgcatcgct ctatctcggg ctagtgatcc tatcataaga gggtattctt tgttactcag     840
gttcagattc ttcccagtga aatgcatgca aagacaaata gtttgacaaa agattgatt     900 ctttagatcc ccttgatgtg tttgggatta acattgtcca ttgaaagttt aggttttatt     960
tgaaagtttg tattctttt atattggagc gtgttgatta gaattcattg gatatttgat    1020
ttggtctatg tttaatgtat tgaaagttcg ttgacttttt caatagaaga tgtccgttga    1080
cttt                                                                 1084

<210> SEQ ID NO 32
<211> LENGTH: 234
<212> TYPE: PRT
<213> ORGANISM: Arabidopsis thaliana
```

-continued

```
<400> SEQUENCE: 32

Met Asp Ser Pro Asn Trp Glu Leu Arg Gly Cys Cys Asn Arg Asn Gln
1               5                   10                  15

Asn Thr Phe Leu Ile Thr Ile Gly Val Phe Thr Val Val Ile Leu Leu
            20                  25                  30

Leu Trp Arg Thr Phe Leu Leu Thr Pro Phe Lys Leu Ile Thr Val Phe
        35                  40                  45

Leu His Glu Ala Ser His Ala Val Ala Cys Lys Leu Thr Cys Gly Asp
    50                  55                  60

Val Glu Gly Met Glu Val Asn Ala Asn Glu Gly Gly Ser Thr Thr Thr
65                  70                  75                  80

Arg Gly Gly Ile Tyr Trp Leu Ile Leu Pro Ala Gly Tyr Leu Gly Ser
                85                  90                  95

Ser Phe Trp Gly Met Ala Leu Ile Leu Ala Ser Thr Asn Leu Leu Thr
            100                 105                 110

Ala Arg Ile Ala Ala Ala Gly Leu Gly Leu Ala Leu Phe Ile Val Leu
        115                 120                 125

Phe Ile Ala Lys Asn Trp Thr Leu Arg Gly Leu Cys Ile Gly Phe Ile
130                 135                 140

Val Phe Leu Ala Val Ile Trp Val Leu Gln Glu Leu Thr Thr Val Lys
145                 150                 155                 160

Ile Leu Arg Tyr Val Ile Leu Phe Ile Gly Val Met Asn Ser Leu Phe
                165                 170                 175

Ser Val Tyr Asp Ile Tyr Asp Asp Leu Ile Ser Arg Arg Val His Ser
            180                 185                 190

Ser Asp Ala Glu Lys Phe Ala Glu Ile Cys Pro Cys Cys Thr Gly Cys
        195                 200                 205

Gly Trp Gly Val Ile Trp Gly Met Ile Ser Phe Ala Phe Leu Cys Ala
    210                 215                 220

Ser Leu Tyr Leu Gly Leu Val Ile Leu Ser
225                 230

<210> SEQ ID NO 33
<211> LENGTH: 233
<212> TYPE: PRT
<213> ORGANISM: Vitis vinifera

<400> SEQUENCE: 33

Met Ala Asn Trp Glu Leu Lys Asn Cys Cys Lys His Asp Gln Val Val
1               5                   10                  15

Phe Leu Ala Thr Ile Gly Val Phe Thr Val Val Ile Leu Leu Leu Trp
            20                  25                  30

Arg Thr Phe Leu Leu Thr Pro Phe Lys Leu Ile Thr Val Phe Leu His
        35                  40                  45

Glu Ala Ser His Ala Ile Ala Cys Lys Leu Thr Cys Gly Gln Val Glu
    50                  55                  60

Gly Ile Gln Val Asn Ala Asp Glu Gly Val Thr Gln Thr Arg Gly
65                  70                  75                  80

Gly Val Tyr Trp Leu Ile Leu Pro Ala Gly Tyr Leu Gly Ser Ser Phe
                85                  90                  95

Trp Gly Met Val Phe Ile Leu Ala Ser Thr Asn Leu Leu Thr Ser Arg
            100                 105                 110

Ile Ala Ala Gly Cys Phe Ala Val Ala Leu Ile Val Val Leu Phe Ile
        115                 120                 125
```

```
Ala Lys Asn Trp Thr Leu Arg Gly Leu Cys Ile Gly Phe Ile Ile Phe
    130                 135                 140

Leu Ala Ile Ile Trp Val Leu Gln Glu Thr Thr Lys Val Arg Ile Leu
145                 150                 155                 160

Arg Phe Phe Ile Leu Phe Met Gly Val Met Asn Ser Leu Phe Ser Val
                165                 170                 175

Tyr Asp Ile Tyr Asp Asp Leu Ile Ser Arg Arg Val His Ser Ser Asp
            180                 185                 190

Ala Glu Lys Phe Ala Glu Ile Cys Pro Cys Pro Cys Asn Gly Val Gly
        195                 200                 205

Trp Gly Val Ile Trp Gly Met Ile Ser Phe Ile Phe Leu Ala Ala Ala
    210                 215                 220

Met Tyr Leu Gly Leu Val Ile Leu Ser
225                 230

<210> SEQ ID NO 34
<211> LENGTH: 233
<212> TYPE: PRT
<213> ORGANISM: Vitis vinifera

<400> SEQUENCE: 34

Met Ala Asn Trp Glu Leu Lys Lys Cys Cys Asn His Glu Gln Val Val
1               5                   10                  15

Phe Leu Thr Thr Ile Ser Ile Cys Thr Val Val Ile Leu Ala Leu Trp
                20                  25                  30

Arg Thr Ile Leu Leu Thr Pro Phe Lys Leu Val Thr Val Phe Leu His
            35                  40                  45

Glu Ala Ser His Ala Ile Ala Cys Lys Leu Thr Cys Gly His Val Glu
        50                  55                  60

Gly Ile Gln Val His Ala Asp Glu Gly Gly Thr Thr Gln Thr Arg Gly
65                  70                  75                  80

Gly Ile Tyr Trp Leu Ile Leu Pro Ala Gly Tyr Leu Gly Ser Ser Phe
                85                  90                  95

Trp Gly Met Val Leu Ile Ile Ala Ser Thr Asn Val Leu Thr Ala Lys
                100                 105                 110

Ile Ala Ala Gly Cys Phe Ala Phe Ala Leu Leu Val Val Leu Phe Val
            115                 120                 125

Ala Lys Asn Trp Thr Leu Arg Gly Leu Cys Ile Gly Phe Ile Ile Leu
    130                 135                 140

Ile Ala Val Val Trp Leu Leu Gln Glu Thr Thr Glu Ile Arg Ile Leu
145                 150                 155                 160

Arg Tyr Ile Ile Leu Phe Ile Gly Val Met Asn Ser Leu Phe Ser Val
                165                 170                 175

Tyr Asp Ile Tyr Asp Asp Leu Ile Ser Arg Arg Val Asn Ser Ser Asp
            180                 185                 190

Ala Glu Lys Phe Ala Glu Val Cys Pro Cys Pro Cys Asn Gly Val Gly
        195                 200                 205

Trp Gly Val Ile Trp Gly Leu Ile Ser Phe Leu Phe Leu Cys Gly Ala
    210                 215                 220

Met Tyr Leu Gly Leu Val Ile Leu Ser
225                 230

<210> SEQ ID NO 35
<211> LENGTH: 55
<212> TYPE: DNA
<213> ORGANISM: Artificial
<220> FEATURE:
```

```
<223> OTHER INFORMATION: At1g67060-5' attB F primer

<400> SEQUENCE: 35
ttaaacaagt ttgtacaaaa aagcaggctc aacaatggat tcgccaaact gggaa        55

<210> SEQ ID NO 36
<211> LENGTH: 50
<212> TYPE: DNA
<213> ORGANISM: artificial
<220> FEATURE:
<223> OTHER INFORMATION: At1g67060-3' attB R primer

<400> SEQUENCE: 36
ttaaaccact ttgtacaaga aagctgggtt tatgatagga tcactagccc              50

<210> SEQ ID NO 37
<211> LENGTH: 234
<212> TYPE: PRT
<213> ORGANISM: Zea mays

<400> SEQUENCE: 37
```

Met Ala Val Asn Trp Glu Leu Gln Gly Cys Cys His Arg Asp Gln Arg
1               5                   10                  15

Ile Phe Ile Ala Ala Val Gly Val Ser Thr Val Val Ile Leu Leu Leu
            20                  25                  30

Trp Arg Thr Phe Leu Leu Thr Pro Phe Lys Leu Ile Thr Val Phe Leu
        35                  40                  45

His Glu Thr Ser His Ala Leu Ala Cys Lys Leu Thr Cys Gly Asp Val
    50                  55                  60

Glu Gly Met Gln Val His Ala Asn Glu Gly Val Thr Gln Thr Arg
65                  70                  75                  80

Gly Gly Ile Tyr Trp Ile Ile Leu Pro Ala Gly Tyr Leu Gly Ser Ser
                85                  90                  95

Phe Trp Gly Met Val Phe Ile Leu Ala Ser Thr Asn Leu Leu Thr Thr
            100                 105                 110

Arg Ile Ala Ala Gly Cys Phe Ile Leu Ala Leu Phe Ile Val Leu Phe
        115                 120                 125

Val Ala Asp Asn Trp Phe Leu Arg Trp Leu Cys Leu Gly Phe Ile Val
    130                 135                 140

Phe Ile Ala Val Val Trp Val Ile Gln Glu Phe Thr Ser Phe His Ile
145                 150                 155                 160

Leu Lys Tyr Val Ile Leu Phe Ile Gly Val Met Asn Ser Leu Phe Ser
                165                 170                 175

Val Tyr Asp Ile Tyr Asp Asp Leu Ile Ser Arg Arg Val Asn Thr Ser
            180                 185                 190

Asp Ala Glu Lys Phe Ala Glu Ile Cys Pro Cys Pro Cys Asn Gly Phe
        195                 200                 205

Ala Trp Gly Val Ile Trp Gly Phe Ile Ser Phe Ile Phe Leu Cys Ala
    210                 215                 220

Ser Ile Tyr Leu Gly Leu Val Ile Leu Ser
225                 230

US 8,541,650 B2

PLANTS HAVING ALTERED AGRONOMIC CHARACTERISTICS UNDER NITROGEN LIMITING CONDITIONS AND RELATED CONSTRUCTS AND METHODS INVOLVING GENES ENCODING LNT1 POLYPEPTIDES AND HOMOLOGS THEREOF

CROSS REFERENCE TO RELATED APPLICATIONS

This application claims the benefit of U.S. Provisional Application No. 61/078949, filed Jul. 8, 2008, the entire content of which is herein incorporated by reference.

FIELD OF THE INVENTION

The field of invention relates to plant breeding and genetics and, in particular, relates to recombinant DNA constructs useful in plants for conferring nitrogen use efficiency and/or tolerance to nitrogen limiting conditions.

BACKGROUND OF THE INVENTION

Abiotic stressors significantly limit crop production worldwide. Cumulatively, these factors are estimated to be responsible for an average 70% reduction in agricultural production. Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors.

The adsorption of nitrogen by plants plays an important role in their growth (Gallais et al., *J. Exp. Bot.* 55(396):295-306 (2004)). Plants synthesize amino acids from inorganic nitrogen in the environment. Consequently, nitrogen fertilization has been a powerful tool for increasing the yield of cultivated plants, such as maize and soybean. Today farmers desire to reduce the use of nitrogen fertilizer, in order to avoid pollution by nitrates and to maintain a sufficient profit margin. If the nitrogen assimilation capacity of a plant can be increased, then increases in plant growth and yield increase are also expected. In summary, plant varieties that have a better nitrogen use efficiency (NUE) are desirable.

Activation tagging can be utilized to identify genes with the ability to affect a trait. This approach has been used in the model plant species *Arabidopsis thaliana* (Weigel et al., *Plant Physiol.* 122:1003-1013 (2000)). Insertions of transcriptional enhancer elements can dominantly activate and/or elevate the expression of nearby endogenous genes. This method can be used to identify genes of interest for a particular trait (e.g. nitrogen use efficiency in a plant), genes that when placed in an organism as a transgene can alter that trait.

SUMMARY OF THE INVENTION

The present invention includes:

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37, and wherein said plant exhibits increased nitrogen stress tolerance when compared to a control plant not comprising said recombinant DNA construct.

In another embodiment, a method of increasing nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct and exhibits increased nitrogen stress tolerance when compared to a control plant not comprising the recombinant DNA construct; and optionally, (c) obtaining a progeny plant derived from the transgenic plant, wherein said progeny plant comprises in its genome the recombinant DNA construct and exhibits increased nitrogen stress tolerance when compared to a control plant not comprising the recombinant DNA construct.

In another embodiment, a method of evaluating nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct; and (c) evaluating the transgenic plant for nitrogen stress tolerance compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating the progeny plant for nitrogen stress tolerance compared to a control plant not comprising the recombinant DNA construct.

In another embodiment, a method of evaluating nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for nitrogen stress tolerance compared to a control plant not comprising the recombinant DNA construct.

In another embodiment, the present invention includes any of the methods of the present invention wherein the plant is a maize plant or a soybean plant.

In another embodiment, the present invention includes an isolated polynucleotide comprising: (a) a nucleotide sequence encoding an LNT1 or LNT1-like polypeptide, wherein the polypeptide has an amino acid sequence of at least 90% or 95% sequence identity, based on the Clustal V method of alignment, when compared to one of SEQ ID NO:26, 28 or 30, or (b) a full complement of the nucleotide sequence, wherein the full complement and the nucleotide sequence consist of the same number of nucleotides and are 100% complementary. The polypeptide may comprise the amino acid sequence of SEQ ID NO: 26, 28 or 30. The nucleotide sequence may comprise the nucleotide sequence of SEQ ID NO: 25, 27 or 29.

In another embodiment, the present invention concerns a recombinant DNA construct comprising any of the isolated polynucleotides of the present invention operably linked to at least one regulatory sequence, and a cell, a plant, and a seed comprising the recombinant DNA construct.

In another embodiment, the present invention includes a vector comprising any of the isolated polynucleotides of the present invention.

In another embodiment, the present invention concerns a cell, plant or seed comprising any of the recombinant DNA constructs of the present invention. The cell may be eukaryotic, e.g., a yeast, insect or plant cell, or prokaryotic, e.g., a bacterium.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 11 shows a typical grid pattern for five lines (labeled 1 through 5—eleven individuals for each line), plus wild-type control C1 (nine individuals), used in screens.

FIG. 13 shows the growth medium used for semi-hydroponics maize growth in Example 18.

FIG. 14 shows a chart setting forth data relating to the effect of different nitrate concentrations on the growth and development of Gaspe Flint derived maize lines in Example 18.

FIGS. 15A-15C show the multiple alignment of the full length amino acid sequences of the *Arabidopsis thaliana* LNT1 polypeptide (SEQ ID NO:32) and the LNT1 homologs of SEQ ID NOs: 18, 20, 22, 24, 26, 28, 30, 33, 34, and 37.

FIG. 16 shows a chart of the percent sequence identity and the divergence values for each pair of amino acids sequences displayed in FIGS. 15A-15C.

FIGS. 17A-E shows an evaluation of individual Gaspe Flint derived maize lines transformed with PHP30116.

FIG. 18 shows a summary evaluation of Gaspe Flint derived maize lines transformed with PHP30116.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

Table 1 lists certain polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing.

TABLE 1

Low Nitrogen tolerant proteins (LNT)

| | | SEQ ID NO: | |
|---|---|---|---|
| | Clone Designation | Nucleotide | Amino Acid |
| LNT1-like | cfp7n.pk064.p15:fis | 17 | 18 |
| LNT1-like | cr1.pk0018.c9:fis | 19 | 20 |
| LNT1-like | srr1c.pk002.g4:fis | 21 | 22 |
| LNT1-like | sfl1.pk0086.d10:fis | 23 | 24 |
| LNT1-like | hso1c.pk016.m11:fis | 25 | 26 |
| LNT1-like | hhs1c.pk009.j19:fis | 27 | 28 |
| LNT1-like | rl0n.pk135.l9:fis | 29 | 30 |

Figure 1:
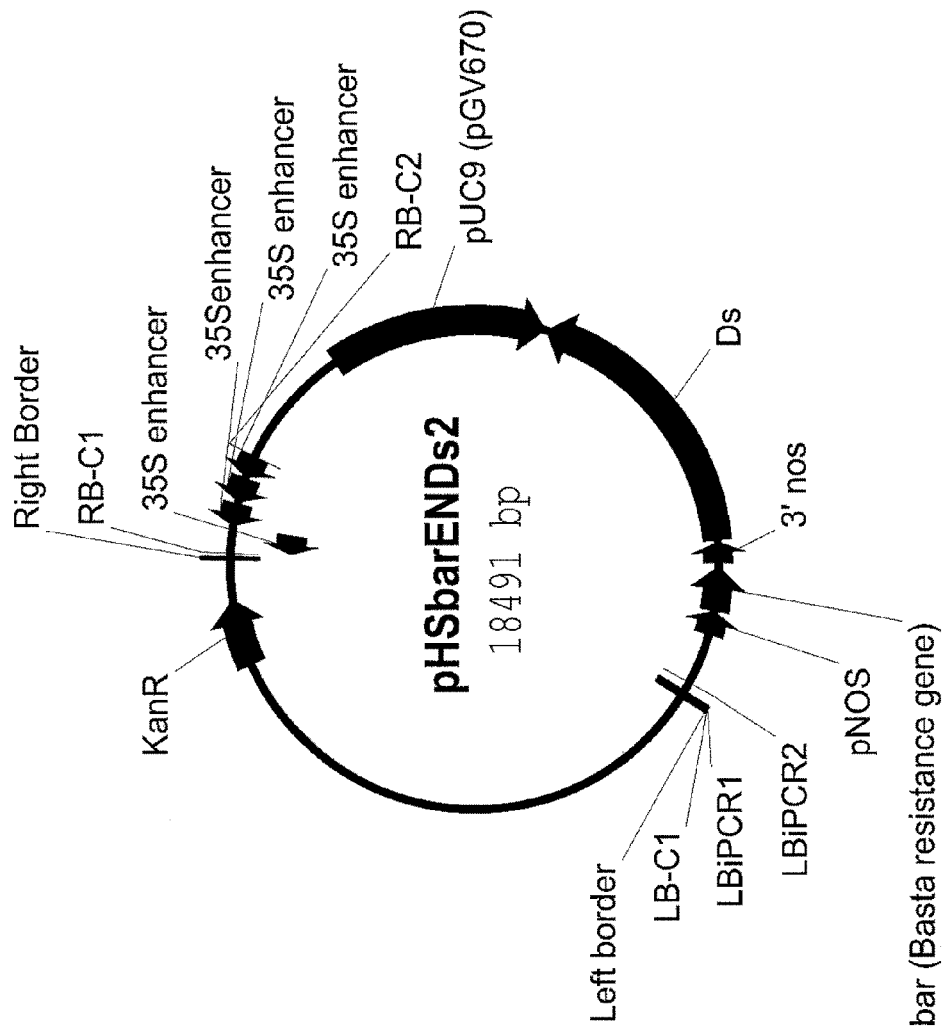
FIG. 1 shows a schematic of the pHSbarENDs2 activation tagging construct used to make the *Arabidopsis* populations (SEQ ID NO:1).

SEQ ID NO:1 is the nucleotide sequence of the pHSbarENDs2 activation tagging vector (FIG. 1).

Figure 2:
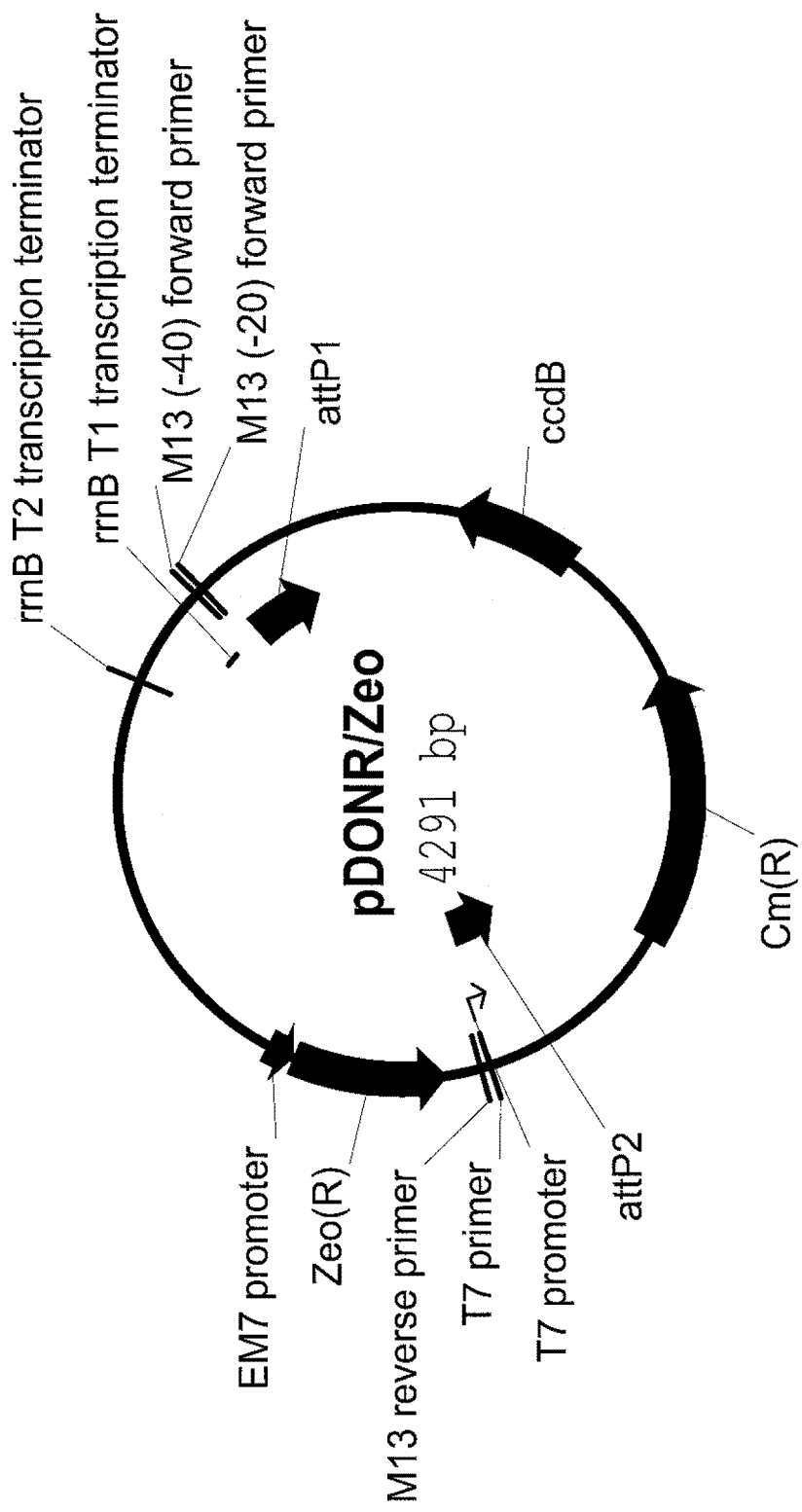
FIG. 2 shows a schematic of the vector pDONR™Zeo (SEQ ID NO:2), GATEWAY® donor vector. The attP1 site is at nucleotides 570-801; the attP2 site is at nucleotides 2754-2985 (complementary strand).

SEQ ID NO:2 is the nucleotide sequence of the pDONR™Zeo construct (FIG. 2).

Figure 3:
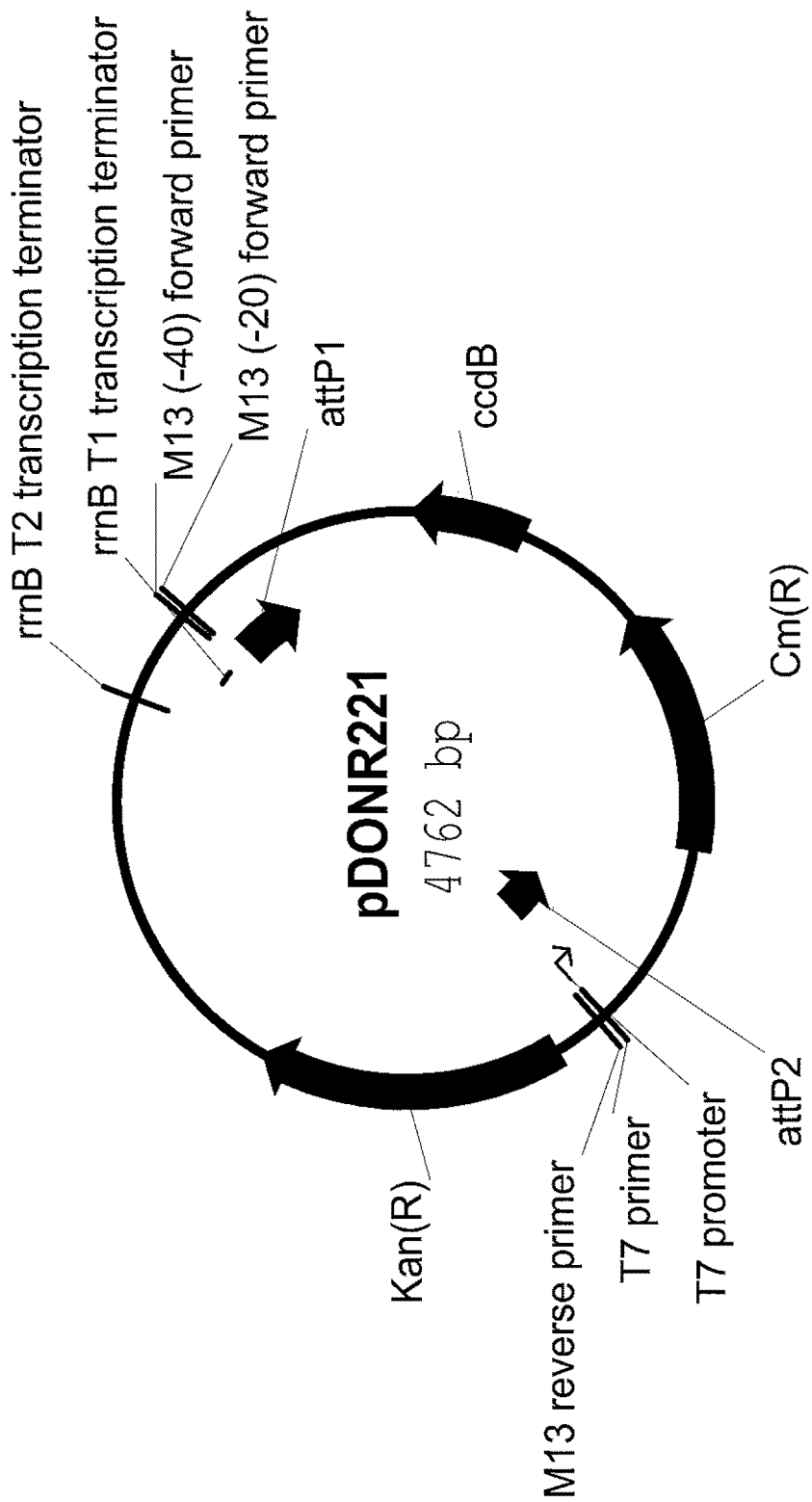
FIG. 3 shows a schematic of the vector pDONR™221 (SEQ ID NO:3), GATEWAY® donor vector. The attP1 site is at nucleotides 570-801; the attP2 site is at nucleotides 2754-2985 (complementary strand).

SEQ ID NO:3 is the nucleotide sequence of the pDONR™221 construct (FIG. 3).

Figure 4:
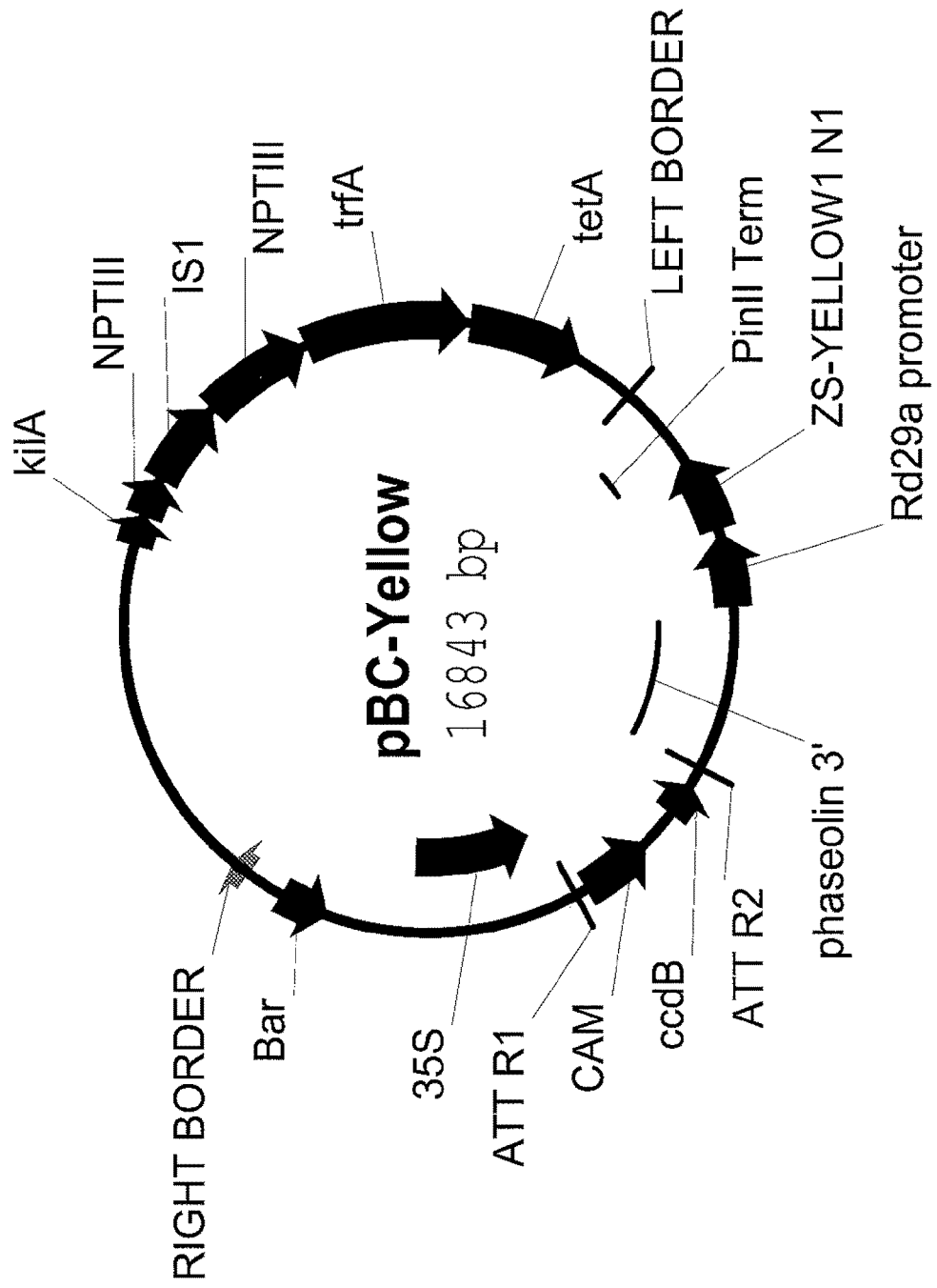
FIG. 4 shows a schematic of the vector pBC-yellow (SEQ ID NO:4), a destination vector for use in construction of expression vectors for *Arabidopsis*. The attR1 site is at nucleotides 11276-11399 (complementary strand); the attR2 site is at nucleotides 9695-9819 (complementary strand).

SEQ ID NO:4 is the nucleotide sequence of the pBC-yellow vector (FIG. 4).

Figure 5:
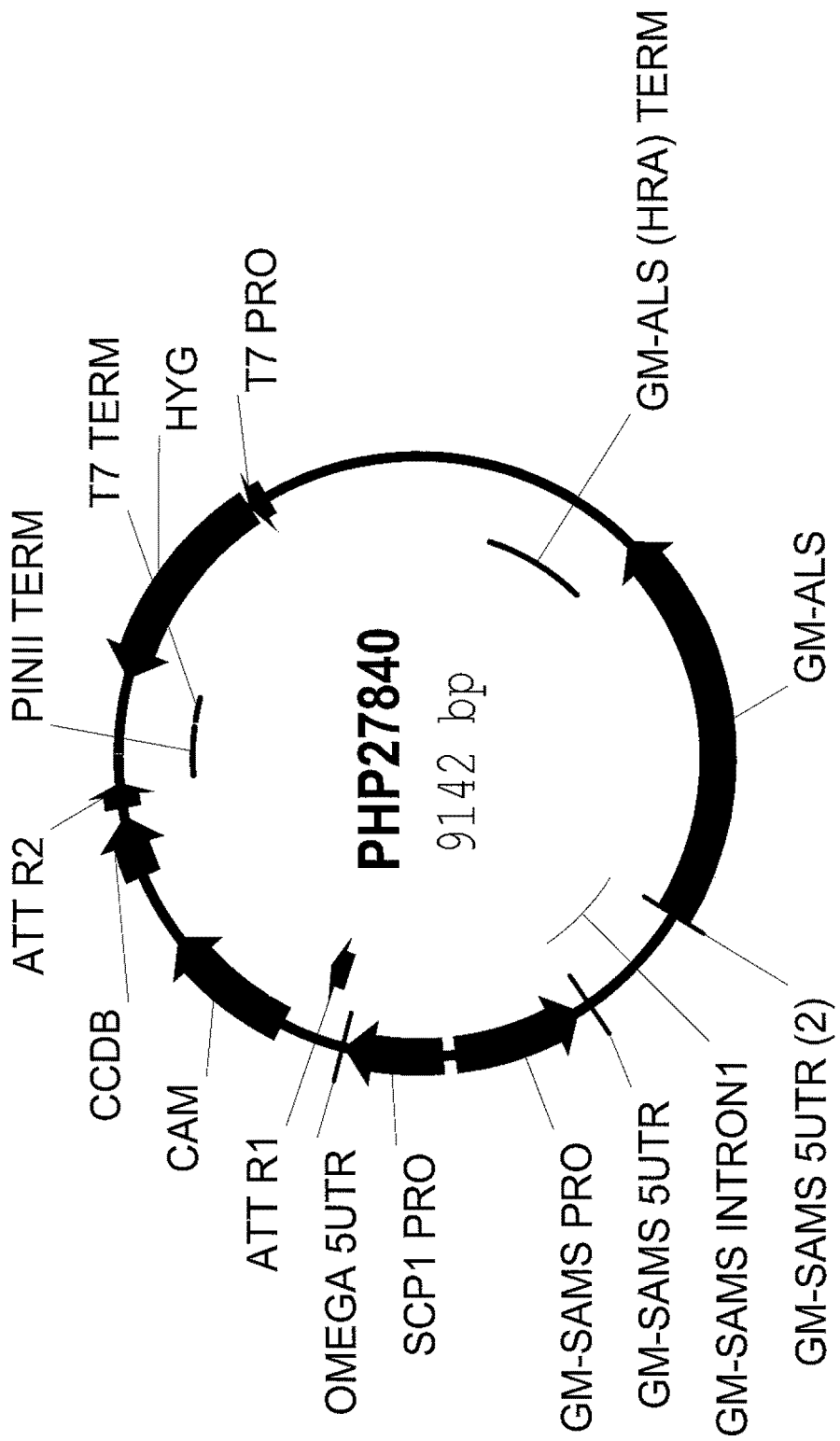
FIG. 5 shows a schematic of the vector PHP27840 (SEQ ID NO:5), a destination vector for use in construction of expression vectors for soybean. The attR1 site is at nucleotides 7310-7434; the attR2 site is at nucleotides 8890-9014.

SEQ ID NO:5 is the nucleotide sequence of the PHP27840 vector (FIG. 5).

Figure 6:
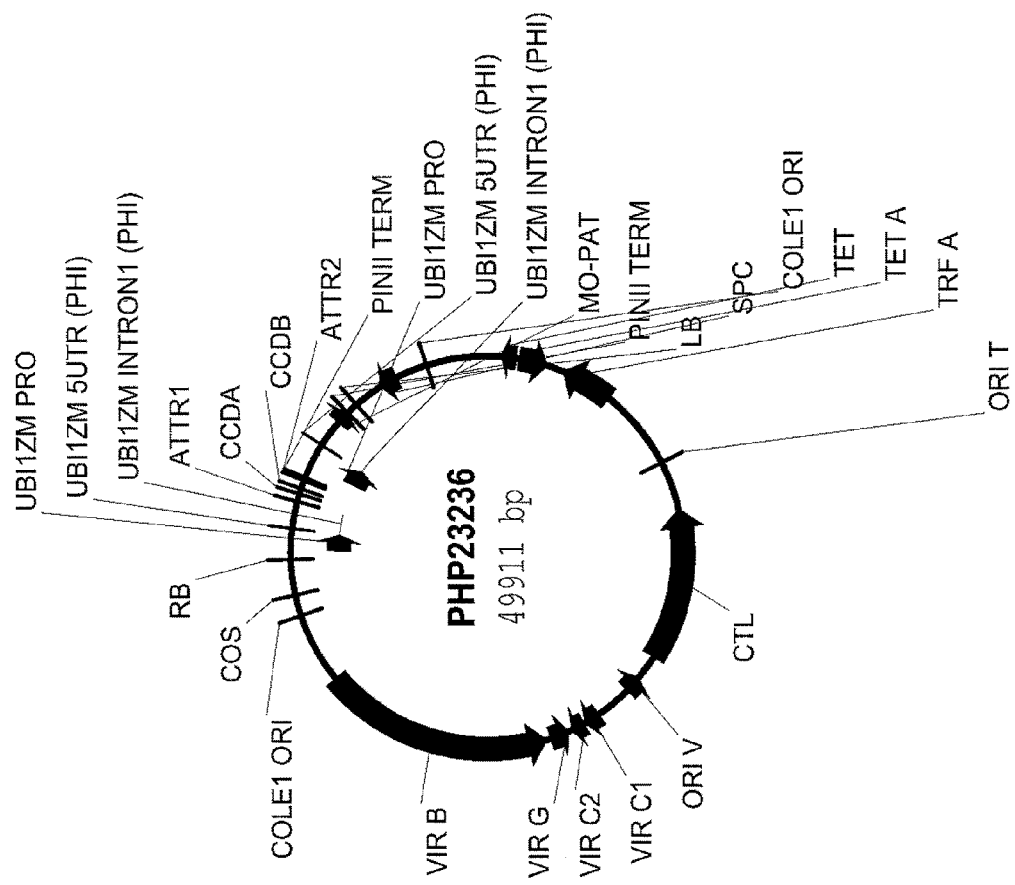
FIG. 6 shows a schematic of the vector PHP23236 (SEQ ID NO:6), a destination vector for use in construction of expression vectors for Gaspe Flint derived maize lines. The attR1 site is at nucleotides 2006-2130; the attR2 site is at nucleotides 2899-3023.

SEQ ID NO:6 is the nucleotide sequence of the destination vector PHP23236 (FIG. 6).

Figure 7:
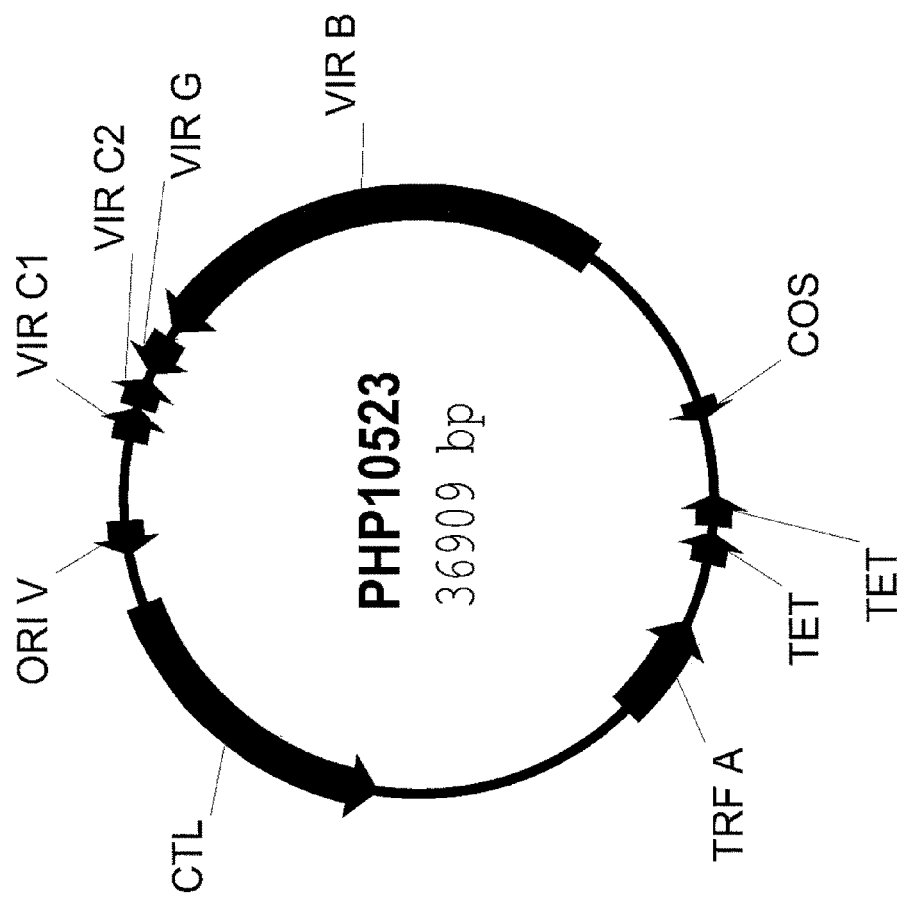
FIG. 7 shows a schematic of the vector PHP10523 (SEQ ID NO:7), a plasmid DNA present in *Agrobacterium* strain LBA4404 (Komari et al., *Plant J.* 10:165-174 (1996); NCBI General Identifier No. 59797027).

SEQ ID NO:7 is the nucleotide sequence of the PHP10523 vector (FIG. 7).

Figure 8:
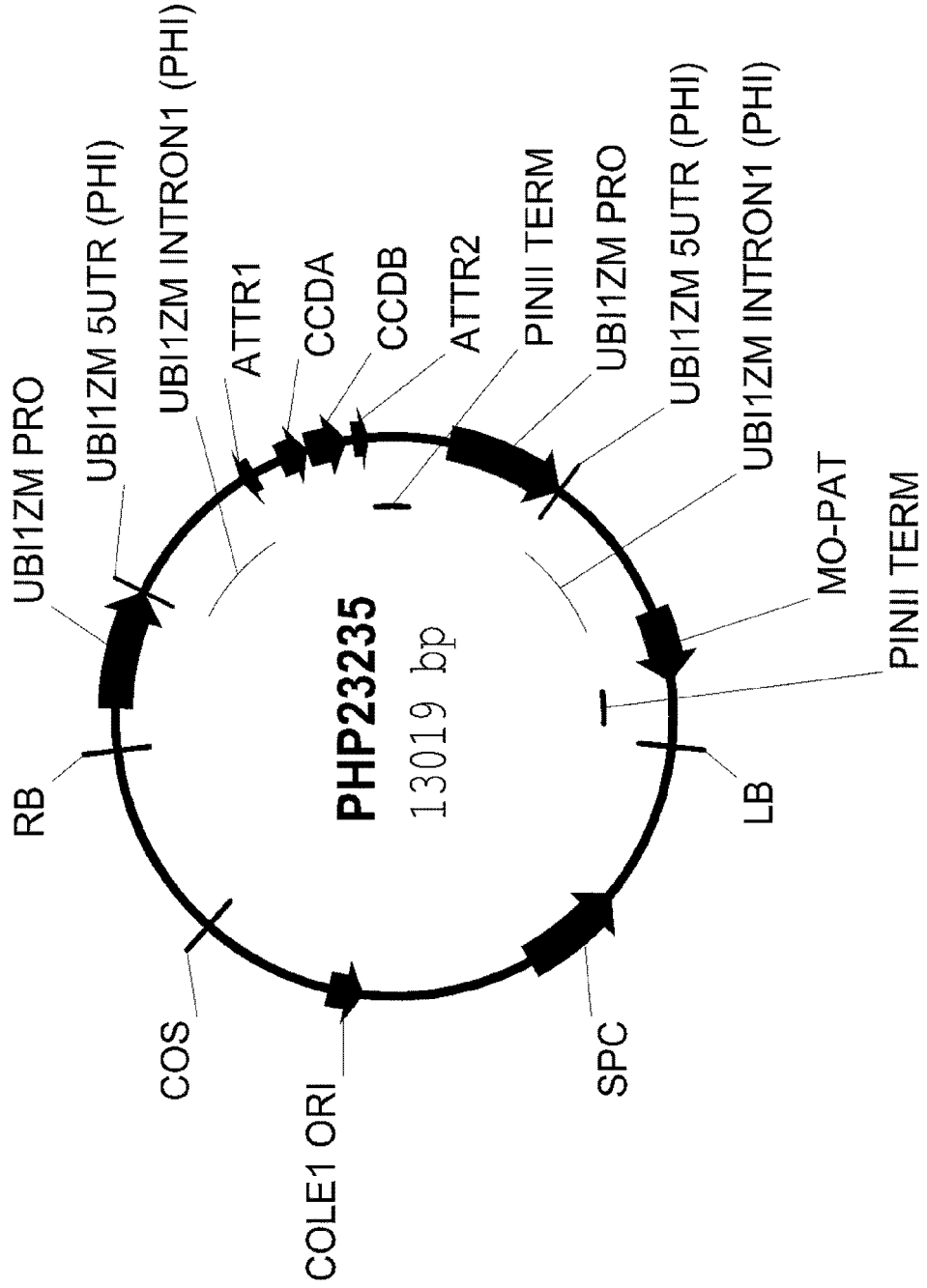
FIG. 8 shows a schematic of the vector PHP23235 (SEQ ID NO:8), a vector used to construct the destination vector PHP23236.

SEQ ID NO:8 is the nucleotide sequence of the PHP23235 vector (FIG. 8).

Figure 9:
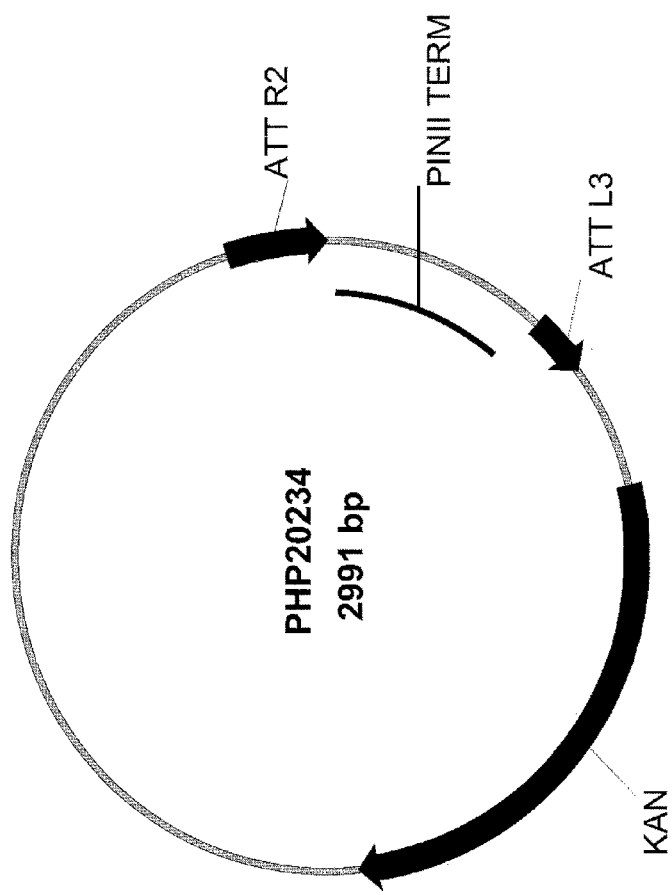
FIG. 9 shows a schematic of the vector PHP20234 (SEQ ID NO:9).

SEQ ID NO:9 is the nucleotide sequence of the PHP20234 vector (FIG. 9).

Figure 10:
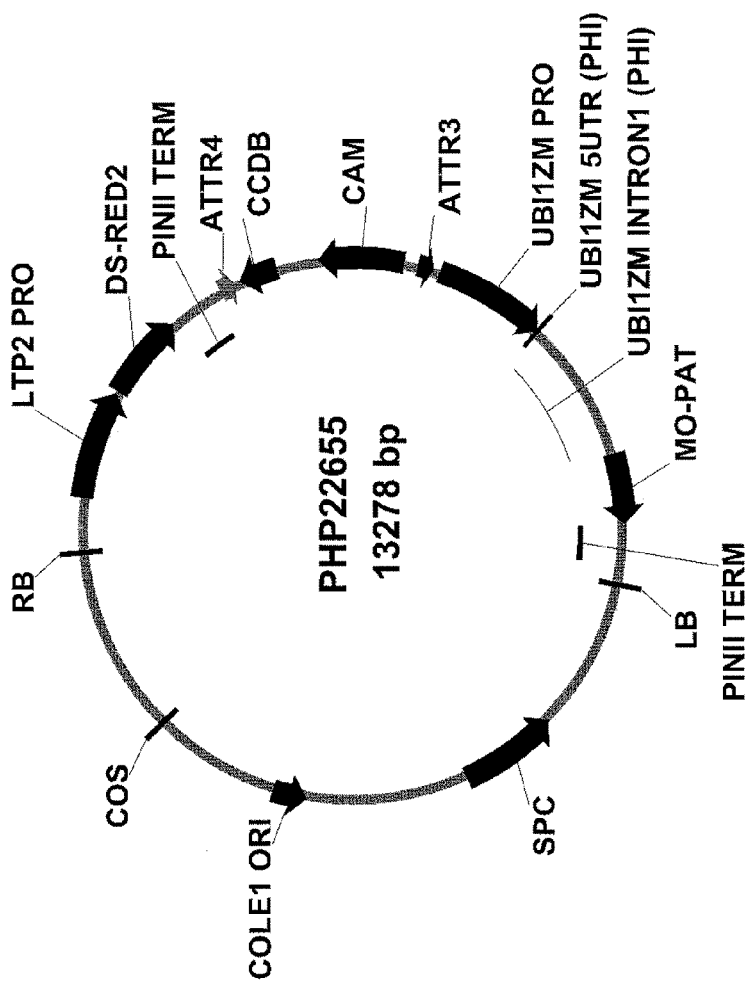
FIG. 10 shows a schematic of the destination vector PHP22655 (SEQ ID NO:10).

SEQ ID NO:10 is the nucleotide sequence of the destination vector PHP22655 (FIG. 10).

SEQ ID NO:11 is the nucleotide sequence of the polylinker used to substitute the PacI restriction site at position 5775 of pHSbarENDs2.

SEQ ID NO:12 is the nucleotide sequence of the attB1 sequence.

SEQ ID NO:13 is the nucleotide sequence of the attB2 sequence.

SEQ ID NO:14 is the nucleotide sequence of the entry clone PHP23112.

SEQ ID NO:15 is the forward primer VC062 in Example 9.

SEQ ID NO:16 is the reverse primer VC063 in Example 9.

SEQ ID NOs:17-30 (see Table 1).

SEQ ID NO:31 is the nucleotide sequence of the gene that encodes the *Arabidopsis thaliana* "unknown protein" (LNT1) (At1g67060; NCBI General Identifier No. 145337238).

SEQ ID NO:32 is the amino acid sequence of the *Arabidopsis thaliana* "unknown protein" (LNT1) (At1g67060; NCBI General Identifier No. 42563004).

SEQ ID NO:33 corresponds to NCBI GI No. 157341431, which is the amino acid sequence of a *Vitis vinifera* LNT1-like polypeptide.

SEQ ID NO:34 corresponds to NCBI GI No. 157343572, which is the amino acid sequence of a *Vitis vinifera* LNT1-like polypeptide.

SEQ ID NO:35 is the nucleotide sequence of the At1g67060-5' attB forward primer.

SEQ ID NO:36 is the nucleotide sequence of the At1g67060-3' attB reverse primer.

SEQ ID NO:37 corresponds to NCBI GI No. 212275704, which is the amino acid sequence of a *Zea mays* "hypothetical protein".

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in vegetative tissue, whole plant amino acid content, vegetative tissue free amino acid content, fruit free amino acid content, total plant protein content, seed free amino acid content, fruit protein content, seed protein content, protein content in a vegetative tissue, drought tolerance, nitrogen uptake, resistance to root lodging, harvest index, stalk lodging, plant height, ear height, and ear length.

"Harvest index" refers to the grain weight divided by the total plant weight.

"Int1" refers to the *Arabidopsis thaliana* locus, At1g67060 (SEQ ID NO: 31). "LNT1" refers to the protein (SEQ ID NO:32) encoded by At1g67060.

"Int1-like" refers to nucleotide homologs from different species, such as corn and soybean, of the *Arabidopsis thaliana* "Int1" locus, At1g67060 (SEQ ID NO: 31) and includes without limitation any of the nucleotide sequences of SEQ ID NOs: 17, 19, 21, 23, 25, 27, and 29.

"LNT1-like" refers to protein homologs from different species, such as corn and soybean, of the *Arabidopsis thaliana* "LNT1" (SEQ ID NO: 32) and includes without limitation any of the amino acid sequences of SEQ ID NOs: 18, 20, 22, 24, 26, 28, 30, 33, 34, and 37.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Nitrogen stress tolerance" is a trait of a plant and refers to the ability of the plant to survive under nitrogen limiting conditions.

"Increased nitrogen stress tolerance" of a plant is measured relative to a reference or control plant, and means that the nitrogen stress tolerance of the plant is increased by any amount or measure when compared to the nitrogen stress tolerance of the reference or control plant.

A "nitrogen stress tolerant plant" is a plant that exhibits nitrogen stress tolerance. A nitrogen stress tolerant plant may be a plant that exhibits an increase in at least one agronomic characteristic relative to a control plant under nitrogen limiting conditions.

"Environmental conditions" refer to conditions under which the plant is grown, such as the availability of water, availability of nutrients (for example nitrogen), or the presence of insects or disease.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/ transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS*. 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs, compositions (such as plants or seeds) comprising these recombinant DNA constructs, and methods utilizing these recombinant DNA constructs.

Isolated Polynucleotides and Polypeptides

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is preferably an LNT1 or LNT1-like protein.

An isolated polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37. The polypeptide is preferably an LNT1 or LNT1-like protein.

An isolated polynucleotide comprising (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:17, 19, 21, 23, 25, 27, 29, or 31; or (ii) a full complement of the nucleic acid sequence of (i). Any of the foregoing isolated polynucleotides may be utilized in any recombinant DNA constructs (including suppression DNA constructs) of the present invention. The isolated polynucleotide preferably encodes an LNT1 or LNT1-like protein.

Recombinant DNA Constructs and Suppression DNA Constructs

In one aspect, the present invention includes recombinant DNA constructs (including suppression DNA constructs).

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 17, 19, 21, 23, 25, 27, 29, or 31; or (ii) a full complement of the nucleic acid sequence of (i).

FIGS. 15A-15C show the multiple alignment of the amino acid sequences of SEQ ID NOs:18, 20, 22, 24, 26, 28, 30, 32, 33, 34, and 37. The multiple alignment of the sequences was performed using the MEGALIGN® program of the LASERGENE® bioinformatics computing suite (DNASTAR® Inc., Madison, Wis.); in particular, using the Clustal V method of alignment (Higgins and Sharp, *CABIOS*. 5:151-153 (1989)) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 16 is a chart of the percent sequence identity and the divergence values for each pair of amino acids sequences displayed in FIGS. 15A-15C.

In another embodiment, a recombinant DNA construct comprises a polynucleotide operably linked to at least one regulatory sequence (e.g., a promoter functional in a plant), wherein said polynucleotide encodes an LNT1 or LNT1-like protein. The LNT1 or LNT1-like polypeptide may be from *Arabidopsis thaliana, Zea mays, Glycine max, Glycine tabacina, Glycine soja*, and *Glycine tomentella*.

In another aspect, the present invention includes suppression DNA constructs.

A suppression DNA construct may comprise at least one regulatory sequence (e.g., a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like protein; or (c) all or part of: (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:17, 19, 21, 23, 25, 27, 29, or 31; or (ii) a full complement of the nucleic acid sequence of (c)(i). The suppression DNA construct may comprise a cosuppression construct, antisense construct, viral-suppression construct, hairpin suppression construct, stem-loop suppression construct, double-stranded RNA-producing construct, RNAi construct, or small RNA construct (e.g., an sRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as sRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107, 065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

Regulatory Sequences:

A recombinant DNA construct (including a suppression DNA construct) of the present invention may comprise at least one regulatory sequence.

A regulatory sequence may be a promoter.

A number of promoters can be used in recombinant DNA constructs (and suppression DNA constructs) of the present invention. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to enhance nitrogen tolerance. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W. G., et al., *Mol. Gen. Genet.* 259:149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci. U.S.A.* 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., Plant Mol. Biol. 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current invention include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228(1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7):729-737 (1993); "Structural characterization, chromosomal localization and phylogenetic evaluation of two pairs of AGAMOUS-like MADS-box genes from maize", Theissen et al., *Gene* 156(2):155-166 (1995); NCBI GenBank Accession No. X80206)). Zag2 transcripts can be detected five days prior to pollination to seven to eight days after pollination ("DAP"), and directs expression in the carpel of developing female inflorescences and CimI which is specific to the nucleus of developing maize kernels. CimI transcript is detected four to five days before pollination to six to eight DAP. Other useful promoters include any promoter which can be derived from a gene whose expression is maternally associated with developing female florets.

Additional promoters for regulating the expression of the nucleotide sequences of the present invention in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current invention may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOTMET2 promoter (WO 2005/063998, published Jul. 14, 2005), the CR1BIO promoter (WO 2006/055487, published May 26, 2006), the CRWAQ81 (WO 2005/035770, published Apr. 21, 2005) and the maize ZRP2.47 promoter (NCBI Accession No. U38790; NCBI GI No. 1063664).

Recombinant DNA constructs (and suppression DNA constructs) of the present invention may also include other regulatory sequences including, but not limited to, translation leader sequences, introns, and polyadenylation recognition sequences. In another embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

Any plant can be selected for the identification of regulatory sequences and genes to be used in recombinant DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, maize, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions:

A composition of the present invention is a plant comprising in its genome any of the recombinant DNA constructs (including any of the suppression DNA constructs) of the present invention (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic optionally under nitrogen limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct may be stably integrated into the genome of the plant.

Embodiments include but are not limited to the following:

1. A plant (for example, a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37, and wherein said plant exhibits increased nitrogen stress tolerance when compared to a control plant not comprising said recombinant DNA construct. The plant may further exhibit an alteration of at least one agronomic characteristic when compared to the control plant.

2. A plant (for example, a maize or soybean plant) comprising in its genome a recombinant DNA construct comprising:

(a) a polynucleotide operably linked to at least one regulatory element, wherein said polynucleotide encodes a polypeptide having an amino acid sequence of at least 50% sequence identity, based on the Clustal V method of alignment, when compared to SEQ ID NO:18, 20, 22, 24, 26, 28, 30, 32, 33, 34, or 37; or (b) a suppression DNA construct comprising at least one regulatory element operably linked to:

(i) all or part of: (A) a nucleic acid sequence encoding a polypeptide having an amino acid sequence of at least 50% sequence identity, based on the Clustal V method of alignment, when compared to SEQ ID NO:18, 20, 22, 24, 26, 28, 30, 32, 33, 34, or 37, or (B) a full complement of the nucleic acid sequence of (b)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes an LNT1 or LNT1-like polypeptide, and wherein said plant exhibits an alteration of at least one agronomic characteristic when compared to a control plant not comprising said recombinant DNA construct.

3. A plant (for example, a maize or soybean plant) comprising in its genome a recombinant DNA construct comprising a polynucleotide operably linked to at least one regulatory sequence, wherein said polynucleotide encodes an LNT1 or LNT1-like polypeptide, and wherein said plant exhibits increased nitrogen stress tolerance when compared to a control plant not comprising said recombinant DNA construct. The plant may further exhibit an alteration of at least one agronomic characteristic when compared to the control plant. The LNT1 polypeptide may be from *Arabidopsis thaliana, Zea mays, Glycine max, Glycine tabacina, Glycine soja* or *Glycine tomentella*.

4. A plant (for example, a maize or soybean plant) comprising in its genome a recombinant DNA construct comprising a polynucleotide operably linked to at least one regulatory sequence, wherein said polynucleotide encodes an LNT1 or LNT1-like polypeptide, and wherein said plant exhibits an alteration of at least one agronomic characteristic under nitrogen limiting conditions when compared to a control plant not comprising said recombinant DNA construct. The LNT1 polypeptide may be from *Arabidopsis thaliana, Zea mays, Glycine max, Glycine tabacina, Glycine soja* or *Glycine tomentella*.

5. A plant (for example, a maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37, and wherein said plant exhibits an alteration of at least one agronomic characteristic under nitrogen limiting conditions when compared to a control plant not comprising said recombinant DNA construct.

6. A plant (for example, a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide, and wherein said plant exhibits an alteration of at least one agronomic characteristic under nitrogen limiting conditions when compared to a control plant not comprising said suppression DNA construct.

7. A plant (for example, a maize or soybean plant) comprising in its genome a suppression DNA construct comprising at least one regulatory element operably linked to all or part of: (a) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (b) a full complement of the nucleic acid sequence of (a), and wherein said plant exhibits an alteration of at least one agronomic characteristic under nitrogen limiting conditions when compared to a control plant not comprising said suppression DNA construct.

8. Any progeny of the above plants in embodiments 1-7, any seeds of the above plants in embodiments 1-7, any seeds of progeny of the above plants in embodiments 1-7, and cells from any of the above plants in embodiments 1-7 and progeny thereof.

In any of the foregoing embodiments 1-8 or any other embodiments of the present invention, the recombinant DNA construct (or suppression DNA construct) may comprise at least a promoter functional in a plant as a regulatory sequence.

In any of the foregoing embodiments 1-8 or any other embodiments of the present invention, the alteration of at least one agronomic characteristic is either an increase or decrease.

In any of the foregoing embodiments 1-8 or any other embodiments of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, early seedling vigor, and seedling emergence under low temperature stress. For example, the alteration of at least one agronomic characteristic may be an increase in yield, greenness, or biomass.

In any of the foregoing embodiments 1-8 or any other embodiments of the present invention, the plant may exhibit the alteration of at least one agronomic characteristic when compared, under nitrogen stress conditions, to a control plant not comprising said recombinant DNA construct (or suppression DNA construct).

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/or physical condition, including (but not limited to) vigor, growth, size, or root length, or in particular, leaf color or leaf area size. Other techniques for evaluating such plants include measuring chlorophyll fluorescence, photosynthetic rates, root growth or gas exchange rates.

The Examples below describe some representative protocols and techniques for simulating nitrogen limiting conditions and/or evaluating plants under such conditions.

One can also evaluate nitrogen stress tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods

Methods include but are not limited to methods for increasing nitrogen stress tolerance in a plant, methods for evaluating nitrogen stress tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize or soybean plant. The plant may also be sunflower, sorghum, canola, wheat, alfalfa, cotton, rice, barley, or millet. The seed may be a maize or soybean seed, for example a maize hybrid seed or maize inbred seed.

Methods include but are not limited to the following:

A method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

A method for isolating a polypeptide of the invention from a cell or culture medium of the cell, wherein the cell comprises a recombinant DNA construct comprising a polynucleotide of the invention operably linked to at least one regulatory sequence, and wherein the transformed host cell is grown under conditions that are suitable for expression of the recombinant DNA construct.

A method of altering the level of expression of a polypeptide of the invention in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide of the invention in the transformed host cell.

A method of increasing nitrogen stress tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; and (b) regenerating a transgenic plant from the regenerable plant cell after step (a), wherein the transgenic plant comprises in its genome the recombinant DNA construct and exhibits increased nitrogen stress tolerance when compared to a control plant not comprising the recombinant DNA construct. The method may further comprise (c) obtaining a progeny plant derived from the transgenic plant, wherein said progeny plant comprises in its genome the suppression DNA construct and exhibits increased nitrogen stress tolerance when compared to a control plant not comprising the recombinant DNA construct.

A method of increasing nitrogen stress tolerance in a plant, comprising: (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37, or (ii) a full complement of the nucleic acid sequence of (a)(i); and (b) regenerating a transgenic plant from the regenerable plant cell after step (a), wherein the transgenic plant comprises in its genome the suppression DNA construct and exhibits increased nitrogen stress tolerance when compared to a control plant not comprising the suppression DNA construct. The method may further comprise (c) obtaining a progeny plant derived from the transgenic plant, wherein said progeny plant comprises in its genome the suppression DNA construct and exhibits increased nitrogen stress tolerance when compared to a control plant not comprising the suppression DNA construct.

A method of increasing nitrogen stress tolerance in a plant, comprising: (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; and (b) regenerating a transgenic plant from the regenerable plant cell after step (a), wherein the transgenic plant comprises in its genome the suppression DNA construct and exhibits increased nitrogen stress tolerance when compared to a control plant not comprising the suppression DNA construct. The method may further comprise (c) obtaining a progeny plant derived from the transgenic plant, wherein said progeny plant comprises in its genome the suppression DNA construct and exhibits increased nitrogen stress tolerance when compared to a control plant not comprising the suppression DNA construct.

A method of evaluating nitrogen stress tolerance in a plant, comprising (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct; and (c) evaluating the transgenic plant for nitrogen stress tolerance compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (a)(i); (b) regenerating a transgenic plant from the regenerable plant cell after step (a), wherein the transgenic plant comprises in its genome the suppression DNA construct; and (c) evaluating the transgenic plant for nitrogen stress tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for nitrogen stress tolerance compared to a control plant not comprising the suppression DNA construct.

A method of evaluating nitrogen stress tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; (b) regenerating a transgenic plant from the regenerable plant cell after step (a), wherein the transgenic plant comprises in its genome the suppression DNA construct; and (c) evaluating the transgenic plant for nitrogen stress tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for nitrogen stress tolerance compared to a control plant not comprising the suppression DNA construct.

A method of evaluating nitrogen stress tolerance in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (a)(i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) evaluating the progeny plant for nitrogen stress tolerance compared to a control plant not comprising the recombinant DNA construct.

A method of determining an alteration of an agronomic characteristic in a plant, comprising (a) introducing into a regenerable plant cell a recombinant DNA construct comprising a polynucleotide operably linked to at least on regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome said recombinant DNA construct; and (c) determining whether the transgenic plant exhibits an alteration of at least one agronomic characteristic when compared, optionally under nitrogen limiting conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristic when compared, optionally under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared, optionally under nitrogen limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration of at least one agronomic characteristic when compared, optionally under nitrogen limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; (b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared, optionally under nitrogen limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration of at least one agronomic characteristic when compared, optionally under nitrogen limiting conditions, to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration of at least one agronomic characteristic when compared, optionally under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 30, 32, 33, 34, or 37; or (ii) a full complement of the nucleic acid sequence of (i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration of at least one agronomic characteristic when compared, optionally under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT1 or LNT1-like polypeptide; (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration of at least one agronomic characteristic when compared, optionally under nitrogen limiting conditions, to a control plant not comprising the suppression DNA construct.

A method of producing seed (for example, seed that can be sold as a nitrogen stress tolerant product offering) comprising any of the preceding methods, and further comprising obtaining seeds from said progeny plant, wherein said seeds comprise in their genome said recombinant DNA construct (or suppression DNA construct).

In any of the foregoing methods or any other embodiments of methods of the present invention, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the foregoing methods or any other embodiments of methods of the present invention, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present invention, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present invention, said regenerating step may comprise: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present invention, the at least one agronomic characteristic is preferably selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, early seedling vigor, and seedling emergence under low temperature stress. The alteration of at least one agronomic characteristic may be an increase in yield, greenness, or biomass.

In any of the preceding methods or any other embodiments of methods of the present invention, the plant may exhibit the alteration of at least one agronomic characteristic when compared, under nitrogen stress conditions, to a control plant not comprising said recombinant DNA construct (or suppression DNA construct).

In any of the preceding methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

An 18.49-kb T-DNA based binary construct was created, pHSbarENDs2 (SEQ ID NO:1; FIG. 1), that contains four multimerized enhancer elements derived from the Cauliflower Mosaic Virus 35S promoter (corresponding to sequences −341 to −64, as defined by Odell et al., *Nature* 313:810-812 (1985)). The construct also contains vector sequences (pUC9) and a poly-linker (SEQ ID NO:11) to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

Arabidopsis activation-tagged populations were created by whole plant Agrobacterium transformation. The pHSbarENDs2 construct was transformed into Agrobacterium tumefaciens strain C58, grown in lysogeny broth medium at 25° C. to OD600~1.0. Cells were then pelleted by centrifugation and resuspended in an equal volume of 5% sucrose/ 0.05% Silwet L-77 (OSI Specialties, Inc). At early bolting, soil grown Arabidopsis thaliana ecotype Col-0 were top watered with the Agrobacterium suspension. A week later, the same plants were top watered again with the same Agrobacterium strain in sucrose/Silwet. The plants were then allowed to set seed as normal. The resulting T1 seed were sown on soil, and transgenic seedlings were selected by spraying with glufosinate (FINALE®; AgrEvo; Bayer Environmental Science). A total of 100,000 glufosinate resistant T1 seedlings were selected. T2 seed from each line was kept separate.

Example 2

Screens to Identify Lines with Tolerance to Low Nitrogen

From each of 100,000 separate T1 activation-tagged lines, eleven T2 plants are sown on square plates (15 mm×15 mm) containing 0.5× N-Free Hoagland's, 0.4 mM potassium nitrate, 0.1% sucrose, 1 mM MES and 0.25% Phytagel™ (Low N medium). Five lines are plated per plate, and the inclusion of 9 wild-type individuals on each plate makes for a total of 64 individuals in an 8×8 grid pattern (see FIG. 11). Plates are kept for three days in the dark at 4° C. to stratify seeds and then placed horizontally for nine days at 22° C. light and 20° C. dark. Photoperiod is sixteen hours light and eight hours dark, with an average light intensity of ~200 mmol/m$^2$/s. Plates are rotated and shuffled daily within each shelf. At day twelve (nine days of growth), seedling status is evaluated by imaging the entire plate.

Figure 12:
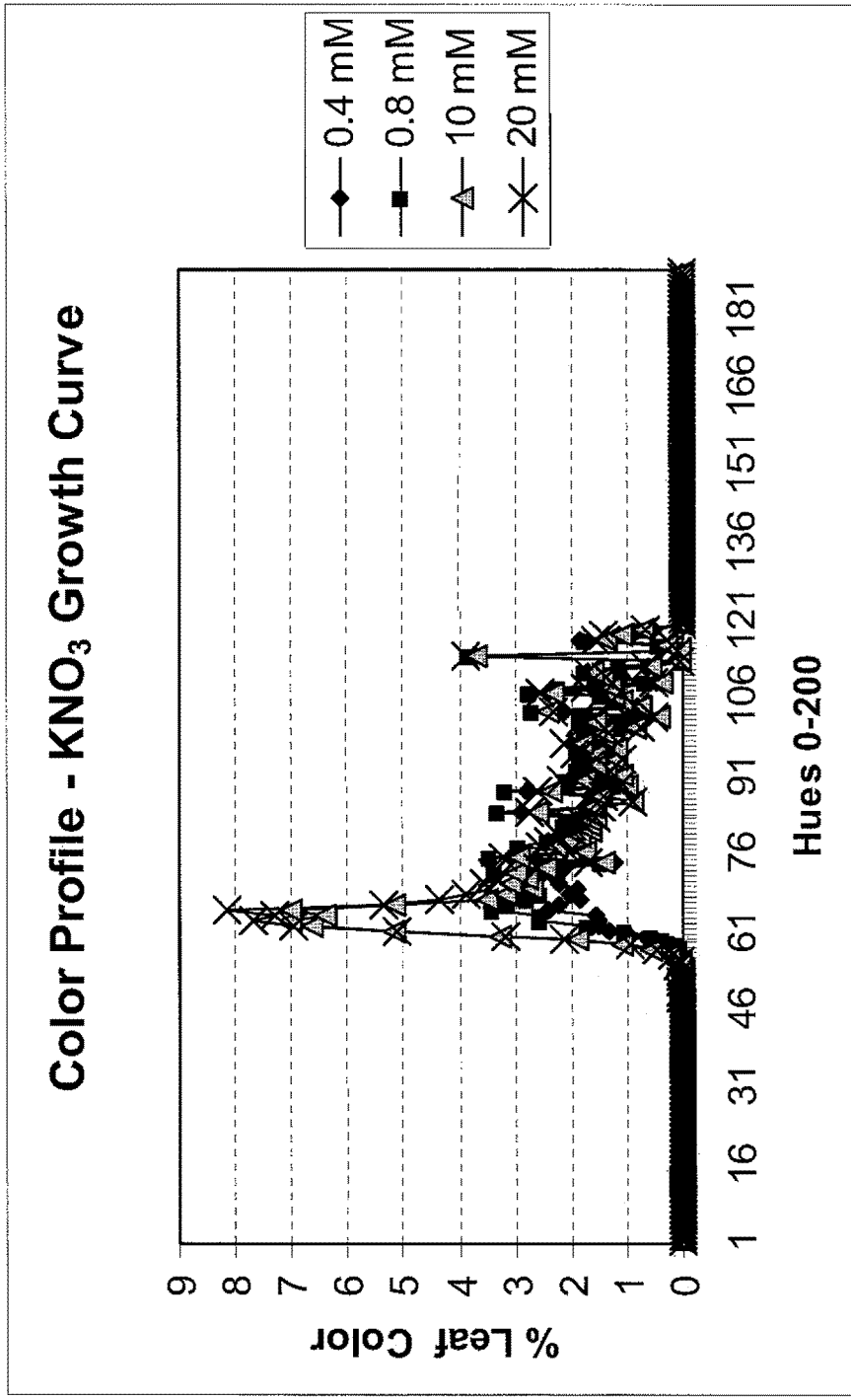
FIG. 12 shows a graph showing the effect of several different potassium nitrate concentrations on plant color as determined by image analysis. The response of the green color bin (hues 50 to 66) to nitrate dosage demonstrates that this bin can be used as an indicator of nitrogen assimilation.

After masking the plate image to remove background color, two different measurements are collected for each individual: total rosette area, and the percentage of color that falls into a green color bin. Using hue, saturation and intensity data (HSI), the green color bin consists of hues 50 to 66. Total rosette area is used as a measure of plant biomass, whereas the green color bin has been shown by dose-response studies to be an indicator of nitrogen assimilation (see FIG. 12).

Lines with a significant increase in total rosette area and/or green color bin, when compared to the wild-type controls, are designated as Phase 1 hits. Phase 1 hits are re-screened in duplicate under the same assay conditions (Phase 2 screen). A Phase 3 screen is also employed to further validate mutants that pass through Phases 1 and 2. In Phase 3, each line is plated separately on Low N medium, such that 32 T2 individuals are grown next to 32 wild-type individuals on one plate, providing greater statistical rigor to the analysis. If a line shows a significant difference from the controls in Phase 3, the line is then considered a validated nitrogen-deficiency tolerant line.

Example 3

Identification of Activation-Tagged Genes

Genes flanking the T-DNA insert in nitrogen tolerant lines are identified using one, or both, of the following two standard procedures: (1) thermal asymmetric interlaced (TAIL) PCR (Liu et al., Plant J. 8:457-63 (1995)); and (2) SAIFF PCR (Siebert et al., Nucleic Acids Res. 23:1087-1088 (1995)). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and Arabidopsis genomic sequence. Once a tag of genomic sequence flanking a T-DNA insert is obtained, candidate genes are identified by alignment to publicly available Arabidopsis genome sequence. Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged Int1 Gene

An activation tagged-line (line 110629) showing nitrogen-deficiency tolerance was further analyzed. DNA from the line was extracted, and genes flanking the T-DNA insert in the mutant line were identified using ligation-mediated PCR (Siebert et al., Nucleic Acids Res. 23:1087-1088 (1995)). A single amplified fragment was identified that contained a T-DNA border sequence and Arabidopsis genomic sequence. Once a tag of genomic sequence flanking a T-DNA insert was obtained, a candidate gene was identified by alignment to the completed Arabidopsis genome. Specifically, the annotated gene nearest the 35S enhancer elements/T-DNA RB was the candidate for the gene activated in the line. In the case of line 110629 the gene nearest the 35S enhancers was At1g67060 (SEQ ID NO:31; NCBI GI No: 145337238), encoding the Arabidopsis thaliana "unknown protein" referred to herein as LNT1 (SEQ ID NO:32; NCBI GI 42563004).

Example 5

Validation of Candidate Arabidopsis Gene (At1g67060) via Transformation into Arabidopsis Candidate genes can be transformed into Arabidopsis and overexpressed under the 35S promoter. If the same or similar phenotype is observed in the transgenic line as in the parent activation-tagged line, then the candidate gene is considered to be a validated "lead gene" in Arabidopsis.

The Arabidopsis At1g67060 gene (SEQ ID NO:31) was tested for its ability to confer nitrogen-deficiency tolerance in the following manner.

The At1g67060 cDNA was amplified by RT-PCR with the following primers:

1. At1g67060-5' attB forward primer (SEQ ID NO:35) The forward primer contains the attB1 sequence (ACAAGTTTGTACAAAAAAGCAGGCT; SEQ ID NO:12) and a consensus Kozak sequence (CAACA) upstream of the first 21 nucleotides of the protein-coding region, beginning with the ATG start codon, of said cDNA.

2. At1g67060-3' attB reverse primer (SEQ ID NO:36) The reverse primer contains the attB2 sequence (ACCACTTTG-TACAAGAAAGCTGGGT; SEQ ID NO:13) adjacent to the reverse complement of the last 21 nucleotides of the protein-coding region, beginning with the reverse complement of the stop codon, of said cDNA.

Using the INVITROGEN™ GATEWAY® CLONASE™ technology, a BP Recombination Reaction was performed for the RT-PCR product with pDONR™Zeo (SEQ ID NO:2; FIG. 2). This process removes the bacteria lethal ccdB gene, as well as the chloramphenicol resistance gene (CAM) from pDONR™Zeo and directionally clones the PCR product with flanking attB1 and attB2 sites, creating an entry clone. This entry clone was used for a subsequent LR Recombination Reaction with a destination vector, as follows.

A 16.8-kb T-DNA based binary vector (destination vector), called pBC-yellow (SEQ ID NO:4; FIG. 4), was constructed with a 1.3-kb 35S promoter immediately upstream of the INVITROGEN™ GATEWAY C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed on the entry clone containing the directionally cloned PCR product and pBC-yellow. This amplification allowed for rapid and directional cloning of the At1g67060 gene (SEQ ID NO:31) behind the 35S promoter in pBC-yellow.

Applicants then introduced the 35S promoter::At1g67060 expression construct into wild-type *Arabidopsis* ecotype Col-0, using the same *Agrobacterium*-mediated transformation procedure described in Example 1. Transgenic T1 seeds were selected by yellow fluorescence, and 32 of these T1 seeds were plated next to 32 wild-type *Arabidopsis* ecotype Col-0 seeds on low nitrogen medium. All subsequent growth conditions and imaging analyses were performed as described in Example 1. It was found that the original phenotype from activation tagging, tolerance to nitrogen limiting conditions, could be recapitulated in wild-type *Arabidopsis* plants that were transformed with a construct where At1g67060 was directly expressed by the 35S promoter.

Example 6

Composition of cDNA Libraries, Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBLUESCRIPT®. In addition, the cDNAs may be introduced directly into precut BLUESCRIPT® II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBLUESCRIPT® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., *Science* 252:1651-1656 (1991)). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke, *Nucleic Acids Res.* 22:3765-3772 (1994)). The in vitro transposition system places unique binding sites randomly throughout a population of large DNA molecules. The transposed DNA is then used to transform DH10B electro-competent cells (GIBCO BRL/Life Technologies, Rockville, Md.) via electroporation. The transposable element contains an additional selectable marker (named DHFR; Fling and Richards, *Nucleic Acids Res.* 11:5147-5158 (1983)), allowing for dual selection on agar plates of only those subclones containing the integrated transposon. Multiple subclones are randomly selected from each transposition reaction, plasmid DNAs are prepared via alkaline lysis, and templates are sequenced (ABI PRISM dye-terminator ReadyReaction mix) outward from the transposition event site, utilizing unique primers specific to the binding sites within the transposon.

Sequence data is collected (ABI PRISM® Collections) and assembled using Phred and Phrap (Ewing et al., *Genome Res.* 8:175-185 (1998); Ewing et al., *Genome Res.* 8:186-194 (1998)). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al., *Genome Res.* 8:195-202 (1998)).

In some of the clones the cDNA fragment corresponds to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries sometimes are chosen based on previous knowledge that the specific gene should be found in a certain tissue and sometimes are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBLUE-SCRIPT® vector using a commercial kit and following the manufacturer's protocol. This kit is selected from many available from several vendors including INVITROGEN™ (Carlsbad, Calif.), Promega Biotech (Madison, Wis.), and GIBCO-BRL (Gaithersburg, Md.). The plasmid DNA is isolated by alkaline lysis method and submitted for sequencing and assembly using Phred/Phrap, as above.

Example 7

Identification of cDNA Clones cDNA clones encoding LNT1-like polypeptides were identified by conducting BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States, *Nat. Genet.* 3:266-272 (1993)) provided by the NCBI. Alternatively, the polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expection) of observing a match of a cDNA-encoded sequence to a sequence contained in the searched databases merely by chance as calculated by BLAST are reported herein as "pLog" values, which represent the negative of the logarithm of the reported P-value or E-value. Accordingly, the greater the pLog value, the greater the likelihood that the cDNA-encoded sequence and the BLAST "hit" represent homologous proteins.

EST sequences can be compared to the GenBank database as described above. ESTs that contain sequences more 5- or 3-prime can be found by using the BLASTN algorithm (Altschul et al., *Nucleic Acids Res.* 25:3389-3402 (1997)) against the DUPONT proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described above.

Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 8

Characterization of cDNA Clones Encoding LNT1-Like Polypeptides cDNA libraries representing mRNAs from various tissues of *Zea mays* (maize), *Oryza sativa* (rice), *Glycine max* (soybean), and *Helianthus annuus* (sunflower) were prepared. The characteristics of the libraries are described below.

TABLE 2 cDNA Libraries from Maize, Soybean, and Sunflower

| Library | Description (tissue) | Clone |
|---|---|---|
| cfp7n | Maize Root, Pooled stages, Full-length enriched, normalized | cfp7n.pk064.p15:fis |
| cr1 | Corn (Zea mays L.) root from 7 day seedlings grown in light | cr1.pk0018.c9:fis |
| srr1c | Soybean (Glycine max L., 9281) roots control for src1c. | srr1c.pk002.g4:fis |
| sfl1 | Soybean (Glycine max L.) immature flower | sfl1.pk0086.d10:fis |
| hso1c | Oxalate oxidase-transgenic sunflower plants | hso1c.pk016.m11:fis |
| hhs1c | Sunflower (Helianthus sp.) head tissue infected with sclerotinia | hhs1c.pk009.j19:fis |
| rl0n | Rice 15 Day Old Leaf* | rl0n.pk135.l9 |

*These libraries were normalized essentially as described in U.S. Pat. No. 5,482,845

As shown in Table 3, FIGS. 15A-15C, and FIG. 16, cDNAs identified in Table 2 encode polypeptides similar to the LNT1 polypeptide from *Arabidopsis thaliana* (At1g67060; NCBI General Identifier No. 42563004; SEQ ID NO:32) and to two unknown polypeptides from *Vitis vinifera* (NCBI General Identifier No. 157343572 (SEQ ID NO:34) and NCBI General Identifier No. 157341431 (SEQ ID NO:33)) and one polypeptide from *Zea mays* (NCBI General Identifier No. 212275704).

Shown in Table 3 (non-patent literature) and Table 4 (patent literature) are the BLAST results for individual ESTs ("EST"), the sequences of the entire cDNA inserts comprising the indicated cDNA clones ("FIS"), the sequences of contigs assembled from two or more EST, FIS or PCR sequences ("Contig"), or sequences encoding an entire or functional protein derived from an FIS or a contig ("CGS"). Also shown in Tables 3 and 4 are the percent sequence identity values for each pair of amino acid sequences using the Clustal V method of alignment with default parameters (described below).

TABLE 3

BLASTP Results for Polypeptides Homologous to LNT1

| Sequence (SEQ ID NO: #) | Status | NCBI GI No. | % identity | BLASTP pLog Score |
|---|---|---|---|---|
| cfp7n.pk064.p15:fis (SEQ ID NO: 18) | CGS | 157341431 (SEQ ID NO: 33) | 78.1 | 108 |
| cr1.pk0018.c9:fis (SEQ ID NO: 20) | CGS | 157341431 (SEQ ID NO: 33) | 78.1 | 109 |
| srr1c.pk002.g4:fis (SEQ ID NO: 22) | CGS | 157341431 (SEQ ID NO: 33) | 82.8 | 114 |

TABLE 3-continued

BLASTP Results for Polypeptides Homologous to LNT1

| Sequence (SEQ ID NO: #) | Status | NCBI GI No. | % identity | BLASTP pLog Score |
|---|---|---|---|---|
| sfl1.pk0086.d10:fis (SEQ ID NO: 24) | CGS | 157341431 (SEQ ID NO: 33) | 82.8 | 115 |
| hso1c.pk016.m11:fis (SEQ ID NO: 26) | CGS | 157341431 (SEQ ID NO: 33) | 82.8 | 113 |
| hhs1c.pk009.j19:fis (SEQ ID NO: 28) | CGS | 157343572 (SEQ ID NO: 34) | 78.5 | 106 |
| rl0n.pk135.l9:fis (SEQ ID NO: 30) | CGS | 212275704 (SEQ ID NO: 37) | 92.9 | 87 |

TABLE 4

BLASTP Results for Polypeptides Homologous to LNT1

| Sequence (SEQ ID NO: #) | Status | Reference | % Identity | BLAST pLog Score |
|---|---|---|---|---|
| cfp7n.pk064.p15:fis (SEQ ID NO: 18) | CGS | SEQ ID NO: 302196 in US2004214272 | 100.0 | 135 |
| cr1.pk0018.c9:fis (SEQ ID NO: 20) | CGS | SEQ ID NO: 7336 in US2004216190 | 97.9 | 133 |
| srr1c.pk002.g4:fis (SEQ ID NO: 22) | CGS | SEQ ID NO: 279794 in US2004031072 | 99.1 | 134 |
| sfl1.pk0086.d10:fis (SEQ ID NO: 24) | CGS | SEQ ID NO: 279794 in US2004031072 | 100.0 | 134 |
| hso1c.pk016.m11:fis (SEQ ID NO: 26) | CGS | SEQ ID NO: 27974 in US2004031072 | 82.9 | 114 |
| hhs1c.pk009.j19:fis (SEQ ID NO: 28) | CGS | SEQ ID NO: 279794 in US2004031072 | 73.5 | 103 |
| rl0n.pk135.l9:fis (SEQ ID NO: 32) | CGS | SEQ ID NO: 302199 in US20040214272 and in US20090087878 | 92.9 | 88 |

FIGS. 15A-15C present an alignment of the amino acid sequences set forth in SEQ ID NOs:18, 20, 22, 24, 26, 28, 30, 33, 34, and 37, and the amino acid sequence of the LNT1 polypeptide from *Arabidopsis thaliana* (GI No. 42563004) (SEQ ID NO: 32). FIG. 16 is a chart of the percent sequence identity and the divergence values for each pair of amino acids sequences presented in FIGS. 15A-15C.

Sequence alignments and percent identity calculations were performed using the MEGALIGN® program of the LASERGENE® bioinformatics computing suite (DNAS-TAR® Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Example 9

Preparation of a Plant Expression Vector Containing a Homolog to the *Arabidopsis* Lead Gene Sequences homologous to the lead LNT1 gene can be identified using sequence comparison algorithms such as BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health). Homologous LNT1-like sequences, such as the ones described in Example 8, can be PCR-amplified by either of the following methods.

Method 1 (RNA-based): If the 5' and 3' sequence information for the protein-coding region of an LNT1 homolog is available, gene-specific primers can be designed as outlined in Example 5. RT-PCR can be used with plant RNA to obtain a nucleic acid fragment containing the protein-coding region flanked by attB1 (SEQ ID NO:12) and attB2 (SEQ ID NO:13) sequences. The primer may contain a consensus Kozak sequence (CAACA) upstream of the start codon.

Method 2 (DNA-based): Alternatively, if a cDNA clone is available for the LNT1 homolog, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBLUESCRIPT SK+, the forward primer VC062 (SEQ ID NO:15) and the reverse primer VC063 (SEQ ID NO:16) can be used.

Methods 1 and 2 can be modified according to procedures known by one skilled in the art. For example, the primers of Method 1 may contain restriction sites instead of attB1 and attB2 sites, for subsequent cloning of the PCR product into a vector containing attB1 and attB2 sites. Additionally, Method 2 can involve amplification from a cDNA clone, a lambda clone, a BAC clone or genomic DNA.

A PCR product obtained by either method above can be combined with a GATEWAY® donor vector, such as pDONR™Zeo (SEQ ID NO:2; FIG. 2) or pDONR™221 (SEQ ID NO:3; FIG. 3), using a BP Recombination Reaction. This process removes the bacteria lethal ccdB gene, as well as the chloramphenicol resistance gene (CAM), from pDONR™Zeo or pDONR™221 and directionally clones the PCR product with flanking attB1 and attB2 sites to create an entry clone. Using the INVITROGEN™ GATEWAY® CLONASE™ technology, the sequence encoding the homologous LNT1 polypeptide from the entry clone can then be transferred to a suitable destination vector, such as pBC-Yellow (SEQ ID NO:4; FIG. 4), PHP27840 (SEQ ID NO:5; FIG. 5), or PHP23236 (SEQ ID NO:6; FIG. 6), to obtain a plant expression vector for use with *Arabidopsis*, soybean, and corn, respectively.

The attP1 and attP2 sites of donor vectors pDONR™/Zeo or pDONR™221 are shown in FIGS. 2 and 3, respectively. The attR1 and attR2 sites of destination vectors pBC-Yellow, PHP27840 and PHP23236 are shown in FIGS. 4, 5, and 6, respectively.

Alternatively a MultiSite GATEWAY® LR recombination reaction between multiple entry clones and a suitable destination vector can be performed to create an expression vector.

Example 10

Preparation of Soybean Expression Vectors and Transformation of Soybean with Validated *Arabidopsis* Lead Genes Soybean plants can be transformed to overexpress each validated *Arabidopsis* gene or the corresponding homologs from various species in order to examine the resulting phenotype.

The same GATEWAY® entry clone described in Example 5 can be used to directionally clone each gene into the PHP27840 vector (SEQ ID NO:5; FIG. 5) such that expression of the gene is under control of the SCP1 promoter.

Soybean embryos may then be transformed with the expression vector comprising sequences encoding the instant polypeptides.

To induce somatic embryos, cotyledons, 3-5 mm in length dissected from surface sterilized, immature seeds of the soybean cultivar A2872, can be cultured in the light or dark at 26° C. on an appropriate agar medium for six to ten weeks. Somatic embryos, which produce secondary embryos, are then excised and placed into a suitable liquid medium. After repeated selection for clusters of somatic embryos which multiply as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium. Soybean embryogenic suspension cultures may then be transformed by the method of particle gun bombardment (Klein et al., *Nature* (London) 327:70-73 (1987), U.S. Pat. No. 4,945, 050). A DUPONT BIOLISTIC™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al., *Nature* 313:810-812 (1985)), the hygromycin phosphotransferase gene from plasmid pJR225 (from *E. coli*; Gritz et al., *Gene* 25:179-188 (1983)) and the 3' region of the nopaline synthase gene from the T-DNA of the Ti plasmid of *Agrobacterium tumefaciens*. Another selectable marker gene which can be used to facilitate soybean transformation is an herbicide-resistant acetolactate synthase (ALS) gene from soybean or *Arabidopsis*. ALS is the first common enzyme in the biosynthesis of the branched-chain amino acids valine, leucine and isoleucine. Mutations in ALS have been identified that convey resistance to some or all of three classes of inhibitors of ALS (U.S. Pat. No. 5,013,659; the entire contents of which are herein incorporated by reference). Expression of the herbicide-resistant ALS gene can be under the control of a SAM synthetase promoter (U.S. Patent Application No. US-2003-0226166-A1; the entire contents of which are herein incorporated by reference).

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment, with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Soybean plants transformed with validated genes can be assayed to study agronomic characteristics relative to control or reference plants. For example, yield enhancement and/or stability under low and high nitrogen conditions (e.g., nitrogen limiting conditions and nitrogen-sufficient conditions) can be assayed.

Example 11

Transformation of Maize with Validated *Arabidopsis* Lead Genes Using Particle Bombardment Maize plants can be transformed to overexpress a validated *Arabidopsis* lead gene or the corresponding homologs from various species in order to examine the resulting phenotype.

The same GATEWAY® entry clone described in Example 5 can be used to directionally clone each gene into a maize transformation vector. Expression of the gene in the maize transformation vector can be under control of a constitutive promoter such as the maize ubiquitin promoter (Christensen et al., *Plant Mol. Biol.* 12:619-632 (1989) and Christensen et al., *Plant Mol. Biol.* 18:675-689 (1992))

The recombinant DNA construct described above can then be introduced into maize cells by the following procedure. Immature maize embryos can be dissected from developing caryopses derived from crosses of the inbred maize lines H99 and LH132. The embryos are isolated ten to eleven days after pollination when they are 1.0 to 1.5 mm long. The embryos are then placed with the axis-side facing down and in contact with agarose-solidified N6 medium (Chu et al., *Sci. Sin. Peking* 18:659-668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every two to three weeks.

The plasmid, p35S/Ac (obtained from Dr. Peter Eckes, Hoechst Ag, Frankfurt, Germany) may be used in transformation experiments in order to provide for a selectable marker. This plasmid contains the pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al., *Nature* 313:810-812 (1985)) and the 3' region of the nopaline synthase gene from the T-DNA of the Ti plasmid of *Agrobacterium tumefaciens*.

The particle bombardment method (Klein et al., *Nature* 327:70-73 (1987)) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After ten minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a KAPTON™ flying disc (Bio-Rad Labs). The particles are then accelerated into the maize tissue with a BIOLISTIC™ PDS-1000/He (Bio-Rad Instruments, Hercules Calif.), using a helium pressure of 1000 psi, a gap distance of 0.5 cm, and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional two weeks the tissue can be transferred to fresh N6 medium containing bialaphos. After six weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2.4-D. After two weeks the tissue can be transferred to regeneration medium (Fromm et al., *Bio/Technology* 8:833-839 (1990)). Transgenic T0 plants can be regenerated and their phenotype determined following HTP procedures. T1 seed can be collected.

T1 plants can be grown under nitrogen limiting conditions, for example 1 mM nitrate, and analyzed for phenotypic changes. The following parameters can be quantified using image analysis: plant area, volume, growth rate and color analysis can be collected and quantified. Overexpression constructs that result in an alteration, compared to suitable control plants, in greenness (green color bin), yield, growth rate, biomass, fresh or dry weight at maturation, fruit or seed yield, total plant nitrogen content, fruit or seed nitrogen content, nitrogen content in vegetative tissue, free amino acid content in the whole plant, free amino acid content in vegetative tissue, free amino acid content in the fruit or seed, protein content in the fruit or seed, or protein content in a vegetative tissue can be considered evidence that the *Arabidopsis* lead gene functions in maize to enhance tolerance to nitrogen deprivation (increased nitrogen stress tolerance).

Furthermore, a recombinant DNA construct containing a validated *Arabidopsis* gene can be introduced into a maize inbred line either by direct transformation or introgression from a separately transformed line.

Example 12

Electroporation of *Agrobacterium tumefaciens* LBA4404 (General Description)

Electroporation competent cells (40 µL), such as *Agrobacterium tumefaciens* LBA4404 (containing PHP10523), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 µL parental DNA at a concentration of 0.2 µg-1.0 µg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., FALCON™ tube). The cells are incubated at 28-30° C., 200-250 rpm for 3 h.

Aliquots of 250 µL are spread onto plates containing YM medium and 50 µg/mL spectinomycin and incubated three days at 28-30° C. To increase the number of transformants one of two optional steps can be performed:

Option 1: Overlay plates with 30 µL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 µg/mL spectinomycin for isolation of single colonies. The plates are incubated at 28° C. for two to three days. A single colony for each putative cointegrate is picked and inoculated with 4 mL of 10 g/L bactopeptone, 10 g/L yeast extract, 5 g/L sodium chloride, and 50 mg/L spectinomycin. The mixture is incubated for 24 h at 28° C. with shaking. Plasmid DNA from 4 mL of culture is isolated using QIAGEN Miniprep and an optional Buffer PB wash. The DNA is eluted in 30 µL. Aliquots of 2 µL are used to electroporate 20 µL of DH10b+20 µL of twice distilled $H_2O$ as per above. Optionally a 15 µL aliquot can be used to transform 75-100 µL of INVITROGEN™ Library Efficiency DH5α. The cells are spread on plates containing LB medium and 50 µg/mL spectinomycin and incubated at 37° C. overnight.

Three to four independent colonies are picked for each putative cointegrate and inoculated 4 mL of 2×YT medium (10 g/L bactopeptone, 10 g/L yeast extract, 5 g/L sodium chloride) with 50 µg/mL spectinomycin. The cells are incubated at 37° C. overnight with shaking. Next, plasmid DNA is isolated from 4 mL of culture using QiAprep® Miniprep with optional Buffer PB wash (elute in 50 µL). 8 µL are used for digestion with SalI (using parental DNA and PHP10523 as controls). Three more digestions using restriction enzymes BamHI, EcoRI, and HindIII are performed for 4 plasmids that represent 2 putative cointegrates with correct SalI digestion pattern (using parental DNA and PHP10523 as controls). Electronic gels are recommended for comparison.

Alternatively, for high throughput applications, such as that described for Gaspe Flint Derived Maize Lines (Example 16), instead of evaluating the resulting cointegrate vectors by restriction analysis, three colonies can be simultaneously used for the infection step as described in Example 13 (transformation via *Agrobacterium*).

Example 13

Transformation of Maize Using *Agrobacterium*

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium inoculation, co-cultivation, resting, selection, and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-Culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation, and the dishes are sealed with parafilm. The plates are incubated in darkness at 28° C. Actively growing putative events, evinced as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L GELRITE®, 100 µM acetosyringone (filter-sterilized), pH 5.8.
3. PHI-C: PHI-B without GELRITE® and acetosyringonee, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L GELRITE®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected. T1 plants can be grown under nitrogen limiting conditions, for example 1 mM nitrate, and analyzed for phenotypic changes. The following parameters can be quantified using image analysis: plant area, volume, growth rate and color analysis can be collected and quantified. Overexpression constructs that result in an alteration, compared to suitable control plants, in greenness (green color bin), yield, growth rate, biomass, fresh or dry weight at maturation, fruit or seed yield, total plant nitrogen content, fruit or seed nitrogen content, nitrogen content in vegetative tissue, free amino acid content in the whole plant, free amino acid content in vegetative tissue, free amino acid content in the fruit or seed, protein content in the fruit or seed, or protein content in a vegetative tissue can be considered evidence that the *Arabidopsis* lead gene functions in maize to enhance tolerance to nitrogen deprivation (increased nitrogen stress tolerance).

Furthermore, a recombinant DNA construct containing a validated *Arabidopsis* gene can be introduced into a maize inbred line either by direct transformation or introgression from a separately transformed line.

Example 14A

Preparation of Expression Vector for Transformation of Maize Lines with Validated Candidate *Arabidopsis* Gene (At1q67060) Using *Agrobacterium*

Using the INVITROGEN™ GATEWAY® technology, an LR Recombination Reaction can be performed with the same GATEWAY® entry clone described in Example 5 (containing the *Arabidopsis* LNT1 gene), entry clone PHP23112 (SEQ ID NO:14), entry clone PHP20234 (SEQ ID NO:9; FIG. 9), and destination vector PHP22655 (SEQ ID NO:10) to create a precursor plasmid with the following expression cassettes:

1. Ubiquitin promoter::moPAT::PinII terminator cassette expressing the PAT herbicide resistance gene used for selection during the transformation process.

2. LTP2 promoter::DS-RED2::PinII terminator cassette expressing the DS-RED color marker gene used for seed sorting.

3. Ubiquitin promoter::AT-LNT1::PinII terminator cassette over expressing the gene of interest, *Arabidopsis* LNT1 (At1g67060).

Example 14B

Transformation of Maize Lines with Validated Candidate *Arabidopsis* Gene (At1g67060) Using *Agrobacterium*

The LNT1 expression cassette described in Example 14A can be introduced into a maize inbred line, or a transformable maize line derived from an elite maize inbred line, using *Agrobacterium*-mediated transformation as described in Examples 12 and 13.

The expression vector can be electroporated into the LBA4404 *Agrobacterium* strain containing vector PHP10523 (SEQ ID NO:7, FIG. 7) to create a co-integrate vector, formed by recombination via COS sites contained on each vector. The cointegrate vector would contain the same three expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation. The electroporation protocol in, but not limited to, Example 12 may be used.

Example 15

Preparation of the Destination Vector PHP23236 for Transformation into Gaspe Flint derived Maize Lines Destination vector PHP23236 (FIG. 6; SEQ ID NO:6) was obtained by transformation of *Agrobacterium* strain LBA4404 containing PHP10523 (FIG. 7; SEQ ID NO:7) with vector PHP23235 (FIG. 8; SEQ ID NO:8) and isolation of the resulting co-integration product.

Destination vector PHP23236 can be used in a recombination reaction with an entry clone, as described in Example 16, to create a maize expression vector for transformation of Gaspe Flint derived maize lines.

Example 16

Preparation of Expression Constructs for Transformation into Gaspe Flint Derived Maize Lines Using the INVITROGEN™ GATEWAY® LR Recombination technology, the same entry clone described in Example 5 (containing the *Arabidopsis* LNT1 gene) can be directionally cloned into the GATEWAY® destination vector PHP23236 (SEQ ID NO:6; FIG. 6) to create an expression vector. This expression vector contains the cDNA of interest under control of the UBI promoter and is a T-DNA binary for *Agrobacterium*-mediated transformation into maize as described, but not limited to, the examples described herein.

Example 17A

Transformation of Gaspe Flint Derived Maize Lines with Validated Candidate *Arabidopsis* Gene (At1g67060)

Maize plants can be transformed to overexpress the *Arabidopsis* At1g67060 gene (and the corresponding homologs from other species) in order to examine the resulting phenotype. Expression constructs such as the one described in Example 16 may be used.

Recipient Plants

Recipient plant cells can be from a uniform maize line having a short life cycle ("fast cycling"), a reduced size, and high transformation potential. Typical of these plant cells for maize are plant cells from any of the publicly available Gaspe Flint (GF) line varieties. One possible candidate plant line variety is the F1 hybrid of GF×QTM (Quick Turnaround Maize, a publicly available form of Gaspe Flint selected for growth under greenhouse conditions) disclosed in Tomes et al. (U.S. application Ser. No. 10/367,416 filed Feb. 13, 2003; U.S. Patent Publication No. 2003/0221212 A1 published Nov. 27, 2003). Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line includes but is not limited to a double haploid line of GS3 (a highly transformable line) X Gaspe Flint. Yet another suitable line is a transformable elite maize inbred line carrying a transgene which causes early flowering, reduced stature, or both.

Transformation Protocol

Any suitable method may be used to introduce the transgenes into the maize cells, including but not limited to, inoculation type procedures using *Agrobacterium* based vectors (see, for example, Examples 12 and 13). Transformation may be performed on immature embryos of the recipient (target) plant.

Precision Growth and Plant Tracking

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location within the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location within the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. application Ser. No. 10/324,288 filed Dec. 19, 2002 (U.S. Patent Publication No. 2004/0122592 A1 published Jun. 24, 2004), incorporated herein by reference.

Phenotypic Analysis using Three-Dimensional Imaging

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. A digital imaging analyzer may be used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate, for example, the biomass, size, and morphology of each plant.

Due to the change in size of the plants from the time the first leaf appears from the soil to the time the plants are at the end of their development, the early stages of plant development are best documented with a higher magnification from the top. This imaging may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture, and motor focus. All camera settings may be made using LemnaTec software. For example, the instrumental variance of the imaging analyzer is less than about 5% for major components and less than about 10% for minor components.

Software

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g., Matlab, others) can be used for quantitative interpretation of the imaging data, and any of these software systems can be applied to the image data set.

Conveyor System

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores).

Biomass Estimation Based on Three-Dimensional Imaging

For best estimation of biomass the plant images should be taken from at least three axes, for example, the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green (for example, hues 50-66, see FIG. 12) and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis

Transgenes which modify plant architecture parameters may also be identified using the present invention, including such parameters as maximum height and width, internodal distances, angle between leaves and stem, number of leaves starting at nodes, and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g., pollination date, first silk date) can be recorded by the personnel responsible for performing plant care. To maximize data integrity and process efficiency, this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition. Example 17B Transformation of Gaspe Flint Derived Maize Lines with Maize Homologs Using the INVITROGEN™ GATEWAY® LR Recombination technology, an entry clone may be created for a maize homolog (SEQ ID NO:17 OR SEQ ID NO:19) (see Example 5 for entry clone preparation) and then directionally cloned into the GATEWAY® destination vector PHP23236 (SEQ ID NO:6; FIG. 6) to create a corresponding expression vector. Hence, the expression vectors PHP30106 and PHP30116 were constructed from SEQ ID NO:17 and SEQ ID NO:19, respectively. Each expression vector contains the cDNA of interest under control of the UBI promoter and is a T-DNA binary for *Agrobacterium*-mediated transformation into maize as described, but not limited to, the examples described herein.

Example 18A

Screening of Gaspe Flint Derived Maize Lines under Nitrogen Limiting Conditions

Transgenic plants can contain two or three doses of Gaspe Flint-3 with one dose of GS3 (GS3/(Gaspe-3)2× or GS3/(Gaspe-3)3×) and segregate 1:1 for a dominant transgene. Transgenic plants can be planted in 100% TURFACE, a commercial potting medium, and can be watered four times each day with 1 mM $KNO_3$ growth medium and with 2 mM $KNO_3$, or higher, growth medium (see FIG. 13). Control plants grown in 1 mM $KNO_3$ medium would be less green, produce less biomass, and have a smaller ear at anthesis (see FIG. 14 for an illustration of sample data).

Statistics would be used to decide if differences seen between treatments are really different. FIG. 14 illustrates one method which places letters after the values. Those values in the same column that have the same letter (not group of letters) following them are not significantly different. Using this method, if there are no letters following the values in a column, then there are no significant differences between any of the values in that column or, in other words, all the values in that column are equal.

Expression of a transgene would result in plants with improved plant growth in 1 mM KNO3 when compared to a transgenic null. Thus biomass and greenness (as described in Example 11) would be monitored during growth and compared to a transgenic null. Improvements in growth, greenness, and ear size at anthesis would be indications of increased nitrogen stress tolerance.

Example 18B

Procedure for Evaluation of Gaspe Flint Derived Maize Lines Under Nitrogen Limiting Conditions Gaspe Flint derived maize lines may be transformed via *Agrobacterium*. Typically, four transformation events for each plasmid construct may be evaluated under nitrogen limiting conditions in the following manner. Plants are planted in 100% Turface and watered until emergence. Following emergence, plants are divided equally between treatment groups and watered as appropriate to achieve saturation using drip irrigation. Daily irrigation schedule consists of a 9:00 AM, 12:00 PM, and 3:00 PM nutrient watering for 3 minutes (156 ml) between 13 and 24 days after planting (DAP). A fourth watering is added at 5:00 AM on 25 DAP, and a fifth watering is added at 5:00 PM on 31 DAP. Two treatments are applied, optimal (6.5 mMol KNO3) and reduced nitrogen (1.0 mMol KNO3). pH is monitored at least three times weekly for each table. The target pH for the experiment is 5.75-6.0. Imaging to assess surface area accumulation and specific growth rates (sgr) is performed for each plant three times per week, Monday, Wednesday and Friday. Plants are sampled for ELISA MoPAT on 9 DAP, and for expression and metabolic profiling analysis on 36 DAP. At 50% shed, 36 DAP, destructive ear and shoot phenotypes are collected manually. At 38 DAP, harvested tissue is oven dried (70C for 120 hrs.) to obtain dry weight data. The probability of a greater Student's one tailed t Test is calculated for each transgenic mean compared to the appropriate null mean (either segregant null or construct null). A minimum (P<t) of 0.1 is used as a cut off for a statistically significant result.

Example 18C

Transformation and Evaluation of Gaspe Flint Derived Maize Lines Under Nitrogen Limiting Conditions A Gaspe Flint derived maize line was transformed via *Agrobacterium* with plasmid PHP30116, encoding the *Zea mays* LNT1-like polypeptide (SEQ ID NO:20). Six transformation events were evaluated following a procedure similar to that described in Example 18B.

Tables 5 and 6 show the number of variables for each transgenic event that were significantly altered, as compared to the segregant nulls. A "positive effect" was defined as a statistically significant improvement in that variable for the transgenic event relative to the null control. A "negative effect" was defined as a statistically significant improvement in that variable for the null control relative to the transgenic event. Table 5 presents the number of variables with a significant change for individual events transformed with the PHP30116 construct. Table 6 presents the number of events that showed a significant change for each individual variable. The variables designated with "_end exponential" indicate that the variables were measured at the end of exponential growth. The variables designated with "_harvest" indicate that the variables were measured at the time of harvest.

TABLE 5

Number of Variables with a Significant Change* for Individual Events Transformed with PHP30116 Encoding the Zea mays LNT1-like Polypeptide (SEQ ID NO: 20)

| | 1.0 mMol KNO3 | | 6.5 mMol KNO3 | |
| --- | --- | --- | --- | --- |
| Event | Positive Effect | Negative Effect | Positive Effect | Negative Effect |
| EA2393.375.1.1 | 1 | 0 | 5 | 0 |
| EA2393.375.1.11 | 0 | 0 | 0 | 5 |
| EA2393.375.1.3 | 2 | 1 | 0 | 8 |
| EA2393.375.1.6 | 0 | 2 | 3 | 3 |
| EA2393.375.1.7 | 6 | 0 | 0 | 1 |
| EA2393.375.1.9 | 1 | 4 | 1 | 2 |

*P-value less than or equal to 0.1

TABLE 6

Number of Events Transformed with PHP30116 Encoding the Zea mays LNT1-like polypeptide (SEQ ID NO: 20) with a Significant Change* for Individual Variables

| | 1.0 mMol KNO3 | | 6.5 mMol KNO3 | |
| --- | --- | --- | --- | --- |
| Variable | Positive Effect | Negative Effect | Positive Effect | Negative Effect |
| area_end exponential | 1 | 0 | 1 | 3 |
| area_harvest | 1 | 1 | 0 | 2 |
| ear diameter | 0 | 1 | 2 | 2 |
| ear dry weight | 0 | 0 | 2 | 0 |
| ear fresh weight | 0 | 0 | 2 | 0 |
| maximum area | 1 | 1 | 0 | 2 |
| sgr – r2 > 0.9 | 1 | 1 | 0 | 2 |
| shoot dry weight | 1 | 0 | 1 | 3 |
| shoot fresh weight | 2 | 1 | 0 | 3 |
| shoot + ear dry weight | 1 | 0 | 0 | 1 |
| shoot + ear fresh weight | 1 | 0 | 0 | 1 |
| stalk + ear diameter | 1 | 2 | 1 | 0 |

*P-value less than or equal to 0.1

For construct PHP30116, the statistical value associated with each improved variable is presented in FIGS. 17-18. A significant positive effect had a P-value of less than or equal to 0.1. A significant negative effect is shown in parentheses. A blank entry indicates that a significant difference was not observed between the transgenic event and the null segregant. The results for each of six transformed maize lines are presented in FIGS. 17A-E. Events EA2393.375.1.3 and EA2393.375.1.7 had at least two variables with improved effects under reduced nitrogen conditions, while events EA2393.375.1.1 and EA2393.375.1.6 had at least two variables with improved effects under optimal nitrogen conditions. The summary evaluation for all six events with construct PHP30116 is presented in FIG. 18. When all events are combined, events with construct PHP30116 showed significant increases in area (taken at harvest) and in shoot fresh weight, under reduced nitrogen conditions.

Example 19

Nitrogen Utilization Efficiency (NUE) Maize Seedling Assay

Seeds of transgenic events can also be evaluated using a maize seedling assay. The maize seedling assay is implemented by separating into Transgenic (Treatment 1) and Null (Treatment 2) seed using a seed color marker and randomly assigning each treatment to blocks of 54 pots (experimental units) arranged in 6 rows by 9 columns. Each treatment (Transgenic or Bulked Nulls) can be replicated 9 times.

All seeds are planted in 4 inch, square pots containing Turface on 8 inch, staggered centers and watered four times each day with a solution containing the following nutrients:

| | | | |
|---|---|---|---|
| 1 mM CaCl$_2$ | 2 mM MgSO$_4$ | 0.5 mM KH$_2$PO$_4$ | 83 ppm Sprint330 |
| 3 mM KCl | 1 mM KNO$_3$ | 1 µM ZnSO$_4$ | 1 µM MnCl$_2$ |
| 3 µM H$_3$BO$_4$ | 1 µM MnCl$_2$ | 0.1 µM CuSO$_4$ | 0.1 µM NaMoO$_4$ |

After emergence the plants are thinned to one seed per pot. At harvest, plants are removed from the pots, and the Turface is washed from the roots. The roots are separated from the shoot, placed in a paper bag, and dried at 70° C. for 70 hr. The dried plant parts (roots and shoots) are weighed and placed in a 50 ml conical tube with approximately 20⁵⁄₃₂ inch steel balls and then ground by shaking in a paint shaker. Approximately, 30 mg of the ground tissue (weight recorded for later adjustment) is hydrolyzed in 2 ml of 20% H$_2$O$_2$ and 6M H$_2$SO$_4$ for 30 min at 170° C. After cooling, water is added to 20 ml, mixed thoroughly, and a 50 µl aliquot is removed and added to 950 µl 1M Na$_2$CO$_3$. The ammonia in this solution is used to estimate total reduced plant nitrogen by placing 100 µl of this solution into individual wells of a 96 well plate followed by adding 50 µl of OPA solution. Fluorescence, excitation=360 nM/emission=530 nM, is determined and compared to NH$_4$Cl standards dissolved in a similar solution and treated with OPA solution.

OPA solution—5 µl Mercaptoethanol+1 ml OPA stock solution

OPA stock—50 mg o-phthadialdehyde (OPA—Sigma #P0657) dissolved in 1.5 ml methanol+4.4 ml 1M Borate buffer pH 9.5 (3.09 g H$_3$BO$_4$+1 g NaOH in 50 ml water)+0.55 ml 20% SDS The following parameters are measured, and means of Transgenic parameters are compared to means of Null parameters using a Student's t test:

Total Plant Biomass (Total plant Dwt)

Root Biomass (Root Dwt)

Shoot Biomass (Shoot Dwt)

Root/Shoot Ratio

Plant N concentration ([N}=mg N/plant Dwt)

Total Plant N (Total Plant N)

Variance is calculated within each block using a nearest neighbor calculation as well as by Analysis of Variance (ANOVA) using a completely random design (CRD) model. An overall treatment effect for each block is calculated using an F statistic by dividing overall block treatment mean square by the overall block error mean square. The probability of a greater Student's t test is calculated for each transgenic mean compared to the appropriate null. A minimum (P<t) of 0.1 is used to define variables that show a significant difference (*).

Example 20

Yield Analysis of Maize Lines with the *Arabidopsis* Int1 or an Int1-Like Maize Homolog Transgenic plants, either inbred or hybrid, can undergo more vigorous field-based experiments to study yield enhancement and/or stability under nitrogen limiting and non-limiting conditions.

Subsequent yield analysis can be done to determine whether plants that contain the validated *Arabidopsis* Int1 gene or a maize homolog of Int1 have an improvement in yield performance (under nitrogen limiting or non-limiting conditions), when compared to the control (or reference) plants that do not contain the validated *Arabidopsis* Int1 gene or a maize homolog of Int1. Specifically, nitrogen limiting conditions can be imposed during the flowering and/or grain fill period for plants that contain either the validated *Arabidopsis* lead gene or a maize homolog of Int1 and the control plants. Reduction in yield can be measured for both. Plants containing the validated *Arabidopsis* lead gene or a maize homolog of Int1 would have less yield loss relative to the control plants, for example, at least 25% less yield loss, under nitrogen limiting conditions, or would have increased yield relative to the control plants under nitrogen non-limiting conditions.

Example 21

Transformation and Evaluation of Soybean with Soybean Homologs of Validated Lead Genes Based on homology searches, one or several candidate soybean homologs of validated *Arabidopsis* leads can be identified and also be assessed for their ability to enhance tolerance to nitrogen limiting conditions in soybean. Vector construction, plant transformation and phenotypic analysis will be similar to that in previously described Examples.

Example 22

Transformation of *Arabidopsis* with Maize and Soybean Homologs of Validated Lead Genes Soybean and maize homologs to validated *Arabidopsis* lead genes can be transformed into *Arabidopsis* under control of the 35S promoter and assayed for leaf area and green color bin accumulation when grown on low nitrogen medium. Vector construction and plant transformation can be as described in the examples herein. Assay conditions, data capture and data analysis can be similar to that in previously described Examples.

What is claimed is:

1. A method of increasing nitrogen stress tolerance in a plant, comprising:
    (a) introducing into a regenerable plant cell a recombinant DNA construct comprising a polynucleotide operably linked to at least one regulatory sequence, wherein the polynucleotide encodes a polypeptide having an amino acid sequence of at least 90% sequence identity, based on the Clustal V method of alignment, when compared to SEQ ID NO: 20;
    (b) regenerating a transgenic plant from the regenerable plant cell after step (a); and
    (c) selecting for a transgenic plant that exhibits increased nitrogen stress tolerance when compared to a control plant not comprising the recombinant DNA construct.

2. The method of claim 1, further comprising:
    (d) obtaining a progeny plant derived from the transgenic plant, wherein said progeny plant comprises in its genome the recombinant DNA construct and exhibits increased nitrogen stress tolerance when compared to a control plant not comprising the recombinant DNA construct.

3. A method of evaluating nitrogen stress tolerance in a plant, comprising:
    (a) introducing into a regenerable plant cell a recombinant DNA construct comprising a polynucleotide operably linked to at least one regulatory sequence, wherein the polynucleotide encodes a polypeptide having an amino acid sequence of at least 90% sequence identity, based on the Clustal V method of alignment, when compared to SEQ ID NO:;
    (b) regenerating a transgenic plant from the regenerable plant cell after step (a), wherein the transgenic plant comprises in its genome the recombinant DNA construct; and
    (c) evaluating the transgenic plant for nitrogen stress tolerance compared to a control plant not comprising the recombinant DNA construct.

4. The method of claim 3, further comprising:
    (d) obtaining a progeny plant derived from the transgenic plant, wherein the progeny plant comprises in its genome the recombinant DNA construct; and
    (e) evaluating the progeny plant for nitrogen stress tolerance compared to a control plant not comprising the recombinant DNA construct.

5. A method of evaluating nitrogen stress tolerance in a plant, comprising:
    (a) introducing into a regenerable plant cell a recombinant DNA construct comprising a polynucleotide operably linked to at least one regulatory sequence, wherein the polynucleotide encodes a polypeptide having an amino acid sequence of at least 90% sequence identity, based on the Clustal V method of alignment, when compared to SEQ ID NO:20;
    (b) regenerating a transgenic plant from the regenerable plant cell after step (a), wherein the transgenic plant comprises in its genome the recombinant DNA construct;
    (c) obtaining a progeny plant derived from the transgenic plant, wherein the progeny plant comprises in its genome the recombinant DNA construct; and
    (d) evaluating the progeny plant for nitrogen stress tolerance compared to a control plant not comprising the recombinant DNA construct.

6. The method of claim 1, wherein the plant is a maize plant or a soybean plant.

7. The method of claim 2, wherein the plant is a maize plant or a soybean plant.

8. The method of claim 3, wherein the plant is a maize plant or a soybean plant.

9. The method of claim 4, wherein the plant is a maize plant or a soybean plant.

10. The method of claim 5, wherein the plant is a maize plant or a soybean plant.

* * * * *